United States Patent
Wagner et al.

(10) Patent No.: US 10,912,790 B2
(45) Date of Patent: Feb. 9, 2021

(54) C/EBP ALPHA SARNA COMPOSITIONS AND METHODS OF USE

(71) Applicant: MiNA THERAPEUTICS LIMITED, London (GB)

(72) Inventors: Andreas Wagner, Vienna (AT); Robert Habib, London (GB); Hans E. Huber, Lansdale, PA (US); Pål Sætrom, Trondheim (NO); Endre Bakken Stovner, Trondheim (NO); Markus Hossbach, Kulmbach (DE); Monika Krampert, Bamberg (DE); Hans-Peter Vornlocher, Bayreuth (DE)

(73) Assignee: MiNA THERAPEUTICS LIMITED, London (GB)

( * ) Notice: Subject to any disclaimer, the term of this patent is extended or adjusted under 35 U.S.C. 154(b) by 262 days.

(21) Appl. No.: 15/568,139

(22) PCT Filed: Apr. 21, 2016

(86) PCT No.: PCT/GB2016/051117
§ 371 (c)(1),
(2) Date: Oct. 20, 2018

(87) PCT Pub. No.: WO2016/170349
PCT Pub. Date: Oct. 27, 2016

(65) Prior Publication Data
US 2020/0376020 A1 Dec. 3, 2020

Related U.S. Application Data

(60) Provisional application No. 62/150,889, filed on Apr. 22, 2015, provisional application No. 62/235,778, filed on Oct. 1, 2015, provisional application No. 62/308,521, filed on Mar. 15, 2016.

(51) Int. Cl.
| | | |
|---|---|---|
| A61K 31/7105 | (2006.01) |
| C12N 15/113 | (2010.01) |
| A61P 1/16 | (2006.01) |
| A61P 3/08 | (2006.01) |
| A61K 9/127 | (2006.01) |
| A61P 35/00 | (2006.01) |

(52) U.S. Cl.
CPC .......... *A61K 31/7105* (2013.01); *A61K 9/127* (2013.01); *A61P 1/16* (2018.01); *A61P 3/08* (2018.01); *A61P 35/00* (2018.01); *C12N 15/113* (2013.01); *C12N 2310/113* (2013.01); *C12N 2310/14* (2013.01); *C12N 2310/315* (2013.01); *C12N 2310/351* (2013.01)

(58) Field of Classification Search
CPC .... A61K 45/06; A61K 47/549; C12N 15/113; C12N 15/1135; C12N 2310/11; C12N 2310/113; C12N 2310/141

USPC .......... 435/6.1, 6.12, 91.1, 91.31, 455, 458; 514/44 A; 536/23.1, 24.5
See application file for complete search history.

(56) References Cited

U.S. PATENT DOCUMENTS

| | | | | |
|---|---|---|---|---|
| 10,633,659 B2* | 4/2020 | SÆtrom | ................. | A61P 43/00 |
| 2015/0299803 A1* | 10/2015 | Rodrigueza | ........ | G01N 33/5748 |
| | | | | 424/9.2 |
| 2016/0298113 A1* | 10/2016 | Sætrom | .................... | A61P 1/16 |

FOREIGN PATENT DOCUMENTS

| | | |
|---|---|---|
| JP | 2013-532973 A | 8/2013 |
| JP | 2014-519838 A | 8/2014 |
| WO | 2006/020768 A2 | 2/2006 |
| WO | 2006020768 A2 | 2/2006 |
| WO | 2010/055147 A1 | 5/2010 |
| WO | 2011/161460 A2 | 12/2011 |
| WO | 2011161460 A2 | 12/2011 |
| WO | 2012/175958 A1 | 12/2012 |
| WO | 2012175958 A1 | 12/2012 |
| WO | WO-2012175958 A1 * | 12/2012 ........... A61K 31/713 |
| WO | 2014/078468 A2 | 5/2014 |
| WO | 2014078468 A2 | 5/2014 |
| WO | 2015/075557 A2 | 5/2015 |
| WO | 2015075557 A2 | 5/2015 |
| WO | WO-2015075557 A2 * | 5/2015 ........... C12N 15/113 |
| WO | 2017/004357 A1 | 1/2017 |

OTHER PUBLICATIONS

Reebye et al, Hepatology, vol. 59, No. 1, pp. 216-227. (Year: 2014).*
Vikash Reebye et al: "Novel RNA oligonucleotide improves liver function and inhibits liver carcinogenesis in vivo", Hepatology, vol. 59, No. 1, Dec. 9, 2013, pp. 216-227.
Database Geneseq [Online] Jul. 22, 2010, "Human CEBPA DNA hybridizing probe SEQ ID:2". Database accession No. AYB64923.
Communication pursuant to Rule 164(2)(b) and Article 94(3) EPC dated Feb. 28, 2019 in corresponding European application No. 16 721 209.1, entitled "C/EBP Alpha saRNA Compositions and Methods of Use".
Examination Report No. 1 dated Sep. 17, 2018 in co-pending Australia application No. 2016251415 entitled, "C/EBP Alpha saRNA Compositions and Methods of Use".
Database Geneseq [Online] Jul. 22, 2010, "Human CEBPA DNA hybridizing probe SEQ ID:2". XP002759919.
Hongbo Huan et al: C/EBPA [alpha] Short-Activating RNA Suppresses Metastasis of Hepatocellular Carcinoma through Inhibiting EGFR/[beta-Catenin Signaling Mediated EMT, PLOS ONE, vol. 11, No. 4, 6 Apr. 6, 2016, p. e0153117.
Sorah Yoon et al: "Targeting Delivery of C/EBP [alpha]—saRNA by Pancreatic Ductal Adenocarcinoma-specific RNA Aptamers Inhibits Tumor Growth In Vivo", Molecular Therapy, vol. 24, No. 6, Mar. 17, 2016, pp. 1106-1116.

(Continued)

*Primary Examiner* — Jane J Zara
(74) *Attorney, Agent, or Firm* — DT Ward, PC; Donna T. Ward; Heng Zhu

(57) ABSTRACT

The invention relates to saRNA targeting a C/EBPα transcript and therapeutic compositions comprising said saRNA. Methods of using the therapeutic compositions are also provided.

23 Claims, 53 Drawing Sheets
Specification includes a Sequence Listing.

(56) References Cited

OTHER PUBLICATIONS

International Search Report dated Sep. 29, 2016 received in corresponding PCT Application No. PCT/GB2016/051117.
Office Action dated Apr. 1, 2020 in corresponding Japanese patent application No. 2017-554886 entitled C/EBP Alpha saRNA Compositions and Methods of Use.
Reebye, V. et al., "A novel RNA oligonucleotide improves liver function and inhibits liver carcinogenesis in vivo" (2014) Hepatology 59(1)216-227.
Nishikawa, T. et al., "Resetting the transcription factor network reverses terminal chronic hepatic failure" (2015) The Journal of Clinical Investigation 125(4):1533-1544.
Communication pursuant to Article 94(3) EPC dated Jul. 23, 2020 in corresponding European application 16721209.1, entitled "C/EBP Alpha saRNA Compositions and Methods of Use".
Examination Report dated Aug. 28, 2020 in corresponding India application No. 201717034525, entitled "C/EBP Alpha Sarna Compositions and Methods of Use".

* cited by examiner x-axis      concentration [nM]
y-axis      remaining mRNA x-axis      concentration [nM]
y-axis      remaining mRNA x-axis      concentration [nM]
y-axis      remaining mRNA x-axis concentration [nM]
y-axis remaining mRNA x-axis concentration [nM]
y-axis remaining mRNA x-axis concentration [nM]
y-axis remaining mRNA Data presented as mean ± SEM, $^\#p < 0.001$, $^\$p < 0.01$ and $^\delta p < 0.05$ vs. sham control; $^*p < 0.05$, $^{}p < 0.01$, $^{*}p < 0.001$ vs. NOV340/siFLUC.

p = 0.07455 p = 0.1134 p = 0.04022 p = 0.06455 p = 0.2293 p = 0.09047 p = 0.01467 p = 0.4257 p = 0.04417 p = 0.01264 p = 0.1231

Statistical significance compared to control animals: *, $p < 0.05$; **, $p < 0.01$.

- *p<0.05, p<0.01 & *p<0.001 one-way ANOVA followed by Tukey's multiple comparisons test, when compare to Normal diet group

- Treatment groups showed no significant changes in Body weight and Feed intake compared to MCD diet Control

*p<0.05 & **p<0.01, one-way ANOVA followed by Tukey's multiple comparisons test, when compare to Normal diet control group.

^p<0.05, ^^p<0.01 & ^^^p<0.001, when compared with MCD diet control.

p<0.001, one-way ANOVA followed by Tukey's multiple comparisons test, when compare to Normal diet group (week 6).

***p<0.001, when compared with MCD diet control (week 6).

$$$p<0.001, when compared with Normal diet group (week 4).

Chi square test.
*p<0.05 compared to path control-2

FIG. 39

Duplex:  5'-abasic-GCGGUCAUUGUCACUGGUCUU -3'
         |||||||||||||||||||
      3'- UUCGCCAGUAACAGUGACCAG

FIG. 40B

| Step-No. | TIME | CONDITIONS | ACTIVITY | IPC |
|---|---|---|---|---|
| *(steps 1-9: each separately for sense and antisense strand)* | | | | |
| 1. | 12-15 hours | 24°C ± 3°C | Solid Phase Synthesis | N/A |
| 2. | 1-2 hours | 50% TEA in Acetonitrile 24°C ± 3°C<br>40% Methylamine in H₂O, 40°C ± 2°C | Deprotection / Cleavage from Support | N/A |
| 3. | 2 hours | TEA·3HF (neat), 65°C ± 2°C | Deprotection | UV, RP-HPLC, LCMS |
| 4. | 12-15 hours | A buffer (50mM TEAA)<br>B buffer (Acetonitrile), 65°C ± 1°C | Purification by Reverse-Phase Chromatography | UV, RP-HPLC |
| 5. | ≤ 1 hours | TEAA/Acetonitrile | Pooling of Fractions | UV, RP-HPLC, LCMS |
| 6. | ≤ 8 hours | 10-25°C | Ultra Filtration (Concentration) | UV |
| 7. | ≤ 8 hours | 0.2M Sodium Phosphate, 10-25°C | Ultra Filtration (Salt/Buffer Exchange) | UV |
| 8. | 12-15 hours | 10-25°C | Ultra Filtration (Water Exchange / Concentration) | UV, Conductivity |
| 9. | ≤ 1 hour | 24°C ± 3°C | 0.2 μm Filtration | RP-HPLC |
| *Subsequent steps 10-14 executed once for duplex* | | | | |
| 10. | 1 hour | 24°C ± 3°C | Annealing of Duplex (using sense and antisense strand solution) | SE-HPLC |
| 11. | ≤ 1 hour | 24°C ± 3°C | 0.2 μm Filtration | |

FIG. 41

| Step-No. | TIME | CONDITIONS | ACTIVITY | In-Process Control (IPC) |
|---|---|---|---|---|
| 1. a) | 10 – 18 hours | Lipids (POPC, DOPE, CHEMS) in Ethanol, 55°C ± 5°C | Preparation of Lipids Solution | n.a. |
|  | 1 – 5 hours | Lipids (POPC, DOPE, CHEMS, MOCHOL) in Ethanol, 55°C ± 5°C | Preparation of Lipids Solution | Lipid concentration |
| b) | n.d. | CEBPA-51 (RNA in Sodium Acetate / Sucrose Buffer, pH 4.0), 15-25°C | Preparation of CEBPA-51 Solution | CEBPA-51 conc. |
| 2. | n.d. | 100 mM NaCl/136 mM Na$_2$HPO$_4$, pH 9.0 buffer, 15-25°C | Ethanol dilution and pH adjustment | Particle size, size distribution. |
| 3. | 1 - 4 hours | CEBPA-51 liposomes at pH 7.5 ± 0.5, 15-25°C | Extrusion of Liposomes | Particle size, size distribution. |
| 4. | 2 – 5 hours | CEBPA-51 liposomes in PB-Sucrose at pH 7.5, 15-25°C | Ultra-/Diafiltration and Buffer Exchange | CEBPA-51 conc., lipid conc., pH, osmolality, zeta potential, ribogreen assay, particle size, size distribution. |
| 5. | < 2 hours | Concentrated bulk liposomes in PB-Sucrose buffer, 15-25°C | 0.2 µm Filtration (bioburden reduction) | -as above- |
| 6. | < 2 hours | Dilution wit PB-Sucrose pH 7.5; 15-25°C | Concentration Adjustment and 0.2 µm Filtration (sterile filtration) of Bulk Product | Bioburden testing before sterile filtration |
| 7. | 3 – 8 hours | 15-25°C | Filling and Capping | Visual Inspection |
| 8. |  | ≤ -20°C | Final Drug Product Vials | DP Release Testing |
| 9. | Until use /shipping | ≤ -20°C | Storage |  |

C/EBP ALPHA SARNA COMPOSITIONS AND METHODS OF USE

CROSS-REFERENCE TO RELATED APPLICATIONS

This application is a 35 U.S.C. § 371 U.S. National Stage Entry of International Application No. PCT/GB2016/051117 filed Apr. 21, 2016, entitled C/EBP ALPHA SARNA COMPOSITIONS AND METHODS OF USE, which claims the benefit of priority of U.S. Provisional Application No. 62/150,889 filed Apr. 22, 2015, entitled C/EBP ALPHA COMPOSITIONS AND METHODS OF USE, U.S. Application No. 62/235,778 filed Oct. 1, 2015, entitled C/EBP ALPHA SARNA COMPOSITIONS AND METHODS OF USE, U.S. Application No. 62/308,521 filed Mar. 15, 2016, entitled C/EBP ALPHA SARNA COMPOSITIONS AND METHODS OF USE, the contents of which are each incorporated herein by reference in their entirety.

REFERENCE TO SEQUENCE LISTING

The instant application contains a Sequence Listing which has been submitted electronically in ASCII format and is hereby incorporated by reference in its entirety. Said ASCII copy, created on Oct. 20, 2017 is named 20581015US371 SEQLIST.txt and is 80,877 bytes in size.

FIELD OF THE INVENTION

The invention relates to polynucleotide, specifically saRNA, compositions for the modulating C/EBPα and C/EBPα pathways and to the methods of using the compositions in therapeutic applications such as treating metabolic disorders, hyperproliferative diseases, and regulating stem cell linage.

BACKGROUND OF THE INVENTION

CCAAT/enhancer-binding protein α (C/EBPα, C/EBP alpha, C/EBPA or CEBPA) is a leucine zipper protein that is conserved across humans and rats. This nuclear transcription factor is enriched in hepatocytes, myelomonocytes, adipocytes, as well as other types of mammary epithelial cells [Lekstrom-Himes et al., *J. Bio. Chem*, vol. 273, 28545-28548 (1998)]. It is composed of two transactivation domains in the N-terminal part, and a leucine zipper region mediating dimerization with other C/EBP family members and a DNA-binding domain in the C-terminal part. The binding sites for the family of C/EBP transcription factors are present in the promoter regions of numerous genes that are involved in the maintenance of normal hepatocyte function and response to injury. C/EBPα has a pleiotropic effect on the transcription of several liver-specific genes implicated in the immune and inflammatory responses, development, cell proliferation, anti-apoptosis, and several metabolic pathways [Darlington et al., *Current Opinion of Genetic Development*, vol. 5(5), 565-570 (1995)]. It is essential for maintaining the differentiated state of hepatocytes. It activates albumin transcription and coordinates the expression of genes encoding multiple ornithine cycle enzymes involved in urea production, therefore playing an important role in normal liver function.

In the adult liver, C/EBPα is defined as functioning in terminally differentiated hepatocytes whilst rapidly proliferating hepatoma cells express only a fraction of C/EBPα [Umek et al., *Science*, vol. 251, 288-292 (1991)]. C/EBPα is known to up-regulate p21, a strong inhibitor of cell proliferation through the up-regulation of retinoblastoma and inhibition of Cdk2 and Cdk4 [Timchenko et al., *Genes & Development*, vol. 10, 804-815 (1996); Wang et al., *Molecular Cell*, vol. 8, 817-828 (2001)]. In hepatocellular carcinoma (HCC), C/EBPα functions as a tumor suppressor with anti-proliferative properties [Iakova et al., *Seminars in Cancer Biology*, vol. 21(1), 28-34 (2011)].

Different approaches are carried out to study C/EBPα mRNA or protein modulation. It is known that C/EBPα protein is regulated by post-translational phosphorylation and sumoylation. For example, FLT3 tyrosine kinase inhibitors and extra-cellular signal-regulated kinases 1 and/or 2 (ERK1/2) block serine-21 phosphorylation of C/EBPα, which increases the granulocytic differentiation potential of the C/EBPα protein [Radomska et al., *Journal of Experimental Medicine*, vol. 203(2), 371-381 (2006) and Ross et al., *Molecular and Cellular Biology*, vol. 24(2), 675-686 (2004)]. In addition, C/EBPα translation can be efficiently induced by 2-cyano-3,12-dioxoolean-1,9-dien-28-oic acid (CDDO), which alters the ratio of the C/EBPα protein isoforms in favor of the full-length p42 form over p30 form thereby inducing granulocytic differentiation [Koschmieder et al., *Blood*, vol. 110(10), 3695-3705 (2007)]. The C/EBPα gene is an intronless gene located on chromosome 19q13.1. Most eukaryotic cells use RNA-complementarity as a mechanism for regulating gene expression. One example is the RNA interference (RNAi) pathway which uses double stranded short interfering RNAs to knockdown gene expression via the RNA-induced silencing complex (RISC). It is now established that short duplex RNA oligonucleotides also have the ability to target the promoter regions of genes and mediate transcriptional activation of these genes and they have been referred to as RNA activation (RNAa), antigene RNA (agRNA) or short activating RNA (saRNA) [Li et al., *PNAS*, vol. 103, 17337-17342 (2006)]. saRNA induced activation of genes is conserved in other mammalian species including mouse, rat, and non-human primates and is fast becoming a popular method for studying the effects of endogenous up-regulation of genes. Thus, there is a need for targeted modulation of C/EBPα for therapeutic purposes with saRNA.

SUMMARY OF THE INVENTION

The present invention provides compositions, methods and kits for the design, preparation, manufacture, formulation and/or use of short activating RNA (saRNA) molecules that modulate C/EBPα gene expression and/or function for therapeutic purposes, including diagnosing and prognosis.

One aspect of the invention provides a pharmaceutical composition comprising a saRNA that targets a C/EBPα transcript and at least one pharmaceutically acceptable carrier. Yet another aspect of the invention provides a method of regulating stem cell differentiation and pluripotency comprising contact said stem cell with a saRNA that targets a C/EBPα transcript.

The details of various embodiments of the invention are set forth in the description below. Other features, objects, and advantages of the invention will be apparent from the description and the drawings, and from the claims.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead being placed upon illustrating the principles of various embodiments of the invention.

FIG. 9 comprises FIG. 9A and FIG. 9B showing expression levels.

FIG. 23A is sham control. FIG. 23B is CCL4-treated rats that received NOV340/siFluc treatment (negative control). FIG. 23C is CCL4-treated rats that received MTL-CEBPA treatment.

FIG. 26 shows serum and physical parameters of diabetes rats treated with CEBPA-saRNA.

FIG. 39 shows a duplex of CEBPA-51 (sense and antisense strands).

FIG. 40B is a detailed flow chart of CEBPA-51 synthesis.

FIG. 41 is a flow chart of MTL-CEBPA production (Steps 1-9).

DETAILED DESCRIPTION

Figure 1:
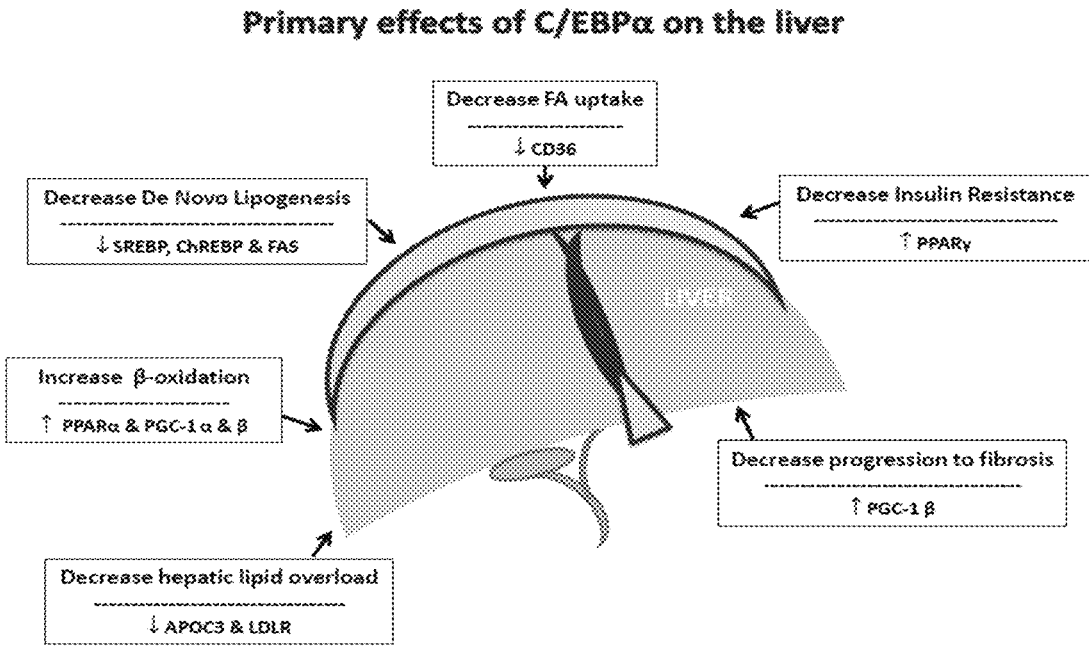
FIG. 1 shows the primary effects of C/EBPα on the liver.

The present invention provides compositions, methods and kits for modulating C/EBPα gene expression and/or function for therapeutic purposes. These compositions, methods and kits comprise nucleic acid constructs that target a C/EBPα transcript.

C/EBPα protein is known as a critical regulator of metabolic processes and cell proliferation. Modulating C/EBPα gene has great potentials for therapeutic purposes. The present invention addresses this need by providing nucleic acid constructs targeting a C/EBPα transcript, wherein the nucleic acid constructs may include single or double stranded DNA or RNA with or without modifications.

C/EBPα gene as used herein is a double-stranded DNA comprising a coding strand and a template strand. It may also be referred to the target gene in the present application.

The terms "C/EBPα transcript", "C/EBPα target transcript" or "target transcript" in the context may be C/EBPα mRNA encoding C/EBPα protein. C/EBPα mRNA is transcribed from the template strand of C/EBPα gene and may exist in the mitochondria.

The antisense RNA of the C/EBPα gene transcribed from the coding strand of the C/EBPα gene is called a target antisense RNA transcript herein after. The target antisense RNA transcript may be a long non-coding antisense RNA transcript.

The terms "small activating RNA", "short activating RNA", or "saRNA" in the context of the present invention means a single-stranded or double-stranded RNA that upregulates or has a positive effect on the expression of a specific gene. The saRNA may be single-stranded of 14 to 30 nucleotides. The saRNA may also be double-stranded, each strand comprising 14 to 30 nucleotides. The gene is called the target gene of the saRNA. A saRNA that upregulates the expression of the C/EBPα gene is called an "C/EBPα-saRNA" and the C/EBPα gene is the target gene of the C/EBPα-saRNA.

In one embodiment, C/EBPα-saRNA targeting a C/EBPα target antisense RNA transcript upregulates C/EBPα gene expression and/or function.

The terms "target" or "targeting" in the context mean having an effect on a C/EBPα gene. The effect may be direct or indirect. Direct effect may be caused by complete or partial hybridization with the C/EBPα target antisense RNA transcript. Indirect effect may be upstream or downstream.

C/EBPα-saRNA may have a downstream effect on a biological process or activity. In such embodiments, C/EBPα-saRNA may have an effect (either upregulating or downregulating) on a second, non-target transcript.

The term "gene expression" in the context may include the transcription step of generating C/EBPα mRNA from C/EBPα gene or the translation step generating C/EBPα protein from C/EBPα mRNA. An increase of C/EBPα mRNA and an increase of C/EBPα protein both indicate an increase or a positive effect of C/EBPα gene expression.

By "upregulation" or "activation" of a gene is meant an increase in the level of expression of a gene, or levels of the polypeptide(s) encoded by a gene or the activity thereof, or levels of the RNA transcript(s) transcribed from the template strand of a gene above that observed in the absence of the saRNA of the present invention. The saRNA of the present invention may have a direct or indirect upregulating effect on the expression of the target gene.

In one embodiment, the saRNA of the present invention may show efficacy in proliferating cells. As used herein with respect to cells, "proliferating" means cells which are growing and/or reproducing rapidly.

I. Composition of the Invention

One aspect of the present invention provides pharmaceutical compositions comprising a saRNA that upregulates CEBPA gene, and at least one pharmaceutically acceptable carrier. Such a saRNA is referred herein after as "C/EBPα-saRNA", or "saRNA of the present invention", used interchangeably in this application.

saRNA Design

C/EBPα-saRNA upregulates C/EBPα gene. In one embodiment, it is designed to be complementary to a target antisense RNA transcript of C/EBPα gene, and it may exert its effect on C/EBPα gene expression and/or function by down-regulating the target antisense RNA transcript.

The term "complementary to" in the context means being able to hybridize with the target antisense RNA transcript under stringent conditions.

The term "sense" when used to describe a nucleic acid sequence in the context of the present invention means that the sequence has identity to a sequence on the coding strand of a gene. The term "antisense" when used to describe a nucleic acid sequence in the context of the present invention means that the sequence is complementary to a sequence on the coding strand of a gene.

It is to be understood that thymidine of the DNA is replaced by uridine in RNA and that this difference does not alter the understanding of the terms "antisense" or "complementarity".

The target antisense RNA transcript may be transcribed from a locus on the coding strand between up to 100, 80, 60, 40, 20 or 10 kb upstream of a location corresponding to the target gene's transcription start site (TSS) and up to 100, 80, 60, 40, 20 or 10 kb downstream of a location corresponding to the target gene's transcription stop site.

In one embodiment, the target antisense RNA transcript is transcribed from a locus on the coding strand located within +/−1 kb of the target gene's transcription start site.

In another embodiment, the target antisense RNA transcript is transcribed from a locus on the coding strand located within +/−500, +/−250 or +/−100 of the target gene's transcription start site.

In another embodiment, the target antisense RNA transcript is transcribed from a locus on the coding strand located +/−2000 nucleotides of the target gene's transcription start site.

In another embodiment, the locus on the coding strand is no more than 1000 nucleotides upstream or downstream from a location corresponding to the target gene's transcription start site.

In another embodiment, the locus on the coding strand is no more than 500 nucleotides upstream or downstream from a location corresponding to the target gene's transcription start site.

The term "transcription start site" (TSS) as used herein means a nucleotide on the template strand of a gene corresponding to or marking the location of the start of transcription. The TSS may be located within the promoter region on the template strand of the gene.

The term "transcription stop site" as used herein means a region, which can be one or more nucleotides, on the template strand of a gene, which has at least one feature such as, but not limited to, a region which encodes at least one stop codon of the target transcript, a region encoding a sequence preceding the 3'UTR of the target transcript, a region where the RNA polymerase releases the gene, a region encoding a splice site or an area before a splice site and a region on the template strand where transcription of the target transcript terminates.

The phrase "is transcribed from a particular locus" in the context of the target antisense RNA transcript of the invention means the transcription of the target antisense RNA transcript starts at the particular locus.

The target antisense RNA transcript is complementary to the coding strand of the genomic sequence of the target gene, and any reference herein to "genomic sequence" is shorthand for "coding strand of the genomic sequence".

The "coding strand" of a gene has the same base sequence as the mRNA produced, except T is replayed by U in the mRNA. The "template strand" of a gene is therefore complementary and antiparallel to the mRNA produced.

Thus, the target antisense RNA transcript may comprise a sequence which is complementary to a genomic sequence located between 100, 80, 60, 40, 20 or 10 kb upstream of the target gene's transcription start site and 100, 80, 60, 40, 20 or 10 kb downstream of the target gene's transcription stop site.

In one embodiment, the target antisense RNA transcript comprises a sequence which is complementary to a genomic sequence located between 1 kb upstream of the target gene's transcription start site and 1 kb downstream of the target gene's transcription stop site.

In another embodiment, the target antisense RNA transcript comprises a sequence which is complementary to a genomic sequence located between 500, 250 or 100 nucleotides upstream of the target gene's transcription start site and ending 500, 250 or 100 nucleotides downstream of the target gene's transcription stop site.

The target antisense RNA transcript may comprise a sequence which is complementary to a genomic sequence which includes the coding region of the CEBPA gene. The target antisense RNA transcript may comprise a sequence which is complementary to a genomic sequence that aligns with the target gene's promoter region on the template strand. Genes may possess a plurality of promoter regions, in which case the target antisense RNA transcript may align with one, two or more of the promoter regions. An online database of annotated gene loci may be used to identify the promoter regions of genes. The terms 'align' and 'alignment' when used in the context of a pair of nucleotide sequences mean the pair of nucleotide sequences are complementary to each other or have sequence identity with each other.

The region of alignment between the target antisense RNA transcript and the promoter region of the target gene may be partial and may be as short as a single nucleotide in length, although it may be at least 15 or at least 20 nucleotides in length, or at least 25 nucleotides in length, or at least 30, 35, 40, 45 or 50 nucleotides in length, or at least 55, 60, 65, 70 or 75 nucleotides in length, or at least 100 nucleotides in length. Each of the following specific arrangements is intended to fall within the scope of the term "alignment":

a) The target antisense RNA transcript and the target gene's promoter region are identical in length and they align (i.e. they align over their entire lengths).

b) The target antisense RNA transcript is shorter than the target gene's promoter region and aligns over its entire length with the target gene's promoter region (i.e. it aligns over its entire length to a sequence within the target gene's promoter region).

c) The target antisense RNA transcript is longer than the target gene's promoter region and the target gene's promoter region is aligned fully by it (i.e. the target gene's promoter region is aligns over its entire length to a sequence within the target antisense RNA transcript).

d) The target antisense RNA transcript and the target gene's promoter region are of the same or different lengths and the region of alignment is shorter than both the length of the target antisense RNA transcript and the length of the target gene's promoter region.

The above definition of "align" and "alignment" applies mutatis mutandis to the description of other overlapping, e.g., aligned sequences throughout the description. Clearly, if a target antisense RNA transcript is described as aligning with a region of the target gene other than the promoter region then the sequence of the target antisense RNA transcript aligns with a sequence within the noted region rather than within the promoter region of the target gene.

In one embodiment, the target antisense RNA transcript is at least 1 kb, or at least 2, 3, 4, 5, 6, 7, 8, 9 or 10, e.g., 20, 25, 30, 35 or 40 kb long.

In one embodiment, the target antisense RNA transcript comprises a sequence which is at least 75%, or at least 85%, or at least 90%, or at least 95% complementary along its full length to a sequence on the coding strand of the target gene.

The present invention provides saRNAs targeting the target antisense RNA transcript and may effectively and specifically down-regulate such target antisense RNA transcripts. This can be achieved by saRNA having a high degree of complementarity to a region within the target antisense RNA transcript. The saRNA will have no more than 5, or no more than 4 or 3, or no more than 2, or no more than 1, or no mismatches with the region within the target antisense RNA transcript to be targeted.

Figure 3:
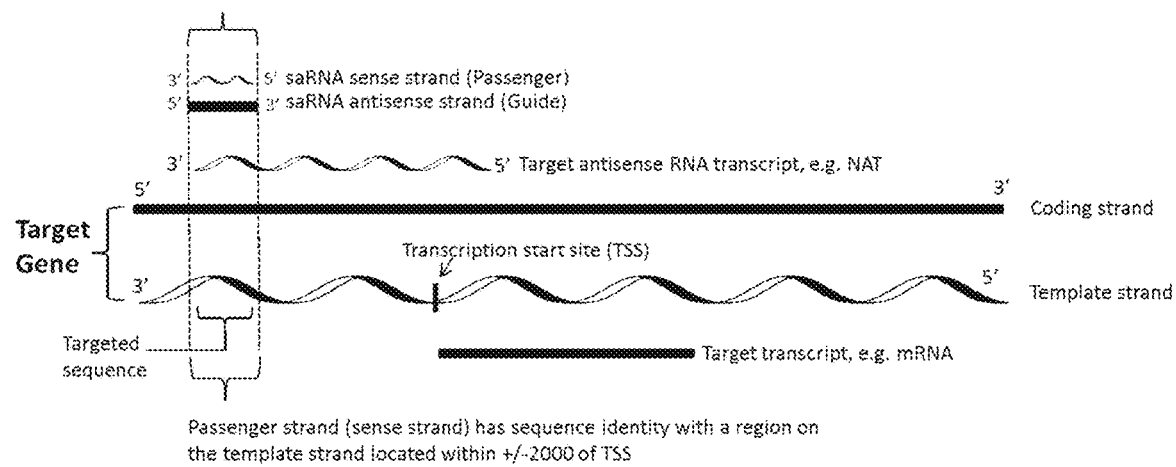
FIG. 3 is a schematic illustrating the relationships among the nucleic acid moieties involved in the function of an saRNA of the invention.
Figure 4A:
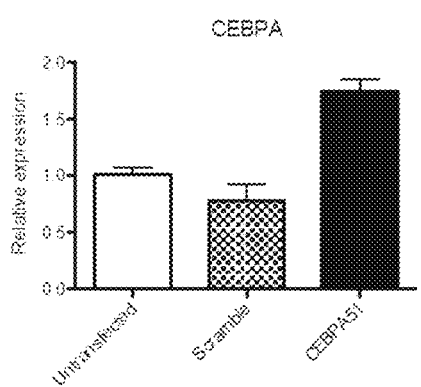
FIG. 4A-4D show upregulation of CEBPA in a panel of HCC cells by CEBPA-saRNA.
Figure 4B:
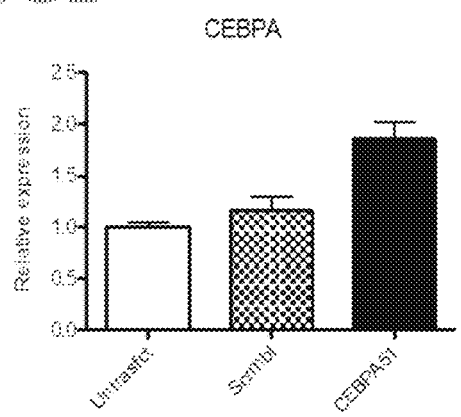
Figure 4C:
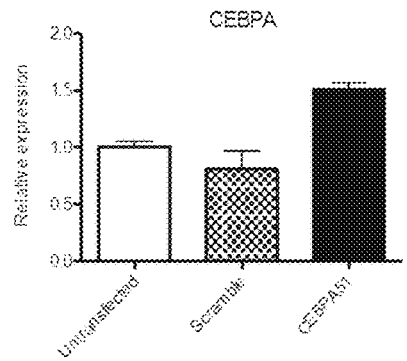
Figure 4D:
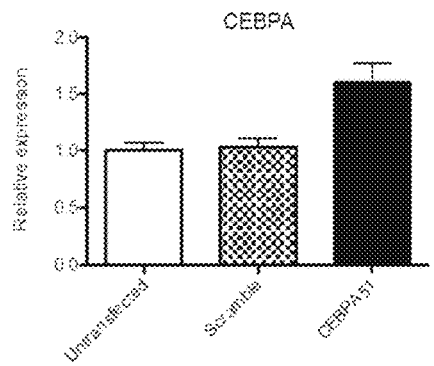
Figure 5A:
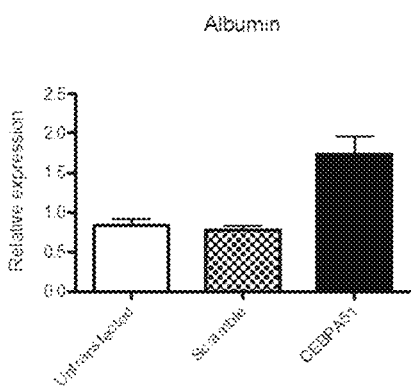
FIG. 5A-5D show upregulation of albumin in a panel of HCC cells by CEBPA-saRNA.
Figure 5B:
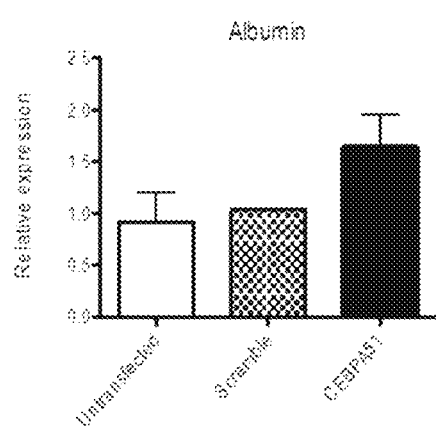
Figure 5C:
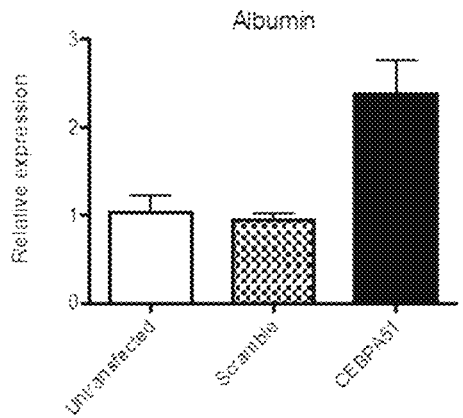
Figure 5D:
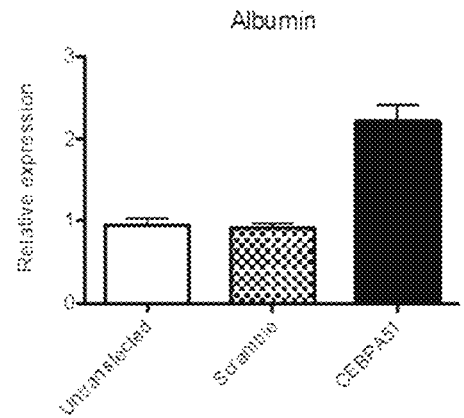

Referring to FIG. 3, as the target antisense RNA transcript has sequence identity with a region of the template strand of the target gene, the target antisense RNA transcript will be in part identical to a region within the template strand of the target gene allowing reference to be made either to the template strand of the gene or to a target antisense RNA transcript. The location at which the saRNA hybridizes or binds to the target antisense RNA transcript (and hence the same location on the template strand) is referred to as the "targeted sequence" or "target site".

The antisense strand of the saRNA (whether single- or double-stranded) may be at least 80%, 90%, 95%, 98%, 99% or 100% identical with the reverse complement of the targeted sequence. Thus, the reverse complement of the antisense strand of the saRNA has a high degree of sequence identity with the targeted sequence. The targeted sequence may have the same length, i.e., the same number of nucleotides, as the saRNA and/or the reverse complement of the saRNA.

In some embodiments, the targeted sequence comprises at least 14 and less than 30 nucleotides.

In some embodiments, the targeted sequence has 19, 20, 21, 22, or 23 nucleotides.

In some embodiments, the location of the targeted sequence is situated within a promoter area of the template strand.

In some embodiments, the targeted sequence is located within a TSS (transcription start site) core of the template stand. A "TSS core" or "TSS core sequence" as used herein, refers to a region between 2000 nucleotides upstream and 2000 nucleotides downstream of the TSS (transcription start site). Therefore, the TSS core comprises 4001 nucleotides and the TSS is located at position 2001 from the 5' end of the TSS core sequence. CEBPA TSS core sequence is show in the table below:

| CEBPA mRNA REF. No. | CEBPA protein REF. No. | CEBPA TSS core genomic location | CEBPA TSS core sequence ID No. |
|---|---|---|---|
| NM_001285829 | NP_001272758 | chr19:33302564 minus strand | SEQ ID No. 77 |
| NM_001287424 | NP_001274353 | | |
| NM_001287435 | NP_001274364 | | |
| NM_004364 | NP_004355 | | |

In some embodiments, the targeted sequence is located between 1000 nucleotides upstream and 1000 nucleotides downstream of the TSS.

In some embodiments, the targeted sequence is located between 500 nucleotides upstream and 500 nucleotides downstream of the TSS.

In some embodiments, the targeted sequence is located between 250 nucleotides upstream and 250 nucleotides downstream of the TSS.

In some embodiments, the targeted sequence is located between 100 nucleotides upstream and 100 nucleotides downstream of the TSS.

In some embodiments, the targeted sequence is located upstream of the TSS in the TSS core. The targeted sequence may be less than 2000, less than 1000, less than 500, less than 250, or less than 100 nucleotides upstream of the TSS.

In some embodiments, the targeted sequence is located downstream of the TSS in the TSS core. The targeted sequence may be less than 2000, less than 1000, less than 500, less than 250, or less than 100 nucleotides downstream of the TSS.

In some embodiments, the targeted sequence is located +/−50 nucleotides surrounding the TSS of the TSS core. In some embodiments, the targeted sequence substantially overlaps the TSS of the TSS core. In some embodiments, the targeted sequence overlaps begins or ends at the TSS of the TSS core. In some embodiments, the targeted sequence overlaps the TSS of the TSS core by 1, 2, 3, 4, 5, 6, 7, 8, 9, 10, 11, 12, 13, 14, 15, 16, 17, 18 or 19 nucleotides in either the upstream or downstream direction.

The location of the targeted sequence on the template strand is defined by the location of the 5' end of the targeted sequence. The 5' end of the targeted sequence may be at any position of the TSS core and the targeted sequence may start at any position selected from position 1 to position 4001 of the TSS core. For reference herein, when the 5' most end of the targeted sequence from position 1 to position 2000 of the TSS core, the targeted sequence is considered upstream of the TSS and when the 5' most end of the targeted sequence is from position 2002 to 4001, the targeted sequence is considered downstream of the TSS. When the 5' most end of the targeted sequence is at nucleotide 2001, the targeted sequence is considered to be a TSS centric sequence and is neither upstream nor downstream of the TSS.

For further reference, for example, when the 5' end of the targeted sequence is at position 1600 of the TSS core, i.e., it is the $1600^{th}$ nucleotide of the TSS core, the targeted sequence starts at position 1600 of the TSS core and is considered to be upstream of the TSS.

In one embodiment, the saRNA of the present invention may have two strands that form a duplex, one strand being a guide strand. The saRNA duplex is also called a double-stranded saRNA. A double-stranded saRNA or saRNA duplex, as used herein, is a saRNA that includes more than one, and preferably, two, strands in which interstrand hybridization can form a region of duplex structure. The two strands of a double-stranded saRNA are referred to as an antisense strand or a guide strand, and a sense strand or a passenger strand.

The antisense strand of a saRNA duplex, used interchangeably with antisense strand saRNA or antisense saRNA, has a high degree of complementarity to a region within the target antisense RNA transcript. The antisense strand may have no more than 5, or no more than 4 or 3, or no more than 2, or no more than 1, or no mismatches with the region within the target antisense RNA transcript or targeted sequence. Therefore, the antisense strand has a high degree of complementary to the targeted sequence on the template strand. The sense strand of the saRNA duplex, used interchangeably with sense strand saRNA or sense saRNA, has a high degree of sequence identity with the targeted sequence on the template strand. In some embodiments, the targeted sequence is located within the promoter area of the template strand. In some embodiments, the targeted sequence is located within the TSS core of the template stand.

The location of the antisense strand and/or sense strand of the saRNA duplex, relative to the targeted sequence is defined by making reference to the TSS core sequence. For example, when the targeted sequence is downstream of the TSS, the antisense saRNA and the sense saRNA start downstream of the TSS. In another example, when the targeted sequence starts at position 200 of the TSS core, the antisense saRNA and the sense saRNA start upstream of the TSS.

The relationships among the saRNAs, a target gene, a coding strand of the target gene, a template strand of the target gene, a target antisense RNA transcript, a target transcript, a targeted sequence/target site, and the TSS are shown in FIG. 3.

A "strand" in the context of the present invention means a contiguous sequence of nucleotides, including non-naturally occurring or modified nucleotides. Two or more strands may be, or each form a part of, separate molecules, or they may be connected covalently, e.g., by a linker such as a polyethyleneglycol linker. At least one strand of a saRNA may comprise a region that is complementary to a target antisense RNA. Such a strand is called an antisense or guide strand of the saRNA duplex. A second strand of a saRNA that comprises a region complementary to the antisense strand of the saRNA is called a sense or passenger strand.

A saRNA duplex may also be formed from a single molecule that is at least partly self-complementary forming a hairpin structure, including a duplex region. In such case, the term "strand" refers to one of the regions of the saRNA that is complementary to another internal region of the saRNA. The guide strand of the saRNA will have no more than 5, or no more than 4 or 3, or no more than 2, or no more than 1, or no mismatches with the sequence within the target antisense RNA transcript.

In some embodiments, the passenger strand of a saRNA may comprise at least one nucleotide that is not complementary to the corresponding nucleotide on the guide strand, called a mismatch with the guide strand. The mismatch with the guide strand may encourage preferential loading of the guide strand (Wu et al., *PLoS ONE*, vol. 6(12):e28580 (2011), the contents of which are incorporated herein by reference in their entirety). In one embodiment, the at least one mismatch with the guide strand may be at 3' end of the passenger strand. In one embodiment, the 3' end of the passenger strand may comprise 1-5 mismatches with the guide strand. In one embodiment, the 3' end of the passenger strand may comprise 2-3 mismatches with the guide strand. In one embodiment, the 3' end of the passenger strand may comprise 6-10 mismatches with the guide strand.

In one embodiment, an saRNA duplex may show efficacy in proliferating cells

A saRNA duplex may have siRNA-like complementarity to a region of a target antisense RNA transcript; that is, 100% complementarity between nucleotides 2-6 from the 5' end of the guide strand in the saRNA duplex and a region of the target antisense RNA transcript. Other nucleotides of the saRNA may, in addition, have at least 80%, 90%, 95%, 98%, 99% or 100% complementarity to a region of the target antisense RNA transcript. For example, nucleotides 7 (counted from the 5' end) until the 3' end of the saRNA may have least 80%, 90%, 95%, 98%, 99% or 100% complementarity to a region of the target antisense RNA transcript.

The terms "small interfering RNA" or "siRNA" in the context mean a double-stranded RNA typically 20-25 nucleotides long involved in the RNA interference (RNAi) pathway and interfering with or inhibiting the expression of a specific gene. The gene is the target gene of the siRNA. For example, siRNA that interferes the expression of APOA1 gene is called "APOA1-siRNA" and the APOA1 gene is the target gene. siRNA is usually about 21 nucleotides long, with 3' overhangs (e.g., 2 nucleotides) at each end of the two strands.

siRNA inhibits target gene expression by binding to and promoting the cleavage of one or more RNA transcripts of the target gene at specific sequences. Typically in RNAi the RNA transcripts are mRNA, so cleavage of mRNA results in the down-regulation of gene expression. In the present invention, not willing to be bound with any theory, one of the possible mechanisms is that saRNA of the present invention may modulate the target gene expression by cleavage of the target antisense RNA transcript.

A double-stranded saRNA may include one or more single-stranded nucleotide overhangs. The term "overhang" or "tail" in the context of double-stranded saRNA and siRNA refers to at least one unpaired nucleotide that protrudes from the duplex structure of saRNA or siRNA. For example, when a 3'-end of one strand of a saRNA extends beyond the 5'-end of the other strand, or vice versa, there is a nucleotide overhang. A saRNA may comprise an overhang of at least one nucleotide; alternatively the overhang may comprise at least two nucleotides, at least three nucleotides, at least four nucleotides, at least five nucleotides or more. A nucleotide overhang may comprise of consist of a nucleotide/nucleoside analog, including a deoxynucleotide/nucleoside. The overhang(s) may be on the sense strand, the antisense strand or any combination thereof. Furthermore, the nucleotide(s) of an overhang can be present on the 5' end, 3' end or both ends of either an antisense or sense strand of a saRNA. Where two oligonucleotides are designed to form, upon hybridization, one or more single-stranded overhangs, such overhangs shall not be regarded as mismatches with regard to the determination of complementarity. For example, a saRNA comprising one oligonucleotide 19 nucleotides in length and another oligonucleotide 21 nucleotides in length, wherein the longer oligonucleotide comprises a sequence of 19 nucleotides that is fully complementary to the shorter oligonucleotide, can yet be referred to as "fully complementary" for the purposes described herein.

In one embodiment, the antisense strand of a double-stranded saRNA has a 1-10 nucleotide overhang at the 3' end and/or the 5' end. In one embodiment, the antisense strand of a double-stranded saRNA has 1-4 nucleotide overhang at its 3' end, or 1-2 nucleotide overhang at its 3' end. In one embodiment, the sense strand of a double-stranded saRNA has a 1-10 nucleotide overhang at the 3' end and/or the 5' end. In one embodiment, the sense strand of a double-stranded saRNA has 1-4 nucleotide overhang at its 3' end, or 1-2 nucleotide overhang at its 3' end. In one embodiment, both the sense strand and the antisense strand of a double-stranded saRNA have 3' overhangs. The 3' overhangs may comprise one or more uracils, e.g., the sequences UU or UUU. In one embodiment, one or more of the nucleotides in the overhang is replaced with a nucleoside thiophosphate, wherein the internucleoside linkage is thiophosphate. In one embodiment, the overhang comprises one or more deoxyribonucleoside, e.g., the sequence dTdT or dTdTdT. In one embodiments, the overhang comprises the sequence dT*dT, wherein * is a thiophosphate internucleoside linkage.

The skilled person will appreciate that it is convenient to define the saRNA of the present invention by reference to the target antisense RNA transcript or the targeted sequence, regardless of the mechanism by which the saRNA modulates the target gene expression. However, the saRNA of the present invention may alternatively be defined by reference to the target gene. The target antisense RNA transcript is complementary to a genomic region on the coding strand of the target gene, and the saRNA of the present invention is in turn complementary to a region of the target antisense RNA transcript, so the saRNA of the present invention may be defined as having sequence identity to a region on the coding strand of the target gene. All of the features discussed herein with respect to the definition of the saRNA of the present invention by reference to the target antisense RNA transcript apply mutatis mutandis to the definition of the saRNA of the present invention by reference to the target gene so any discussion of complementarity to the target antisense RNA transcript should be understood to include identity to the genomic sequence of the target gene. Thus, the saRNA of the present invention may have a high percent identity, e.g. at least 80%, 90%, 95%, 98% or 99%, or 100% identity, to a genomic sequence on the target gene. The genomic sequence may be up to 2000, 1000, 500, 250, or 100 nucleotides upstream or downstream of the target gene's transcription start site. It may align with the target gene's promoter region. Thus, the saRNA may have sequence identity to a sequence that aligns with the promoter region of the target gene.

In one embodiment, the existence of the target antisense RNA transcript does not need to be determined to design the saRNA of the present invention. In another word, the design of the saRNA does not require the identification of the target antisense RNA transcript. For example, the nucleotide sequence of the TSS core, i.e., the sequence in the region 2000 nucleotides upstream of the target gene's transcription start site to 2000 nucleotides downstream of the target gene's transcription start may be obtained by the genomic sequence of the coding strand of the target gene, by sequencing or by searching in a database. Targeted sequence within the TSS core starting at any position from position 1 to position 4001 of the TSS core on the template strand can be selected and can then be used to design saRNA sequences. As discussed above, the saRNA has a high degree of sequence identity with the reverse complement of the targeted sequence.

The saRNA sequence's off-target hit number in the whole genome, 0 mismatch (0 mm) hit number, and 1 mismatch (1 mm) hit number are then determined. The term "off-target hit number" refers to the number of other sites in the whole genome that are identical to the saRNA's targeted sequence on the template strand of the target gene. The term "0 mm hit number" refers to the number of known protein coding transcript other than the target transcript of the saRNA, the complement of which the saRNA may hybridize with or bind to with 0 mismatch. In another word, "0 mm hit number" counts the number of known protein coding transcript, other than the target transcript of the saRNA that comprises a region completely identical with the saRNA sequence. The term "1 mm hit number" refers to the number of known protein coding transcript other than the target transcript of the saRNA, the complement of which the saRNA may hybridize with or bind to with 1 mismatch. In another word, "1 mm hit number" counts the number of known protein coding transcript, other than the target transcript of the saRNA that comprises a region identical with the saRNA sequence with only 1 mismatch. In one embodiment, only saRNA sequences that have no off-target hit, no 0 mm hit and no 1 mm hit are selected. For those saRNA sequences disclosed in the present application, each has no off-target hit, no 0 mm hit and no 1 mm hit.

The method disclosed in US 2013/0164846 filed Jun. 23, 2011 (saRNA algorithm), the contents of which are incorporated herein by reference in their entirety, may also be used to design saRNA. The design of saRNA is also disclosed in U.S. Pat. Nos. 8,324,181 and 7,709,566 to Corey et al., US Pat. Pub. No. 2010/0210707 to Li et al., and Voutila et al., *Mol Ther Nucleic Acids*, vol. 1, e35 (2012), the contents of each of which are incorporated herein by reference in their entirety.

"Determination of existence" means either searching databases of ESTs and/or antisense RNA transcripts around the locus of the target gene to identify a suitable target antisense RNA transcript, or using RT PCR or any other known technique to confirm the physical presence of a target antisense RNA transcript in a cell.

In some embodiments, the saRNA of the present invention may be single or, double-stranded. Double-stranded molecules comprise a first strand and a second strand. If double-stranded, each strand of the duplex may be at least 14, or at least 18, e.g. 19, 20, 21 or 22 nucleotides in length. The duplex may be hybridized over a length of at least 12, or at least 15, or at least 17, or at least 19 nucleotides. Each strand may be exactly 19 nucleotides in length. Preferably, the length of the saRNA is less than 30 nucleotides since oligonucleotide duplex exceeding this length may have an increased risk of inducing the interferon response. In one embodiment, the length of the saRNA is 19 to 25 nucleotides. The strands forming the saRNA duplex may be of equal or unequal lengths.

In one embodiment, the saRNAs of the present invention comprise a sequence of at least 14 nucleotides and less than 30 nucleotides which has at least 80%, 90%, 95%, 98%, 99% or 100% complementarity to the targeted sequence. In one embodiment, the sequence which has at least 80%, 90%, 95%, 98%, 99% or 100% complementarity to the targeted sequence is at least 15, 16, 17, 18 or 19 nucleotides in length, or 18-22 or 19 to 21, or exactly 19.

The saRNA of the present invention may include a short 3' or 5' sequence which is not complementary to the target antisense RNA transcript. In one embodiment, such a sequence is at 3' end of the strand. The sequence may be 1-5 nucleotides in length, or 2 or 3. The sequence may comprises uracil, so it may be a 3' stretch of 2 or 3 uracils. The sequence may comprise one or more deoxyribonucleoside, such as dT. In one embodiment, one or more of the nucleotides in the sequence is replaced with a nucleoside thiophosphate, wherein the internucleoside linkage is thiophosphate. As a non-limiting example, the sequence comprises the sequence dT*dT, wherein * is a thiophosphate internucleoside linkage. This non-complementary sequence may be referred to as "tail". If a 3' tail is present, the strand may be longer, e.g., 19 nucleotides plus a 3' tail, which may be UU or UUU. Such a 3' tail shall not be regarded as mismatches with regard to determine complementarity between the saRNA and the target antisense RNA transcript.

Thus, the saRNA of the present invention may consist of (i) a sequence having at least 80% complementarity to a region of the target antisense RNA transcript; and (ii) a 3' tail of 1-5 nucleotides, which may comprise or consist of uracil residues. The saRNA will thus typically have complementarity to a region of the target antisense RNA transcript over its whole length, except for the 3' tail, if present. Any of the saRNA sequences disclosed in the present application may optionally include such a 3' tail. Thus, any of the saRNA sequences disclosed in the saRNA Tables and Sequence Listing may optionally include such a 3' tail. The saRNA of the present invention may further comprise Dicer or Drosha substrate sequences.

The saRNA of the present invention may contain a flanking sequence. The flanking sequence may be inserted in the 3' end or 5' end of the saRNA of the present invention. In one embodiment, the flanking sequence is the sequence of a miRNA, rendering the saRNA to have miRNA configuration and may be processed with Drosha and Dicer. In a non-limiting example, the saRNA of the present invention has two strands and is cloned into a microRNA precursor, e.g., miR-30 backbone flanking sequence.

The saRNA of the present invention may comprise a restriction enzyme substrate or recognition sequence. The restriction enzyme recognition sequence may be at the 3' end or 5' end of the saRNA of the present invention. Non-limiting examples of restriction enzymes include NotI and AscI.

In one embodiment, the saRNA of the present invention consists of two strands stably base-paired together. In some embodiments, the passenger strand may comprise at least one nucleotide that is not complementary to the corresponding nucleotide on the guide strand, called a mismatch with the guide strand. In one embodiment, the at least one mismatch with the guide strand may be at 3' end of the passenger strand. In one embodiment, the 3' end of the passenger strand may comprise 1-5 mismatches with the guide strand. In one embodiment, the 3' end of the passenger strand may comprise 2-3 mismatches with the guide strand. In one embodiment, the 3' end of the passenger strand may comprise 6-10 mismatches with the guide strand.

In some embodiments, the double-stranded saRNA may comprise a number of unpaired nucleotides at the 3' end of each strand forming 3' overhangs. The number of unpaired nucleotides forming the 3' overhang of each strand may be in the range of 1 to 5 nucleotides, or 1 to 3 nucleotides, or 2 nucleotides. The 3' overhang may be formed on the 3' tail mentioned above, so the 3' tail may be the 3' overhang of a double-stranded saRNA.

Thus, the saRNA of the present invention may be single-stranded and consists of (i) a sequence having at least 80% complementarity to a region of the target antisense RNA transcript; and (ii) a 3' tail of 1-5 nucleotides, which may comprise uracil residues. The saRNA of the present invention may have complementarity to a region of the target antisense RNA transcript over its whole length, except for the 3' tail, if present. As mentioned above, instead of "complementary to the target antisense RNA transcript" the saRNA of the present invention may also be defined as having "identity" to the coding strand of the target gene. The saRNA of the present invention may be double-stranded and consists of a first strand comprising (i) a first sequence having at least 80% complementarity to a region of the target antisense RNA transcript and (ii) a 3' overhang of 1-5 nucleotides; and a second strand comprising (i) a second sequence that forms a duplex with the first sequence and (ii) a 3' overhang of 1-5 nucleotides.

As described herein, the sequence for C/EBPα gene is used to design C/EBPα-saRNA. The sequence of a target antisense RNA transcript of CEBPA gene may be determined from the sequence of C/EBPα gene for designing C/EBPα-saRNA. However, the existence of such a target antisense RNA transcript does not need to be determined. Sequences of suitable C/EBPα-saRNA of the present invention are provided in Table 1. Thus, provided is C/EBPα-saRNA having a first strand comprising a sequence selected from SEQ ID Nos: 2, 4, 6, 8, 10, and 12. Optionally, the C/EBPα-saRNA may comprise a 3' tail at the 3' end of these sequences.

Single stranded C/EBPα-saRNA only consists of a first strand, whereas double stranded C/EBPα-saRNA also has a second strand. The single stranded CEBPA-saRNA comprises a sequence selected from the anti-sense strands in Tables 1 and 1A. The double-stranded C/EBPα-saRNA comprises a first strand, wherein the first strand comprises a sequence selected from the anti-sense strands in Tables 1 and 1A, and a second strand, wherein the second strand comprises a sequence which is the corresponding sense strand in Tables 1 and 1A. The anti-sense and/or sense strands may comprise a 3' overhang.

TABLE 1 saRNA sequences

| | ID | Sense strand (Passenger) | SEQ ID NO | Anti-sense strand (Guide) | SEQ ID NO |
|---|---|---|---|---|---|
| Human C/EBPα | AW1 | CGGUCAUUGUCACUGGUCA | 1 | UGACCAGUGACAAUGACCG | 2 |
| | AW2 | AGCUGAAAGGAUUCAUCCU | 3 | AGGAUGAAUCCUUCCAGCU | 4 |
| | NR1 | ACAUAGUCCCAGUGAUUAA | 5 | UUAAUCACUGGGACUAUGU | 6 |
| | NR2 | GAAUAAGACUUUGUCCAAU | 7 | AUUGGACAAAGUCUUAUUC | 8 |
| | pR1 | GCGCGGAUUCUCUUUCAAA | 9 | UUUGAAAGAGAAUCCGCGC | 10 |
| | pR2 | CCAGGAACUCGUCGUUGAA | 11 | UUCAACGACGAGUUCCUGG | 12 |

TABLE 1A additional saRNA sequences

| Sense strand (Passenger) | SEQ ID NO | Anti-sense strand (Guide) | SEQ ID NO |
|---|---|---|---|
| GGUAUACAUCCUCAGAGCU | 34 | AGCUCUGAGGAUGUAUACC | 35 |
| CUAGCUUUCUGGUGUGACU | 36 | AGUCACACCAGAAAGCUAG | 37 |
| CGGGCUUGUCGGGAUCUCA | 38 | UGAGAUCCCGACAAGCCCG | 39 |
| GCAUUGGAGCGGUGAGUUU | 40 | AAACUCACCGCUCCAAUGC | 41 |
| GGCACAAGGUUAUCCUAAA | 42 | UUUAGGAUAACCUUGUGCC | 43 |
| GCACAAGGUUAUCCUAAAU | 44 | AUUUAGGAUAACCUUGUGC | 45 |
| CGGUCAUUGUCACUGGUCA | 46 | UGACCAGUGACAAUGACCG | 47 |
| CCAGGAACUCGUCGUUGAA | 48 | UUCAACGACGAGUUCCUGG | 49 |

Bifunction or dual-functional oligonucleotides are also designed to up-regulate C/EBPα gene expression and down-regulate C/EBPβ gene expression. One strand of the dual-functional oligonucleotide activates C/EBPα gene expression and the other inhibits C/EBPβ gene expression. Preferred dual-functional oligonucleotide sequences are shown in Table 2A. Each strand might further comprise a Dicer substrate sequence as shown in Table 2B.

TABLE 2a

Bifunction oligonucleotide sequences

| ID | 19 mer 1 (Target C/ EBPβ (NM_005194)) | 19 mer 2 (Target C/ EBPα-AS (NM_004364)) |
|---|---|---|
| sa-CEBPA_si-CEBPB-1 | AGAAGUUGGCCACUUCCAU (SEQ ID NO. 13) | AUGGAGUCGGCCGACUUCU (SEQ ID NO. 14) |
| sa-CEBPA_si-CEBPB-2 | AAGAGGUCGGAGAGGAAGU (SEQ ID NO. 15) | AGUUCCUGGCCGACCUGUU (SEQ ID NO. 16) |
| sa-CEBPA_si-CEBPB-3 | UUGUACUCGUCGCUGUGCU (SEQ ID NO. 17) | AGAACAGCAACGAGUACCG (SEQ ID NO. 18) |
| sa-CEBPA_si-CEBPB-4 | UACUCGUCGCUGUGCUUGU (SEQ ID NO. 19) | ACAAGAACAGCAACGAGUA (SEQ ID NO. 20) |

Table 2B

Dice substrate sequences of bifunction oligonucleotide sequences

| ID | DicerSubstrateStrand1 (RNAs in upper case; DNAs in underlined lower case) | DicerSubstrateStrand2 (RNAs in upper case; DNAs in underlined lower case) |
|---|---|---|
| sa-CEBPA_si-CEBPB-1 | AGAAGUUGGCCACUUCCAUGGGGga (SEQ ID NO. 21) | tcCCCCAUGGAGUCGGCCGACUUCUAC (SEQ ID NO. 22) |
| sa-CEBPA_si-CEBPB-2 | AAGAGGUCGGAGAGGAAGUCGUCgt (SEQ ID NO. 23) | acGACGAGUUCCUGGCCGACCUGUUCC (SEQ ID NO. 24) |
| sa-CEBPA_si-CEBPB-3 | UUGUACUCGUCGCUGUGCUUGUCca (SEQ ID NO. 25) | tgGACAAGAACAGCAACGAGUACCGGG (SEQ ID NO. 26) |
| sa-CEBPA_si-CEBPB-4 | UACUCGUCGCUGUGCIJUGUCCACcg (SEQ ID NO. 27) | cgGUGGACAAGAACAGCAACGAGUACC (SEQ ID NO. 28) |

The saRNA of the present invention may be produced by any suitable method, for example synthetically or by expression in cells using standard molecular biology techniques which are well-known to a person of ordinary skill in the art. For example, the saRNA of the present invention may be chemically synthesized or recombinantly produced using methods known in the art.

Chemical Modifications of saRNA

Herein, in saRNA, the terms "modification" or, as appropriate, "modified" refer to structural and/or chemical modifications with respect to A, G, U or C ribonucleotides. Nucleotides in the saRNA of the present invention may comprise non-standard nucleotides, such as non-naturally occurring nucleotides or chemically synthesized nucleotides or deoxynucleotides. The saRNA of the present invention may include any useful modification, such as to the sugar, the nucleobase, or the internucleoside linkage (e.g. to a linking phosphate/to a phosphodiester linkage/to the phosphodiester backbone). One or more atoms of a pyrimidine nucleobase may be replaced or substituted with optionally substituted amino, optionally substituted thiol, optionally substituted alkyl (e.g., methyl or ethyl), or halo (e.g., chloro or fluoro). In certain embodiments, modifications (e.g., one or more modifications) are present in each of the sugar and the internucleoside linkage. Modifications according to the present invention may be modifications of ribonucleic acids (RNAs) to deoxyribonucleic acids (DNAs), threose nucleic acids (TNAs), glycol nucleic acids (GNAs), peptide nucleic acids (PNAs), locked nucleic acids (LNAs) or hybrids thereof.

In one embodiment, the saRNAs of the present invention may comprise at least one modification described herein.

In another embodiment, the saRNA is an saRNA duplex and the sense strand and antisense sequence may independently comprise at least one modification. As a non-limiting example, the sense sequence may comprises a modification and the antisense strand may be unmodified. As another non-limiting example, the antisense sequence may comprises a modification and the sense strand may be unmodified. As yet another non-limiting example, the sense sequence may comprises more than one modification and the antisense strand may comprise one modification. As a non-limiting example, the antisense sequence may comprises more than one modification and the sense strand may comprise one modification.

The saRNA of the present invention can include a combination of modifications to the sugar, the nucleobase, and/or the internucleoside linkage. These combinations can include any one or more modifications described herein or in International Application Publication WO2013/052523 filed Oct.

3, 2012, in particular Formulas (Ia)-(Ia-5), (Ib)-(If), (IIa)-(IIp), (IIb-1), (IIb-2), (IIc-1)-(IIc-2), (IIn-1), (IIn-2), (IVa)-(IVl), and (IXa)-(IXr)), the contents of which are incorporated herein by reference in their entirety.

The saRNA of the present invention may or may not be uniformly modified along the entire length of the molecule. For example, one or more or all types of nucleotide (e.g., purine or pyrimidine, or any one or more or all of A, G, U, C) may or may not be uniformly modified in the saRNA of the invention. In some embodiments, all nucleotides X in a saRNA of the invention are modified, wherein X may be any one of nucleotides A, G, U, C, or any one of the combinations A+G, A+U, A+C, G+U, G+C, U+C, A+G+U, A+G+C, G+U+C or A+G+C.

Different sugar modifications, nucleotide modifications, and/or internucleoside linkages (e.g., backbone structures) may exist at various positions in a saRNA. One of ordinary skill in the art will appreciate that the nucleotide analogs or other modification(s) may be located at any position(s) of a saRNA such that the function of saRNA is not substantially decreased. The saRNA of the present invention may contain from about 1% to about 100% modified nucleotides (either in relation to overall nucleotide content, or in relation to one or more types of nucleotide, i.e. any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%).

In some embodiments, the modification may be on the ribose ring. The 2'-OH group on the ribose may be substituted to protect saRNA against ribonucleases. For example, the 2'-OH group may be substituted with 2'-O-methyl (2'-OMe), 2'-fluoro (2'-F), 2'-O-methoxyethyl (2'-O-MOE), 2'-O-allyl (2'-O-allyl), etc.

In some embodiments, the modifications include bicyclic derivatives of the nucleotides (LNA, ENA, CLNA, CENA, AENA etc.), acyclic nucleotides (UNA, PNA, etc.) or nucleotides containing pyranose ring (ANA, HNA) instead of ribose.

In some embodiments, the modification may be on the backbone to increase nuclease resistance of the saRNA. Non-limiting examples include the replacement of phosphate group (PO) with phosphorothioate (PS) or boranophosphonate (PB) groups, the replacement of the 3', 5'-phosphodiester bond with 2', 5'-bond or the amide bond instead of the ester bond, etc.

In some embodiments, the modification may be on the nucleobases. For example, uridine (U) may be replaced with pseudouridine (ψ), 2-thiouridine (s2U), dihydrouridine (D), 5-bromo-U, 5-iodo-U, etc. Purine may be replaced with 2,6-diaminopurine.

In some embodiments, the modification may be at the termini of saRNA. Any termini modification may be used to increase nuclease resistance, to facilitate asymmetric RISC assembly, to help saRNA accumulation in cells, and to enable saRNA detection. For example, fluorescence labels and biotin may be attached to a terminus of saRNA. In another example, inverted deoxyribose may be employed at a terminus of saRNA.

In some embodiments, the saRNA of the present invention may be modified to be a spherical nucleic acid (SNA) or a circular nucleic acid. The terminals of the saRNA of the present invention may be linked by chemical reagents or enzymes, producing spherical saRNA that has no free ends. Spherical saRNA is expected to be more stable than its linear counterpart and to be resistant to digestion with RNase R exonuclease. Spherical saRNA may further comprise other structural and/or chemical modifications with respect to A, G, U or C ribonucleotides.

In some embodiments, the saRNA of the present invention may comprise inverted dT modifications. The inverted modification may be at 5' terminus or 3' terminus. In some embodiments, the 2'-OH of a nucleotide is substituted with —OMe, referred to as 2'-OMe. In some embodiments, the 2'-OH of a nucleotide is substituted with —F, referred to as 2'-F. In some embodiments, there is phosphorothioate linkage between nucleotides. In some embodiments, the saRNA of the present invention may comprise a basic modifications.

The saRNA of the present invention may comprise a combination of modifications. The saRNA may comprise at least 2, 3, 4, 5, 6, 7, 8, 9, 10, 11, 12, 13, 14, 15, 16, 17, 18, 19, or 20 modifications. For example, the saRNA may comprise alternating 2'-F and 2'-OMe modifications. In some embodiments, the saRNA may be modified across its whole length.

Any suitable modification to render the sense strand inactive and/or to reduce off-targets, which does not interfere with guide strand activity, may be used.

Table 3 includes non-limiting examples of modified CEBPA-saRNA sequences and the unmodified CEBPA-saRNA sequences. In Table 3, lower case letters refer to 2'-OMe modification. '(invdT)' refers to inclusion of an inverted dT at 3' and/or 5' end. 'f' means the nucleotide preceding it has 2'-F modification. 's' means there is a phosphorothioate linkage between the nucleotides. 'dT' refers to deoxy-thymine. 'dG' refers to deoxy-guanosine. 'dA' refers to deoxy-adenosine.

TABLE 3-1

Modified saRNA sequences-sense sequences

| Duplex-ID | Sense-ID | Sense Sequence | SEQ ID | Notes |
|---|---|---|---|---|
| XD-03287 | X09198 | CGGUCAUUGUCACUGGUCAUU | 50 | Unmodified |
| XD-04353 | X12716 | cgGfuCfaUfuGfuCfaCfuGfgUfcAfusu | 52 | |
| XD-04354 | X12718 | csgGfuCfaUfuGfuCfaCfuGfgUfcAf(invdT) | 54 | |
| XD-04355 | X12720 | (invdT)cgGfuCfaUfuGfuCfaCfuGfgUfcAf(invdT) | 56 | |

TABLE 3-1-continued

Modified saRNA sequences-sense sequences

| Duplex-ID | Sense-ID | Sense Sequence | SEQ ID | Notes |
|---|---|---|---|---|
| XD-04356 | X12721 | (invdT)CfdGdGUfCfdAUfUfdGUfCfdACfUfdGdGUfCfdA(invdT) | 57 | |
| XD-03302 | X09316 | GCGGUCAUUGUCACUGGUCUU | 73 | Unmodified |
| XD-04358 | X12723 | gcGfgUfcAfuUfgUfcAfcUfgGfuCfuUfusu | 59 | |
| XD-04359 | X12725 | gscGfgUfcAfuUfgUfcAfcUfgGfuCfuUf(invdT) | 61 | |
| XD-04360 | X12727 | (invdT)gcGfgUfcAfuUfgUfcAfcUfgGfuCfuUf(invdT) | 63 | |
| XD-04361 | X12728 | (invdT)dGCfdGdGUfCfdAUfUfdGUfCfdACfUfdGdGUfCfUfUf(invdT) | 64 | |
| XD-03317 | X09346 | UGAAAGGAUUCAUCCUCCUUU | 74 | Unmodified |
| XD-04363 | X12730 | ugAfaAfgGfaUfuCfaUfcCfuCfcUfuUfusu | 66 | |
| XD-04364 | X12732 | usgAfaAfgGfaUfuCfaUfcCfuCfcUfuUf(invdT) | 68 | |
| XD-04365 | X12734 | (invdT)ugAfaAfgGfaUfuCfaUfcCfuCfcUfuUf(invdT) | 70 | |
| XD-04366 | X12735 | (invdT)UfdGdAdAdAdGdGdAUfUfCfdAUfCfCfUfCfCfUtUfUf(invdT) | 71 | |

TABLE 3-2

Modified saRNA sequences-antisense sequences

| Duplex-ID | Antisense-ID | Antisense Sequence | SEQ ID | Notes |
|---|---|---|---|---|
| XD-03287 | X09199 | UGACCAGUGACAAUGACCGUU | 51 | Unmodified |
| XD-04353 | X12717 | UltUfaCfcAfgUfgAfcAfaUfgAfcCfgusu | 53 | |
| XD-04354 | X12719 | UfsGfaCfcAfgUfgAfcAfaUfgAfcCfgsusu | 55 | |
| XD-04355 | X12719 | UfsGfaCfcAfgUfgAfcAfaUfgAfcCfgsusu | 55 | |
| XD-04356 | X12722 | UfgaCfCfagUfgaCfaaUfgaCfCfgusu | 58 | |
| XD-03302 | X09317 | GACCAGUGACAAUGACCGCUU | 75 | Unmodified |
| XD-04358 | X12724 | AfAfgAfcCfaGfuGfaCfaAfuGfaCfcGfcusu | 60 | |
| XD-04359 | X12726 | AfAfgAfcCfaGfuGfaCfaAfuGfaCfcGfscusu | 62 | |
| XD-04360 | X12726 | AfAfgAfcCfaGfuGfaCfaAfuGfaCfcGfscusu | 62 | |
| XD-04361 | X12729 | gaCfCfagUfgaCfaaUfgaCfCfgCfUfUfusu | 65 | |
| XD-03317 | X09347 | AGGAGGAUGAAUCCUUUCAUU | 76 | Unmodified |
| XD-04363 | X12731 | AfAfaGfgAfgGfaUfgAfaUfcCfuUfuCfausu | 67 | |
| XD-04364 | X12733 | AfAfaGfgAfgGfaUfgAfaUfcCfuUfuCfasusu | 69 | |
| XD-04365 | X12733 | AfAfaGfgAfgGfaUfgAfaUfcCfuUfuCfasusu | 69 | |
| XD-04366 | X12736 | aggaggaUfgaaUfCfCfUfUfUfCfaUfUfusu | 72 | | saRNA Conjugates and Combinations

Conjugation may result in increased stability and/or half life and may be particularly useful in targeting the saRNA of the present invention to specific sites in the cell, tissue or organism. The saRNA of the present invention can be designed to be conjugated to other polynucleotides, dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases, proteins, e.g., glycoproteins, or peptides, e.g., molecules having a specific affinity for a co-ligand, or antibodies e.g., an antibody, that binds to a specified cell type such as a cancer cell, endothelial cell, or bone cell, hormones and hormone receptors, non-peptidic species, such as lipids, lectins, carbohydrates, vitamins, cofactors, or a drug. Suitable conjugates for nucleic acid molecules are disclosed in International Publication WO 2013/090648 filed Dec. 14, 2012, the contents of which are incorporated herein by reference in their entirety.

According to the present invention, C/EBPα-saRNA may be administered with, or further encode one or more of RNAi agents, small interfering RNAs (siRNAs), small hairpin RNAs (shRNAs), long non-coding RNAs (lncRNAs), enhancer RNAs, enhancer-derived RNAs or enhancer-driven RNAs (eRNAs), microRNAs (miRNAs), miRNA binding sites, antisense RNAs, ribozymes, catalytic DNA, tRNA, RNAs that induce triple helix formation, aptamers or vectors, and the like to achieve different functions. The one or more RNAi agents, small interfering RNAs (siRNAs), small hairpin RNAs (shRNAs), long non-coding RNAs (lncRNA), microRNAs (miRNAs), miRNA binding sites, antisense RNAs, ribozymes, catalytic DNA, tRNA, RNAs that induce triple helix formation, aptamers or vectors may comprise at least one modification or substitution. In some embodiments, the modification is selected from a chemical substitution of the nucleic acid at a sugar position, a chemical substitution at a phosphate position and a chemical substitution at a base position. In other embodiments, the chemical modification is selected from incorporation of a modified nucleotide; 3' capping; conjugation to a high molecular weight, non-immunogenic compound; conjugation to a lipophilic compound; and incorporation of phosphorothioate into the phosphate backbone. In a preferred embodiment, the high molecular weight, non-immunogenic compound is polyalkylene glycol, and more preferably is polyethylene glycol (PEG).

In one embodiment, C/EBPα-saRNA may be attached to a transgene so it can be co-expressed from an RNA polymerase II promoter. In a non-limiting example, C/EBPα-saRNA is attached to green fluorescent protein gene (GFP).

In one embodiment, C/EBPα-saRNA may be attached to a DNA or RNA aptamer, thereby producing C/EBPα-saRNA-aptamer conjugate. Aptamers are oligonucleotides or peptides with high selectivity, affinity and stability. They assume specific and stable three-dimensional shapes, thereby providing highly specific, tight binding to target molecules. An aptamer may be a nucleic acid species that has been engineered through repeated rounds of in vitro selection or equivalently, SELEX (systematic evolution of ligands by exponential enrichment) to bind to various molecular targets such as small molecules, proteins, nucleic acids, and even cells, tissues and organisms. Nucleic acid aptamers have specific binding affinity to molecules through interactions other than classic Watson-Crick base pairing. Nucleic acid aptamers, like peptides generated by phage display or monoclonal antibodies (mAbs), are capable of specifically binding to selected targets and, through binding, block their targets' ability to function. In some cases, aptamers may also be peptide aptamers. For any specific molecular target, nucleic acid aptamers can be identified from combinatorial libraries of nucleic acids, e.g. by SELEX. Peptide aptamers may be identified using a yeast two hybrid system. A skilled person is therefore able to design suitable aptamers for delivering the saRNAs or cells of the present invention to target cells such as liver cells. DNA aptamers, RNA aptamers and peptide aptamers are contemplated. Administration of saRNA of the present invention to the liver using liver-specific aptamers is particularly preferred.

As used herein, a typical nucleic acid aptamer is approximately 10-15 kDa in size (20-45 nucleotides), binds its target with at least nanomolar affinity, and discriminates against closely related targets. Nucleic acid aptamers may be ribonucleic acid, deoxyribonucleic acid, or mixed ribonucleic acid and deoxyribonucleic acid. Aptamers may be single stranded ribonucleic acid, deoxyribonucleic acid or mixed ribonucleic acid and deoxyribonucleic acid. Aptamers may comprise at least one chemical modification.

A suitable nucleotide length for an aptamer ranges from about 15 to about 100 nucleotides (nt), and in various other preferred embodiments, 15-30 nt, 20-25 nt, 30-100 nt, 30-60 nt, 25-70 nt, 25-60 nt, 40-60 nt, 25-40 nt, 30-40 nt, any of 22, 23, 24, 25, 26, 27, 28, 29, 30, 31, 32, 33, 34, 35, 36, 37, 38, 39 or 40 nt or 40-70 nt in length. However, the sequence can be designed with sufficient flexibility such that it can accommodate interactions of aptamers with two targets at the distances described herein. Aptamers may be further modified to provide protection from nuclease and other enzymatic activities. The aptamer sequence can be modified by any suitable methods known in the art.

The C/EBPα-saRNA-aptamer conjugate may be formed using any known method for linking two moieties, such as direct chemical bond formation, linkage via a linker such as streptavidin and so on.

In one embodiment, C/EBPα-saRNA may be attached to an antibody. Methods of generating antibodies against a target cell surface receptor are well known. The saRNA molecules of the invention may be attached to such antibodies with known methods, for example using RNA carrier proteins. The resulting complex may then be administered to a subject and taken up by the target cells via receptor-mediated endocytosis.

In one embodiment, C/EBPα-saRNA may be conjugated with lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4:1053-1060), a thioether, e.g., beryl-5-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-Hphosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylamino-carbonyloxycholesterol moiety (Crooke et al., J. Pharmacol. Exp. Ther., 1996, 277:923-937), the content of each of which is herein incorporated by reference in its entirety.

In one embodiment, the saRNA of the present invention is conjugated with a ligand disclosed in US 20130184328 to Manoharan et al., the contents of which are incorporated herein by reference in their entirety. The conjugate has a formula of Ligand-[linker]$_{optional}$-[tether]$_{optional}$-oligonucleotide agent. The oligonucleotide agent may comprise a subunit having formulae (I) disclosed by US 20130184328 to Manoharan et al., the contents of which are incorporated herein by reference in their entirety.

Representative U.S. patents that teach the preparation of such nucleic acid/lipid conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, the content of each of which is herein incorporated by reference in its entirety.

In on embodiment, the saRNA is conjugated with a carbohydrate ligand, such as any carbohydrate ligand disclosed in U.S. Pat. Nos. 8,106,022 and 8,828,956 to Manoharan et al. (Alnylam Pharmaceuticals), the contents of which are incorporated herein by reference in their entirety. For example, the carbohydrate ligand may be monosaccharide, disaccharide, trisaccharide, tetrasaccharide, oligosaccharide, or polysaccharide. These carbohydrate-conjugated RNA agents may target the parenchymal cells of the liver. In one embodiment, the saRNA is conjugated with more than one carbohydrate ligand, preferably two or three. In one embodiment, the saRNA is conjugated with one or more galactose moiety. In another embodiment, the saRNA is conjugated at least one (e.g., two or three or more) lactose molecules (lactose is a glucose coupled to a galactose). In another embodiment, the saRNA is conjugated with at least one (e.g., two or three or more) N-Acetyl-Galactosamine (GalNAc), N-Ac-Glucosamine (GluNAc), or mannose (e.g., mannose-6-phosphate). In one embodiment, the saRNA is conjugated with at least one mannose ligand, and the conjugated saRNA targets macrophages.

The saRNA of the present invention may be provided in combination with other active ingredients known to have an effect in the particular method being considered. The other active ingredients may be administered simultaneously, separately, or sequentially with the saRNA of the present invention. In one embodiment, C/EBPα-saRNA is administered with saRNA modulating a different target gene. Non-limiting examples include saRNA that modulates albumin, insulin or HNF4A genes. Modulating any gene may be achieved using a single saRNA or a combination of two or more different saRNAs. Non-limiting examples of saRNA that can be administered with C/EBPα-saRNA of the present invention include saRNA modulating albumin or HNF4A disclosed in International Publication WO 2012/175958 filed Jun. 20, 2012, saRNA modulating insulin disclosed in International Publications WO 2012/046084 and WO 2012/046085 both filed Oct. 10, 2011, saRNA modulating human progesterone receptor, human major vault protein (hMVP), E-cadherin gene, p53 gene, or PTEN gene disclosed in U.S. Pat. No. 7,709,456 filed Nov. 13, 2006 and US Pat. Publication US 2010/0273863 filed Apr. 23, 2010, and saRNAs targeting p21 gene disclosed in International Publication WO 2006/113246 filed Apr. 11, 2006, the contents of each of which are incorporated herein by reference in their entirety.

In one embodiment, C/EBPα-saRNA is administered with a small interfering RNA or siRNA that inhibits the expression of C/EBPβ gene, i.e., C/EBPβ-siRNA. Preferred sequences of suitable siRNAs of the invention are provided in Table 4.

TABLE 4

| | siRNA sequences | |
|---|---|---|
| ID | C/EBPβ-si-1 | C/EBPβ-si-2 |
| Target | ctgagtaatcgcttaaaga | gaaactttagcgagtcaga |
| Efficacy | 0.7 | 0.52 |
| Location | 1892 | 239 |
| Sense (passenger) | CUGAGUAAUCGCUUAAAGAUU (SEQ ID NO. 29) | GAAACUUUAGCGAGUCAGAUU (SEQ ID NO. 31) |
| Antisense (guide) | UCUUUAAGCGAUUACUCAGUU (SEQ ID NO. 30) | UCUGACUCGCUAAAGUUUCUU (SEQ ID NO. 32) |

In one embodiment, C/EBPα-saRNA is administered with one or more drugs that regulate metabolics, particularly liver function. In a non-limiting example, C/EBPα-saRNA of the present invention is administered with drugs that decrease low density lipoprotein (LDL) cholesterol levels, such as statin, simvastatin, atorvastatin, rosuvastatin, ezetimibe, niacin, PCSK9 inhibitors, CETP inhibitors, clofibrate, fenofibric, tocotrienols, phytosterols, bile acid sequestrants, probucol, or a combination thereof. C/EBPα-saRNA may also be administered with vanadium biguanide complexes disclosed in U.S. Pat. No. 6,287,586 to Orvig et al. In another example, C/EBPα-saRNA may be administered with a composition disclosed in WO 201102838 to Rhodes, the contents of which are incorporated by reference in their entirety, to lower serum cholesterol. The composition comprises an antigen binding protein that selectively binds to and inhibits a PCSK9 protein; and an RNA effector agent which inhibits the expression of a PCSK9 gene in a cell. In yet another example, C/EBPα-saRNA may be administered with an ABC1 polypeptide having ABC1 biological activity, or a nucleic acid encoding an ABC1 polypeptide having ABC1 activity to modulate cholesterol levels as described in EP1854880 to Brooks-Wilson et al., the contents of which are incorporated herein by reference in their entirety.

In another embodiment, C/EBPα-saRNA of the present invention is administered with drugs that increase insulin sensitivity or treat type II diabetes mellitus, such as metformin, sulfonylurea, nonsulfonylurea secretagogues, α glucosidase inhibitors, thiazolidinediones, pioglitazone, rosiglitazone, glucagon-like peptide-1 analog, and dipeptidyl peptidase-4 inhibitors or a combination thereof. Other hepato-protective agents that may be administered in combination with the saRNA of the present invention are disclosed in Adams et al., *Postgraduate Medical Journal*, vol. 82, 315-322 (2006), the contents of which are incorporated herein by reference in their entirety.

Gankyrin and FXR Protein

The development of hepatocellular carcinoma (HCC) is a multistep process which involves progressive changes of gene expression leading to liver hyperproliferation and to liver cancer. During carcinogenesis of liver cancer, tumor suppressor proteins Rb, p53, hepatocyte nuclear factor 4α (HNF4α), and C/EBP-α are neutralized. The elimination of these proteins is mediated by a small subunit of 26S proteasome, gankyrin, which is activated by cancer. Wang et al. discloses that gankyrin interacts with S193-ph isoform of C/EBPα and targets it for ubiquitinproteasome system (UPS)-mediated degradation. Gankyrin level is elevated during the early stages of liver cancer development (Wang et al., *J. Clin. Invest*, vol. 120(7):2549-2562 (2010), the contents of which are incorporated herein by reference in their entireties). Inhibiting gankyrin, e.g., using siRNA of the gankyrin gene (also known as PSMD10 gene) and/or gankyrin inhibitors, may prevent and/or treat HCC.

Jiang et al. found that farnesoid X receptor (FXR), also known as bile acid receptor (BAR) or NR1H4, inhibits expression of gankyrin in quiescent livers by silencing the gankyrin promoter through HDAC1-C/EBPβ complexes (Jiang et al., *Hepatology*, vol. 57(3):1098-1106 (2013), the contents of which are incorporated herein by reference in their entireties). Deletion of FXR signaling in mice leads to de-repression of the gankyrin promoter and to spontaneous development of liver cancer at 12 months of age. Diethylnitrosoamine (DEN)-mediated liver cancer in wild-type mice also involves the reduction of FXR and activation of gankyrin. Examination of liver cancer in old mice and liver cancer in human patients revealed that FXR is reduced, while gankyrin is elevated during spontaneous development of liver cancer. Jiang et al. concluded that FXR prevents liver cancer by inhibiting the gankyrin promoter via C/EBPβ-HDAC1 complexes leading to subsequent protection of tumor suppressor proteins from degradation. Stabilization and nuclear translocation of FXR inhibits gankyrin. Activating FXR, e.g., using FXR agonists or activators, or activator of NR1H4 gene, may prevent and/or treat HCC.

C/EBPα-saRNA of the present invention may be used in combination with one or more of therapeutic agents that down-regulate gankyrin or up-regulate FXR. The combination may have synergistic effect on preventing and/or treating HCC. In some embodiments, C/EBPα-saRNA of the present invention may be used in combination with gankyrin-siRNA. Double-stranded Gankyrin-siRNA may be produced using the method disclosed by Higashitsuji et al. in the 'Inhibition of endogenous gene expression by RNAi' section (Higashitsuji et al., *Cancer Cell*, vol. 8:75-87 (2005), the contents of which are incorporated herein by reference in their entireties). In some embodiments, C/EBPα-saRNA of the present invention may be used in combination with FXR agonists. Non-limiting examples of FXR agonists or activators include taurocholic acid, obeticholic acid (OCA), INT-767 (Intercept Pharmaceuticals), INT-777 (Intercept Pharmaceuticals), and any FXR agonist or activator disclosed in US Pat. App. No. 20140057886, U.S. Pat. Nos. 8,546,365, 7,932,244, US Pat. App. No. 20140100209, U.S. Pat. Nos. 8,445,472, 8,114,862, US Pat. App. No. 20140094443, U.S. Pat. Nos. 8,410,083, 8,796,249, US Pat. App. No. 20140024631, U.S. Pat. Nos. 8,377,916, 8,258, 267, 7,786,102, 7,138,390, 7,994,352, 7,858,608, 7,812,011, US Pat. App. No. 20140148428, and US Pat. App. No. 20060252670 (the contents of each of which are incorporated herein by reference in their entirety).

Formulation, Delivery, Administration, and Dosing

Pharmaceutical formulations may additionally comprise a pharmaceutically acceptable excipient, which, as used herein, includes, but is not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21$^{st}$ Edition, A. R. Gennaro, Lippincott, Williams & Wilkins, Baltimore, Md., 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

In some embodiments, compositions are administered to humans, human patients or subjects. For the purposes of the present disclosure, the phrase "active ingredient" generally refers to C/EBPα-saRNA to be delivered as described herein.

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys.

In one embodiment, the efficacy of the formulated saRNA described herein may be determined in proliferating cells.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

In some embodiments, the formulations described herein may contain at least one saRNA. As a non-limiting example, the formulations may contain 1, 2, 3, 4 or 5 saRNAs with different sequences. In one embodiment, the formulation contains at least three saRNAs with different sequences. In one embodiment, the formulation contains at least five saRNAs with different sequences.

The saRNA of the invention can be formulated using one or more excipients to: (1) increase stability; (2) increase cell transfection; (3) permit the sustained or delayed release (e.g., from a depot formulation of the saRNA); (4) alter the biodistribution (e.g., target the saRNA to specific tissues or cell types); (5) increase the translation of encoded protein in vivo; and/or (6) alter the release profile of encoded protein in vivo. In addition to traditional excipients such as any and all solvents, dispersion media, diluents, or other liquid vehicles, dispersion or suspension aids, surface active agents, isotonic agents, thickening or emulsifying agents, preservatives, excipients of the present invention can include, without limitation, lipidoids, liposomes, lipid nanoparticles, polymers, lipoplexes, core-shell nanoparticles, peptides, proteins, cells transfected with saRNA (e.g., for transplantation into a subject), hyaluronidase, nanoparticle mimics and combinations thereof. Accordingly, the formulations of the invention can include one or more excipients, each in an amount that together increases the stability of the saRNA and/or increases cell transfection by the saRNA. Further, the saRNA of the present invention may be formulated using self-assembled nucleic acid nanoparticles. Pharmaceutically acceptable carriers, excipients, and delivery agents for nucleic acids that may be used in the formulation with the saRNA of the present invention are disclosed in International Publication WO 2013/090648 filed Dec. 14, 2012, the contents of which are incorporated herein by reference in their entirety.

In one embodiment, the saRNA of the present invention comprises two single RNA strands that are 21 nucleotides in length each that are annealed to form a double stranded C/EBPα-saRNA as the active ingredient. The composition further comprises a salt buffer composed of 50 mM Tris-HCl, pH 8.0, 100 mM NaCl and 5 mM EDTA.

In another embodiment, the saRNA of the present invention may be delivered with dendrimers. Dendrimers are highly branched macromolecules. In a preferred embodiment, the saRNA of the present invention is complexed with structurally flexible poly(amidoamine) (PAMAM) dendrimers for targeted in vivo delivery. The complex is called C/EBPα-saRNA-dendrimers. Dendrimers have a high degree of molecular uniformity, narrow molecular weight distribution, specific size and shape characteristics, and a highly-functionalized terminal surface. The manufacturing process is a series of repetitive steps starting with a central initiator core. Each subsequent growth step represents a new generation of polymers with a larger molecular diameter and molecular weight, and more reactive surface sites than the preceding generation. PAMAM dendrimers are efficient nucleotide delivery systems that bear primary amine groups on their surface and also a tertiary amine group inside of the structure. The primary amine group participates in nucleotide binding and promotes their cellular uptake, while the buried tertiary amino groups act as a proton sponge in endosomes and enhance the release of nucleic acid into the cytoplasm. These dendrimers protect the saRNA carried by them from ribonuclease degradation and achieves substantial release of saRNA over an extended period of time via endocytosis for efficient gene targeting. The in vivo efficacy of these nanoparticles have previously been evaluated where biodistribution studies show that the dendrimers preferentially accumulate in peripheral blood mononuclear cells and live with no discernible toxicity (see Zhou et al., Molecular Ther. 2011 Vol. 19, 2228-2238, the contents of which are incorporated herein by reference in their entirety). PAMAM dendrimers may comprise a triethanolamine (TEA) core, a diaminobutane (DAB) core, a cystamine core, a diaminohexane (HEX) core, a diamonododecane (DODE) core, or an ethylenediamine (EDA) core. Preferably, PAMAM dendrimers comprise a TEA core or a DAB core.

Lipidoids

The synthesis of lipidoids has been extensively described and formulations containing these compounds are particularly suited for delivery of oligonucleotides or nucleic acids (see Mahon et al., Bioconjug Chem. 2010 21:1448-1454; Schroeder et al., J Intern Med. 2010 267:9-21; Akinc et al., Nat Biotechnol. 2008 26:561-569; Love et al., Proc Natl Acad Sci USA. 2010 107:1864-1869; Siegwart et al., Proc Natl Acad Sci USA. 2011 108:12996-3001; all of which are incorporated herein in their entireties).

While these lipidoids have been used to effectively deliver double stranded small interfering RNA molecules in rodents and non-human primates (see Akinc et al., Nat Biotechnol. 2008 26:561-569; Frank-Kamenetsky et al., Proc Natl Acad Sci USA. 2008 105:11915-11920; Akinc et al., Mol Ther. 2009 17:872-879; Love et al., Proc Natl Acad Sci USA. 2010 107:1864-1869; Leuschner et al., Nat Biotechnol. 2011 29:1005-1010; all of which is incorporated herein in their entirety), the present disclosure describes their formulation and use in delivering saRNA. Complexes, micelles, liposomes or particles can be prepared containing these lipidoids and therefore, can result in an effective delivery of the saRNA following the injection of a lipidoid formulation via localized and/or systemic routes of administration. Lipidoid complexes of saRNA can be administered by various means including, but not limited to, intravenous, intramuscular, or subcutaneous routes.

In vivo delivery of nucleic acids may be affected by many parameters, including, but not limited to, the formulation composition, nature of particle PEGylation, degree of loading, oligonucleotide to lipid ratio, and biophysical parameters such as, but not limited to, particle size (Akinc et al., Mol Ther. 2009 17:872-879; the contents of which are herein incorporated by reference in its entirety). As an example, small changes in the anchor chain length of poly(ethylene glycol) (PEG) lipids may result in significant effects on in vivo efficacy. Formulations with the different lipidoids, including, but not limited to penta[3-(1-laurylaminopropionyl)]-triethylenetetramine hydrochloride (TETA-5LAP; aka 98N12-5, see Murugaiah et al., Analytical Biochemistry, 401:61 (2010); the contents of which are herein incorporated by reference in its entirety), C12-200 (including derivatives and variants), and MD1, can be tested for in vivo activity.

The lipidoid referred to herein as "98N12-5" is disclosed by Akinc et al., Mol Ther. 2009 17:872-879 and the contents of which is incorporated by reference in its entirety. (See FIG. 2)

The lipidoid referred to herein as "C12-200" is disclosed by Love et al., Proc Natl Acad Sci USA. 2010 107:1864-1869 (see FIG. 2) and Liu and Huang, Molecular Therapy. 2010 669-670 (see FIG. 2); the contents of both of which are herein incorporated by reference in their entirety. The lipidoid formulations can include particles comprising either 3 or 4 or more components in addition to the saRNA. As an example, formulations with certain lipidoids, include, but are not limited to, 98N12-5 and may contain 42% lipidoid, 48% cholesterol and 10% PEG (C14 alkyl chain length). As another example, formulations with certain lipidoids, include, but are not limited to, C12-200 and may contain 50% lipidoid, 10% disteroylphosphatidyl choline, 38.5% cholesterol, and 1.5% PEG-DMG.

In one embodiment, a saRNA formulated with a lipidoid for systemic intravenous administration can target the liver. For example, a final optimized intravenous formulation using saRNA and comprising a lipid molar composition of 42% 98N12-5, 48% cholesterol, and 10% PEG-lipid with a final weight ratio of about 7.5 to 1 total lipid to saRNA and a C14 alkyl chain length on the PEG lipid, with a mean particle size of roughly 50-60 nm, can result in the distribution of the formulation to be greater than 90% to the liver. (see, Akinc et al., Mol Ther. 2009 17:872-879; the contents of which are herein incorporated by reference in its entirety). In another example, an intravenous formulation using a C12-200 (see U.S. provisional application 61/175,770 and published international application WO2010129709, the contents of each of which is herein incorporated by reference in their entirety) lipidoid may have a molar ratio of 50/10/38.5/1.5 of C12-200/disteroylphosphatidyl choline/cholesterol/PEG-DMG, with a weight ratio of 7 to 1 total lipid to nucleic acid and a mean particle size of 80 nm may be effective to deliver saRNA (see, Love et al., Proc Natl Acad Sci USA. 2010 107:1864-1869, the contents of which are herein incorporated by reference in its entirety). In another embodiment, an MD1 lipidoid-containing formulation may be used to effectively deliver saRNA to hepatocytes in vivo. The characteristics of optimized lipidoid formulations for intramuscular or subcutaneous routes may vary significantly depending on the target cell type and the ability of formulations to diffuse through the extracellular matrix into the blood stream. While a particle size of less than 150 nm may be desired for effective hepatocyte delivery due to the size of the endothelial fenestrae (see, Akinc et al., Mol Ther. 2009 17:872-879, the contents of which are herein incorporated by reference in its entirety), use of a lipidoid-formulated saRNA to deliver the formulation to other cells types including, but not limited to, endothelial cells, myeloid cells, and muscle cells may not be similarly size-limited. Use of lipidoid formulations to deliver siRNA in vivo to other non-hepatocyte cells such as myeloid cells and endothelium has been reported (see Akinc et al., Nat Biotechnol. 2008 26:561-569; Leuschner et al., Nat Biotechnol. 2011 29:1005-1010; Cho et al. Adv. Funct. Mater. 2009 19:3112-3118; 8$^{th}$ International Judah Folkman Conference, Cambridge, Mass. Oct. 8-9, 2010; the contents of each of which is herein incorporated by reference in its entirety). Effective delivery to myeloid cells, such as monocytes, lipidoid formulations may have a similar component molar ratio. Different ratios of lipidoids and other components including, but not limited to, disteroylphosphatidyl choline, cholesterol and PEG-DMG, may be used to optimize the formulation of saRNA for delivery to different cell types including, but not limited to, hepatocytes, myeloid cells, muscle cells, etc. For example, the component molar ratio may include, but is not limited to, 50% C12-200, 10% disteroylphosphatidyl choline, 38.5% cholesterol, and %1.5 PEG-DMG (see Leuschner et al., Nat Biotechnol 2011 29:1005-1010; the contents of which are herein incorporated by reference in its entirety). The use of lipidoid formulations for the localized delivery of nucleic acids to cells (such as, but not limited to, adipose cells and muscle cells) via either subcutaneous or intramuscular delivery, may not require all of the formulation components desired for systemic delivery, and as such may comprise only the lipidoid and saRNA.

Liposomes, Lipoplexes, and Lipid Nanoparticles

The saRNA of the invention can be formulated using one or more liposomes, lipoplexes, or lipid nanoparticles. In one embodiment, pharmaceutical compositions of saRNA include liposomes. Liposomes are artificially-prepared vesicles which may primarily be composed of a lipid bilayer and may be used as a delivery vehicle for the administration of nutrients and pharmaceutical formulations. Liposomes can be of different sizes such as, but not limited to, a multilamellar vesicle (MLV) which may be hundreds of nanometers in diameter and may contain a series of concentric bilayers separated by narrow aqueous compartments, a small unicellular vesicle (SUV) which may be smaller than 50 nm in diameter, and a large unilamellar vesicle (LUV) which may be between 50 and 500 nm in diameter. Liposome design may include, but is not limited to, opsonins or ligands in order to improve the attachment of liposomes to unhealthy tissue or to activate events such as, but not limited to, endocytosis. Liposomes may contain a low or a high pH in order to improve the delivery of the pharmaceutical formulations.

The formation of liposomes may depend on the physicochemical characteristics such as, but not limited to, the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimization size, polydispersity and the shelf-life of the vesicles for the intended application, and the batch-to-batch reproducibility and possibility of large-scale production of safe and efficient liposomal products.

In one embodiment, pharmaceutical compositions described herein may include, without limitation, liposomes such as those formed from 1,2-dioleyloxy-N,N-dimethylaminopropane (DODMA) liposomes, DiLa2 liposomes from Marina Biotech (Bothell, Wash.), 1,2-dilinoleyloxy-3-dimethylaminopropane (DLin-DMA), 2,2-dilinoleyl-4-(2-dimethylaminoethyl)-[1,3]-dioxolane (DLin-KC2-DMA), and MC3 (US20100324120; the contents of which are herein incorporated by reference in its entirety) and liposomes which may deliver small molecule drugs such as, but not limited to, DOXIL® from Janssen Biotech, Inc. (Horsham, Pa.).

In one embodiment, pharmaceutical compositions described herein may include, without limitation, liposomes such as those formed from the synthesis of stabilized plasmid-lipid particles (SPLP) or stabilized nucleic acid lipid particle (SNALP) that have been previously described and shown to be suitable for oligonucleotide delivery in vitro and in vivo (see Wheeler et al. Gene Therapy. 1999 6:271-281; Zhang et al. Gene Therapy. 1999 6:1438-1447; Jeffs et al. Pharm Res. 2005 22:362-372; Morrissey et al., Nat Biotechnol. 2005 2:1002-1007; Zimmermann et al., Nature. 2006 441:111-114; Heyes et al. J Contr Rel. 2005 107:276-287; Semple et al. Nature Biotech. 2010 28:172-176; Judge et al. J Clin Invest. 2009 119:661-673; deFougerolles Hum Gene Ther. 2008 19:125-132; the contents of each of which are incorporated herein in their entireties). The original manufacture method by Wheeler et al. was a detergent dialysis method, which was later improved by Jeffs et al. and is referred to as the spontaneous vesicle formation method. The liposome formulations may be composed of 3 to 4 lipid components in addition to the saRNA. As an example a liposome can contain, but is not limited to, 55% cholesterol, 20% disteroylphosphatidyl choline (DSPC), 10% PEG-S-DSG, and 15% 1,2-dioleyloxy-N,N-dimethylaminopropane (DODMA), as described by Jeffs et al. In another example, certain liposome formulations may contain, but are not limited to, 48% cholesterol, 20% DSPC, 2% PEG-c-DMA, and 30% cationic lipid, where the cationic lipid can be 1,2-distearloxy-N,N-dimethylaminopropane (DSDMA), DODMA, DLin-DMA, or 1,2-dilinolenyloxy-3-dimethylaminopropane (DLenDMA), as described by Heyes et al. In another example, the nucleic acid-lipid particle may comprise a cationic lipid comprising from about 50 mol % to about 85 mol % of the total lipid present in the particle; a non-cationic lipid comprising from about 13 mol % to about 49.5 mol % of the total lipid present in the particle; and a conjugated lipid that inhibits aggregation of particles comprising from about 0.5 mol % to about 2 mol % of the total lipid present in the particle as described in WO2009127060 to Maclachlan et al, the contents of which are incorporated herein by reference in their entirety. In another example, the nucleic acid-lipid particle may be any nucleic acid-lipid particle disclosed in US2006008910 to Maclachlan et al., the contents of which are incorporated herein by reference in their entirety. As a non-limiting example, the nucleic acid-lipid particle may comprise a cationic lipid of Formula I, a non-cationic lipid, and a conjugated lipid that inhibits aggregation of particles.

In one embodiment, the saRNA may be formulated in a lipid vesicle which may have crosslinks between functionalized lipid bilayers.

In one embodiment, the liposome may contain a sugar-modified lipid disclosed in U.S. Pat. No. 5,595,756 to Bally et al., the contents of which are incorporated herein by reference in their entirety. The lipid may be a ganglioside and cerebroside in an amount of about 10 mol percent.

In one embodiment, the saRNA may be formulated in a liposome comprising a cationic lipid. The liposome may have a molar ratio of nitrogen atoms in the cationic lipid to the phosphates in the saRNA (N:P ratio) of between 1:1 and 20:1 as described in International Publication No. WO2013006825, the contents of which are herein incorporated by reference in its entirety. In another embodiment, the liposome may have a N:P ratio of greater than 20:1 or less than 1:1.

In one embodiment, the saRNA may be formulated in a lipid-polycation complex. The formation of the lipid-polycation complex may be accomplished by methods known in the art and/or as described in U.S. Pub. No. 20120178702, the contents of which are herein incorporated by reference in its entirety. As a non-limiting example, the polycation may include a cationic peptide or a polypeptide such as, but not limited to, polylysine, polyornithine and/or polyarginine and the cationic peptides described in International Pub. No. WO2012013326; herein incorporated by reference in its entirety. In another embodiment, the saRNA may be formulated in a lipid-polycation complex which may further include a neutral lipid such as, but not limited to, cholesterol or dioleoyl phosphatidylethanolamine (DOPE).

The liposome formulation may be influenced by, but not limited to, the selection of the cationic lipid component, the degree of cationic lipid saturation, the nature of the PEGy-lation, ratio of all components and biophysical parameters such as size. In one example by Semple et al. (Semple et al. Nature Biotech. 2010 28:172-176; the contents of which are herein incorporated by reference in its entirety), the liposome formulation was composed of 57.1% cationic lipid, 7.1% dipalmitoylphosphatidylcholine, 34.3% cholesterol, and 1.4% PEG-c-DMA.

In some embodiments, the ratio of PEG in the lipid nanoparticle (LNP) formulations may be increased or decreased and/or the carbon chain length of the PEG lipid may be modified from C14 to C18 to alter the pharmacokinetics and/or biodistribution of the LNP formulations. As a non-limiting example, LNP formulations may contain 1-5% of the lipid molar ratio of PEG-c-DOMG as compared to the cationic lipid, DSPC and cholesterol. In another embodiment the PEG-c-DOMG may be replaced with a PEG lipid such as, but not limited to, PEG-DSG (1,2-Distearoyl-sn-glycerol, methoxypolyethylene glycol) or PEG-DPG (1,2-Dipalmitoyl-sn-glycerol, methoxypolyethylene glycol). The cationic lipid may be selected from any lipid known in the art such as, but not limited to, DLin-MC3-DMA, DLin-DMA, C12-200 and DLin-KC2-DMA.

In one embodiment, the saRNA may be formulated in a lipid nanoparticle such as the lipid nanoparticles described in International Publication No. WO2012170930, the contents of which are herein incorporated by reference in its entirety.

In one embodiment, the cationic lipid which may be used in formulations of the present invention may be selected from, but not limited to, a cationic lipid described in International Publication Nos. WO2012040184, WO2011153120, WO2011149733, WO2011090965, WO2011043913, WO2011022460, WO2012061259, WO2012054365, WO2012044638, WO2010080724, WO201021865 and WO2008103276, U.S. Pat. Nos. 7,893,302, 7,404,969 and 8,283,333 and US Patent Publication No. US20100036115 and US20120202871; the contents of each of which is herein incorporated by reference in their entirety. In another embodiment, the cationic lipid may be selected from, but not limited to, formula A described in International Publication Nos. WO2012040184, WO2011153120, WO2011149733, WO2011090965, WO2011043913, WO2011022460, WO2012061259, WO2012054365 and WO2012044638; the contents of each of which is herein incorporated by reference in their entirety. In yet another embodiment, the cationic lipid may be selected from, but not limited to, formula CLI-CLXXIX of International Publication No. WO2008103276, formula CLI-CLXXIX of U.S. Pat. No. 7,893,302, formula CLI-CLXXXII of U.S. Pat. No. 7,404,969 and formula I-VI of US Patent Publication No. US20100036115; the contents of each of which is herein incorporated by reference in their entirety. In yet another embodiment, the cationic lipid may be a multivalent cationic lipid such as the cationic lipid disclosed in U.S. Pat. No. 7,223,887 to Gaucheron et al., the contents of which are incorporated herein by reference in their entirety. The cationic lipid may have a positively-charged head group including two quaternary amine groups and a hydrophobic portion including four hydrocarbon chains as described in U.S. Pat. No. 7,223,887 to Gaucheron et al., the contents of which are incorporated herein by reference in their entirety. In yet another embodiment, the cationic lipid may be biodegradable as the biodegradable lipids disclosed in US20130195920 to Maier et al., the contents of which are incorporated herein by reference in their entirety. The cationic lipid may have one or more biodegradable groups located in a lipidic moiety of the cationic lipid as described in formula I-IV in US 20130195920 to Maier et al., the contents of which are incorporated herein by reference in their entirety. As a non-limiting example, the cationic lipid may be selected from (20Z,23Z)—N,N-dimethylnonacosa-20,23-dien-10-amine, (17Z,20Z)—N,N-dimemylhexacosa-17,20-dien-9-amine, (1Z,19Z)—N5N-dimethylpentacosa-16, 19-dien-8-amine, (13Z,16Z)—N,N-dimethyldocosa-13,16-dien-5-amine, (12Z,15Z)—N,N-dimethylhenicosa-12,15-dien-4-amine, (14Z,17Z)—N,N-dimethyltricosa-14,17-dien-6-amine, (15Z,18Z)—N,N-dimethyltetracosa-15,18-dien-7-amine, (18Z,21Z)—N,N-dimethylheptacosa-18,21-dien-10-amine, (15Z,18Z)—N,N-dimethyltetracosa-15,18-dien-5-amine, (14Z,17Z)—N,N-dimethyltricosa-14,17-dien-4-amine, (19Z,22Z)—N,N-dimethyloctacosane-19,22-dien-9-amine, (18Z,21 Z)—N,N-dimethylheptacosa-18,21-dien-8-amine, (17Z,20Z)—N,N-dimethylhexacosa-17,20-dien-7-amine, (16Z,19Z)—N,N-dimethylpentacosa-16,19-dien-6-amine, (22Z,25Z)—N,N-dimethylhentriaconta-22,25-dien-10-amine, (21 Z,24Z)—N,N-dimethyltriaconta-21,24-dien-9-amine, (18Z)—N,N-dimetylheptacos-18-en-10-amine, (17Z)—N,N-dimethylhexacos-17-en-9-amine, (19Z,22Z)—N,N-dimethyloctacosa-19,22-dien-7-amine, N,N-dimethyl-heptacosan-10-amine, (20Z,23Z)—N-ethyl-N-methylnonacosa-20,23-dien-10-amine, 1-[(11Z,14Z)-1-nonylicosa-11,14-dien-1-yl] pyrrolidine, (20Z)—N,N-dimethylheptacos-20-en-10-amine, (15Z)—N,N-dimethyl eptacos-15-en-10-amine, (14Z)—N,N-dimethylnonacos-14-en-10-amine, (17Z)—N,N-dimethylnonacos-17-en-10-amine, (24Z)—N,N-dimethyltritriacont-24-en-10-amine, (20Z)—N,N-dimethylnonacos-20-en-10-amine, (22Z)—N,N-dimethylhentriacont-22-en-10-amine, (16Z)—N,N-dimethylpentacos-16-en-8-amine, (12Z,15Z)—N,N-dimethyl-2-nonylhenicosa-12,15-dien-1-amine, (13Z,16Z)—N,N-dimethyl-3-nonyldocosa-13,16-dien-1-amine, N,N-dimethyl-1-[(1S,2R)-2-octylcyclopropyl] eptadecan-8-amine, 1-[(1S,2R)-2-hexylcyclopropyl]-N,N-dimethylnonadecan-10-amine, N,N-dimethyl-1-[(1S,2R)-2-octylcyclopropyl]nonadecan-10-amine, N,N-dimethyl-21-[(1S,2R)-2-octylcyclopropyl]henicosan-10-amine, N,N-dimethyl-1-[(1S,2S)-2-{[(1R,2R)-2-pentylcyclopropyl]methyl}cyclopropyl]nonadecan-10-amine, N,N-dimethyl-1-[(1S,2R)-2-octylcyclopropyl]hexadecan-8-amine, N,N-dimethyl-[(1R,2S)-2-undecylcyclopropyl]tetradecan-5-amine, N,N-dimethyl-3-{7-[(1S,2R)-2-octylcyclopropyl] heptyl} dodecan-1-amine, 1-[(1R,2S)-2-heptylcyclopropyl]-N,N-dimethyloctadecan-9-amine, 1-[(1S,2R)-2-decylcyclopropyl]-N,N-dimethylpentadecan-6-amine, N,N-dimethyl-1-[(1S,2R)-2-octylcyclopropyl]pentadecan-8-amine, R—N,N-dimethyl-1-[(9Z,12Z)-octadeca-9,12-dien-1-yloxy]-3-(octyloxy)propan-2-amine, S—N,N-dimethyl-1-[(9Z,12Z)-octadeca-9,12-dien-1-yloxy]-3-(octyloxy) propan-2-amine, 1-{2-[(9Z,12Z)-octadeca-9,12-dien-1-yloxy]-1-[(octyloxy)methyl]ethyl}pyrrolidine, (2S)—N,N-dimethyl-1-[(9Z,12Z)-octadeca-9,12-dien-1-yloxy]-3-[(5Z)-oct-5-en-1-yloxy]propan-2-amine, 1-{2-[(9Z,12Z)-octadeca-9,12-dien-1-yloxy]-1-[(octyloxy)methyl] ethyl}azetidine, (2S)-1-(hexyloxy)-N,N-dimethyl-3-[(9Z,12Z)-octadeca-9,12-dien-1-yloxy]propan-2-amine, (2S)-1-(heptyloxy)-N,N-dimethyl-3-[(9Z,12Z)-octadeca-9,12-dien-1-yloxy]propan-2-amine, N,N-dimethyl-1-(nonyloxy)-3-[(9Z,12Z)-octadeca-9,12-dien-1-yloxy]propan-2-amine, N,N-dimethyl-1-[(9Z)-octadec-9-en-1-yloxy]-3-(octyloxy) propan-2-amine; (2S)—N,N-dimethyl-1-[(6Z,9Z,12Z)-octadeca-6,9,12-trien-1-yloxy]-3-(octyloxy)propan-2-amine, (2S)-1-[(11Z,14Z)-icosa-11,14-dien-1-yloxy]-N,N-dimethyl-3-(pentyloxy)propan-2-amine, (2S)-1-(hexyloxy)-3-[(11Z,14Z)-icosa-11,14-dien-1-yloxy]-N,N-dimethylpropan-2-amine, 1-[(11Z,14Z)-icosa-11,14-dien-1-yloxy]-N,N-dimethyl-3-(octyloxy)propan-2-amine, 1-[(13Z,16Z)-docosa-13,16-dien-1-yloxy]-N,N-dimethyl-3-(octyloxy) propan-2-amine, (2S)-1-[(13Z,16Z)-docosa-13,16-dien-1-yloxy]-3-(hexyloxy)-N,N-dimethylpropan-2-amine, (2S)-1-[(13Z)-docos-13-en-1-yloxy]-3-(hexyloxy)-N,N-dimethylpropan-2-amine, 1-[(13Z)-docos-13-en-1-yloxy]-N,N-dimethyl-3-(octyloxy)propan-2-amine, 1-[(9Z)-hexadec-9-en-1-yloxy]-N,N-dimethyl-3-(octyloxy)propan-2-amine, (2R)—N,N-dimethyl-H(1-metoylo ctyl)oxy]-3-[(9Z,12Z)-octadeca-9,12-dien-1-yloxy]propan-2-amine, (2R)-1-[(3,7-dimethyloctyl)oxy]-N,N-dimethyl-3-[(9Z,12Z)-octadeca-9,12-dien-1-yloxy]propan-2-amine, N,N-dimethyl-1-(octyloxy)-3-({8-[(1S,2S)-2-{[(1R,2R)-2-pentylcyclopropyl]methyl}cyclopropyl]octyl}oxy)propan-2-amine, N,N-dimethyl-1-{[8-(2-oclylcyclopropyl)octyl]oxy}-3-(octyloxy)propan-2-amine and (11E,20Z,23Z)—N,N-dimethylnonacosa-11,20,2-trien-10-amine or a pharmaceutically acceptable salt or stereoisomer thereof.

In one embodiment, the lipid may be a cleavable lipid such as those described in International Publication No. WO2012170889, the contents of which is herein incorporated by reference in its entirety.

In one embodiment, the nanoparticles described herein may comprise at least one cationic polymer described herein and/or known in the art.

In one embodiment, the cationic lipid may be synthesized by methods known in the art and/or as described in International Publication Nos. WO2012040184, WO2011153120, WO2011149733, WO2011090965, WO2011043913, WO2011022460, WO2012061259, WO2012054365, WO2012044638, WO2010080724 and WO201021865; the contents of each of which is herein incorporated by reference in their entirety.

In one embodiment, the LNP formulations of the saRNA may contain PEG-c-DOMG at 3% lipid molar ratio. In another embodiment, the LNP formulations of the saRNA may contain PEG-c-DOMG at 1.5% lipid molar ratio.

In one embodiment, the pharmaceutical compositions of the saRNA may include at least one of the PEGylated lipids described in International Publication No. 2012099755, the contents of which is herein incorporated by reference in its entirety.

In one embodiment, the LNP formulation may contain PEG-DMG 2000 (1,2-dimyristoyl-sn-glycero-3-phophoethanolamine-N-[methoxy(polyethylene glycol)-2000). In one embodiment, the LNP formulation may contain PEG-DMG 2000, a cationic lipid known in the art and at least one other component. In another embodiment, the LNP formulation may contain PEG-DMG 2000, a cationic lipid known in the art, DSPC and cholesterol. As a non-limiting example, the LNP formulation may contain PEG-DMG 2000, DLin-DMA, DSPC and cholesterol. As another non-limiting example the LNP formulation may contain PEG-DMG 2000, DLin-DMA, DSPC and cholesterol in a molar ratio of 2:40:10:48 (see e.g., Geall et al., Nonviral delivery of self-amplifying RNA vaccines, PNAS 2012; PMID: 22908294; herein incorporated by reference in its entirety). As another non-limiting example, the saRNA described herein may be formulated in a nanoparticle to be delivered by a parenteral route as described in U.S. Pub. No. 20120207845; the contents of which is herein incorporated by reference in its entirety. The cationic lipid may also be the cationic lipids disclosed in US20130156845 to Manoharan et al. and US 20130129785 to Manoharan et al., WO 2012047656 to Wasan et al., WO 2010144740 to Chen et al., WO 2013086322 to Ansell et al., or WO 2012016184 to Manoharan et al., the contents of each of which are incorporated herein by reference in their entirety.

In one embodiment, the saRNA of the present invention may be formulated with a plurality of cationic lipids, such as a first and a second cationic lipid as described in US20130017223 to Hope et al., the contents of which are incorporated herein by reference in their entirety. The first cationic lipid can be selected on the basis of a first property and the second cationic lipid can be selected on the basis of a second property, where the properties may be determined as outlined in US20130017223, the contents of which are herein incorporated by reference in its entirety. In one embodiment, the first and second properties are complementary.

In another embodiment, the saRNA may be formulated with a lipid particle comprising one or more cationic lipids and one or more second lipids, and one or more nucleic acids, wherein the lipid particle comprises a solid core, as described in US Patent Publication No. US20120276209 to Cullis et al., the contents of which are incorporated herein by reference in their entirety.

In one embodiment, the saRNA of the present invention may be complexed with a cationic amphiphile in an oil-in-water (o/w) emulsion such as described in EP2298358 to Satishchandran et al., the contents of which are incorporated herein by reference in their entirety. The cationic amphiphile may be a cationic lipid, modified or unmodified spermine, bupivacaine, or benzalkonium chloride and the oil may be a vegetable or an animal oil. As a non-limiting example, at least 10% of the nucleic acid-cationic amphiphile complex is in the oil phase of the oil-in-water emulsion (see e.g., the complex described in European Publication No. EP2298358 to Satishchandran et al., the contents of which are herein incorporated by reference in its entirety).

In one embodiment, the saRNA of the present invention may be formulated with a composition comprising a mixture of cationic compounds and neutral lipids. As a non-limiting example, the cationic compounds may be formula (I) disclosed in WO 1999010390 to Ansell et al., the contents of which are disclosed herein by reference in their entirety, and the neutral lipid may be selected from the group consisting of diacylphosphatidylcholine, diacylphosphatidylethanolamine, ceramide and sphingomyelin.

In one embodiment, the LNP formulation may be formulated by the methods described in International Publication Nos. WO2011127255 or WO2008103276, each of which are herein incorporated by reference in their entirety. As a non-limiting example, the saRNA of the present invention may be encapsulated in any of the lipid nanoparticle (LNP) formulations described in WO2011127255 and/or WO2008103276; the contents of each of which are herein incorporated by reference in their entirety.

In one embodiment, the LNP formulations described herein may comprise a polycationic composition. As a non-limiting example, the polycationic composition may be selected from formula 1-60 of US Patent Publication No. US20050222064; the contents of which is herein incorporated by reference in its entirety. In another embodiment, the LNP formulations comprising a polycationic composition may be used for the delivery of the saRNA described herein in vivo and/or in vitro.

In one embodiment, the LNP formulations described herein may additionally comprise a permeability enhancer molecule. Non-limiting permeability enhancer molecules are described in US Patent Publication No. US20050222064; the contents of which is herein incorporated by reference in its entirety.

In one embodiment, the pharmaceutical compositions may be formulated in liposomes such as, but not limited to, DiLa2 liposomes (Marina Biotech, Bothell, Wash.), SMARTICLES®/NOV340 (Marina Biotech, Bothell, Wash.), neutral DOPC (1,2-dioleoyl-sn-glycero-3-phosphocholine) based liposomes (e.g., siRNA delivery for ovarian cancer (Landen et al. Cancer Biology & Therapy 2006 5(12)1708-1713); the contents of which is herein incorporated by reference in its entirety) and hyaluronan-coated liposomes (Quiet Therapeutics, Israel). In some embodiments, the pharmaceutical compositions may be formulated with any amphoteric liposome disclosed in WO 2008/043575 to Panzner and U.S. Pat. No. 8,580,297 to Essler et al., the contents of which are incorporated herein by reference in their entirety. The amphoteric liposome may comprise a mixture of lipids including a cationic amphiphile, an anionic amphiphile and optional one or more neutral amphiphiles. The amphoteric liposome may comprise amphoteric compounds based on amphiphilic molecules, the head groups of which being substituted with one or more amphoteric groups. In some embodiments, the pharmaceutical compositions may be formulated with an amphoteric lipid comprising one or more amphoteric groups having an isoelectric point between 4 and 9, as disclosed in US 20140227345 to Essler et al., the contents of which are incorporated herein by reference in their entirety.

The nanoparticle formulations may be a carbohydrate nanoparticle comprising a carbohydrate carrier and a nucleic acid molecule (e.g., saRNA). As a non-limiting example, the carbohydrate carrier may include, but is not limited to, an anhydride-modified phytoglycogen or glycogen-type material, phtoglycogen octenyl succinate, phytoglycogen beta-dextrin, anhydride-modified phytoglycogen beta-dextrin. (See e.g., International Publication No. WO2012109121; the contents of which is herein incorporated by reference in its entirety).

Lipid nanoparticle formulations may be improved by replacing the cationic lipid with a biodegradable cationic lipid which is known as a rapidly eliminated lipid nanoparticle (reLNP). Ionizable cationic lipids, such as, but not limited to, DLinDMA, DLin-KC2-DMA, and DLin-MC3-DMA, have been shown to accumulate in plasma and tissues over time and may be a potential source of toxicity. The rapid metabolism of the rapidly eliminated lipids can improve the tolerability and therapeutic index of the lipid nanoparticles by an order of magnitude from a 1 mg/kg dose to a 10 mg/kg dose in rat. Inclusion of an enzymatically degraded ester linkage can improve the degradation and metabolism profile of the cationic component, while still maintaining the activity of the reLNP formulation. The ester linkage can be internally located within the lipid chain or it may be terminally located at the terminal end of the lipid chain. The internal ester linkage may replace any carbon in the lipid chain.

In one embodiment, the saRNA may be formulated as a lipoplex, such as, without limitation, the ATUPLEX™ system, the DACC system, the DBTC system and other siRNA-lipoplex technology from Silence Therapeutics (London, United Kingdom), STEMFECT™ from STEMGENT® (Cambridge, Mass.), and polyethylenimine (PEI) or protamine-based targeted and non-targeted delivery of nucleic acids (Aleku et al. Cancer Res. 2008 68:9788-9798; Strumberg et al. Int J Clin Pharmacol Ther 2012 50:76-78; Santel et al., Gene Ther 2006 13:1222-1234; Santel et al., Gene Ther 2006 13:1360-1370; Gutbier et al., Pulm Pharmacol.

Ther. 2010 23:334-344; Kaufmann et al. Microvasc Res 2010 80:286-293 Weide et al. J Immunother. 2009 32:498-507; Weide et al. J Immunother. 2008 31:180-188; Pascolo Expert Opin. Biol. Ther. 4:1285-1294; Fotin-Mleczek et al., 2011 J. Immunother. 34:1-15; Song et al., Nature Biotechnol. 2005, 23:709-717; Peer et al., Proc Natl Acad Sci USA. 2007 6; 104:4095-4100; deFougerolles Hum Gene Ther. 2008 19:125-132; the contents of each of which are incorporated herein by reference in its entirety).

In one embodiment such formulations may also be constructed or compositions altered such that they passively or actively are directed to different cell types in vivo, including but not limited to hepatocytes, immune cells, tumor cells, endothelial cells, antigen presenting cells, and leukocytes (Akinc et al. Mol Ther. 2010 18:1357-1364; Song et al., Nat Biotechnol. 2005 23:709-717; Judge et al., J Clin Invest. 2009 119:661-673; Kaufmann et al., Microvasc Res 2010 80:286-293; Santel et al., Gene Ther 2006 13:1222-1234; Santel et al., Gene Ther 2006 13:1360-1370; Gutbier et al., Pulm Pharmacol. Ther. 2010 23:334-344; Basha et al., Mol. Ther. 2011 19:2186-2200; Fenske and Cullis, Expert Opin Drug Deliv. 2008 5:25-44; Peer et al., Science. 2008 319: 627-630; Peer and Lieberman, Gene Ther. 2011 18:1127-1133; the contents of each of which are incorporated herein by reference in its entirety). One example of passive targeting of formulations to liver cells includes the DLin-DMA, DLin-KC2-DMA and DLin-MC3-DMA-based lipid nanoparticle formulations which have been shown to bind to apolipoprotein E and promote binding and uptake of these formulations into hepatocytes in vivo (Akinc et al. Mol Ther. 2010 18:1357-1364; the contents of which is herein incorporated by reference in its entirety). Formulations can also be selectively targeted through expression of different ligands on their surface as exemplified by, but not limited by, folate, transferrin, N-acetylgalactosamine (GalNAc), and antibody targeted approaches (Kolhatkar et al., Curr Drug Discov Technol. 2011 8:197-206; Musacchio and Torchilin, *Front Biosci*. 2011 16:1388-1412; Yu et al., Mol Membr Biol. 2010 27:286-298; Patil et al., Crit Rev Ther Drug Carrier Syst. 2008 25:1-61; Benoit et al., Biomacromolecules. 2011 12:2708-2714; Zhao et al., Expert Opin Drug Deliv. 2008 5:309-319; Akinc et al., Mol Ther. 2010 18:1357-1364; Srinivasan et al., Methods Mol Biol. 2012 820:105-116; Ben-Arie et al., Methods Mol Biol. 2012 757:497-507; Peer 2010 J Control Release. 20:63-68; Peer et al., Proc Natl Acad Sci USA. 2007 104:4095-4100; Kim et al., Methods Mol Biol. 2011 721:339-353; Subramanya et al., Mol Ther. 2010 18:2028-2037; Song et al., Nat Biotechnol. 2005 23:709-717; Peer et al., Science. 2008 319:627-630; Peer and Lieberman, Gene Ther. 2011 18:1127-1133; the contents of each of which are incorporated herein by reference in its entirety).

In one embodiment, the saRNA is formulated as a solid lipid nanoparticle. A solid lipid nanoparticle (SLN) may be spherical with an average diameter between 10 to 1000 nm. SLN possess a solid lipid core matrix that can solubilize lipophilic molecules and may be stabilized with surfactants and/or emulsifiers. In a further embodiment, the lipid nanoparticle may be a self-assembly lipid-polymer nanoparticle (see Zhang et al., ACS Nano, 2008, 2 (8), pp 1696-1702; the contents of which are herein incorporated by reference in its entirety).

In one embodiment, the saRNA of the present invention can be formulated for controlled release and/or targeted delivery. As used herein, "controlled release" refers to a pharmaceutical composition or compound release profile that conforms to a particular pattern of release to effect a therapeutic outcome. In one embodiment, the saRNA may be encapsulated into a delivery agent described herein and/or known in the art for controlled release and/or targeted delivery. As used herein, the term "encapsulate" means to enclose, surround or encase. As it relates to the formulation of the compounds of the invention, encapsulation may be substantial, complete or partial. The term "substantially encapsulated" means that at least greater than 50, 60, 70, 80, 85, 90, 95, 96, 97, 98, 99, 99.9, 99.9 or greater than 99.999% of the pharmaceutical composition or compound of the invention may be enclosed, surrounded or encased within the delivery agent. "Partially encapsulated" means that less than 10, 10, 20, 30, 40 50 or less of the pharmaceutical composition or compound of the invention may be enclosed, surrounded or encased within the delivery agent. Advantageously, encapsulation may be determined by measuring the escape or the activity of the pharmaceutical composition or compound of the invention using fluorescence and/or electron micrograph. For example, at least 1, 5, 10, 20, 30, 40, 50, 60, 70, 80, 85, 90, 95, 96, 97, 98, 99, 99.9, 99.99 or greater than 99.99% of the pharmaceutical composition or compound of the invention are encapsulated in the delivery agent.

In another embodiment, the saRNA may be encapsulated into a lipid nanoparticle or a rapidly eliminated lipid nanoparticle and the lipid nanoparticles or a rapidly eliminated lipid nanoparticle may then be encapsulated into a polymer, hydrogel and/or surgical sealant described herein and/or known in the art. As a non-limiting example, the polymer, hydrogel or surgical sealant may be PLGA, ethylene vinyl acetate (EVAc), poloxamer, GELSITE® (Nanotherapeutics, Inc. Alachua, Fla.), HYLENEX® (Halozyme Therapeutics, San Diego Calif.), surgical sealants such as fibrinogen polymers (Ethicon Inc. Cornelia, Ga.), TISSELL® (Baxter International, Inc Deerfield, Ill.), PEG-based sealants, and COSEAL® (Baxter International, Inc Deerfield, Ill.).

In another embodiment, the lipid nanoparticle may be encapsulated into any polymer known in the art which may form a gel when injected into a subject. As another non-limiting example, the lipid nanoparticle may be encapsulated into a polymer matrix which may be biodegradable.

In one embodiment, the saRNA formulation for controlled release and/or targeted delivery may also include at least one controlled release coating. Controlled release coatings include, but are not limited to, OPADRY®, polyvinylpyrrolidone/vinyl acetate copolymer, polyvinylpyrrolidone, hydroxypropyl methylcellulose, hydroxypropyl cellulose, hydroxyethyl cellulose, EUDRAGIT RL®, EUDRAGIT RS® and cellulose derivatives such as ethylcellulose aqueous dispersions (AQUACOAT® and SURELEASE®).

In one embodiment, the controlled release and/or targeted delivery formulation may comprise at least one degradable polyester which may contain polycationic side chains. Degradeable polyesters include, but are not limited to, poly(serine ester), poly(L-lactide-co-L-lysine), poly(4-hydroxy-L-proline ester), and combinations thereof. In another embodiment, the degradable polyesters may include a PEG conjugation to form a PEGylated polymer.

In one embodiment, the saRNA of the present invention may be formulated with a targeting lipid with a targeting moiety such as the targeting moieties disclosed in US20130202652 to Manoharan et al., the contents of which are incorporated herein by reference in their entirety. As a non-limiting example, the targeting moiety of formula I of US 20130202652 to Manoharan et al. may selected in order to favor the lipid being localized with a desired organ, tissue, cell, cell type or subtype, or organelle. Non-limiting targeting moieties that are contemplated in the present invention include transferrin, anisamide, an RGD peptide, prostate specific membrane antigen (PSMA), fucose, an antibody, or an aptamer.

In one embodiment, the saRNA of the present invention may be encapsulated in a therapeutic nanoparticle. Therapeutic nanoparticles may be formulated by methods described herein and known in the art such as, but not limited to, International Pub Nos. WO2010005740, WO2010030763, WO2010005721, WO2010005723, WO2012054923, US Pub. Nos. US20110262491, US20100104645, US20100087337, US20100068285, US20110274759, US20100068286 and US20120288541 and U.S. Pat. Nos. 8,206,747, 8,293,276, 8,318,208 and 8,318,211; the contents of each of which are herein incorporated by reference in their entirety. In another embodiment, therapeutic polymer nanoparticles may be identified by the methods described in US Pub No. US20120140790, the contents of which are herein incorporated by reference in its entirety.

In one embodiment, the therapeutic nanoparticle may be formulated for sustained release. As used herein, "sustained release" refers to a pharmaceutical composition or compound that conforms to a release rate over a specific period of time. The period of time may include, but is not limited to, hours, days, weeks, months and years. As a non-limiting example, the sustained release nanoparticle may comprise a polymer and a therapeutic agent such as, but not limited to, the saRNA of the present invention (see International Pub No. 2010075072 and US Pub No. US20100216804, US20110217377 and US20120201859, the contents of each of which are herein incorporated by reference in their entirety).

In one embodiment, the therapeutic nanoparticles may be formulated to be target specific. As a non-limiting example, the therapeutic nanoparticles may include a corticosteroid (see International Pub. No. WO2011084518; the contents of which are herein incorporated by reference in its entirety). In one embodiment, the therapeutic nanoparticles may be formulated to be cancer specific. As a non-limiting example, the therapeutic nanoparticles may be formulated in nanoparticles described in International Pub No. WO2008121949, WO2010005726, WO2010005725, WO2011084521 and US Pub No. US20100069426, US20120004293 and US20100104655, the contents of each of which are herein incorporated by reference in their entirety.

In one embodiment, the nanoparticles of the present invention may comprise a polymeric matrix. As a non-limiting example, the nanoparticle may comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester) or combinations thereof.

In one embodiment, the therapeutic nanoparticle comprises a diblock copolymer. In one embodiment, the diblock copolymer may include PEG in combination with a polymer such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester) or combinations thereof.

As a non-limiting example the therapeutic nanoparticle comprises a PLGA-PEG block copolymer (see US Pub. No. US20120004293 and U.S. Pat. No. 8,236,330, each of which is herein incorporated by reference in their entirety). In another non-limiting example, the therapeutic nanoparticle is a stealth nanoparticle comprising a diblock copolymer of PEG and PLA or PEG and PLGA (see U.S. Pat. No. 8,246,968 and International Publication No. WO2012166923, the contents of each of which is herein incorporated by reference in its entirety).

In one embodiment, the therapeutic nanoparticle may comprise a multiblock copolymer such as, but not limited to the multiblock copolymers described in U.S. Pat. Nos. 8,263,665 and 8,287,910; the contents of each of which is herein incorporated by reference in its entirety.

In one embodiment, the block copolymers described herein may be included in a polyion complex comprising a non-polymeric micelle and the block copolymer. (See e.g., U.S. Pub. No. 20120076836; the contents of which are herein incorporated by reference in its entirety).

In one embodiment, the therapeutic nanoparticle may comprise at least one acrylic polymer. Acrylic polymers include but are not limited to, acrylic acid, methacrylic acid, acrylic acid and methacrylic acid copolymers, methyl methacrylate copolymers, ethoxyethyl methacrylates, cyanoethyl methacrylate, amino alkyl methacrylate copolymer, poly (acrylic acid), poly(methacrylic acid), polycyanoacrylates and combinations thereof.

In one embodiment, the therapeutic nanoparticles may comprise at least one amine-containing polymer such as, but not limited to polylysine, polyethylene imine, poly(amidoamine) dendrimers, poly(beta-amino esters) (See e.g., U.S. Pat. No. 8,287,849; the contents of which are herein incorporated by reference in its entirety) and combinations thereof.

In one embodiment, the therapeutic nanoparticles may comprise at least one degradable polyester which may contain polycationic side chains. Degradable polyesters include, but are not limited to, poly(serine ester), poly(L-lactide-co-L-lysine), poly(4-hydroxy-L-proline ester), and combinations thereof. In another embodiment, the degradable polyesters may include a PEG conjugation to form a PEGylated polymer.

In another embodiment, the therapeutic nanoparticle may include a conjugation of at least one targeting ligand. The targeting ligand may be any ligand known in the art such as, but not limited to, a monoclonal antibody. (Kirpotin et al, Cancer Res. 2006 66:6732-6740; the contents of which are herein incorporated by reference in its entirety).

In one embodiment, the therapeutic nanoparticle may be formulated in an aqueous solution which may be used to target cancer (see International Pub No. WO2011084513 and US Pub No. US20110294717, the contents of each of which is herein incorporated by reference in their entirety).

In one embodiment, the saRNA may be encapsulated in, linked to and/or associated with synthetic nanocarriers. Synthetic nanocarriers include, but are not limited to, those described in International Pub. Nos. WO2010005740, WO2010030763, WO201213501, WO2012149252, WO2012149255, WO2012149259, WO2012149265, WO2012149268, WO2012149282, WO2012149301, WO2012149393, WO2012149405, WO2012149411, WO2012149454 and WO2013019669, and US Pub. Nos.

US20110262491, US20100104645, US20100087337 and US20120244222, the contents of each of which are herein incorporated by reference in their entirety. The synthetic nanocarriers may be formulated using methods known in the art and/or described herein. As a non-limiting example, the synthetic nanocarriers may be formulated by the methods described in International Pub Nos. WO2010005740, WO2010030763 and WO201213501 and US Pub. Nos. US20110262491, US20100104645, US20100087337 and US2012024422, the contents of each of which are herein incorporated by reference in their entirety. In another embodiment, the synthetic nanocarrier formulations may be lyophilized by methods described in International Pub. No. WO2011072218 and U.S. Pat. No. 8,211,473; the contents of each of which are herein incorporated by reference in their entirety.

In one embodiment, the synthetic nanocarriers may contain reactive groups to release the saRNA described herein (see International Pub. No. WO20120952552 and US Pub No. US20120171229, the contents of each of which are herein incorporated by reference in their entirety).

In one embodiment, the synthetic nanocarriers may be formulated for targeted release. In one embodiment, the synthetic nanocarrier may be formulated to release the saRNA at a specified pH and/or after a desired time interval. As a non-limiting example, the synthetic nanoparticle may be formulated to release the saRNA after 24 hours and/or at a pH of 4.5 (see International Pub. Nos. WO2010138193 and WO2010138194 and US Pub Nos. US20110020388 and US20110027217, the contents of each of which is herein incorporated by reference in their entireties).

In one embodiment, the synthetic nanocarriers may be formulated for controlled and/or sustained release of the saRNA described herein. As a non-limiting example, the synthetic nanocarriers for sustained release may be formulated by methods known in the art, described herein and/or as described in International Pub No. WO2010138192 and US Pub No. 20100303850, the contents each of which is herein incorporated by reference in their entirety.

In one embodiment, the nanoparticle may be optimized for oral administration. The nanoparticle may comprise at least one cationic biopolymer such as, but not limited to, chitosan or a derivative thereof. As a non-limiting example, the nanoparticle may be formulated by the methods described in U.S. Pub. No. 20120282343; the contents of which are herein incorporated by reference in its entirety.

In one embodiment, the saRNA of the present invention may be formulated in a modular composition such as described in U.S. Pat. No. 8,575,123 to Manoharan et al., the contents of which are herein incorporated by reference in their entirety. As a non-limiting example, the modular composition may comprise a nucleic acid, e.g., the saRNA of the present invention, at least one endosomolytic component, and at least one targeting ligand. The modular composition may have a formula such as any formula described in U.S. Pat. No. 8,575,123 to Manoharan et al., the contents of which are herein incorporated by reference in their entirety.

In one embodiment, the saRNA of the present invention may be encapsulated in the lipid formulation to form a stable nucleic acid-lipid particle (SNALP) such as described in U.S. Pat. No. 8,546,554 to de Fougerolles et al., the contents of which are incorporated here by reference in their entirety. The lipid may be cationic or non-cationic. In one non-limiting example, the lipid to nucleic acid ratio (mass/mass ratio) (e.g., lipid to saRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1, or 5:1, 6:1, 7:1, 8:1, 9:1, 10:1, or 11:1. In another example, the SNALP includes 40% 2,2-Dilinoleyl-4-dimethylaminoethyl-[1,3]-dioxolane (Lipid A), 10% dioleoylphosphatidylcholine (DSPC), 40% cholesterol, 10% polyethyleneglycol (PEG)-C-DOMG (mole percent) with a particle size of 63.0±20 nm and a 0.027 nucleic acid/lipid ratio. In another embodiment, the saRNA of the present invention may be formulated with a nucleic acid-lipid particle comprising an endosomal membrane destabilizer as disclosed in U.S. Pat. No. 7,189,705 to Lam et al., the contents of which are incorporated herein by reference in their entirety. As a non-limiting example, the endosomal membrane destabilizer may be a $Ca^{2+}$ ion.

In one embodiment, the saRNA of the present invention may be formulated with formulated lipid particles (FLiPs) disclosed in U.S. Pat. No. 8,148,344 to Akine et al., the contents of which are herein incorporated by reference in their entirety. Akine et al. teach that FLiPs may comprise at least one of a single or double stranded oligonucleotide, where the oligonucleotide has been conjugated to a lipophile and at least one of an emulsion or liposome to which the conjugated oligonucleotide has been aggregated, admixed or associated. These particles have surprisingly been shown to effectively deliver oligonucleotides to heart, lung and muscle disclosed in U.S. Pat. No. 8,148,344 to Akine et al., the contents of which are herein incorporated by reference in their entirety.

In one embodiment, the saRNA of the present invention may be delivered to a cell using a composition comprising an expression vector in a lipid formulation as described in U.S. Pat. No. 6,086,913 to Tam et al., the contents of which are incorporated herein by reference in their entirety. The composition disclosed by Tam is serum-stable and comprises an expression vector comprising first and second inverted repeated sequences from an adeno associated virus (AAV), a rep gene from AAV, and a nucleic acid fragment. The expression vector in Tam is complexed with lipids.

In one embodiment, the saRNA of the present invention may be formulated with a lipid formulation disclosed in US 20120270921 to de Fougerolles et al., the contents of which are incorporated herein by reference in their entirety. In one non-limiting example, the lipid formulation may include a cationic lipid having the formula A described in US 20120270921, the contents of which are herein incorporated by reference in its entirety. In another non-limiting example, the compositions of exemplary nucleic acid-lipid particles disclosed in Table A of US 20120270921, the contents of which are incorporated herein by reference in their entirety, may be used with the saRNA of the present invention.

In one embodiment, the saRNA of the present invention may be fully encapsulated in a lipid particle disclosed in US 20120276207 to Maurer et al., the contents of which are incorporated herein by reference in their entirety. The particles may comprise a lipid composition comprising preformed lipid vesicles, a charged therapeutic agent, and a destabilizing agent to form a mixture of preformed vesicles and therapeutic agent in a destabilizing solvent, wherein said destabilizing solvent is effective to destabilize the membrane of the preformed lipid vesicles without disrupting the vesicles.

In one embodiment, the saRNA of the present invention may be formulated with a conjugated lipid. In a non-limiting example, the conjugated lipid may have a formula such as described in US 20120264810 to Lin et al., the contents of which are incorporated herein by reference in their entirety.

The conjugate lipid may form a lipid particle which further comprises a cationic lipid, a neutral lipid, and a lipid capable of reducing aggregation.

In one embodiment, the saRNA of the present invention may be formulated in a neutral liposomal formulation such as disclosed in US 20120244207 to Fitzgerald et al., the contents of which are incorporated herein by reference in their entirety. The phrase "neutral liposomal formulation" refers to a liposomal formulation with a near neutral or neutral surface charge at a physiological pH. Physiological pH can be, e.g., about 7.0 to about 7.5, or, e.g., about 7.5, or, e.g., 7.0, 7.1, 7.2, 7.3, 7.4, or 7.5, or, e.g., 7.3, or, e.g., 7.4. An example of a neutral liposomal formulation is an ionizable lipid nanoparticle (iLNP). A neutral liposomal formulation can include an ionizable cationic lipid, e.g., DLin-KC2-DMA.

In one embodiment, the saRNA of the present invention may be formulated with a charged lipid or an amino lipid. As used herein, the term "charged lipid" is meant to include those lipids having one or two fatty acyl or fatty alkyl chains and a quaternary amino head group. The quaternary amine carries a permanent positive charge. The head group can optionally include an ionizable group, such as a primary, secondary, or tertiary amine that may be protonated at physiological pH. The presence of the quaternary amine can alter the pKa of the ionizable group relative to the pKa of the group in a structurally similar compound that lacks the quaternary amine (e.g., the quaternary amine is replaced by a tertiary amine) In some embodiments, a charged lipid is referred to as an "amino lipid." In a non-limiting example, the amino lipid may be amino lipids described in US20110256175 to Hope et al., the contents of which are incorporated herein by reference in their entirety. For example, the amino lipids may have the structure disclosed as structure (II), DLin-K-C2-DMA, DLin-K2-DMA, DLin-K6-DMA disclosed in US20110256175 to Hope et al., the contents of which are incorporated herein by reference in their entirety. In another example, the amino lipid may have the structure (I), (II), (III), or (IV), or 4-(R)-DUn-K-DMA (VI), 4-(S)-DUn-K-DMA (V) as described in WO2009132131 to Muthiah et al., the contents of which are incorporated herein by reference in their entirety. In another example, the charged lipid used in any of the formulations described herein may be any charged lipid described in EP2509636 to Manoharan et al., the contents of which are incorporated herein by reference in their entirety.

In one embodiment, the saRNA of the present invention may be formulated with an association complex containing lipids, liposomes, or lipoplexes. In a non-limiting example, the association complex comprises one or more compounds each having a structure defined by formula (I), a PEG-lipid having a structure defined by formula (XV), a steroid and a nucleic acid disclosed in U.S. Pat. No. 8,034,376 to Manoharan et al., the contents of which are incorporated herein by reference in their entirety. The saRNA may be formulated with any association complex described in U.S. Pat. No. 8,034,376, the contents of which are herein incorporated by reference in its entirety.

In one embodiment, the saRNA of the present invention may be formulated with reverse head group lipids. As a non-limiting example, the saRNA may be formulated with a zwitterionic lipid comprising a headgroup wherein the positive charge is located near the acyl chain region and the negative charge is located at the distal end of the head group, such as a lipid having structure (A) or structure (I) described in WO2011056682 to Leung et al., the contents of which are incorporated herein by reference in their entirety.

In one embodiment, the saRNA of the present invention may be formulated in a lipid bilayer carrier. As a non-limiting example, the saRNA may be combined with a lipid-detergent mixture comprising a lipid mixture of an aggregation-preventing agent in an amount of about 5 mol % to about 20 mol %, a cationic lipid in an amount of about 0.5 mol % to about 50 mol %, and a fusogenic lipid and a detergent, to provide a nucleic acid-lipid-detergent mixture; and then dialyzing said nucleic acid-lipid-detergent mixture against a buffered salt solution to remove said detergent and to encapsulate said nucleic acid in a lipid bilayer carrier and provide a lipid bilayer-nucleic acid composition, wherein said buffered salt solution has an ionic strength sufficient to encapsulate of from about 40% to about 80% of said nucleic acid, described in WO1999018933 to Cullis et al., the contents of which are incorporated herein by reference in their entirety.

In one embodiment, the saRNA of the present invention may be formulated in a nucleic acid-lipid particle capable of selectively targeting the saRNA to a heart, liver, or tumor tissue site. For example, the nucleic acid-lipid particle may comprise (a) a nucleic acid; (b) 1.0 mole % to 45 mole % of a cationic lipid; (c) 0.0 mole % to 90 mole % of another lipid; (d) 1.0 mole % to 10 mole % of a bilayer stabilizing component; (e) 0.0 mole % to 60 mole % cholesterol; and (f) 0.0 mole % to 10 mole % of cationic polymer lipid as described in EP1328254 to Cullis et al., the contents of which are incorporated herein by reference in their entirety. Cullis teaches that varying the amount of each of said cationic lipid, bilayer stabilizing component, another lipid, cholesterol, and cationic polymer lipid can impart tissue selectivity for heart, liver, or tumor tissue site, thereby identifying a nucleic acid-lipid particle capable of selectively targeting a nucleic acid to said heart, liver, or tumor tissue site.

Delivery

The present disclosure encompasses the delivery of saRNA for any of therapeutic, pharmaceutical, diagnostic or imaging by any appropriate route taking into consideration likely advances in the sciences of drug delivery. Delivery may be naked or formulated.

The saRNA of the present invention may be delivered to a cell naked. As used herein in, "naked" refers to delivering saRNA free from agents which promote transfection. For example, the saRNA delivered to the cell may contain no modifications. The naked saRNA may be delivered to the cell using routes of administration known in the art and described herein.

The saRNA of the present invention may be formulated, using the methods described herein. The formulations may contain saRNA which may be modified and/or unmodified. The formulations may further include, but are not limited to, cell penetration agents, a pharmaceutically acceptable carrier, a delivery agent, a bioerodible or biocompatible polymer, a solvent, and a sustained-release delivery depot. The formulated saRNA may be delivered to the cell using routes of administration known in the art and described herein.

The compositions may also be formulated for direct delivery to an organ or tissue in any of several ways in the art including, but not limited to, direct soaking or bathing, via a catheter, by gels, powder, ointments, creams, gels, lotions, and/or drops, by using substrates such as fabric or biodegradable materials coated or impregnated with the compositions, and the like. The saRNA of the present invention may also be cloned into a retroviral replicating vector (RRV) and transduced to cells.

Administration

The saRNA of the present invention may be administered by any route which results in a therapeutically effective outcome. These include, but are not limited to enteral, gastroenteral, epidural, oral, transdermal, epidural (peridural), intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection, (into the base of the penis), intravaginal administration, intrauterine, extra-amniotic administration, transdermal (diffusion through the intact skin for systemic distribution), transmucosal (diffusion through a mucous membrane), insufflation (snorting), sublingual, sublabial, enema, eye drops (onto the conjunctiva), or in ear drops. In specific embodiments, compositions may be administered in a way which allows them cross the blood-brain barrier, vascular barrier, or other epithelial barrier. Routes of administration disclosed in International Publication WO 2013/090648 filed Dec. 14, 2012, the contents of which are incorporated herein by reference in their entirety, may be used to administer the saRNA of the present invention.

Dosage Forms

A pharmaceutical composition described herein can be formulated into a dosage form described herein, such as a topical, intranasal, intratracheal, or injectable (e.g., intravenous, intraocular, intravitreal, intramuscular, intracardiac, intraperitoneal, subcutaneous). Liquid dosage forms, injectable preparations, pulmonary forms, and solid dosage forms described in International Publication WO 2013/090648 filed Dec. 14, 2012, the contents of which are incorporated herein by reference in their entirety may be used as dosage forms for the saRNA of the present invention.

II. Methods of Use

One aspect of the present invention provides methods of using C/EBPα-saRNA and pharmaceutical compositions comprising said C/EBPα-saRNA and at least one pharmaceutically acceptable carrier. C/EBPα-saRNA modulates C/EBPα gene expression. In one embodiment, the expression of C/EBPα gene is increased by at least 20, 30, 40%, more preferably at least 45, 50, 55, 60, 65, 70, 75%, even more preferably at least 80% in the presence of the saRNA of the present invention compared to the expression of C/EBPα gene in the absence of the saRNA of the present invention. In a further preferable embodiment, the expression of C/EBPα gene is increased by a factor of at least 2, 3, 4, 5, 6, 7, 8, 9, 10, more preferably by a factor of at least 15, 20, 25, 30, 35, 40, 45, 50, even more preferably by a factor of at least 60, 70, 80, 90, 100, in the presence of the saRNA of the present invention compared to the expression of C/EBPα gene in the absence of the saRNA of the present invention.

In one embodiment, the increase in gene expression of the saRNA descried herein is shown in proliferating cells.

Metabolics Regulation

Hepatocytes are generally perceived as being important for maintenance of several vital functions. For example, they can regulate carbohydrate and lipid metabolism and detoxification of exogenous and endogenous compounds. C/EBPα is expressed in a variety of tissues where it plays an important role in the differentiation of many cell types including adipocytes, type II alveolar cells and hepatocytes. In the mouse, C/EBPα is found most abundantly in fat, liver and lung tissues. The function role of C/EBPα includes, but not limited to, regulation of alpha-1-antitrypsin, transthyretin and albumin. Furthermore, expression of C/EBPα gene in the liver cell line (HepG2) results in increased levels of cytochrome P450 (CYP), a superfamily of monooxygenases that participates in the metabolism of endogenous substrates and plays a key role in detoxification and metabolic activation of key xenobiotics [Dover et al., *FEBS Letters*, vol. 431(2), 227-230 (1998), the contents of which are incorporated herein by reference in their entirety].

Non-alcoholic fatty liver disease (NAFLD) is a major global health concern and affects 1 in 3 people in the United States. NAFLD is the build-up of extra fat (lipid) in liver cells that is not caused by excessive alcohol use. It is called a fatty liver (steatosis) if more than 5%-10% of the liver's weight is fat. NAFLD may progress to steatoheptitis, cirrhosis, and liver cancer. It is associated with metabolic disorders, such as metabolic syndrome, insulin resistance, type II diabetes, hyperlipidemia, hypertension, obesity, etc. Treatment methods include lowering low-density lipoprotein (LDL) cholesterol levels, improving insulin sensitivity, treating metabolic risk factors, weight loss and so on. [Adams et al., *Postgraduate Medical Journal*, vol. 82, 315-322 (2006); Musso et al., *Curr. Opin. Lipidol.*, vol. 22(6), 489-496 (2011), the contents of which are incorporated herein by reference in their entirety]

Figure 2:
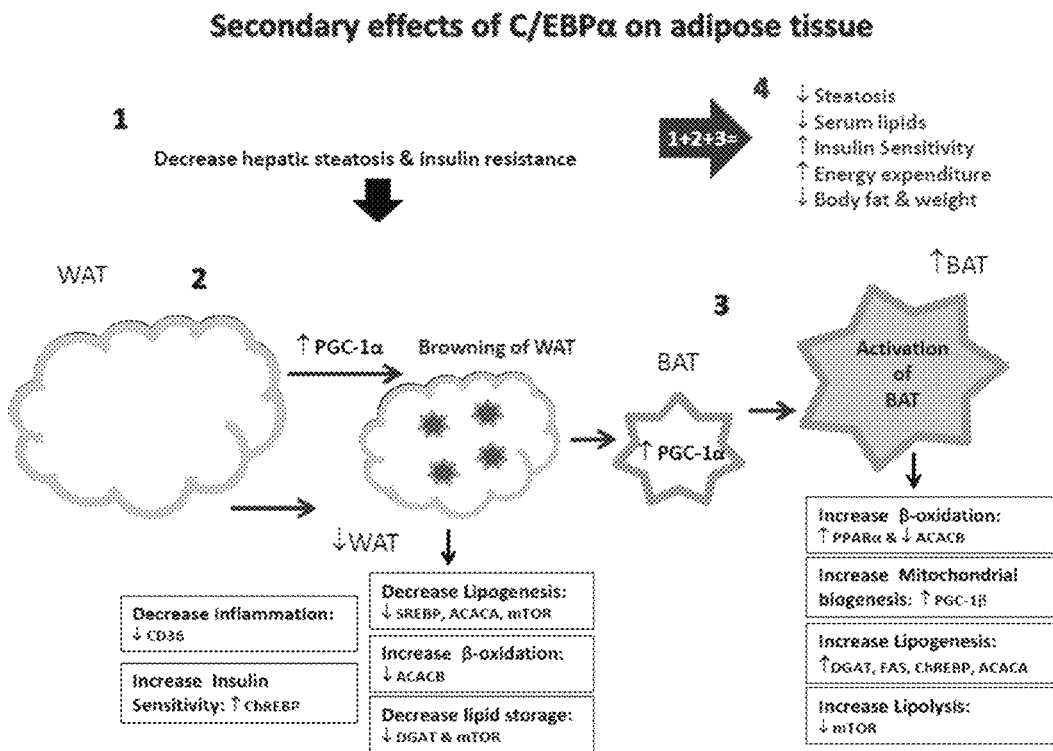
FIG. 2 shows the secondary effects of C/EBPα on the adipose tissue.

C/EBPα protein plays an important role in regulating liver function and metabolics. The primary effects of C/EBPα on the liver are shown in FIG. 1, including decreasing fatty acid uptake by lowering CD36 protein level, decreasing de novo lipogenesis by lowering sterol regulatory element-binding proteins (SREBP), carbohydrate-responsive element-binding protein (ChREBP) and fatty acid synthase (FAS) protein levels, increasing β-oxidation by increasing peroxisome proliferator-activated receptor alpha (PPARα) and peroxisome proliferator-activated receptor gamma coactivator 1-alpha & -beta (PGC-1α & β) protein levels, decreasing hepatic lipid overload by lowering apolipoprotein C-III (APOC3) and low density lipoprotein receptor (LDLR) protein levels, decreasing progression to fibrosis by increasing PGC-1β protein level, and decreasing insulin resistance by increasing peroxisome proliferator-activated receptor gamma (PPARγ) protein level. Furthermore, C/EBPα has secondary effects on adipose tissues as shown in FIG. 2. White adipose tissue (WAT) is not only a lipogenic and fat storage tissue but also an important endocrine organ that regulates energy homeostasis, lipid metabolism, appetite, fertility, and immune and stress responses. Brown adipose tissue (BAT) contains numerous smaller lipid droplets and a much higher number of iron-containing mitochondria compared with WAT. It plays a significant role in nutritional energetics, energy balance and body weight. There is evidence that the atrophy of BAT is related to obesity. In particular, studies have indicated that impaired thermogenesis in BAT is important in the aetiology of obesity in rodents [Trayhurn P., *J. Biosci.*, vol. 18(2), 161-173 (1993)]. C/EBPα decreases hepatic steatosis and insulin resistance and increases PGC-1α protein level, which may in turn cause browning of WAT, turn WAT into BAT, and then activate BAT, thereby reducing body fat and weight. Therefore, C/EBPα-saRNA of the present invention may be used to regulate liver function, reduce steatosis, reduce serum lipids, treat NAFLD, treat insulin resistance, increase energy expenditure, and treat obesity.

In one embodiment, provided is a method of regulating liver metabolism genes in vitro and in vivo by treatment of C/EBPα-saRNA of the present invention. Also provided is a method of regulating liver genes involved in NAFLD in vitro and in vivo by treatment of C/EBPα-saRNA of the present invention. The genes include, but are not limited to sterol regulatory element-binding factor 1 (SREBF-1 or SREBF), cluster of differentiation 36 (CD36), acetyl-CoA carboxylase 2 (ACACB), apolipoprotein C-III (APOC3), microsomal triglyceride transfer protein (MTP), peroxisome proliferator-activated receptor gamma coactivator 1 alpha (PPARγ-CoA1α or PPARGC1A), low density lipoprotein receptor (LDLR), peroxisome proliferator-activated receptor gamma coactivator 1 beta (PPARγ-CoA1β or PERC), peroxisome proliferator-activated receptor gamma (PPARγ), acetyl-CoA carboxylase 1 (ACACA), carbohydrate-responsive element-binding protein (ChREBP or MLX1PL), peroxisome proliferator-activated receptor alpha (PPARα or PPARA), FASN (fatty acid synthase), diglyceride acyltransferase-2 (DGAT2), and mammalian target of rapamycin (mTOR). In one embodiment, C/EBPα-saRNA decreases the expression of SREBF-1 gene in liver cells by at least 20%, 30%, preferably at least 40%. In one embodiment, C/EBPα-saRNA decreases the expression of CD36 gene in liver cells by at least 20%, 30%, 40%, 50%, preferably at least 75%, 90%. In one embodiment, C/EBPα-saRNA increases the expression of ACACB gene in liver cells by at least 20%, 30%, 40%, 50%, preferably at least 75%, 90%, 100%, 125%, 150%. In one embodiment, C/EBPα-saRNA decreases the expression of APOC3 gene in liver cells by at least 20%, 30%, 40%, 50%, preferably at least 75%, 90%. In one embodiment, C/EBPα-saRNA decreases the expression of MTP gene in liver cells by at least 20%, 30%, 40%, 50%, preferably at least 75%, 90%. In one embodiment, C/EBPα-saRNA increases the expression of PPARγ-CoA1α gene in liver cells by at least 20%, 30%, 40%, 50%, preferably at least 75%, 90%, 100%, 125%, 150%, more preferably at least 175%, 200%, 250%, 300%. In one embodiment, C/EBPα-saRNA increases the expression of PPARγ gene in liver cells by at least 20%, 30%, 40%, 50%, preferably at least 75%, 90%, 100%, 125%, 150%, more preferably at least 175%, 200%, 250%, 300%. In one embodiment, C/EBPα-saRNA increases the expression of PPARα gene in liver cells by at least 20%, 30%, 40%, 50%, preferably at least 75%, 90%, 100%, 125%, 150%, more preferably at least 175%, 200%, 250%, 300%. In one embodiment, C/EBPα-saRNA decreases the expression of MLX1PL gene in liver cells by at least 20%, 30%, 40%, 50%, preferably at least 75%. In one embodiment, C/EBPα-saRNA decreases the expression of FASN gene in liver cells by at least 20%, 30%, 40%, 50%, preferably at least 75%, 90%. In one embodiment, C/EBPα-saRNA decreases the expression of DGAT2 gene in liver cells by at least 10%, 20%, preferably at least 30%, 40%, 50%.

C/EBPα-saRNA also modulates the expression of liver metabolism genes disclosed above in BAT cells. In another embodiment, C/EBPα-saRNA decreases the expression of SREBP gene in BAT cells by at least 20%, 30%, preferably at least 40%. In one embodiment, C/EBPα-saRNA decreases the expression of CD36 gene in BAT cells by at least 20%, 30%, 40%, 50%, preferably at least 75%, 90%. In one embodiment, C/EBPα-saRNA decreases the expression of LDLR gene in BAT cells by at least 20%, 30%, 40%, 50%, preferably at least 75%, 90%. In one embodiment, C/EBPα-saRNA increases the expression of PPARGC1A gene in BAT cells by at least 20%, 30%, preferably at least 40%. In one embodiment, C/EBPα-saRNA decreases the expression of APOC gene in BAT cells by at least 20%, 30%, 40%, 50%, preferably at least 75%, 90%, more preferably at least 95%, 99%. In one embodiment, C/EBPα-saRNA decreases the expression of ACACB gene in BAT cells by at least 20%, 30%, 40%, 50%, preferably at least 75%. In one embodiment, C/EBPα-saRNA decreases the expression of PERC gene in BAT cells by at least 20%, 30%, 40%, 50%, preferably at least 75%. In one embodiment, C/EBPα-saRNA increases the expression of ACACA gene in BAT cells by at least 20%, 30%, 40%, 50%, preferably at least 75%, 90%, 100%, 125%, 150%. In one embodiment, C/EBPα-saRNA decreases the expression of MLXP1 gene in BAT cells by at least 20%, 30%, 40%, preferably at least 50%. In one embodiment, C/EBPα-saRNA decreases the expression of MTOR gene in BAT cells by at least 20%, 30%, 40%, preferably at least 50%, 75%. In one embodiment, C/EBPα-saRNA increases the expression of PPARA gene in BAT cells by at least 20%, 30%, 40%, 50%, preferably at least 75%, 90%, 100%, 125%, 150%, more preferably at least 200%, 250%, 300%, 350%, 400%. In one embodiment, C/EBPα-saRNA increases the expression of FASN gene in BAT cells by at least 20%, 30%, 40%, 50%, preferably at least 75%, 90%. In one embodiment, C/EBPα-saRNA increases the expression of DGAT gene in BAT cells by at least 20%, 30%, 40%, 50%, preferably at least 75%, 90%, 100%, 125%, 150%, more preferably at least 200%, 250%, 300%.

C/EBPα-saRNA also modulates the expression of liver metabolism genes disclosed above in WAT cells. In another embodiment, C/EBPα-saRNA decreases the expression of SREBP gene in WAT cells by at least 20%, 30%, preferably at least 40%. In one embodiment, C/EBPα-saRNA decreases the expression of CD36 gene in WAT cells by at least 20%, 30%, 40%, 50%, preferably at least 75%, 90%. In one embodiment, C/EBPα-saRNA decreases the expression of LDLR gene in WAT cells by at least 20%, 30%, 40%, 50%, preferably at least 75%, 90%. In one embodiment, C/EBPα-saRNA increases the expression of PPARGC1A gene in WAT cells by at least 20%, 30%, preferably at least 40%. In one embodiment, C/EBPα-saRNA increases the expression of MTP gene in WAT cells by at least 20%, 30%, 40%, 50%, preferably at least 75%, 90%, more preferably at least 95%, more preferably at least by a factor of 1.5, 2.0, 2.5, 3.0, 3.5, 4.0, more preferably by at least a factor of 5.0, 6.0, 7.0, 8.0, 9.0, 10.0. In one embodiment, In one embodiment, C/EBPα-saRNA increases the expression of APOC gene in WAT cells by at least 20%, 30%, 40%, 50%, preferably at least 75%, 90%, more preferably at least 95%, 99%. In one embodiment, C/EBPα-saRNA decreases the expression of ACACB gene in WAT cells by at least 20%, 30%, 40%, 50%, preferably at least 75%. In one embodiment, C/EBPα-saRNA decreases the expression of PERC gene in WAT cells by at least 20%, 30%, 40%, 50%, preferably at least 75%. In one embodiment, C/EBPα-saRNA decreases the expression of ACACA gene in WAT cells by at least 20%, 30%, 40%, 50%, preferably at least 75%, 90%, 95%. In one embodiment, C/EBPα-saRNA decreases the expression of MLX1PL gene in WAT cells by at least 20%, 30%, 40%, preferably at least 50%. In one embodiment, C/EBPα-saRNA decreases the expression of MTOR gene in WAT cells by at least 20%, 30%, 40%, preferably at least 50%, 75%. In one embodiment, C/EBPα-saRNA decreases the expression of FASN gene in WAT cells by at least 5%, 10%, preferably at least 15%, 20%. In one embodiment, C/EBPα-saRNA decreases the expression of DGAT gene in WAT cells by at least 10%, 20%, 30%, more preferably 40%, 50%.

In another embodiment, provided is a method of reducing insulin resistance (IR) or increasing insulin sensitivity by administering C/EBPα-saRNA of the present invention to a patient in need thereof. Also provided is a method of treating type II diabetes, hyperinsulinaemia and steatosis by administering C/EBPα-saRNA of the present invention to a patient in need thereof. If liver cells are resistance to insulin and cannot use insulin effectively, hyperglycemia develops. Subsequently, beta cells in pancreas increase their production of insulin leading to hyperinsulinemia and type II diabetes. Many regulators affect insulin resistance of liver cells. For example, sterol regulatory element-binding proteins 1 (SREBP1 or SREBP) is the master regulator of cholesterol and associated with increased insulin resistance. The up-regulation of cholesteryl ester transfer protein (CETP) is associated with increased insulin resistance. The up-regulation of hepatic fatty acid translocase/cluster of differentiation 36 (FAT/CD36) is associated with insulin resistance, hyperinsulinaemia, increased steatosis in patients with non-alcoholic steatohepatitis (NASH). Liver-specific overexpression of lipoprotein lipase gene (LPL) causes liver-specific insulin resistance. Liver X receptor gene (LXR) has a central role in insulin-mediated activation of sterol regulatory element-binding protein (SREBP)-1c-induced fatty acid synthesis in liver. Other factors include diglyceride acyltransferase-2 (DGAT2) that regulates triglyceride synthesis and fatty acid synthase (FASN) that regulates fatty acid biosynthesis. In one embodiment, C/EBPα-saRNA reduces the expression of FAT/CD36 gene in liver cells by at least 25%, preferably at least 50%, more preferably at least 75%, even more preferably 90% compared to liver cells with no treatment. In another embodiment, C/EBPα-saRNA increases the expression of LPL gene in liver cells by at least 20, 30, 40%, preferably at least 45, 50, 55, 60, 65, 70, 75, 80, 85, 90, 95%, more preferably at least 100, 150, 200, 250, 300, 350 and 400% compared to liver cells with no treatment. In another embodiment, C/EBPα-saRNA increases the expression of LXR gene in liver cells by at least 45, 50, 55, 60, 65, 70, 75, 80, 85, 90, 95%, more preferably at least 100, 150, 200, 250, 300, 350 and 400%, even more preferably at least 450, 500, 550, 600% compared to liver cells with no treatment. In another embodiment, C/EBPα-saRNA decreases SREBP1 gene expression. In another embodiment, C/EBPα-saRNA decreases DGAT2 gene expression. In another embodiment, C/EBPα-saRNA decreases CETP gene expression. In yet another embodiment, C/EBPα-saRNA decreases FASN gene expression.

A summary of NAFLD and IR genes that may be modulated with C/EBPα-saRNA is shown in Table 5. Abbreviations in Table 5: NAFLD: non-alcoholic fatty liver disease; IR: insulin resistance; DNL: de novo lipogenesis; FA: fatty acid; TG: triglycerides; LPL: lipoprotein lipase; HP: hepatic lipase; CHOL: cholesterol.

TABLE 5

NAFLD and IR genes that may be modulated with C/EBPα-saRNA

| Gene name | Mechanism | Function/encoded products - References | Deregulation in NAFLD | Deregulation in IR |
|---|---|---|---|---|
| CD36 | FAs uptake | Scavenger receptor, free FAs transporter in liver and adipose tissue; regulates adipose tissue apoptosis and inflammation | up | up |
| PPARγ | DNL | Activates genes involved in lipid storage and metabolism; required for lipid homeostasis; high expressed in adipose tissue and very low in the liver; implicated in adipocyte differentiation and insulin sensitivity | up | down |
| PPARγ-CoA 1β (PERC) | DNL | Transcriptional coactivator for SREBP-1; enhances lipogenesis and VLDL synthesis; highly expressed in brown fat and heart and induced in the liver during fasting; master regulator of mitochondrial biogenesis and oxidative metabolism, lipogenesis, and TG secretion | up | up |
| SREBP-1c | DNL | Transcription factor, induces genes involved in glucose utilization and FA synthesis; major mediator of insulin action on lipogenic genes; regulates adipogenesis | up | up |
| ChREBP (MLX1PL) | DNL | Transcription factors activated by glucose; induces glycolytic and lipogenic genes; major determinant of adipose tissue fatty acid synthesis and systemic insulin sensitivity | up | up |
| FAS | DNL | Enzyme that catalyzes the last step in FA biosynthesis | up | up |
| ACACA (ACC1) | DNL | Enzyme that catalyzes the synthesis of malonyl-CoA for the synthesis of FAs in the cytosol | up | up |
| ACACB (ACC2) | β-oxidation | Enzyme that catalyzes the synthesis of malonyl-CoA, which functions as inhibitor of mitochondrial β-oxidation | up | up |
| PPARα | β-oxidation | Activates the genes involved in the oxidation of FAs, major regulator of lipid metabolism in the liver; predominantly expressed in the liver; involved in the regulation of glucose homeostasis, insulin sensitivity, fat accumulation, and adipose tissue glucose use | down | down |

TABLE 5-continued

NAFLD and IR genes that may be modulated with C/EBPα-saRNA

| Gene name | Mechanism | Function/encoded products - References | Deregulation in NAFLD | Deregulation in IR |
|---|---|---|---|---|
| PPARγ-CoA 1α | β-oxidation | Transcriptional co-activator that regulates mitochondrial biology and energy homeostasis; crucial role in mitochondrial biogenesis; interacts with PPARa to increase the mitochondrial (3-oxidation of FAs | down | down |
| DGAT2 | TG synthesis | Enzyme that catalyzes the final reaction in the synthesis of TG | up | up |
| APOC3 | TG concentration | Protein that inhibits LPL and HP; involved in the regulation of plasma TG concentrations; pro-steatosic | up | up |
| LDLR | CHOL concentration | Low-density lipoprotein receptor; critical role in regulating blood CHOL levels; abundant in the liver, which is the organ responsible for removing most excess CHOL from the body | down | no change |
| MTP (MTTP1) | Lipoprotein assembly | Carrier of TG; central role in VLDL assembly; prevalently expressed in the liver | down | no change |
| mTOR | Adipose mass | Possible regulator of adipose tissue mass; central role in lipolysis, lipogenesis, and adipogenesis | up | up |

TABLE 5

NAFLD and IR genes that may be modulated with C/EBPα-saRNA (continued)

| | Effects of Ezetimibe | Effects of C/EBPα | | |
|---|---|---|---|---|
| Gene name | in the liver | Liver | WAT | BAT |
| CD36 | minor down | down | down | down |
| PPARγ | up | up | no change | no change |
| PPARγ-CoA 1β(PERC) | up | up | down | up |
| SREBP-1c | up | down | down | down |
| ChREBP (MLX1PL) | up | down | up | up |
| FAS | down | down | minor up | up |
| ACACA (ACC1) | minor up | no change | down | up |
| ACACB (ACC2) | up | up | down | down |
| PPARα | up | up | up | up |
| PPARγ-CoA 1α | up | up | up | up |
| DGAT2 | minor down | minor down | down | up |
| APOC3 | down | down | up | down |
| LDLR | minor down | down | up | minor down |
| MTP (MTTP1) | up | down | up | down |
| mTOR | no change | no change | down | down |

In one embodiment of the present invention, provided is a method of lowering serum cholesterol level in vitro by treatment of C/EBPα-saRNA of the present invention. The serum cholesterol level with C/EBPα-saRNA reduces at least 25%, preferably 50%, more preferably 75% compared to serum cholesterol level with no treatment. Also provided is a method of lowering LDL and triglyceride levels in hepatocyte cells and increasing circulating levels of LDL in vivo by administering C/EBPα-saRNA of the present invention. The circulation LDL level may increase at least by a factor of 2, preferably by a factor of 3, preferably by a factor of 4, preferably by a factor of 5, preferably by a factor of 10, and preferably by a factor of 15 compared to circulating LDL level in the absence of C/EBPα-saRNA. The liver triglyceride level may be reduced by at least 10%, 20%, 30%, 40%, 50%, 60%, or 70% compared to the liver triglyceride level in the absence of C/EBPα-saRNA. The liver LDL level may be reduced by at least 10%, 20%, 30%, 40%, 50%, 60%, or 70% compared to the liver LDL level in the absence of C/EBPα-saRNA.

In one embodiment of the present invention, provided is a method of treating NAFLD and reducing fatty liver size by administering C/EBPα-saRNA of the present invention to a patient in need thereof. The size of a fatty liver of a patient treated with C/EBPα-saRNA is reduced by at least 10%, 20%, 30%, 40%, or 50% compared with a patient without treatment. Also provided is a method of reducing body weight and treating obesity by administering C/EBPα-saRNA of the present invention to a patient in need thereof. The body weight of a patient treated with C/EBPα-saRNA is lower than the body weight of a patient without treatment of C/EBPα-saRNA by at least 10%, 20%, 30%, 40%, 50%, 60%, or 70%. C/EBPα-saRNA of the present invention may be administered in a dose, 2 doses, 3 does or more. Also provided is a method of decreasing hepatic uptake of free fatty acids by treatment of C/EBPα-saRNA of the present invention. Also provided is a method of reducing white adipose tissue (WAT) inflammation by treatment of C/EBPα-saRNA of the present invention. Also provided is a method of reducing de novo lipogenesis by treatment of C/EBPα-saRNA of the present invention. Also provided is a method of increasing beta-oxidation in the liver by treatment of C/EBPα-saRNA of the present invention. Also provided is a method of increasing brown adipose tissue (BAT) in the liver by treatment of C/EBPα-saRNA of the present invention. Also provided is a method of reducing hepatic lipid uptake by treatment of C/EBPα-saRNA of the present invention. Also provided is a method of decreasing lipogenesis in WAT by treatment of C/EBPα-saRNA of the present invention. Also provided is a method of decreasing lipid storage in liver by treatment of C/EBPα-saRNA of the present invention. Also provided is a method of reducing lipid overload in the liver by treatment of C/EBPα-saRNA of the present invention.

In another embodiment, C/EBPα-saRNA of the present invention is used to increase liver function. In one non-limiting example, C/EBPα-saRNA increases albumin gene expression and thereby increasing serum albumin and unconjugated bilirubin levels. The expression of albumin gene may be increased by at least 20, 30, 40%, more preferably at least 45, 50, 55, 60, 65, 70, 75%, even more preferably at least 80% in the presence of the saRNA of the present invention compared to the expression of albumin gene in the absence of the saRNA of the present invention. In a further preferable embodiment, the expression of albumin gene is increased by a factor of at least 2, 3, 4, 5, 6, 7, 8, 9, 10, more preferably by a factor of at least 15, 20, 25, 30, 35, 40, 45, 50, even more preferably by a factor of at least 60, 70, 80, 90, 100, in the presence of the saRNA of the present invention compared to the expression of albumin gene in the absence of the saRNA of the present invention. In another non-limiting example, C/EBPα-saRNA decreases the amount of alanine transaminase (ALT), aspartate aminotransferase (AST), gamma glutamyl transpeptidase (GGT), alphafectoprotein (AFP) and hepatocyte growth factor (HGF). The amount of ALT, AST, GGT, AFP, or HGF may be decreased by at least 20, 30, 40%, more preferably at least 45, 50, 55, 60, 65, 70, 75%, even more preferably at least 80% in the presence of the saRNA of the present invention compared to the amount of any of ALT, AST, GGT, AFP, or HGF in the absence of the saRNA of the present invention.

In another embodiment, C/EBPα-saRNA of the present invention is administered to regulate the levels of other members of the C/EBP family. C/EBPα-saRNA increases the expression of C/EBPβ, C/EBPγ, C/EBPδ and C/EBζ depending on the dose of C/EBPα-saRNA. In yet another embodiment, the ratio of C/EBPα or C/EBPβ protein isoforms in a cell is regulated by contacting said cell with C/EBPα-saRNA of the present invention. In one embodiment, the 42 KDa isoform of C/EBPα is increased. In one embodiment, the 30 kDa isoform of C/EBPβ is increased.

ecCEBPA

Extra coding CEBPA (ecCEBPA), a functional ncRNA transcribed from the CEBPA locus, regulates CEBPA methylation by interacting with DNA methyltransferase (DNMT1) thus preventing CEBPA gene methylation. It has been found that ecCEBPA knockdown led to a decrease of CEBPA mRNA expression and to a significant increase in DNA methylation (Ruscio et al., Nature, vol. 503:371-376 (2013), the contents of which are incorporated herein by reference in their entirety). In another embodiment, C/EBPα-saRNA of the present invention is used to upregulate ecCEBPA levels.

Surgical Care

Hepatectomy, surgical resection of the liver or hepatic tissue might cause liver failure, reduced production of albumin and coagulation factors. Proper surgical care after hepatectomy is needed. In some embodiments, C/EBPα-saRNA of the present invention is used for surgical care after hepatectomy to promote liver regeneration and increase survival rate.

Hyperproliferation Disorders

In one embodiment of the invention, C/EBPα-saRNA of the present invention is used to reduce cell proliferation of hyperproliferative cells. Examples of hyperproliferative cells include cancerous cells, e.g., carcinomas, sarcomas, lymphomas and blastomas. Such cancerous cells may be benign or malignant. Hyperproliferative cells may result from an autoimmune condition such as rheumatoid arthritis, inflammatory bowel disease, or psoriasis. Hyperproliferative cells may also result within patients with an oversensitive immune system coming into contact with an allergen. Such conditions involving an oversensitive immune system include, but are not limited to, asthma, allergic rhinitis, eczema, and allergic reactions, such as allergic anaphylaxis. In one embodiment, tumor cell development and/or growth is inhibited. In a preferred embodiment, solid tumor cell proliferation is inhibited. In another preferred embodiment, metastasis of tumor cells is prevented. In another preferred example, undifferentiated tumor cell proliferation is inhibited.

Inhibition of cell proliferation or reducing proliferation means that proliferation is reduced or stops altogether. Thus, "reducing proliferation" is an embodiment of "inhibiting proliferation". Proliferation of a cell is reduced by at least 20%, 30% or 40%, or preferably at least 45, 50, 55, 60, 65, 70 or 75%, even more preferably at least 80, 90 or 95% in the presence of the saRNA of the invention compared to the proliferation of said cell prior to treatment with the saRNA of the invention, or compared to the proliferation of an equivalent untreated cell. In embodiments wherein cell proliferation is inhibited in hyperproliferative cells, the "equivalent" cell is also a hyperproliferative cell. In preferred embodiments, proliferation is reduced to a rate comparable to the proliferative rate of the equivalent healthy (non-hyperproliferative) cell. Alternatively viewed, a preferred embodiment of "inhibiting cell proliferation" is the inhibition of hyperproliferation or modulating cell proliferation to reach a normal, healthy level of proliferation.

In one non-limiting example, C/EBPα-saRNA is used to reduce the proliferation of leukemia and lymphoma cells. Preferably, the cells include Jurkat cells (acute T cell lymphoma cell line), K562 cells (erythroleukemia cell line), U373 cells (glioblastoma cell line), and 32Dp210 cells (myeloid leukemia cell line).

In another non-limiting example, C/EBPα-saRNA is used to reduce the proliferation of ovarian cancer cells, liver cancer cells, pancreatic cancer cells, breast cancer cells, prostate cancer cells, rat liver cancer cells, and insulinoma cells. Preferably, the cells include PEO1 and PEO4 (ovarian cancer cell line), HepG2 (hepatocellular carcinoma cell line), Panc1 (human pancreatic carcinoma cell line), MCF7 (human breast adenocarcinoma cell line), DU145 (human metastatic prostate cancer cell line), rat liver cancer cells, and MIN6 (rat insulinoma cell line).

In another non-limiting example, C/EBPα-saRNA is used in combination with a siRNA targeting C/EBPβ gene to reduce tumor cell proliferation. Tumor cell may include hepatocellular carcinoma cells such as HepG2 cells and breast cancer cells such as MCF7 cells.

In one embodiment, the saRNA of the present invention is used to treat hyperproliferative disorders. Tumors and cancers represent a hyperproliferative disorder of particular interest, and all types of tumors and cancers, e.g. solid tumors and haematological cancers are included. Examples of cancer include, but not limited to, cervical cancer, uterine cancer, ovarian cancer, kidney cancer, gallbladder cancer, liver cancer, head and neck cancer, squamous cell carcinoma, gastrointestinal cancer, breast cancer, prostate cancer, testicular cancer, lung cancer, non-small cell lung cancer, non-Hodgkin's lymphoma, multiple myeloma, leukemia (such as acute lymphocytic leukemia, chronic lymphocytic leukemia, acute myelogenous leukemia, and chronic myelogenous leukemia), brain cancer (e.g. astrocytoma, glioblastoma, medulloblastoma), neuroblastoma, sarcomas, colon cancer, rectum cancer, stomach cancer, anal cancer, bladder cancer, endometrial cancer, plasmacytoma, lymphomas, retinoblastoma, Wilm's tumor, Ewing sarcoma, melanoma and other skin cancers. The liver cancer may include, but not limited to, cholangiocarcinoma, hepatoblastoma, haemangiosarcoma, or hepatocellular carcinoma (HCC). HCC is of particular interest.

Primary liver cancer is the fifth most frequent cancer worldwide and the third most common cause of cancer-related mortality. HCC represents the vast majority of primary liver cancers [El-Serag et al., *Gastroenterology*, vol. 132(7), 2557-2576 (2007), the contents of which are disclosed herein in their entirety]. HCC is influenced by the interaction of several factors involving cancer cell biology, immune system, and different aetiologies (viral, toxic and generic). The majority of patients with HCC develop malignant tumors from a background of liver cirrhosis. Currently most patients are diagnosed at an advanced stage and therefore the 5 year survival for the majority of HCC patients remains dismal. Surgical resection, loco-regional ablation and liver transplantation are currently the only therapeutic options which have the potential to cure HCC. However, based on the evaluation of individual liver function and tumor burden only about 5-15% of patients are eligible for surgical intervention. The binding sites for the family of C/EBP transcription factors are present in the promoter regions of numerous genes that are involved in the maintenance of normal hepatocyte function and response to injury (including albumin, interleukin 6 response, energy homeostasis, ornithine cycle regulation and serum amyloid A expression). The present invention utilizes C/EBPα-saRNA to modulate the expression of C/EBPα gene and treat liver cirrhosis and HCC.

The method of the present invention may reduce tumor volume by at least 10, 20, 30, 40, 50, 60, 70, 80 or 90%. Preferably, the development of one or more new tumors is inhibited, e.g. a subject treated according to the invention develops fewer and/or smaller tumors. Fewer tumors means that he develops a smaller number of tumors than an equivalent subject over a set period of time. For example, he develops at least 1, 2, 3, 4 or 5 fewer tumors than an equivalent control (untreated) subject. Smaller tumor means that the tumors are at least 10, 20, 30, 40, 50, 60, 70, 80 or 90% smaller in weight and/or volume than tumors of an equivalent subject. The method of the present invention reduces tumor burden by at least 10, 20, 30, 40, 50, 60, 70, 80 or 90%.

The set period of time may be any suitable period, e.g. 1, 2, 3, 4, 5, 6, 7, 8, 9 or 10 months or years.

In one non-limiting example, provided is a method of treating an undifferentiated tumor, comprising contacting a cell, tissue, organ or subject with C/EBPα-saRNA of the present invention. Undifferentiated tumors generally have a poorer prognosis compared to differentiated ones. As the degree of differentiation in tumors has a bearing on prognosis, it is hypothesized that the use of a differentiating biological agent could be a beneficial anti-proliferative drug. C/EBPα is known to restore myeloid differentiation and prevent hyperproliferation of hematopoietic cells in acute myeloid leukemia. Preferably, undifferentiated tumors that may be treated with C/EBPα-saRNA include undifferentiated small cell lung carcinomas, undifferentiated pancreatic adenocarcinomas, undifferentiated human pancreatic carcinoma, undifferentiated human metastatic prostate cancer, and undifferentiated human breast cancer.

In one non-limiting example, C/EBPα-saRNA is complexed into PAMAM dendrimer, referred to as C/EBPα-saRNA-dendrimer for targeted in vivo delivery. The therapeutic effect of intravenously injected C/EBPα-saRNA-dendrimers is demonstrated in a clinically relevant rat liver tumor model as shown in Example 1. After three doses through tail vein injection at 48 hour intervals, the treated cirrhotic rats showed significantly increased serum albumin levels within one week. The liver tumor burden was significantly decreased in the C/EBPα-saRNA dendrimer treated groups. This study demonstrates, for the first time, that gene targeting by small activating RNA molecules can be used by systemic intravenous administration to simultaneously ameliorate liver function and reduce tumor burden in cirrhotic rats with HCC.

In one embodiment, C/EBPα-saRNA is used to regulate oncogenes and tumor suppressor genes. Preferably, the expression of the oncogenes may be down-regulated. The expression of the oncogenes reduces by at least 20, 30, 40%, more preferably at least 45, 50, 55, 60, 65, 70, 75, 80, 85, 90, 95% in the presence of C/EBPα-saRNA of the invention compared to the expression in the absence of C/EBPα-saRNA of the invention. In a further preferable embodiment, the expression of the oncogenes is reduced by a factor of at least 2, 3, 4, 5, 6, 7, 8, 9, 10, more preferably by a factor of at least 15, 20, 25, 30, 35, 40, 45, 50, even more preferably by a factor of at least 60, 70, 80, 90, 100, in the presence of C/EBPα-saRNA of the invention compared to the expression in the absence of C/EBPα-saRNA of the invention. Preferably, the expressions of tumor suppressor genes may be inhibited. The expression of the tumor suppressor genes increase by at least 20, 30, 40%, more preferably at least 45, 50, 55, 60, 65, 70, 75, 80, 85, 90, 95%, even more preferably at least 100% in the presence of C/EBPα-saRNA of the invention compared to the expression in the absence of C/EBPα-saRNA of the invention. In a further preferable embodiment, the expression of tumor suppressor genes is increased by a factor of at least 2, 3, 4, 5, 6, 7, 8, 9, 10, more preferably by a factor of at least 15, 20, 25, 30, 35, 40, 45, 50, even more preferably by a factor of at least 60, 70, 80, 90, 100 in the presence of C/EBPα-saRNA of the invention compared to the expression in the absence of C/EBPα-saRNA of the invention. Non-limiting examples of oncogenes and tumor suppressor genes include Bcl-2-associated X protein (BAX), BH3 interacting domain death agonist (BID), caspase 8 (CASP8), disabled homolog 2-interacting protein (DAB21P), deleted in liver cancer 1 (DLC1), Fas surface death receptor (FAS), fragile histidine triad (FHIT), growth arrest and DNA-damage-inducible-beta (GADD45B), hedgehog interacting protein (HHIP), insulin-like growth factor 2 (IGF2), lymphoid enhancer-binding factor 1 (LEF1), phosphatase and tensin homolog (PTEN), protein tyrosine kinase 2 (PTK2), retinoblastoma 1 (RB1), runt-related transcription factor 3 (RUNX3), SMAD family member 4 (SMAD4), suppressor of cytokine signaling (3SOCS3), transforming growth factor, beta receptor II (TGFBR2), tumor necrosis factor (ligand) superfamily, member 10 (TNFSF10), P53, disintegrin and metalloproteinase domain-containing protein 17 (ADAM17), v-akt murine thymoma viral oncogene homolog 1 (AKT1), angiopoietin 2 (ANGPT2), B-cell CLL/lymphoma 2 (BCL2), BCL2-like 1 (BCL2L1), baculoviral IAP repeat containing 2 (BIRC2), baculoviral IAP repeat containing 5 (BIRC5), chemokine (C-C motif) ligand 5 (CCL5), cyclin D1 (CCND1), cyclin D2 (CCND2), cadherin 1 (CDH1), cadherin 13 (CDH13), cyclin-dependent kinase inhibitor 1A (CDKN1A), cyclin-dependent kinase inhibitor 1B (CDKN1B), cyclin-dependent kinase inhibitor 2A (CDKN2A), CASP8 and FADD-like apoptosis regulator (CFLAR), catenin (cadherin-associated protein) beta 1 (CTNNB1), chemokine receptor 4 (CXCR4), E2F transcription factor 1 (E2F1), epidermal growth factor (EGF), epidermal growth factor receptor (EGFR), E1A binding protein p300 (EP300), Fas (TNFRSF6)-associated via death domain (FADD), fms-related tyrosine kinase 1 (FLT1), frizzled family receptor 7 (FZD7), glutathione S-transferase pi 1 (GSTP1), hepatocyte growth factor (HGF), Harvey rat sarcoma viral oncogene homolog (HRAS), insulin-like growth factor binding protein 1 (IGFBP1), insulin-like growth factor binding protein 3 (IGFBP3), insulin receptor substrate 1 (IRS1), integrin beta 1 (ITGB1), kinase insert domain receptor (KDR), myeloid cell leukemia sequence 1 (MCL1), met proto-oncogene (MET), mutS homolog 2 (MSH2), mutS homolog 3 (MSH3), metadherin (MTDH), v-myc avian myelocytomatosis viral oncogene homolog (MYC), nuclear factor of kappa light polypeptide gene enhancer in B-cells 1 (NFKB1), neuroblastoma RAS viral (v-ras) oncogene homolog (NRAS), opioid binding protein/cell adhesion molecule-like (OPCML), platelet-derived growth factor receptor, alpha polypeptide (PDGFRA), peptidylprolyl cis/trans isomerase, NIMA-interacting 1 (PIN1), prostaglandin-endoperoxide synthase 2 (PTGS2), PYD and CARD domain containing (PYCARD), ras-related C3 botulinum toxin substrate 1 (RAC1), Ras association (RalGDS/AF-6) domain family member 1 (RASSFI), reelin (RELN), ras homolog family member A (RHOA), secreted frizzled-related protein 2 (SFRP2), SMAD family member 7 (SMAD7), suppressor of cytokine signaling 1 (SOCS1), signal transducer and activator of transcription 3 (STAT3), transcription factor 4 (TCF4), telomerase reverse transcriptase (TERT), transforming growth factor alpha (TGFA), transforming growth factor beta 1 (TGFB1), toll-like receptor 4 (TLR4), tumor necrosis factor receptor superfamily member 10b (TNFRSF10B), vascular endothelial growth factor A (VEGFA), Wilms tumor 1 (WT1), X-linked inhibitor of apoptosis (XIAP), and Yes-associated protein 1 (YAP1).

In one embodiment, provided is a method of increasing white blood cell count by administering C/EBPα-saRNA of the present invention to a patient in need thereof. Also provided is a method of treating leukopaenia for patients having sepsis or chronic inflammation diseases (e.g., hepatitis and liver cirrhosis) and for immunocompromised patients (e.g., patients undergoing chemotherapy) by administering C/EBPα-saRNA of the present invention to said patient. Also provided is a method of treating pre B cell and B cell malignancies including leukaemia and lymphoma by administering C/EBPα-saRNA of the present invention to a patient in need thereof. Also provided is a method of mobilize white blood cells, haematopoietic or mesenchymal stem cells by administering C/EBPα-saRNA of the present invention to a patient in need thereof. In one embodiment, the white blood cell count in a patient treated with C/EBPα-saRNA is increased by at least 50%, 75%, 100%, more preferably by at least a factor of 1.5, 2, 2.5, 3, 3.5, 4, 4.5, 5, more preferably by at least a factor of 6, 7, 8, 9, 10 compared to no C/EBPα-saRNA treatment.

In one embodiment, C/EBPα-saRNA is used to regulate micro RNAs (miRNA or miR) in the treatment of hepatocellular carcinoma. MicroRNAs are small non-coding RNAs that regulate gene expression. They are implicated in important physiological functions and they may be involved in every single step of carcinogenesis. They typically have 21 nucleotides and regulate gene expression at the post transcriptional level via blockage of mRNA translation or induction of mRNA degradation by binding to the 3'-untranslated regions (3'-UTR) of said mRNA.

In tumors, regulation of miRNA expression affects tumor development. In HCC, as in other cancers, miRNAs function either as oncogenes or tumor suppressor genes influencing cell growth and proliferation, cell metabolism and differentiation, apoptosis, angiogenesis, metastasis and eventually prognosis. [Lin et al., *Biochemical and Biophysical Research Communications*, vol. 375, 315-320 (2008); Kutay et al., *J. Cell. Biochem.*, vol. 99, 671-678 (2006); Meng et al., *Gastroenterology*, vol. 133(2), 647-658 (2007), the contents of each of which are incorporated herein by reference in their entirety] C/EBPα-saRNA of the present invention modulates C/EBPα gene expression and/or function and also regulates miRNA levels in HCC cells. Non-limiting examples of miRNAs that may be regulated by C/EBPα-saRNA of the present invention include hsa-let-7a-5p, hsa-miR-133b, hsa-miR-122-5p, hsa-miR-335-5p, hsa-miR-196a-5p, hsa-miR-142-5p, hsa-miR-96-5p, hsa-miR-184, hsa-miR-214-3p, hsa-miR-15a-5p, hsa-let-7b-5p, hsa-miR-205-5p, hsa-miR-181a-5p, hsa-miR-140-5p, hsa-miR-146b-5p, hsa-miR-34c-5p, hsa-miR-134, hsa-let-7g-5p, hsa-let-7c, hsa-miR-218-5p, hsa-miR-206, hsa-miR-124-3p, hsa-miR-100-5p, hsa-miR-10b-5p, hsa-miR-155-5p, hsa-miR-1, hsa-miR-150-5p, hsa-let-7i-5p, hsa-miR-27b-3p, hsa-miR-127-5p, hsa-miR-191-5p, hsa-let-7f-5p, hsa-miR-10a-5p, hsa-miR-15b-5p, hsa-miR-16-5p, hsa-miR-34a-5p, hsa-miR-144-3p, hsa-miR-128, hsa-miR-215, hsa-miR-193a-5p, hsa-miR-23b-3p, hsa-miR-203a, hsa-miR-30c-5p, hsa-let-7e-5p, hsa-miR-146a-5p, hsa-let-7d-5p, hsa-miR-9-5p, hsa-miR-181b-5p, hsa-miR-181c-5p, hsa-miR-20b-5p, hsa-miR-125a-5p, hsa-miR-148b-3p, hsa-miR-92a-3p, hsa-miR-378a-3p, hsa-miR-130a-3p, hsa-miR-20a-5p, hsa-miR-132-3p, hsa-miR-193b-3p, hsa-miR-183-5p, hsa-miR-148a-3p, hsa-miR-138-5p, hsa-miR-373-3p, hsa-miR-29b-3p, hsa-miR-135b-5p, hsa-miR-21-5p, hsa-miR-181d, hsa-miR-301a-3p, hsa-miR-200c-3p, hsa-miR-7-5p, hsa-miR-29a-3p, hsa-miR-210, hsa-miR-17-5p, hsa-miR-98-5p, hsa-miR-25-3p, hsa-miR-143-3p, hsa-miR-19a-3p, hsa-miR-18a-5p, hsa-miR-125b-5p, hsa-miR-126-3p, hsa-miR-27a-3p, hsa-miR-372, hsa-miR-149-5p, and hsa-miR-32-5p.

In one non-limiting example, the miRNAs are oncogenic miRNAs and are downregulated by a factor of at least 0.01, 0.02, 0.05, 0.1, 0.2, 0.3, 0.5, 1, 1.5, 2, 2.5, and 3, in the presence of C/EBPα-saRNA of the invention compared to in the absence of C/EBPα-saRNA. In another non-limiting example, the miRNAs are tumor suppressing miRNAs and are upregulated by a factor of at least 0.01, 0.02, 0.05, 0.1, 0.2, 0.3, 0.5, 1, more preferably by a factor of at least 2, 3, 4, 5, 6, 7, 8, 9, 10, more preferably by a factor of at least 15, 20, 25, 30, 35, 40, 45, 50, even more preferably by a factor of at least 60, 70, 80, 90, 100, in the presence of C/EBPα-saRNA of the invention compared to in the absence of C/EBPα-saRNA.

Stem Cell Regulation

In some embodiments of the present invention, C/EBPα-saRNA is used to regulate self-renewal pluripotency factors and affect stem cell differentiation. Altering the phenotype of cells in order to express a protein of interest or to change a cell to a different cell phenotype has been used in different clinical, therapeutic and research settings. Altering a phenotype of a cell is currently accomplished by expressing protein from DNA or viral vectors. Currently there are studies being done to evaluate the use of human embryonic stem cells as a treatment option for various diseases such as Parkinson's disease and diabetes and injuries such as a spinal cord injury. Embryonic stem cells have the ability to grow indefinitely while maintaining Pluripotency to generate any differentiated cell type.

Many factors such as pluripotency factors, cell phenotype altering factors, transdifferentiation factors, differentiation factors and dedifferentiation factors, are utilized to alter cell phenotype, which is useful in the field of personal regenerative medicine, cell therapy and therapies for other diseases. For example, the self-renewal and pluripotency properties of stem cells are regulated by an array of genes, such as transcription factors and chromatin remodeling enzymes, in a core regulatory circuitry including OCT4, SOX2, NANOG, and KLF genes [Bourillot et al., *BMC Biology*, 8:125 (2010), the contents of which are incorporated herein by reference in their entirety]. This regulatory circuitry for self-regulatory networks also affects downstream genes. Oligonucleotides have been utilized to regulate the core regulatory circuitry. Xu et al. disclosed that miRNA-145 targets the 3'-UTR of OCT4, SOX2, and KLF4. Reducing miRNA-145 impairs differentiation and elevates OCT4, SOX2, and KLF4. [Xu et al., *Cell*, vol. 137, 1-12 (2009), the contents of which are incorporated herein by reference in their entirety]

In one embodiment, C/EBPα-saRNA of the present invention is used to regulate self-renewal pluripotency genes. Non-limiting examples of pluripotency genes include SOX2, OCT4, cKit, KLF4, KLF2, KLF5, NANOG, CDX2, and SALL4. In one embodiment, the expression of the pluripotency gene is reduced by at least 20%, 30% or 40%, or preferably at least 45, 50, 55, 60, 65, 70 or 75%, even more preferably at least 80, 90 or 95%, in the presence of C/EBPα-saRNA of the invention compared to in the absence of C/EBPα-saRNA. In another embodiment, the expression of the pluripotency gene is increased by at least 20, 30, 40%, more preferably at least 45, 50, 55, 60, 65, 70, 75%, even more preferably at least 80%, in the presence of C/EBPα-saRNA of the invention compared to in the absence of C/EBPα-saRNA. In a preferable embodiment, the expression of the pluripotency gene is increased by a factor of at least 2, 3, 4, 5, 6, 7, 8, 9, 10, more preferably by a factor of at least 15, 20, 25, 30, 35, 40, 45, 50, even more preferably by a factor of at least 60, 70, 80, 90, 100, in the presence of C/EBPα-saRNA of the invention compared to the expression in the absence of C/EBPα-saRNA.

In one embodiment, C/EBPα-saRNA is used to regulate epithelial-mesenchymal transition (EMT) of a cell. Some tumors contain cancer stem cells or cancer stem-like cells that can self-renew and maintain tumor-initiating capacity through differentiation into a different lineage of cancer cells. It has been demonstrated that EMT is associated with cancer stem-like cells, tumor aggressiveness and metastasis, and tumor recurrence. [Kong et al., *Cancers*, vol. 3(1), 716-729 (2011)] There are many factors that regulate EMT, including miRNAs such as miR-200 and miR-134, growth factors such as fibroblast growth factor (FGF), epidermal growth factor (EGF), platelet-derived growth factor (PDGF), as well as factors such as Notch-1 and Wnt signaling pathway. In one non-limiting example, C/EBPα-saRNA regulates EMT by modulating the expression of miR-134. In another non-limiting example, C/EBPα-saRNA regulates EMT by modulating the expression of RUNX3, CTNB1, HGF, SMAD7 or TGFB1 genes.

III. Kits and Devices

Kits

The invention provides a variety of kits for conveniently and/or effectively carrying out methods of the present invention. Typically kits will comprise sufficient amounts and/or numbers of components to allow a user to perform multiple treatments of a subject(s) and/or to perform multiple experiments.

In one embodiment, the kits comprising saRNA described herein may be used with proliferating cells to show efficacy.

In one embodiment, the present invention provides kits for regulate the expression of genes in vitro or in vivo, comprising C/EBPα-saRNA of the present invention or a combination of C/EBPα-saRNA, saRNA modulating other genes, siRNAs, or miRNAs. The kit may further comprise packaging and instructions and/or a delivery agent to form a formulation composition. The delivery agent may comprise a saline, a buffered solution, a lipidoid, a dendrimer or any delivery agent disclosed herein. Non-limiting examples of genes include C/EBPα, other members of C/EBP family, albumin gene, alphafectoprotein gene, liver specific factor genes, growth factors, nuclear factor genes, tumor suppressing genes, pluripotency factor genes.

In one non-limiting example, the buffer solution may include sodium chloride, calcium chloride, phosphate and/or EDTA. In another non-limiting example, the buffer solution may include, but is not limited to, saline, saline with 2 mM calcium, 5% sucrose, 5% sucrose with 2 mM calcium, 5% Mannitol, 5% Mannitol with 2 mM calcium, Ringer's lactate, sodium chloride, sodium chloride with 2 mM calcium and mannose (See U.S. Pub. No. 20120258046; herein incorporated by reference in its entirety). In yet another non-limiting example, the buffer solutions may be precipitated or it may be lyophilized. The amount of each component may be varied to enable consistent, reproducible higher concentration saline or simple buffer formulations. The components may also be varied in order to increase the stability of saRNA in the buffer solution over a period of time and/or under a variety of conditions.

In another embodiment, the present invention provides kits to regulate the proliferation of cells, comprising C/EBPα-saRNA of the present invention, provided in an amount effective to inhibit the proliferation of cells when introduced into said cells; optionally siRNAs and miRNAs to further regulate the proliferation of target cells; and packaging and instructions and/or a delivery agent to form a formulation composition.

In another embodiment, the present invention provides kits for reducing LDL levels in cells, comprising saRNA molecules of the present invention; optionally LDL reducing drugs; and packaging and instructions and/or a delivery agent to form a formulation composition.

In another embodiment, the present invention provides kits for regulating miRNA expression levels in cells, comprising C/EBPα-saRNA of the present invention; optionally siRNAs, eRNAs and lncRNAs; and packaging and instructions and/or a delivery agent to form a formulation composition.

Devices

The present invention provides for devices which may incorporate C/EBPα-saRNA of the present invention. These devices contain in a stable formulation available to be immediately delivered to a subject in need thereof, such as a human patient. Non-limiting examples of such a subject include a subject with hyperproliferative disorders such as cancer, tumor, or liver cirrhosis; and metabolics disorders such as NAFLD, obesity, high LDL cholesterol, or type II diabetes.

Non-limiting examples of the devices include a pump, a catheter, a needle, a transdermal patch, a pressurized olfactory delivery device, iontophoresis devices, multi-layered microfluidic devices. The devices may be employed to deliver C/EBPα-saRNA of the present invention according to single, multi- or split-dosing regiments. The devices may be employed to deliver C/EBPα-saRNA of the present invention across biological tissue, intradermal, subcutaneously, or intramuscularly. More examples of devices suitable for delivering oligonucleotides are disclosed in International Publication WO 2013/090648 filed Dec. 14, 2012, the contents of which are incorporated herein by reference in their entirety.

Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

About: As used herein, the term "about" means +/−10% of the recited value.

Administered in combination: As used herein, the term "administered in combination" or "combined administration" means that two or more agents, e.g., saRNA, are administered to a subject at the same time or within an interval such that there may be an overlap of an effect of each agent on the patient. In some embodiments, they are administered within about 60, 30, 15, 10, 5, or 1 minute of one another. In some embodiments, the administrations of the agents are spaced sufficiently close together such that a combinatorial (e.g., a synergistic) effect is achieved.

Amino acid: As used herein, the terms "amino acid" and "amino acids" refer to all naturally occurring L-alpha-amino acids. The amino acids are identified by either the one-letter or three-letter designations as follows: aspartic acid (Asp:D), isoleucine (Ile:I), threonine (Thr:T), leucine (Leu:L), serine (Ser:S), tyrosine (Tyr:Y), glutamic acid (Glu:E), phenylalanine (Phe:F), proline (Pro:P), histidine (His:H), glycine (Gly:G), lysine (Lys:K), alanine (Ala:A), arginine (Arg:R), cysteine (Cys:C), tryptophan (Trp:W), valine (Val:V), glutamine (Gln:Q) methionine (Met:M), asparagines (Asn:N), where the amino acid is listed first followed parenthetically by the three and one letter codes, respectively.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization based connectivity sufficiently stable such that the "associated" entities remain physically associated.

Bifunctional: As used herein, the term "bifunctional" refers to any substance, molecule or moiety which is capable of or maintains at least two functions. The functions may affect the same outcome or a different outcome. The structure that produces the function may be the same or different.

Biocompatible: As used herein, the term "biocompatible" means compatible with living cells, tissues, organs or systems posing little to no risk of injury, toxicity or rejection by the immune system.

Biodegradable: As used herein, the term "biodegradable" means capable of being broken down into innocuous products by the action of living things.

Biologically active: As used herein, the phrase "biologically active" refers to a characteristic of any substance that has activity in a biological system and/or organism. For instance, a substance that, when administered to an organism, has a biological effect on that organism, is considered to be biologically active. In particular embodiments, the saRNA of the present invention may be considered biologically active if even a portion of the saRNA is biologically active or mimics an activity considered biologically relevant.

Cancer: As used herein, the term "cancer" in an individual refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within an individual, or may circulate in the blood stream as independent cells, such as leukemic cells.

Cell growth: As used herein, the term "cell growth" is principally associated with growth in cell numbers, which occurs by means of cell reproduction (i.e. proliferation) when the rate of the latter is greater than the rate of cell death (e.g. by apoptosis or necrosis), to produce an increase in the size of a population of cells, although a small component of that growth may in certain circumstances be due also to an increase in cell size or cytoplasmic volume of individual cells. An agent that inhibits cell growth can thus do so by either inhibiting proliferation or stimulating cell death, or both, such that the equilibrium between these two opposing processes is altered.

Cell type: As used herein, the term "cell type" refers to a cell from a given source (e.g., a tissue, organ) or a cell in a given state of differentiation, or a cell associated with a given pathology or genetic makeup.

Chromosome: As used herein, the term "chromosome" refers to an organized structure of DNA and protein found in cells.

Complementary: As used herein, the term "complementary" as it relates to nucleic acids refers to hybridization or base pairing between nucleotides or nucleic acids, such as, for example, between the two strands of a double-stranded DNA molecule or between an oligonucleotide probe and a target are complementary.

Condition: As used herein, the term "condition" refers to the status of any cell, organ, organ system or organism. Conditions may reflect a disease state or simply the physiologic presentation or situation of an entity. Conditions may be characterized as phenotypic conditions such as the macroscopic presentation of a disease or genotypic conditions such as the underlying gene or protein expression profiles associated with the condition. Conditions may be benign or malignant.

Controlled Release: As used herein, the term "controlled release" refers to a pharmaceutical composition or compound release profile that conforms to a particular pattern of release to effect a therapeutic outcome.

Cytostatic: As used herein, "cytostatic" refers to inhibiting, reducing, suppressing the growth, division, or multiplication of a cell (e.g., a mammalian cell (e.g., a human cell)), bacterium, virus, fungus, protozoan, parasite, prion, or a combination thereof.

Cytotoxic: As used herein, "cytotoxic" refers to killing or causing injurious, toxic, or deadly effect on a cell (e.g., a mammalian cell (e.g., a human cell)), bacterium, virus, fungus, protozoan, parasite, prion, or a combination thereof.

Delivery: As used herein, "delivery" refers to the act or manner of delivering a compound, substance, entity, moiety, cargo or payload.

Delivery Agent: As used herein, "delivery agent" refers to any substance which facilitates, at least in part, the in vivo delivery of a saRNA of the present invention to targeted cells.

Destabilized: As used herein, the term "destable," "destabilize," or "destabilizing region" means a region or molecule that is less stable than a starting, wild-type or native form of the same region or molecule.

Detectable label: As used herein, "detectable label" refers to one or more markers, signals, or moieties which are attached, incorporated or associated with another entity that is readily detected by methods known in the art including radiography, fluorescence, chemiluminescence, enzymatic activity, absorbance and the like. Detectable labels include radioisotopes, fluorophores, chromophores, enzymes, dyes, metal ions, ligands such as biotin, avidin, streptavidin and haptens, quantum dots, and the like. Detectable labels may be located at any position in the peptides, proteins or polynucleotides, e.g, saRNA, disclosed herein. They may be within the amino acids, the peptides, proteins, or polynucleotides located at the N- or C-termini or 5' or 3' termini as the case may be.

Encapsulate: As used herein, the term "encapsulate" means to enclose, surround or encase.

Engineered: As used herein, embodiments of the invention are "engineered" when they are designed to have a feature or property, whether structural or chemical, that varies from a starting point, wild type or native molecule.

Equivalent subject: As used herein, "equivalent subject" may be e.g. a subject of similar age, sex and health such as liver health or cancer stage, or the same subject prior to treatment according to the invention. The equivalent subject is "untreated" in that he does not receive treatment with a saRNA according to the invention. However, he may receive a conventional anti-cancer treatment, provided that the subject who is treated with the saRNA of the invention receives the same or equivalent conventional anti-cancer treatment.

Exosome: As used herein, "exosome" is a vesicle secreted by mammalian cells.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

Feature: As used herein, a "feature" refers to a characteristic, a property, or a distinctive element.

Formulation: As used herein, a "formulation" includes at least a saRNA of the present invention and a delivery agent.

Fragment: A "fragment," as used herein, refers to a portion. For example, fragments of proteins may comprise polypeptides obtained by digesting full-length protein isolated from cultured cells.

Functional: As used herein, a "functional" biological molecule is a biological molecule in a form in which it exhibits a property and/or activity by which it is characterized.

Gene: As used herein, the term "gene" refers to a nucleic acid sequence that comprises control and most often coding sequences necessary for producing a polypeptide or precursor. Genes, however, may not be translated and instead code for regulatory or structural RNA molecules.

A gene may be derived in whole or in part from any source known to the art, including a plant, a fungus, an animal, a bacterial genome or episome, eukaryotic, nuclear or plasmid DNA, cDNA, viral DNA, or chemically synthesized DNA. A gene may contain one or more modifications in either the coding or the untranslated regions that could affect the biological activity or the chemical structure of the expression product, the rate of expression, or the manner of expression control. Such modifications include, but are not limited to, mutations, insertions, deletions, and substitutions of one or more nucleotides. The gene may constitute an uninterrupted coding sequence or it may include one or more introns, bound by the appropriate splice junctions.

Gene expression: As used herein, the term "gene expression" refers to the process by which a nucleic acid sequence undergoes successful transcription and in most instances translation to produce a protein or peptide. For clarity, when reference is made to measurement of "gene expression", this should be understood to mean that measurements may be of the nucleic acid product of transcription, e.g., RNA or mRNA or of the amino acid product of translation, e.g., polypeptides or peptides. Methods of measuring the amount or levels of RNA, mRNA, polypeptides and peptides are well known in the art.

Genome: The term "genome" is intended to include the entire DNA complement of an organism, including the nuclear DNA component, chromosomal or extrachromosomal DNA, as well as the cytoplasmic domain (e.g., mitochondrial DNA).

Homology: As used herein, the term "homology" refers to the overall relatedness between polymeric molecules, e.g. between nucleic acid molecules (e.g. DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). In accordance with the invention, two polynucleotide sequences are considered to be homologous if the polypeptides they encode are at least about 50%, 60%, 70%, 80%, 90%, 95%, or even 99% for at least one stretch of at least about 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. In accordance with the invention, two protein sequences are considered to be homologous if the proteins are at least about 50%, 60%, 70%, 80%, or 90% identical for at least one stretch of at least about 20 amino acids.

The term "hyperproliferative cell" may refer to any cell that is proliferating at a rate that is abnormally high in comparison to the proliferating rate of an equivalent healthy cell (which may be referred to as a "control"). An "equivalent healthy" cell is the normal, healthy counterpart of a cell. Thus, it is a cell of the same type, e.g. from the same organ, which performs the same functions(s) as the comparator cell. For example, proliferation of a hyperproliferative hepatocyte should be assessed by reference to a healthy hepatocyte, whereas proliferation of a hyperproliferative prostate cell should be assessed by reference to a healthy prostate cell.

By an "abnormally high" rate of proliferation, it is meant that the rate of proliferation of the hyperproliferative cells is increased by at least 20, 30, 40%, or at least 45, 50, 55, 60, 65, 70, 75%, or at least 80%, as compared to the proliferative rate of equivalent, healthy (non-hyperproliferative) cells. The "abnormally high" rate of proliferation may also refer to a rate that is increased by a factor of at least 2, 3, 4, 5, 6, 7, 8, 9, 10, or by a factor of at least 15, 20, 25, 30, 35, 40, 45, 50, or by a factor of at least 60, 70, 80, 90, 100, compared to the proliferative rate of equivalent, healthy cells.

The term "hyperproliferative cell" as used herein does not refer to a cell which naturally proliferates at a higher rate as compared to most cells, but is a healthy cell. Examples of cells that are known to divide constantly throughout life are skin cells, cells of the gastrointestinal tract, blood cells and bone marrow cells. However, when such cells proliferate at a higher rate than their healthy counterparts, then they are hyperproliferative.

Hyperproliferative disorder: As used herein, a "hyperproliferative disorder" may be any disorder which involves hyperproliferative cells as defined above. Examples of hyperproliferative disorders include neoplastic disorders such as cancer, psoriatic arthritis, rheumatoid arthritis, gastric hyperproliferative disorders such as inflammatory bowel disease, skin disorders including psoriasis, Reiter's syndrome, pityriasis rubra pilaris, and hyperproliferative variants of the disorders of keratinization.

The skilled person is fully aware of how to identify a hyperproliferative cell. The presence of hyperproliferative cells within an animal may be identifiable using scans such as X-rays, MRI or CT scans. The hyperproliferative cell may also be identified, or the proliferation of cells may be assayed, through the culturing of a sample in vitro using cell proliferation assays, such as MTT, XTT, MTS or WST-1 assays. Cell proliferation in vitro can also be determined using flow cytometry.

Identity: As used herein, the term "identity" refers to the overall relatedness between polymeric molecules, e.g., between oligonucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research,* 12(1), 387 (1984)), BLASTP, BLASTN, and FASTA Altschul, S. F. et al., *J. Molec. Biol.,* 215, 403 (1990)).

Inhibit expression of a gene: As used herein, the phrase "inhibit expression of a gene" means to cause a reduction in the amount of an expression product of the gene. The expression product can be an RNA transcribed from the gene (e.g., an mRNA) or a polypeptide translated from an mRNA transcribed from the gene. Typically a reduction in the level of an mRNA results in a reduction in the level of a polypeptide translated therefrom. The level of expression may be determined using standard techniques for measuring mRNA or protein.

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe or cell or tissue thereof).

Isolated: As used herein, the term "isolated" refers to a substance or entity that has been separated from at least some of the components with which it was associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. Substantially isolated: By "substantially isolated" is meant that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof. Methods for isolating compounds and their salts are routine in the art.

Label: The term "label" refers to a substance or a compound which is incorporated into an object so that the substance, compound or object may be detectable.

Linker: As used herein, a linker refers to a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. The linker can be attached to a modified nucleoside or nucleotide on the nucleobase or sugar moiety at a first end, and to a payload, e.g., a detectable or therapeutic agent, at a second end. The linker may be of sufficient length as to not interfere with incorporation into a nucleic acid sequence. The linker can be used for any useful purpose, such as to form saRNA conjugates, as well as to administer a payload, as described herein. Examples of chemical groups that can be incorporated into the linker include, but are not limited to, alkyl, alkenyl, alkynyl, amido, amino, ether, thioether, ester, alkylene, heteroalkylene, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers and derivatives thereof. Other examples include, but are not limited to, cleavable moieties within the linker, such as, for example, a disulfide bond (—S—S—) or an azo bond (—N=N—), which can be cleaved using a reducing agent or photolysis. Non-limiting examples of a selectively cleavable bond include an amido bond can be cleaved for example by the use of tris(2-carboxyethyl)phosphine (TCEP), or other reducing agents, and/or photolysis, as well as an ester bond can be cleaved for example by acidic or basic hydrolysis.

Metastasis: As used herein, the term "metastasis" means the process by which cancer spreads from the place at which it first arose as a primary tumor to distant locations in the body. Metastasis also refers to cancers resulting from the spread of the primary tumor. For example, someone with breast cancer may show metastases in their lymph system, liver, bones or lungs.

Modified: As used herein "modified" refers to a changed state or structure of a molecule of the invention. Molecules may be modified in many ways including chemically, structurally, and functionally. In one embodiment, the saRNA molecules of the present invention are modified by the introduction of non-natural nucleosides and/or nucleotides.

Naturally occurring: As used herein, "naturally occurring" means existing in nature without artificial aid.

Nucleic acid: The term "nucleic acid" as used herein, refers to a molecule comprised of one or more nucleotides, i.e., ribonucleotides, deoxyribonucleotides, or both. The term includes monomers and polymers of ribonucleotides and deoxyribonucleotides, with the ribonucleotides and/or deoxyribonucleotides being bound together, in the case of the polymers, via 5' to 3' linkages. The ribonucleotide and deoxyribonucleotide polymers may be single or double-stranded. However, linkages may include any of the linkages known in the art including, for example, nucleic acids comprising 5' to 3' linkages. The nucleotides may be naturally occurring or may be synthetically produced analogs that are capable of forming base-pair relationships with naturally occurring base pairs. Examples of non-naturally occurring bases that are capable of forming base-pairing relationships include, but are not limited to, aza and deaza pyrimidine analogs, aza and deaza purine analogs, and other heterocyclic base analogs, wherein one or more of the carbon and nitrogen atoms of the pyrimidine rings have been substituted by heteroatoms, e.g., oxygen, sulfur, selenium, phosphorus, and the like.

Patient: As used herein, "patient" refers to a subject who may seek or be in need of treatment, requires treatment, is receiving treatment, will receive treatment, or a subject who is under care by a trained professional for a particular disease or condition.

Peptide: As used herein, "peptide" is less than or equal to 50 amino acids long, e.g., about 5, 10, 15, 20, 25, 30, 35, 40, 45, or 50 amino acids long.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17$^{th}$ ed., Mack Publishing Company, Easton, Pa., 1985, p. 1418, *Pharmaceutical Salts: Properties, Selection, and Use,* P. H. Stahl and C. G. Wermuth (eds.), Wiley-VCH, 2008, and Berge et al., *Journal of Pharmaceutical Science,* 66, 1-19 (1977), each of which is incorporated herein by reference in its entirety.

Pharmaceutically acceptable solvate: The term "pharmaceutically acceptable solvate," as used herein, means a compound of the invention wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

Pharmacologic effect: As used herein, a "pharmacologic effect" is a measurable biologic phenomenon in an organism or system which occurs after the organism or system has been contacted with or exposed to an exogenous agent. Pharmacologic effects may result in therapeutically effective outcomes such as the treatment, improvement of one or more symptoms, diagnosis, prevention, and delay of onset of disease, disorder, condition or infection. Measurement of such biologic phenomena may be quantitative, qualitative or relative to another biologic phenomenon. Quantitative measurements may be statistically significant. Qualitative measurements may be by degree or kind and may be at least 10%, 20%, 30%, 40%, 50%, 60%, 70%, 80%, 90% or more different. They may be observable as present or absent, better or worse, greater or less. Exogenous agents, when referring to pharmacologic effects are those agents which are, in whole or in part, foreign to the organism or system. For example, modifications to a wild type biomolecule, whether structural or chemical, would produce an exogenous agent. Likewise, incorporation or combination of a wild type molecule into or with a compound, molecule or substance not found naturally in the organism or system would also produce an exogenous agent. The saRNA of the present invention, comprises exogenous agents. Examples of pharmacologic effects include, but are not limited to, alteration in cell count such as an increase or decrease in neutrophils, reticulocytes, granulocytes, erythrocytes (red blood cells), megakaryocytes, platelets, monocytes, connective tissue macrophages, epidermal langerhans cells, osteoclasts, dendritic cells, microglial cells, neutrophils, eosinophils, basophils, mast cells, helper T cells, suppressor T cells, cytotoxic T cells, natural killer T cells, B cells, natural killer cells, or reticulocytes. Pharmacologic effects also include alterations in blood chemistry, pH, hemoglobin, hematocrit, changes in levels of enzymes such as, but not limited to, liver enzymes AST and ALT, changes in lipid profiles, electrolytes, metabolic markers, hormones or other marker or profile known to those of skill in the art.

Physicochemical: As used herein, "physicochemical" means of or relating to a physical and/or chemical property.

Preventing: As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Prodrug: The present disclosure also includes prodrugs of the compounds described herein. As used herein, "prodrugs" refer to any substance, molecule or entity which is in a form predicate for that substance, molecule or entity to act as a therapeutic upon chemical or physical alteration. Prodrugs may by covalently bonded or sequestered in some way and which release or are converted into the active drug moiety prior to, upon or after administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Preparation and use of prodrugs is discussed in T. Higuchi and V. Stella, "Prodrugs as Novel Delivery Systems," Vol. 14 of the A.C.S.

Symposium Series, and in *Bioreversible Carriers in Drug Design*, ed. Edward B. Roche, American Pharmaceutical Association and Pergamon Press, 1987, both of which are hereby incorporated by reference in their entirety.

Prognosing: As used herein, the term "prognosing" means a statement or claim that a particular biologic event will, or is very likely to, occur in the future.

Progression: As used herein, the term "progression" or "cancer progression" means the advancement or worsening of or toward a disease or condition.

Proliferate: As used herein, the term "proliferate" means to grow, expand or increase or cause to grow, expand or increase rapidly. "Proliferative" means having the ability to proliferate. "Anti-proliferative" means having properties counter to or inapposite to proliferative properties.

Protein: A "protein" means a polymer of amino acid residues linked together by peptide bonds. The term, as used herein, refers to proteins, polypeptides, and peptides of any size, structure, or function. Typically, however, a protein will be at least 50 amino acids long. In some instances the protein encoded is smaller than about 50 amino acids. In this case, the polypeptide is termed a peptide. If the protein is a short peptide, it will be at least about 10 amino acid residues long. A protein may be naturally occurring, recombinant, or synthetic, or any combination of these. A protein may also comprise a fragment of a naturally occurring protein or peptide. A protein may be a single molecule or may be a multi-molecular complex. The term protein may also apply to amino acid polymers in which one or more amino acid residues are an artificial chemical analogue of a corresponding naturally occurring amino acid.

Protein expression: The term "protein expression" refers to the process by which a nucleic acid sequence undergoes translation such that detectable levels of the amino acid sequence or protein are expressed.

Purified: As used herein, "purify," "purified," "purification" means to make substantially pure or clear from unwanted components, material defilement, admixture or imperfection.

Regression: As used herein, the term "regression" or "degree of regression" refers to the reversal, either phenotypically or genotypically, of a cancer progression. Slowing or stopping cancer progression may be considered regression.

Sample: As used herein, the term "sample" or "biological sample" refers to a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). A sample further may include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. A sample further refers to a medium, such as a nutrient broth or gel, which may contain cellular components, such as proteins or nucleic acid molecule.

Signal Sequences: As used herein, the phrase "signal sequences" refers to a sequence which can direct the transport or localization of a protein.

Single unit dose: As used herein, a "single unit dose" is a dose of any therapeutic administered in one dose/at one time/single route/single point of contact, i.e., single administration event.

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Split dose: As used herein, a "split dose" is the division of single unit dose or total daily dose into two or more doses.

Stable: As used herein "stable" refers to a compound that is sufficiently robust to survive isolation to a useful degree of purity from a reaction mixture, and preferably capable of formulation into an efficacious therapeutic agent.

Stabilized: As used herein, the term "stabilize", "stabilized," "stabilized region" means to make or become stable.

Subject: As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates, and humans) and/or plants.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantially equal: As used herein as it relates to time differences between doses, the term means plus/minus 2%.

Substantially simultaneously: As used herein and as it relates to plurality of doses, the term means within 2 seconds.

Suffering from: An individual who is "suffering from" a disease, disorder, and/or condition has been diagnosed with or displays one or more symptoms of a disease, disorder, and/or condition.

Susceptible to: An individual who is "susceptible to" a disease, disorder, and/or condition has not been diagnosed with and/or may not exhibit symptoms of the disease, disorder, and/or condition but harbors a propensity to develop a disease or its symptoms. In some embodiments, an individual who is susceptible to a disease, disorder, and/or condition (for example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Sustained release: As used herein, the term "sustained release" refers to a pharmaceutical composition or compound release profile that conforms to a release rate over a specific period of time.

Synthetic: The term "synthetic" means produced, prepared, and/or manufactured by the hand of man. Synthesis of polynucleotides or polypeptides or other molecules of the present invention may be chemical or enzymatic.

Targeted Cells: As used herein, "targeted cells" refers to any one or more cells of interest. The cells may be found in vitro, in vivo, in situ or in the tissue or organ of an organism. The organism may be an animal, preferably a mammal, more preferably a human and most preferably a patient.

Therapeutic Agent: The term "therapeutic agent" refers to any agent that, when administered to a subject, has a therapeutic, diagnostic, and/or prophylactic effect and/or elicits a desired biological and/or pharmacological effect.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Total daily dose: As used herein, a "total daily dose" is an amount given or prescribed in 24 hr period. It may be administered as a single unit dose.

Transcription factor: As used herein, the term "transcription factor" refers to a DNA-binding protein that regulates transcription of DNA into RNA, for example, by activation or repression of transcription. Some transcription factors effect regulation of transcription alone, while others act in concert with other proteins. Some transcription factor can both activate and repress transcription under certain conditions. In general, transcription factors bind a specific target sequence or sequences highly similar to a specific consensus sequence in a regulatory region of a target gene. Transcription factors may regulate transcription of a target gene alone or in a complex with other molecules.

Treating: As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

The phrase "a method of treating" or its equivalent, when applied to, for example, cancer refers to a procedure or course of action that is designed to reduce, eliminate or prevent the number of cancer cells in an individual, or to alleviate the symptoms of a cancer. "A method of treating" cancer or another proliferative disorder does not necessarily mean that the cancer cells or other disorder will, in fact, be completely eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of an individual, is nevertheless deemed an overall beneficial course of action.

Tumor growth: As used herein, the term "tumor growth" or "tumor metastases growth", unless otherwise indicated, is used as commonly used in oncology, where the term is principally associated with an increased mass or volume of the tumor or tumor metastases, primarily as a result of tumor cell growth.

Tumor Burden: As used herein, the term "tumor burden" refers to the total Tumor Volume of all tumor nodules with a diameter in excess of 3 mm carried by a subject.

Tumor Volume: As used herein, the term "tumor volume" refers to the size of a tumor. The tumor volume in $mm^3$ is calculated by the formula: volume=(width)$^2$×length/2.

Unmodified: As used herein, "unmodified" refers to any substance, compound or molecule prior to being changed in any way. Unmodified may, but does not always, refer to the wild type or native form of a biomolecule. Molecules may undergo a series of modifications whereby each modified molecule may serve as the "unmodified" starting molecule for a subsequent modification.

EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

The invention is further illustrated by the following non-limiting examples.

EXAMPLES

Materials and Procedures have been disclosed in PCT Application No. PCT/IB2014/003054.

Example 1. C/EBPα-saRNA In Vitro Studies

AW51 (aka CEBPA-AW1-510000) was transfected in a panel of HCC cell lines such as Hep3B, HepG2, PLC/PRF/5, SNU475 cells. The cells were reverse transfected with 50 nM AW51 at seeding, forward transfected 24 hours later, and harvested at 72 hours. CEBPA mRNA and albumin (ALB) mRNA levels were measured. Upregulation of CEBPA and ALB mRNA were observed as shown in FIG. 4A-4D and FIG. 5A-5D.

| AW51 Antisense sequence (X09317) | GACCAGUGACAAUGACCGCUU | SEQ ID No. 93 |
|---|---|---|
| AW51 Sense sequence (X09316) | GCGGUCAUUGUCACUGGUCUU | SEQ ID No. 94 |

Example 2. Modified CEBPA-saRNA Upregulates CEBPA

Figure 6A:
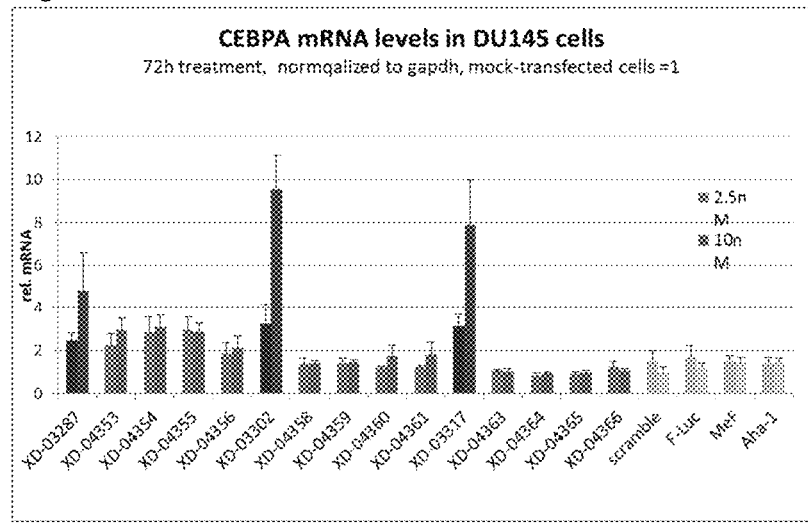
FIG. 6A shows CEBPA mRNA levels in DU145 cells transfected with modified saRNA normalized to GAPDH.
Figure 6B:
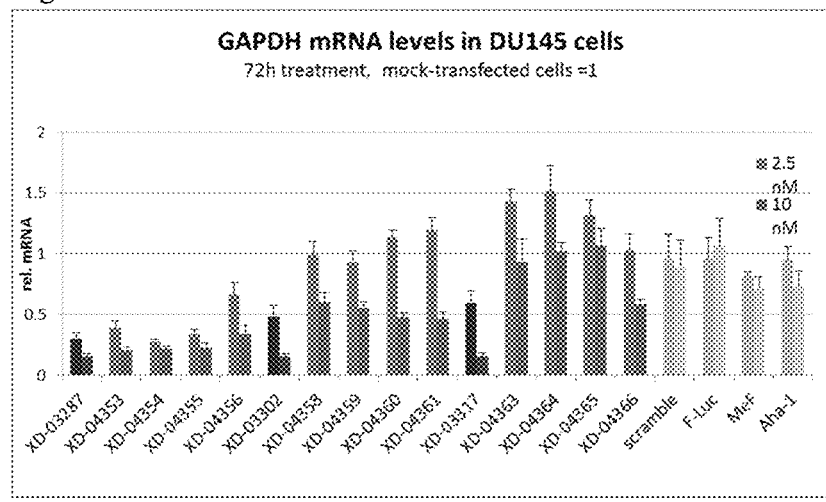
FIG. 6B shows GAPDH mRNA levels in DU145 cells.
Figure 6C:
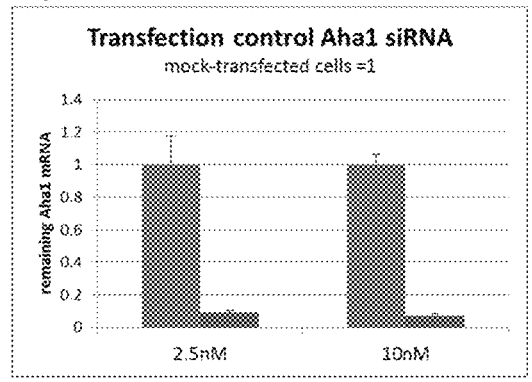
FIG. 6C shows Aha1 mRNA levels as a transfection control.

Modified CEBPA-saRNAs in Table 3 were transfected in DU145 cells. The cells were reverse transfected with 2.5 nM and 10 nM modified CEBPA-saRNA at seeding, forward transfected 24 hours later, and harvested at 72 hours. CEBPA and GAPDH mRNA levels were measured. Results in Table 6, FIG. 6A shows that CEPBA-saRNA could tolerate heavy modifications.

TABLE 6-1

CEBPA mRNA levels in DU145 cells

| Duplex ID | rel. mRNA CEBPA 2.5 nM | SD | rel. mRNA CEBPA 10 nM | SD |
|---|---|---|---|---|
| XD-03287 | 2.47405519 | 0.35441301 | 4.807203057 | 1.77941471 |
| XD-04353 | 2.240846151 | 0.56776333 | 2.948275905 | 0.55264149 |
| XD-04354 | 2.847748677 | 0.7442053 | 3.130235184 | 0.54793146 |
| XD-04355 | 2.946658233 | 0.66053501 | 2.892767048 | 0.37945239 |
| XD-04356 | 1.864020365 | 0.49485233 | 2.109506219 | 0.55126016 |
| XD-03302 | 3.271904091 | 0.84352676 | 9.550389237 | 1.59963498 |
| XD-04358 | 1.35233741 | 0.28653345 | 1.384020564 | 0.13677222 |
| XD-04359 | 1.399054988 | 0.26024787 | 1.486989819 | 0.07346068 |
| XD-04360 | 1.211792463 | 0.06559519 | 1.721136011 | 0.54936887 |
| XD-04361 | 1.221228236 | 0.05912314 | 1.802248329 | 0.58804132 |
| XD-03317 | 3.170377201 | 0.54481336 | 7.878877604 | 2.12261544 |
| XD-04363 | 1.041339997 | 0.06854357 | 1.025008603 | 0.10910861 |
| XD-04364 | 0.810622945 | 0.15207354 | 0.917036666 | 0.07051729 |
| XD-04365 | 0.892397193 | 0.11321896 | 0.960369198 | 0.11671288 |
| XD-04366 | 1.235336205 | 0.24529118 | 1.031610064 | 0.10794732 |
| scramble | 1.50761893 | 0.49259555 | 0.977396047 | 0.25336725 |
| F-Luc | 1.679417472 | 0.53349959 | 1.177929847 | 0.22429314 |
| MeF | 1.519521651 | 0.23368363 | 1.418274737 | 0.26159698 |
| Aha-1 | 1.400196465 | 0.28373253 | 1.44526965 | 0.20604682 |

TABLE 6-2

GAPDH mRNA levels in DU145 cells

| Duplex ID | gapdh 2.5 nM | SD | gapdh 10 nM | SD |
|---|---|---|---|---|
| XD-03287 | 0.30012213 | 0.04872709 | 0.15487859 | 0.021476125 |
| XD-04353 | 0.38430764 | 0.05893013 | 0.21179771 | 0.023662437 |
| XD-04354 | 0.278508 | 0.0151083 | 0.21589058 | 0.025144858 |
| XD-04355 | 0.33891401 | 0.03684563 | 0.23096784 | 0.039633795 |
| XD-04356 | 0.66440667 | 0.09665852 | 0.34165265 | 0.068757809 |
| XD-03302 | 0.48401386 | 0.0938301 | 0.15074631 | 0.023836647 |
| XD-04358 | 0.99270067 | 0.10679351 | 0.60215746 | 0.076308233 |
| XD-04359 | 0.93338175 | 0.08896079 | 0.55308903 | 0.050195732 |
| XD-04360 | 1.14035319 | 0.05727254 | 0.47614574 | 0.040400001 |
| XD-04361 | 1.19595973 | 0.10526669 | 0.46229043 | 0.060483173 |
| XD-03317 | 0.59089619 | 0.10261665 | 0.15368292 | 0.02885901 |
| XD-04363 | 1.42967486 | 0.10493026 | 0.93230015 | 0.188124401 |
| XD-04364 | 1.51612477 | 0.20993157 | 1.02248778 | 0.070857079 |
| XD-04365 | 1.31858062 | 0.12189526 | 1.07045908 | 0.136617289 |
| XD-04366 | 1.02824228 | 0.13557063 | 0.58889998 | 0.03921991 |
| scramble | 0.9596105 | 0.1991626 | 0.88815236 | 0.227402132 |
| F-Luc | 0.95681136 | 0.1749612 | 1.06219451 | 0.229513678 |
| MeF | 0.81949497 | 0.03521342 | 0.71848557 | 0.094709517 |
| Aha-1 | 0.94853936 | 0.10607439 | 0.72142219 | 0.134524626 |

Following table includes the controls used in this example. Aha1 siRNA was used as transfection control and was transfected at concentrations of 2.5 nM and 10 nM.

TABLE 7-1

Controls-sense sequences

| Duplex-ID | Sense-ID | Sense Sequence | SEQ ID No. | Notes |
|---|---|---|---|---|
| XD-03291 | X09206 | ACUACUGAGUGACAGUAGAUU | 33 | Scramble, unmodified |
| XD-03292 | X09208 | CuUACGcUGAGUACUUCGAsusu | 78 | Fluc, modified |
| XD-00033 | X00122 | GGAuGAAGuGGAGAuuAGudTsdT | 79 | AHA1 siRNA, transfection control |

TABLE 7-1-continued

Controls-sense sequences

| Duplex-ID | Sense-ID | Sense Sequence | SEQ ID No. | Notes |
|---|---|---|---|---|
| XD-00376 | X01162 | GGAUfCfAUfCfUfCfAAGUfCfUfUfACfdTsdT | 80 | MeF design, neg. ctrl |

TABLE 7-2

Controls-antisense sequences

| Duplex-ID | Anti-sense-ID | Anti-Sense Sequence | SEQ ID No. | Notes |
|---|---|---|---|---|
| XD-03291 | X09207 | UCUACUGUCACUCAGUAGUUU | 81 | Scramble, unmodified |
| XD-03292 | X09209 | UcGAAGuAcUCAGcGUAAgsusu | 82 | Fluc, modified |
| XD-00033 | X00123 | ACuAAUCUCcACUUcAUCCdTsdT | 83 | AHA1 siRNA, transfection control |
| XD-00376 | X01163 | GUfAAGACtUfUfGAGAUfGAUfCfCfdTsdT | 84 | MeF design, neg. ctrl |

A CEBPA-saRNA is conjugated with GalNac clusters (referred to as GalNac-CEBPA-saRNA) and is transfected in DU145 cells. The cells are reverse transfected with 2.5 nM, 10 nM, or 50 nM GalNac-CEBPA-saRNA at seeding, forward transfected 24 hours later, and harvested at 72 hours. CEBPA and albumin mRNA levels are measured.

AW51 (aka CEBPA-AW1-510000) is conjugated with GalNac clusters and is transfected in DU145 cells. The cells are reverse transfected with 2.5 nM, 10 nM, or 50 nM GalNac-CEBPA-saRNA at seeding, forward transfected 24 hours later, and harvested at 72 hours. CEBPA and albumin mRNA levels are measured.

Example 3. In Vitro Dose Response and Potency Comparison of saRNA and siRNA

EC50 in DU145 cells of three unmodified CEBPA-saRNA (XD-03287, XD-03302, XD-03317) was compared with IC50 of siRNA to AHA1 and CEBPA in DU145 cells.

For EC50 test of saRNA, DU145 cells (p15, 8000 cells/well) were reversed transfected with CEBPA-saRNA at 0 hr (Lipofectamine 2000, 0.4 µl/well), forward transfected at 24 hr, and harvested at 72 hrs. XD-03287, XD-03302, XD-03317 were dosed in 2× dilution series from 100 nM. CEBPA mRNA levels were normalized with GAPDH.

For IC50 test of siRNA, DU145 cells (p15, 8000 cells/well) received a single transfection at 0 hr with harvest at 24 hrs. Life Technologies CEBPA-siRNA and Axo unmod AHA1 were dosed in 5× dilution series from 50 nM.

TABLE 8

Sequences of the saRNA, siRNA and controls:

| Duplex-ID | Sense-ID | Sense Sequence | Antisense-ID | Antisense Sequence | Notes |
|---|---|---|---|---|---|
| XD-03287 | X09198 | CGGUCAUUGUCACUGGUCAUU (SEQ ID NO. 50) | X09199 | UGACCAGUGACAAUGACCGUU (SEQ ID NO. 51) | CEBPA-saRNA |
| XD-03302 | X09316 | GCGGUCAUUGUCACUGGUCUU (SEQ ID NO. 85) | X09317 | GACCAGUGACAAUGACCGCUU (SEQ ID NO. 86) | CEBPA-saRNA |
| XD-03317 | X09346 | UGAAAGGAUUCAUCCUCCUUU (SEQ ID NO. 87) | X09347 | AGGAGGAUGAAUCCUUUCAUU (SEQ ID NO.88) | CEBPA-saRNA |
| XD-01030 | X02807 | GGAUGAAGUGGAGAUUAGUdTsdT (SEQ ID NO.89) | X02812 | ACUAAUCUCCACUUCAUCCdTsdT (SEQ ID NO. 90) | Aha-1 siRNA, unmodified |
| XD-00194 | X00539 | cuuAcGcuGAGuAcuucGAdTsdT (SEQ ID NO. 91) | X00540 | UCGAAGuACUcAGCGuAAGdTsdT (SEQ ID NO. 92) | Fluc, negative control |

TABLE 8-continued

Sequences of the saRNA, siRNA and controls:

| Duplex-ID | Sense-ID | Sense Sequence | Antisense-ID | Antisense Sequence | Notes |
|---|---|---|---|---|---|
| s2890 | | | | | siRNA targeting CEBPA from life technologies |

TABLE 9

Concentrations of saRNA and siRNA in nM:

| siRNA | 50 | 10 | 2 | 0.4 | 0.08 | 0.016 | 0.0032 | 0.00064 | 0.000128 | 0.0000256 |
|---|---|---|---|---|---|---|---|---|---|---|
| saRNA | 100 | 50 | 25 | 12.5 | 6.25 | 3.125 | 1.5625 | 0.78125 | 0.390625 | 0.1953125 |

Figure 7A:
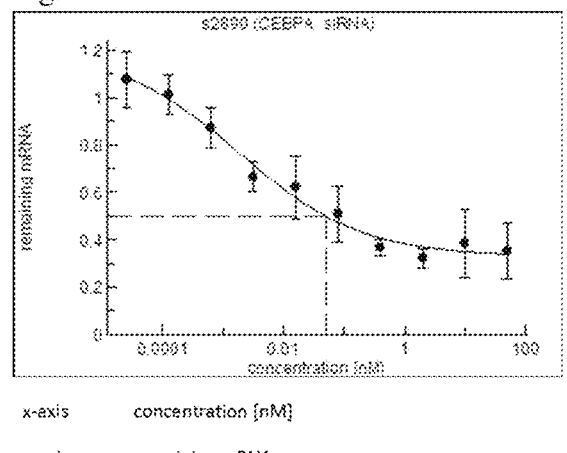
FIG. 7A-7B show CEBPA mRNA levels in DU145 cells transfected with CEBPA-siRNA or Fluc normalized to GAPDH.
Figure 7B:
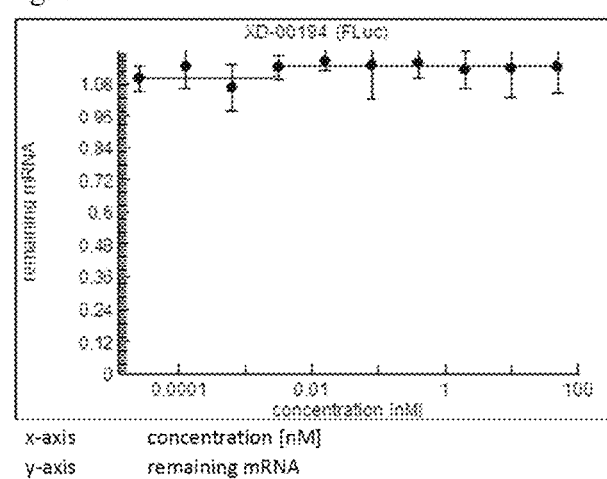
Figure 7C:
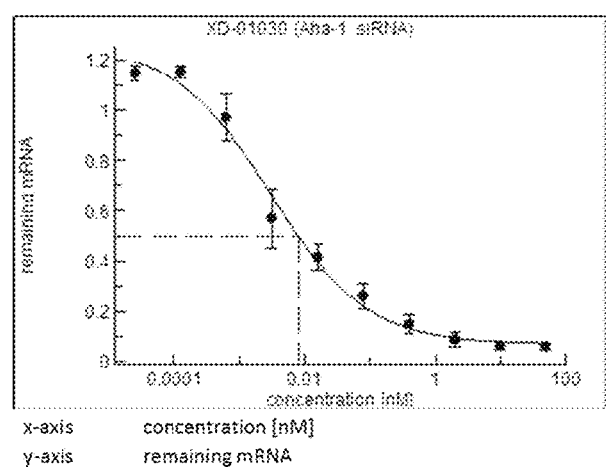
FIG. 7C shows AhA-1 mRNA level in DU145 cells transfected with AhA-1-siRNA normalized to GAPDH.
Figure 8A:
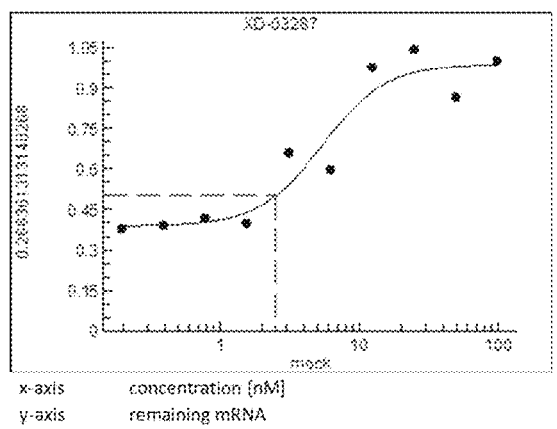
FIG. 8A-8C show CEBPA mRNA levels in DU145 cells transfected with three saRNAs normalized to GAPDH.
Figure 8B:
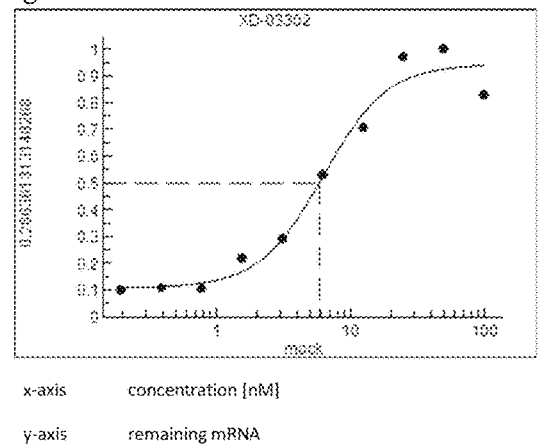
Figure 8C:
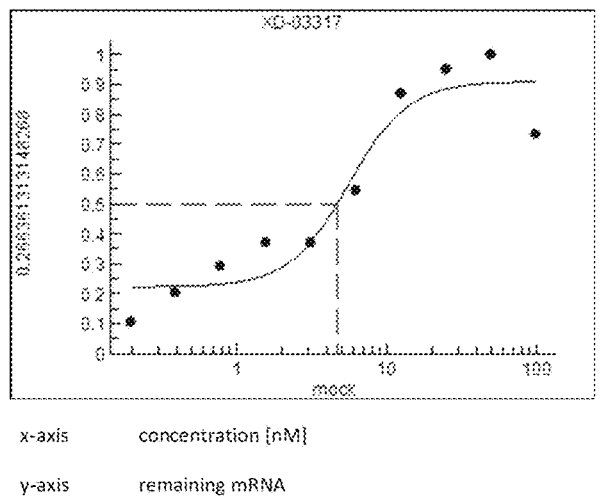

The IC50 values of siRNA were shown in Table 10 and FIG. 7A-7C. The EC50 values of saRNA were shown in Table 11 and FIG. 8A-8C. Slope ratio for saRNA/siRNA of around 5, suggesting a different mechanism. For the calculation of the slope averages and ratios, the slopes were normalized for a Y-axis range of 100%. This results in average slopes of about 0.5 for siRNAs (CEBPA-siRNA and Aha-1-siRNA) and about 2.7 for saRNAs (XD-03287, XD-03302 and XD-03317). EC50 and IC50 are the inflection points (IP), a measure of half-maximal activity. Therefore, CEBPA-saRNAs are highly potent having IC50s in low nM range.

TABLE 10

IC50 values of siRNA and control:

| siRNA Duplex ID | s2890 (CEBPA siRNA) | XD-00194 (FLuc) | XD-01030 (Aha-1 siRNA) |
|---|---|---|---|
| IC50 (nM) | 0.049 | NA | 0.0079 |
| IP (nM) | 0.0018 | NA | 0.0030 |
| slope | −0.43 | NA | −0.59 |

TABLE 11

EC50 values of saRNA

| saRNA Duplex ID | XD-03287 | XD-03302 | XD-03317 |
|---|---|---|---|
| EC50 (nM) | 2.50 | 5.83 | 4.66 |
| IP (nM) | 5.42 | 6.24 | 5.58 |
| slope | 1.91 | 1.82 | 2.19 |

Example 4. In Vitro Studies with CEBPA-saRNA in Human Hepatocytes

Primary human hepatocytes (LifeTechnologies, HMCPTS) were placed in non-proliferation media. On the day of seeding, the cells were subjected to a reverse transfection step where the saRNA transfection complex was added to the cells before they adhered as a monolayer. After 24 hours, the medium was changed and a forward transfection was performed. The next day, the medium was changed and the cells were incubated for a further 24 hours prior to harvesting of cells for analysis. The hepatocytes were transfected with AW51. CEBPA and albumin mRNA levels were measured at 48 hr and 72 hr. Aha-1-siRNA and Fluc were used as controls. Aha1, albumin, CEBPA relative expressions were shown in Table 12 and FIG. 9A.

Materials

Primary hepatocyte thawing medium: Cryopreserved Hepatocyte Recovery Medium (CHRM), 50 mL (Life Technologies Cat. No. CM7000)

Primary hepatocyte plating medium: Fetal bovine serum, heat inactivated—50 mL (Life Technologies Cat. No. 16140-071)

Insulin-Transferrin-Selenium (100×)—5 mL (Life Technologies Cat. No. 41400-045)

HEPES (1 M)—5 mL (Life Technologies Cat. No. 15630-056)

L-Glutamine-Penicillin-Streptomycin solution—5 mL (Sigma Cat. No. G1146)

Dexamethasone—to 40 ng/mL final concentration (Sigma Cat. No. D8893)

William's E Medium, no phenol red—to 500 mL total (Life Technologies Cat. No. A12176-01)

Primary hepatocyte maintenance medium: Primary Hepatocyte Maintenance Supplement (Life Technologies Cat. No. CM4000)

William's E Medium, no phenol red—to 500 mL total (Life Technologies Cat. No. A12176-01)

Primary hepatocyte culture plates:Collagen I, Coated Plate, 24 well (Life Technologies Cat. No. A11428-02)

Transfection reagents:HiPerFect Transfection Reagent (Qiagen Cat. No. 301704)

Opti-MEM I Reduced Serum Medium, no phenol red (Life Technologies Cat. No. 11058-021)

Protocol saRNA Annealing:

Each lyophilised saRNA strand was resuspended to 1 mM in RNase-free 10 mM Tris-HCl, 20 mM NaCl2, 1 mM EDTA. They were mixed well to complete resuspension. Equal volumes of sense and antisense strands were mixed together by gentle vortexing. The tube with combined strands was placed in a beaker of water heated to 95° C. The beaker was covered and allowed to cool to room temperature. Subsequent dilutions were performed using RNAse-free water. Generally for 24 well format, stock solution was diluted to 10 µM. Aliquot annealed saRNA was aliquoted and stored at −20° C.

Thawing and plating of primary hepatocytes:

CHRM and plating medium were warmed to 37° C. in a water bath. Cryopreserved hepatocytes were thawed in a 37° C. water bath until no ice crystals remain. The vial was disinfected with 70% ethanol. In a sterile tissue culture hood, thawed hepatocytes were transferred directly into CHRM. Hepatocytes were centrifuged at 100×g (900 rpm in a Thermo F-G1 fixed-angle rotor) for 10 minutes at room temperature. Supernatant was carefully poured off into a waste bottle. Pellet was resuspended in 1 mL of Plating Medium per 1×106 cryopreserved cells. Cells were counted using a NucleoCounter NC-200 aggregated cells assay to determine cell viability. 2.0×105 viable cells were plated in 500 µL Plating Medium per well in a 24 well plate.

Reverse Transfection (Immediately after Seeding):

For each well to be transfected, 12 µl, of 10 µM saRNA was diluted in 85 µL Opti-MEM. For each well to be transfected, 3 µL HiPerFect was added and mixed well by vortexing. The transfection was incubated for 15 minutes at room temperature. 100 µL transfection complexes was added to each well for a final saRNA concentration of 200 nM. The plate was incubated at 37° C. with 5% CO2 in a humidified incubator. After 5 hours, the medium was changed to 500 µL pre-warmed Maintenance Medium.

Forward Transfection (24 Hours after Seeding):

For each well to be transfected, 12 µL of 10 µM saRNA was diluted in 85 µL Opti-MEM. For each well to be transfected, 3 µL HiPerFect was added and mixed well by vortexing. The transfection was incubated for 15 minutes at room temperature. During incubation, medium was changed to 500 µL fresh pre-warmed Maintenance Medium per well. 100 µL transfection complexes was added to each well for a final saRNA concentration of 200 nM. The plate was returned to incubator. After 24 hours, medium was changed to 500 µL of fresh pre-warmed Maintenance Medium. Peak gene activation occurred 72 hours after cell seeding. Cells and/or supernatant were collected for downstream analysis at this time.

TABLE 12-1

Relative expression of Aha1, albumin and CEBPA genes at 48 hr after aha1-siRNA, Fluc and AW51 transfection

| | Aha1 exprission | Albumin expression | CEBPA expression |
|---|---|---|---|
| Untreated | 1 | 1 | 1 |
| Aha1 | 0.1 | 0.9 | 1.4 |
| Flu | 1.5 | 1.0 | 1.6 |
| AW51 | 1.5 | 1.1 | 1.5 |

TABLE 12-2

Relative expression of Aha1, albumin and CEBPA genes at 72 hr after aha1-siRNA, Fluc and AW51 transfection

| | Aha1 exprission | Albumin expression | CEBPA expression |
|---|---|---|---|
| Untreated | 1 | 1 | 1 |
| Aha1 | 0.1 | 0.6 | 1.0 |
| Flu | 0.8 | 0.7 | 1.4 |
| AW51 | 0.9 | 0.65 | 1.6 | saRNA Transfection Protocol in Proliferating Primary Human Hepatocytes

Primary human hepatocytes (LifeTechnologies, HMCPTS) were placed in proliferation media. On the day of seeding, the cells are subjected to a reverse transfection step where the saRNA transfection complex was added to the cells before they adhere as a monolayer. After 24 hours, the medium was changed and a forward transfection is performed. The next day, the medium was changed and the cells were incubated for a further 24 hours prior to harvesting of cells for analysis. The hepatocytes were transfected with AW51. CEBPA and albumin mRNA levels were measured at 48 hr and 72 hr. Aha-1-siRNA and Fluc were used as controls. Aha1, albumin, CEBPA relative expressions were shown in Table 13 and FIG. 9B.

Materials

Primary Hepatocyte Thawing Medium:
Cryopreserved Hepatocyte Recovery Medium (CHRM), 50 mL (Life Technologies Cat. No. CM7000)
Primary Hepatocyte Plating Medium:
Fetal bovine serum, heat inactivated—50 mL (Life Technologies Cat. No. 16140-071)
Insulin-Transferrin-Selenium (100×)—5 mL (Life Technologies Cat. No. 41400-045)
HEPES (1 M)—5 mL (Life Technologies Cat. No. 15630-056)
L-Glutamine-Penicillin-Streptomycin solution—5 mL (Sigma Cat. No. G1146)
Dexamethasone—to 40 ng/mL final concentration (Sigma Cat. No. D8893)
William's E Medium, no phenol red—to 500 mL total (Life Technologies Cat. No. A12176-01)
Primary Hepatocyte Maintenance Medium:
Primary Hepatocyte Maintenance Supplement (Life Technologies Cat. No. CM4000)
Hepatocyte Growth Factor human—to 40 ng/mL final concentration (Sigma Cat. No. H5791)
Epidermal Growth Factor human—to 20 ng/mL final concentration (Sigma Cat. No. E9644)
Nicotinamide—to 2.5 µg/mL final concentration (Sigma Cat. No. N0636)
William's E Medium, no phenol red—to 500 mL total (Life Technologies Cat. No. A12176-01)
Primary Hepatocyte Culture Plates:
Collagen I, Coated Plate, 24 well (Life Technologies Cat. No. A11428-02)
Transfection Reagents:
HiPerFect Transfection Reagent (Qiagen Cat. No. 301704)
Opti-MEM I Reduced Serum Medium, no phenol red (Life Technologies Cat. No. 11058-021)

Protocol saRNA Annealing:

Each lyophilised saRNA strand was resuspended to 1 mM in RNase-free 10 mM Tris-HCl, 20 mM NaCl2, 1 mM EDTA. They were mixed well to complete resuspension. Equal volumes of sense and antisense strands were mixed together by gentle vortexing. The tube was placed with combined strands in a beaker of water heated to 95° C. The beaker was covered and allowed to cool to room temperature. Subsequent dilutions were performed using RNAse-free water. Generally for 24 well format, stock solution was diluted to 10 µM. Annealed saRNA were aliquoted and store at −20° C.

Thawing and Plating of Primary Hepatocytes:

CHRM and Plating medium were warmed to 37° C. in a water bath. Cryopreserved hepatocytes were thawed in a 37° C. water bath until no ice crystals remain. The vial was disinfected with 70% ethanol. In a sterile tissue culture hood, thawed hepatocytes were transferred directly into CHRM. Hepatocytes were centrifuged at 100×g (900 rpm in a Thermo F-G1 fixed-angle rotor) for 10 minutes at room temperature. Supernatant was carefully poured off into a waste bottle. Resuspend pellet in 1 mL of Plating Medium per 1×106 cryopreserved cells. Cells were counted using a NucleoCounter NC-200 aggregated cells assay to determine cell viability. 1.0×105 viable cells were plated in 500 µL Plating Medium per well in a 24 well plate.

Reverse Transfection (Immediately after Seeding):

For each well to be transfected, 3 µL of 10 µM saRNA was diluted in 94 µL Opti-MEM. For each well to be transfected, 3 µL HiPerFect was added and mixed well by vortexing. The transfection was incubated for 15 minutes at room temperature. 100 µL transfection complexes were added to each well for a final saRNA concentration of 50 nM.

The plate was incubated at 37° C. with 5% $CO_2$ in a humidified incubator. After 5 hours, medium was changed to 500 µL pre-warmed Maintenance Medium.

Forward Transfection (24 Hours after Seeding):

For each well to be transfected, 3 µL of 10 µM saRNA was diluted in 94 µL Opti-MEM. For each well to be transfected, 3 µL HiPerFect was added and mixed well by vortexing.

The transfection was incubated for 15 minutes at room temperature. During incubation, medium was changed to 500 µL fresh pre-warmed Maintenance Medium per well. 100 µL transfection complexes was added to each well for a final saRNA concentration of 50 nM. Plate was returned to incubator. After 24 hours, medium was changed to 500 µL of fresh pre-warmed Maintenance Medium. Peak gene activation occurred 72 hours after cell seeding. Cells and/or supernatant were collected for downstream analysis at this time.

TABLE 13-1

Relative expression of Aha1, albumin and CEBPA genes at 48 hr after aha1-siRNA, Fluc and AW51 transfection

| | Aha1 expression | Albumin expression | CEBPA expression |
|---|---|---|---|
| Untreated | 1 | 1 | 1 |
| Aha1 | 0.1 | 0.8 | 1.1 |
| Flu | 1.6 | 0.7 | 2.0 |
| AW51 | 2.2 | 0.9 | 3.2 |

TABLE 13-2

Relative expression of Aha1, albumin and CEBPA genes at 72 hr after aha1-siRNA, Fluc and AW51 transfection

| | Aha1 expression | Albumin expression | CEBPA expression |
|---|---|---|---|
| Untreated | 1 | 1 | 1 |
| Aha1 | 0.1 | 0.8 | 0.6 |
| Flu | 1.4 | 1.0 | 1.0 |
| AW51 | 1.3 | 5.0 | 2.9 |

Figure 9A:
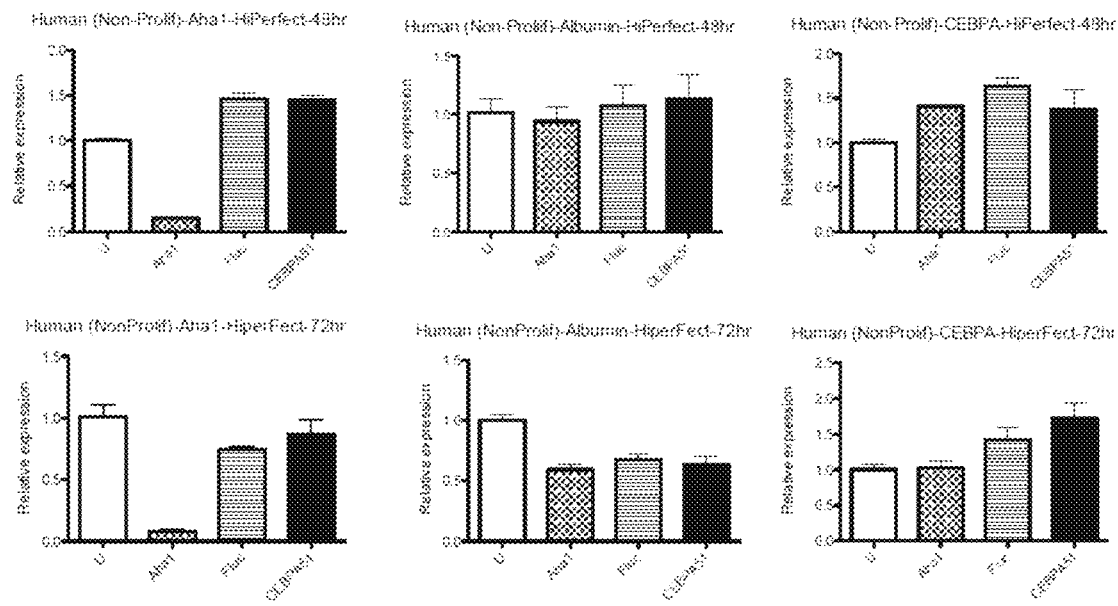
FIG. 9A shows AhA1, albumin and CEBPA relative expression levels in hepatocytes in non-proliferation media.

Tables 12-13 and FIG. 9A/9B show CEBPA-saRNA upregulates CEBPA and albumin in hepatocytes when they are exposed to proliferation media. Therefore, CEBPA-saRNA shows efficacy in proliferating cells. siRNA shows efficacy in both proliferating cells and non-proliferating cells.

Example 5. In Vitro Studies with CEBPA-saRNA

Biological Effects of CEBPA-51 in Hepatic Cell Lines:
Aim of Study:

The aim of this study was to measure the endogenous CEBPA transcript levels in HCC cell lines representative of highly differentiated HCC (HepG2, Hep3B) or of poorly differentiated HCC (PLCPRF5), and to determine the relative increase in CEBPA mRNA and C/EBP-α protein expression following transfection with CEBPA-51. In addition, the effect of C/EBP-α upregulation on cell proliferation was assessed.

Figure 10A:
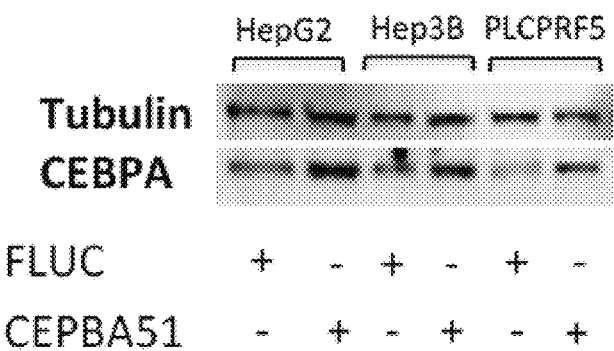
FIG. 10A shows representative Western Blot showing C/EBP-α protein levels in HepG2, Hep3B and PLCPRF5 cells following transfection with CEBPA-51.
Figure 10B:
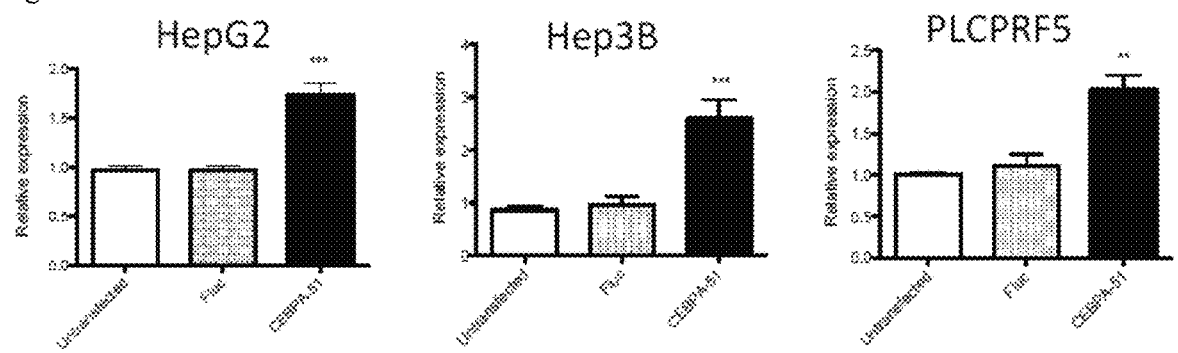
FIG. 10B shows relative CEBPA mRNA expression (*p=0.0002; p=0.0012) in HepG2, Hep3B and PLCPRF5 cells following transfection with CEBPA-51.
Figure 11A:
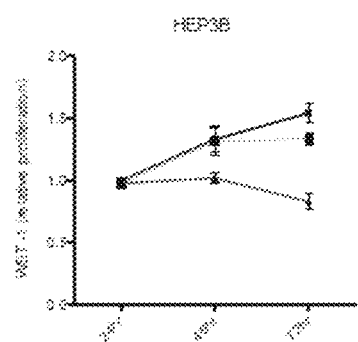
FIG. 11A-11C show WST-1 cell proliferation assay results of AW51 in HEP3B, HEPG2, and PLCPRF5 cell lines.
Figure 11B:
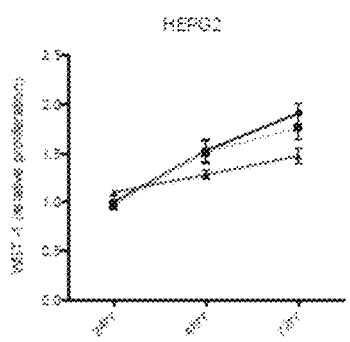
Figure 11C:
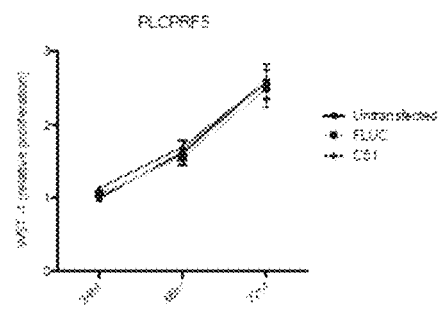
Figure 11D:
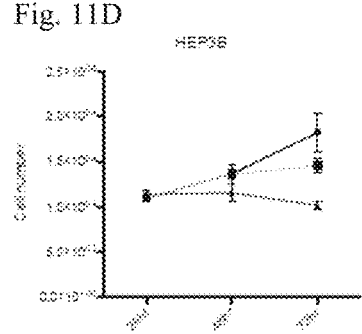
FIG. 11D-11F show sulforhodamine B (SRB) cell number assay results of AW51 in HEP3B, HEPG2 and PLCPRF5 cells.
Figure 11E:
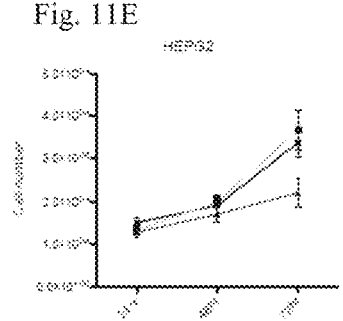
Figure 11F:
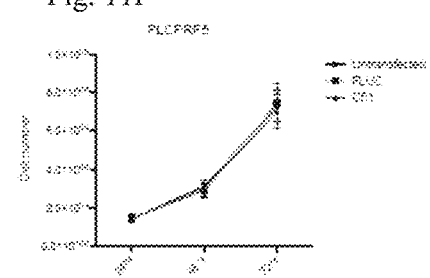

A panel of hepatic cell lines including HEP3B, HEPG, and PLCPRF5 were transfected with CEBPA-51. C/EBP-α protein was detected by Western Blot in cell lysates from 72 hours after transfection (quantification: RC-DC Bradford assay, reference protein: tubulin). The endogenous transcript levels of CEBPA were significantly higher in Hep3B and HepG2 cells compared to PLCPRF5 cells. Treatment with CEBPA-51 led to a significant increase in CEBPA mRNA transcript levels and increased C/EBP-α protein levels in all 3 tested HCC cell lines as compared to untransfected control and treatment with non-specific RNA duplex (siFLUC) (FIGS. 10A and 10B)

Cell proliferations were measured with WST-1 proliferation assay and SRB colorimetric assay. Results were shown in FIG. 11A-11F. CEBPA-51 reduced cell proliferation compared with controls in HEP3B and HEPG2 cell lines, but not in PLCPRF5 cells. Therefore, the capacity of CEBPA-51 to inhibit cell proliferation was confirmed in HepG2 and Hep3B cells. In contrast, PLCPRF5 cells were not affected by CEBPA-51 treatment.

Figure 12A:
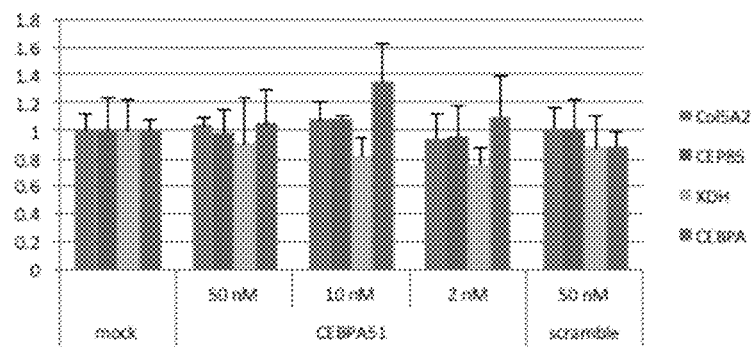
FIG. 12A-12B show AW51 off-targets measured in HuH7 cells (FIG. 12A) and Panc-1 cells (FIG. 12B).
Figure 12B:
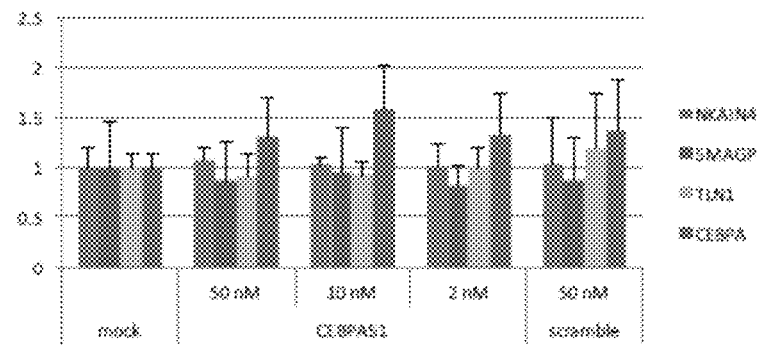

Off-Target Analysis of AW51:

Specificity of AW51 was confirmed from predicted off-target sites. Bioinformatics off-target analysis was conducted. AW51 has at least 2 mismatches of antisense strand with any other human transcript. Only 4 off-targets were predicted with 2 mismatches to antisense strand.—targets were measured in vitro in HuH7 cells and Panc-1 cells with 24 hour incubation. mRNA levels were normalized to gapdh and results were shown in FIG. 12A (HuH7 cells)-12B (Panc-1 cells). Expression pattern of potential off-targets following AW51 transfection showed that none of the genes is significantly affected by AW51.

Example 6. Mechanism Studies of CEBPA-saRNA

Strand Selection/Identification and Cleavage Analysis

Inverted abasic modifications at 5' terminus have been shown to prevent loading into the guide position in Ago2 complex. Antisense strand (AS) and sense strand (SS) of C/EBPA-saRNA were blocked with an inverted abasic modification at 5' end (b) and C/EBPA mRNA expression was measured and the impact of blocking AS and/or SS strands on C/EBPA mRNA expression was determined.

RNAi involves cleavage of target mRNAs. A non-cleaving sequence, mutations of central 3 base pairs, was tested (CEBPA-AW01-510500) to determine whether CEBPA-saRNA cleaves the target EST (AW665812). Mutation of the central 3 base pairs creates a non-cleavable saRNA, regardless of which strand serves as the guide.

All saRNA were synthesized and annealed in water. RP-HPLC has 90% purity. Sequences of the oligonucleotide samples were shown in the following table.

| Oligo ID | Sequence (SS on top) | SEQ ID No. | Notes |
|---|---|---|---|
| NC-500000 | 5'-ACUACUGAGUGACAGUAGAUU-3' | 95 | Non-targeting 'scramble' |
| | 3'-UUUGAUGACUCACUGUCAUCU-5' | 96 | (negative control) |

| Oligo ID | Sequence (SS on top) | SEQ ID No. | Notes |
|---|---|---|---|
| CEBPA-AW01-510000 (AW1-51, AW-51 or AW51) | 5'-GCGGUCAUUGUCACUGGUCUU-3' | 97 | Unmodified 'AW1-51' (positive control) |
| | 3'-UUCGCCAGUAACAGUGACCAG-5' | 98 | |
| CEBPA-AW01-510012 | 5'-bGCGGUCAUUGUCACUGGUCUU-3' | 99 | 5' Inverted abasic modification on SS only |
| | 3'-UUCGCCAGUAACAGUGACCAG-5' | 98 | |
| CEBPA-AW01-510013 | 5'-GCGGUCAUUGUCACUGGUCUU-3' | 97 | 5' Inverted abasic modification on AS only |
| | 3'-UUCGCCAGUAACAGUGACCAGb-5' | 100 | |
| CEBPA-AW01-510014 | 5'-bGCGGUCAUUGUCACUGGUCUU-3' | 99 | Inverted abasic modification on both SS and AS (negative control) |
| | 3'-UUCGCCAGUAACAGUGACCAGb-5' | 100 | |
| CEBPA-AW01-510500 | 5'-GCGGUCAUACACACUGGUCUU-3' | 101 | Mutated central three base pairs |
| | 3'-UUCGCCAGUAUGUGUGACCAG-5' | 102 | |

Critical Reagents

Transfection.

Cells were transfected at 100,000 cells per well in a 24-well dish at a final oligonucleotide concentration of 10 nM with 1 µL Lipofectamine 2000 (Life Technologies, Carlsbad, Calif.). The same conditions were used for forward and reverse transfections.

RNA Isolation.

Total RNA was isolated with the RNeasy Mini Kit according to the manufacturer's protocol (Qiagen, Venlo, Netherlands).

Complementary DNA (cDNA) Synthesis.

cDNA was synthesized using the Quantitect Reverse Transcription kit according to the manufacturer's protocol with 500 ng RNA in a 20 µL reaction (Qiagen).

Quantitative PCR.

Quantitative PCR was performed with QuantiFast SYBR Green PCR master mix (Qiagen) on an Applied Biosystems 7900HT real-time PCR system (Life Technologies) according to the manufacturer's protocol. Reactions were run in triplicate wells with 12.5 ng cDNA in each reaction.

Cell Lines

HepG2 hepatocellular carcinoma cells were maintained in RPMI medium supplemented with 10% Fetal BovineSerum and 1× L-glutamine-penicillin-streptomycin solution (Sigma-Aldrich, St. Louis, Mo.) in an incubator maintained at 37° C. with 5% $CO_2$.

Experimental Design

The experiment was performed in triplicate wells. HepG2 cells were seeded in 24-well dishes at 100,000 cells per well and were reverse transfected with 10 nM (f.c.) of each test item using Lipofectamine 2000. After an incubation period of 24 hours an additional forward transfection step was conducted with 10 nM (f.c.) of each test item using Lipofectamine 2000. Preliminary experiments determined that maximal saRNA activity is observed after a second transfection. Forty-eight hours after the second transfection, cells were lysed and collected to determine the CEBPA and albumin mRNA levels by quantitative reverse transcription-PCR (qRT-PCR).

Data Evaluation

Figure 13A:
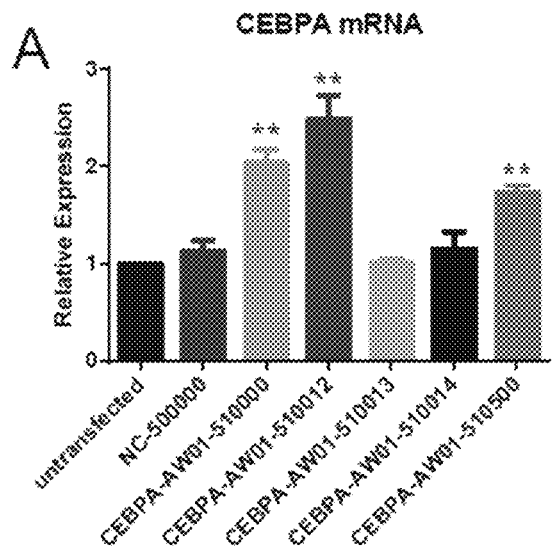
FIG. 13A-13B show CEBPA mRNA and albumin mRNA levels in in cells transfected with non-specific control (NC-500000), the unmodified AW1-51 sequence, the AW1-51 with internal sequence mutations (CEBPA-AW01-510500), the AW1-51 modified on SS (CEBPA-AW01-510012), and the AW1-51 modified on AS (CEBPA-AW01-510013), or modified on both strands (CEBPA-AW01-510014).
Figure 13B:
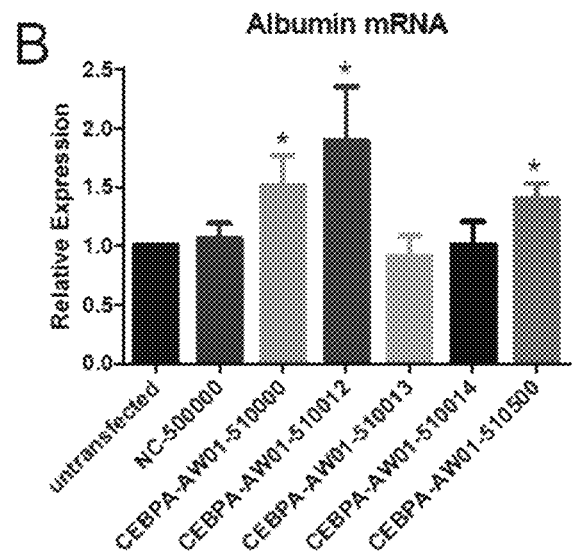

Real-time PCR results were analysed using the ΔΔCt method. Ct values were determined using SDS software (Life Technologies) and relative quantities were calculated by normalization to untransfected cells. Additionally, the housekeeping gene GAPDH served as an internal control. The transfection experiment was conducted with triplicates; determination of qPCR was performed in triplicates. Statistical significance was determined using a t-test with Welch's correction Results and Discussion Compared to untransfected cells, a 2-2.5-fold CEBPA mRNA upregulation was observed in cells transfected with the unmodified AW1-51 sequence, the AW1-51 modified on SS (CEBPA-AW01-510012), and AW1-51 with internal sequence mutations (CEBPA-AW01-510500) (FIG. 13A), all statistically significant at $p<0.01$. No upregulation of CEBPA mRNA was observed after transfection with non-specific control (NC-500000), the AW1-51 modified on AS (CEBPA-AW01-510013), or modified on both strands (CEBPA-AW01-510014). Consistent with this pattern of activation was the upregulation of albumin expression, a downstream target for CEBPA transcriptional activation, also statistically significant at $p<0.05$ (FIG. 13B).

Since 5' inverted abasic modification is known to block Ago2 from loading the strand, the oligo with this modification on both strands, CEBPA-AW01-510014, is expected to be inactive. This could be confirmed in the experiment. The observation of CEBPA activation with the inverted abasic modification on the SS but not on the AS therefore indicates that the AS is the guide strand, which is loaded into Ago2 for triggering CEBPA mRNA expression.

Cleavage of the target by Ago2 is inhibited by central mismatches in sequence between the guide strand and target sequence (genomic DNA or antisense RNA transcripts arising from the gene). The CEBPA-saRNA sequence containing central mutations (CEBPA-AW01-510500) showed no difference in CEBPA activation compared to non-mutated oligo, indicating that cleavage of the CEBPA sequence is not necessary for saRNA activity.

Conclusion

It was demonstrated that the antisense strand of AW1-51 is the guide strand that is responsible for saRNA activity. Further, it was shown that the 5' inverted abasic modification on the sense strand did not have any influence on CEBPA gene activation. In addition, the target antisense RNA cleavage by Ago2 was not necessary for triggering the saRNA activity.

Example 7. CEBPA-51 saRNA Activity in Primary Human Hepatocytes

Figure 9B:
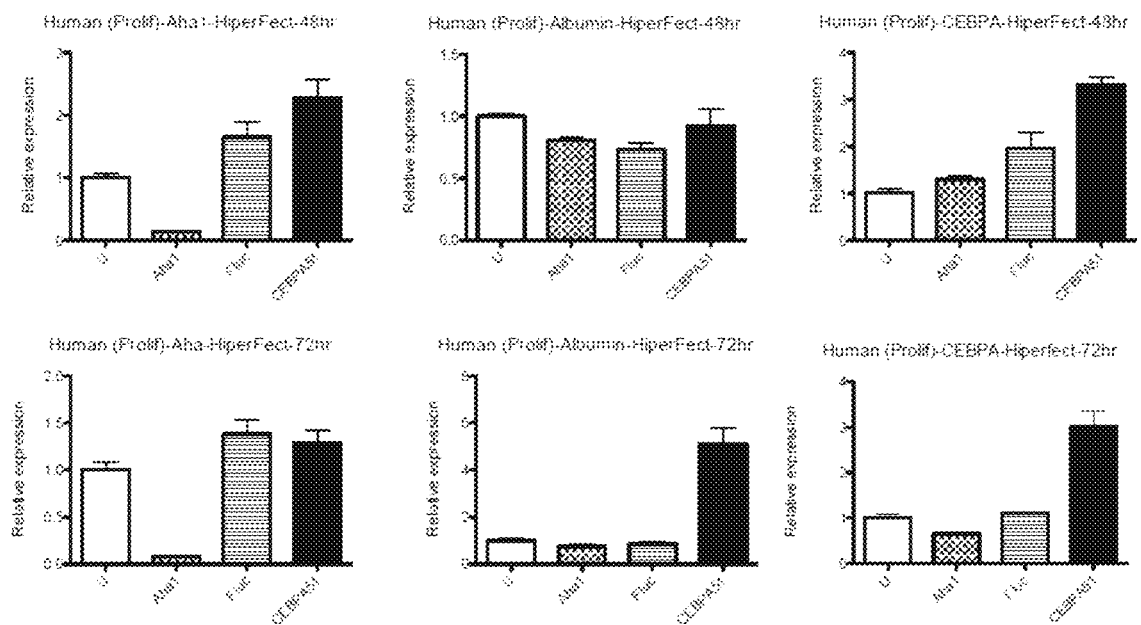
FIG. 9B shows AhA1, albumin and CEBPA relative expression levels in hepatocytes in proliferation media.

As shown previously, CEBPA-saRNA upregulates CEBPA mRNA and albumin mRNA in proliferating but not quiescent hepatocytes (FIG. 9A and FIG. 9B). In this study, the effect of CEBPA-saRNA on proliferating hepatocytes was evaluated again (FIG. 14) and the effect on albumin secretion (FIG. 15) and downstream markers (FIG. 16A-FIG. 16F) were also studied.

The effect of CEBPA-51 in normal human primary human hepatocytes was evaluated. Since primary hepatocytes in culture do not proliferate, this study demonstrates that CEBPA-51 upregulates CEBPA transcript and albumin in primary hepatocytes that are induced to proliferate in the presence of growth factors and cytokines. Furthermore, this study shows CEBPA-51 causes regulation of factors crucial for efficient liver function; these include liver alanine glyoxylate aminotransferase, ornithine transcarbamylases, albumin, CYP3A4 and HNF4A.

The objective of this study was to establish the efficacy of CEBPA-51 in normal human primary hepatocytes on CEBPA and albumin expression. Additionally, factors that are important for liver function were also screened to assess if CEBPA-51 conferred a favorable effect. These factors included:

Alanine-glyoxylate aminotransferase (AGXT). AGXT expression is liver specific and is required for the metabolic function of hepatocytes.

Albumin. Serum albumin is the main protein of human blood plasma and is exclusively synthesized by the liver. Its main function is to regulate the colloidal osmotic pressure of blood as well as acting as a carrier molecule for lipidsoluble hormones, bile salts, unconjugated bilirubin, apoprotein, calcium and certain drugs (warfarin, clofibrate etc).

Cytochrome P450 3A4 (CYP3A4). CYP3A4 is a member of the cytochrome P450 family of oxidizing enzymes involved in drug metabolism. CYP3A4 is predominantly found in the liver. There are several other members of this family of Cytochrome P450, however CYP3A4 is the most common and versatile member.

Ornithine transcarbamylase (OTC). OTC is an enzyme that catalyses the reaction between carbamoyl phosphate and ornithine to form citrulline and phosphate in the mitochondria as part of the urea cycle.

Hepatocyte nuclear factor 4-alpha (HNF4A). HNF4A is a liver specific transcription factor recognized as being a master regulator of liver-specific gene expression for genes involved in lipid transport and drug and glucose metabolism.

To confirm target engagement of CEBPA-51, CEBPA and albumin transcript levels were also confirmed along with the liver function probes. Additionally an ELISA with albumin specific antibodies was carried out to measure albumin secretion in the cell culture medium following transfection with CEBPA-51.

Materials and Methods

The test item for this experiment was CEBPA-51, which is the API of MTL-CEBPA. In addition, a non-targeting duplex, siFLUC, was also used as a negative control and Aha-1 siRNA as a transfection efficiency control. These RNA oligonucleotides (see table below) were commercially synthesized (ST Pharm, Seoul, South Korea, certificate of analysis in appendix), annealed, and stored in 10 μM aliquots at −20° C. in RNase-free $H_2O$.

| Oligo ID | Sequence (SS on top) | SEQ ID No. | Notes |
|---|---|---|---|
| siFLUC | 5'-mCmUmUAmCGmCmUGAGmUAmCmUmUmCGAdTp5dT-3'<br>3'-dTpsdTGAAmUGCGAmCUCAmUGAAGCU-5' | 103<br>104 | Non-targeting control |
| Aha1-siRNA | 5'-GGAmUGAAGmUGGAGAmUmUAGmUdTpsdT-3'<br>3'-dTpsdTCCUAmCUUCAmCCUCUAAmUCA-5' | 105<br>106 | Transfection efficiency control |
| CEBPA-51 | 5'-bmGmCGmGUCAUUmGUCAmCUGGUCmUmU-3'<br>3'-mUmUCGCCAGUAACAGUGACCAG-5' | 107<br>108 | API of MTL-CEBPA | b: 5' inverted abasic sugar cap
m: 2'-O-methyl modified base
d: deoxyribonucleotide
ps: phosphorothioate Critical Reagents Primary Hepatocyte Thawing Medium.

Cryopreserved Hepatocyte Recovery Medium (CHRM) was used for thawing each vial (Life Technologies, CM7000).

Primary Hepatocyte Plating Medium.

Fetal bovine serum, heat inactivated-50 ml (Life Technologies, 16140-071); Insulin-Transferrin-Selenium (100×)-5 ml (Life Technologies, 41400-045); HEPES (1M)-5 ml (Life Technologies, 15630-056); L-Glutamine-Penicillin-Streptomycin solution-5 ml (Sigma, G1146); Dexamethasone-40 ng/ml final concentration (Sigma, D8893); Phenol red free William's E Medium (Life Technologies, A12176-01).

Primary Hepatocyte Maintenance Medium.

Primary Hepatocyte Maintenance Supplement (Life Technologies, CM4000); Human Hepatocyte Growth Factor-40 ng/ml final concentration (Sigma, H5791); Epidermal Growth Factor—20 ng/ml final concentration (Sigma, E9644), Nicotinamide—2.5 ug/ml final concentration (Sigma N0636); Phenol red free William's E Medium—500 ml (Life Technologies, A12176-01).

Transfection.

Cells were transfected at 100,000 cells per well in a 24-well collagen coated dish at a final oligonucleotide concentration of 50 nM with 3 μL of HiPerFect transfection reagent (Qiagen, 301704). The cells were incubated in plating media for 5 hours to allow monolayer formation before replacing with maintenance media. For the second (forward) transfection, the same conditions were used as for reverse transfection. Maintenance media was used for the remaining duration of the experiment.

RNA Isolation.

Total RNA was isolated with the RNeasy Mini Kit according to the manufacturer's protocol (Qiagen, Venlo, Netherlands).

Complementary DNA (cDNA) Synthesis.

cDNA was synthesized using QuantiTect Reverse Transcription kit (Qiagen) according to the manufacturer's protocol with 500 ng RNA in a 20 μL reaction.

Quantitative PCR.

Quantitative PCR was performed with Quantitect SYBR Master Mix (Qiagen) on an Applied Biosystems 7900HT real-time PCR system (Life Technologies) according to the manufacturer's protocol. Reactions were run in triplicate wells.

Albumin Enzyme Linked Immunosorbent Assay (ELISA).

Culture media from primary cells incubated within each experimental groups were measured for albumin content using a human albumin ELISA quantitation set (Bethyl Laboratories Inc, USA) following the manufacturer's instructions. Human specific antibody against albumin was immobilized onto each well of a Costar-3596-96 well plate- (flat bottom, TC treated, nonpyrogenic, polystyrene, sterile plates (Corning, USA). Reagents prepared in-house included:

ELISA plate coating buffer. 0.05M Carbonate-Bicarbonate, (Sigma, C-3041) pH 9.6.

ELISA wash buffer. 50 mM Tris; 0.14M NaCl; 0.05% Tween 20 (Sigma, P1379) pH 8.0).

ELISA blocking buffer. 50 mM Tris; 0.14M NaCl; 1% BSA (Sigma, A-4503), pH8.0).

Sample/Conjugate buffer. 50 nM Tris; 0.14M NaCl; 1% BSA (Sigma, A-4503); 0.05% Tween 20 (Sigma, P1379). Enzyme substrate buffer. 3,3', 5, 5' Tetramethybenzidine (Sigma, T0440). ELISA Stop solution. (Sigma, S5814).

Cell Lines

Human normal primary hepatocytes were purchased from Life technologies (HMCPTS). All repeats were derived from the same batch (HU8200-A).

Experimental Design

Relative Gene Expression

For relative quantitation of target transcript, the experiment was performed in triplicate. Human primary hepatocytes were seeded in 24 collagen-coated well-dishes (Life Technologies, A11428-02) at a density of 100,000 cells per well in primary hepatocyte plating medium following by an initial transfection with 50 nM (f.c) of CEBPA-51 whilst the cells were still in suspension (reverse transfection). The cells were then allowed to form a monolayer for 5 hours before the plating media was replaced with maintenance media. 24 hours following reverse transfection, a second (forward) transfection was carried out with 50 nM of CEBPA-51. Fresh maintenance media was replaced every 24 hour until harvest point at 72 hours following reverse transfection where total RNA extracted from the cells were screened for target gene expression.

ELISA

The culture media at the 72-hour time point of this study was collected for an ELISA using human specific anti-Albumin (Bethyl Laboratories, A80-129A) immobilized onto the wells of a 96 well plate. A standard curve of known albumin amounts (Bethyl Laboratories, RS10-110-4) was added at 10 μg/ml; 400 ng/ml; 200 ng/ml; 100 ng/ml; 50 ng/ml; 25 ng/ml; 12.5 ng/ml and 6.25 ng/ml. The samples and the known control amounts were left to incubated on the ELISA plates on a rotating plate for 3 hours at room temperature (20-25° C.). After the appropriate number of washes as detailed in the manufacturer's protocol, HRP detection antibody (Bethyl Laboratories, A80-129P) was added at a concentration of 1:150,000) and incubated for 1 hour on a rotating plate for 3 hours at room temperature (20-25° C.). After 5 washes, the TMB substrate was added and allowed to incubate at room temperature until the enzymatic color reaction developed. The reaction was stopped by the addition of the ELISA Stop solution where the absorbance at optical density of 450 nm was measured on a plate reader.

Data Evaluation

Relative Expression

Real-time PCR results were analysed using the Livak method ($2\text{-}\Delta\Delta CT$) (Livak K & Schmittgen T D, 2001). Ct values are determined using SDS software (Life Technologies) and relative quantities are calculated by normalization to untransfected cells. The housekeeping gene GAPDH is served as an internal control. The transfection experiment was conducted in triplicate; determination of qPCR was performed in triplicates. Statistical significance was determined using a non-parametric t-test with Welch's correction.

ELISA

A standard curve to determine the amount of human albumin the unknown samples were prepared as the average absorbance value minus the blank value for each standard concentration on the vertical (Y) axis versus the corresponding human albumin concentration on the horizontal (X) axis using a curve-fitting software (Excel). The amount of human albumin concentration in the unknown samples was calculated using the human albumin concentration (X axis) that correlated with the absorbance value (Y axis) obtained for the unknown sample.

Results and Discussion

Figure 14A:
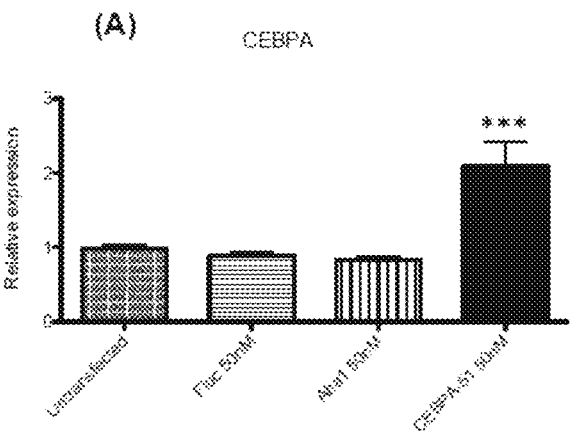
FIG. 14A demonstrates CEBPA51 upregulates CEBPA in primary human hepatocytes.
Figure 14B:
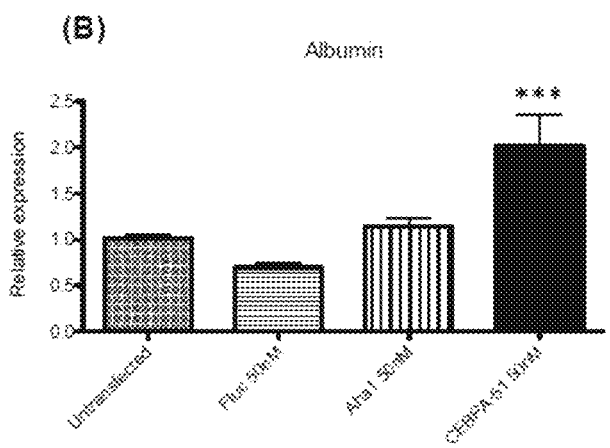
FIG. 14B demonstrates CEBPA51 increases albumin secretion in primary human hepatocytes.
Figure 14C:
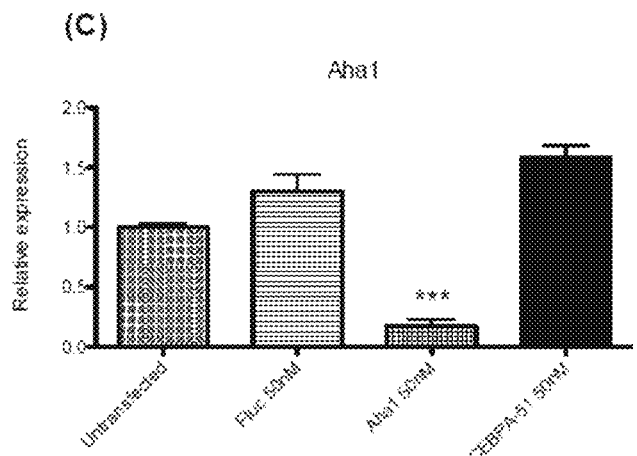
FIG. 14C shows Aha1 levels. Aha1 siRNA was used as a positive control to determine transfection efficiency in primary cells. All statistical significance follows a non-parametric Mann Whitney U test at 95% confidence interval.

Transfection of CEBPA-51 to primary human hepatocytes induces a significant 2.5 fold increase in CEBPA transcript levels as well as albumin, FIGS. 14A and 14B. To confirm efficient transfection efficiency, Aha1-siRNA was used as a control and demonstrated a 7 fold reduction in target transcript, FIG. 14C.

Biological Effect of CEBPA-51 in Normal Human Primary Hepatocyte

Figure 15:
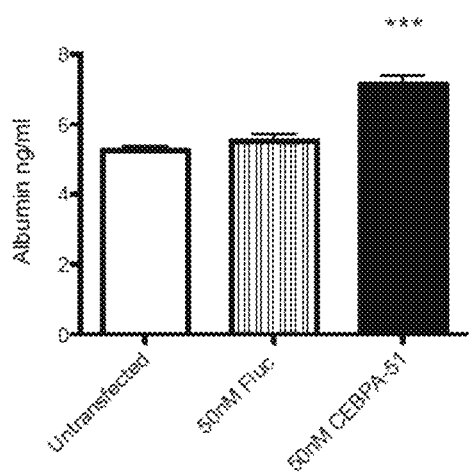
FIG. 15 shows albumin ELISA results from media of cultured primary human hepatocytes transfected with CEBPA51.

After confirming increase in endogenous expression levels of CEBPA transcript following CEBPA-51 transfection, the cultured media from the cells were measured for levels of secreted albumin. An ELISA assay using human specific anti-Albumin antibody confirmed a significant 1.3 fold increase in secretion of albumin from the hepatocytes (FIG. 15).

Figure 16A:
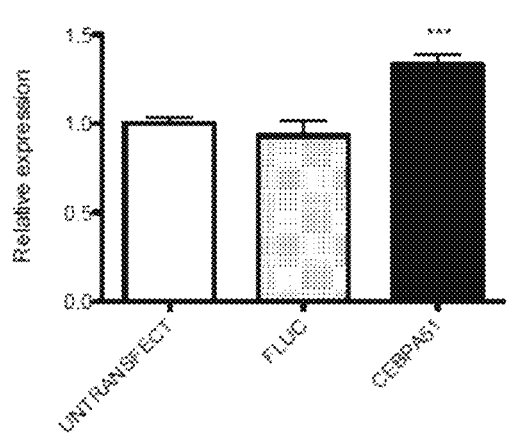
FIG. 16A-16F show relative expression of (A) Alanine-glyoxylate aminotransferase (AGXT); (B) Albumin; (C) Cytochrome P450 3A4 (CYP3A4); (D) Ornithine transcarbamylase (OTC); (E) Hepatocyte nuclear factor 4-alpha (HNF4A) and (F) CEBPA transcript levels detected in primary human hepatocytes transfected with CEBPA-51.
Figure 16B:
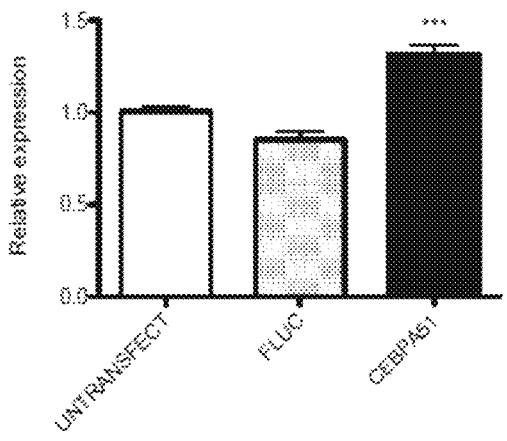
Figure 16C:
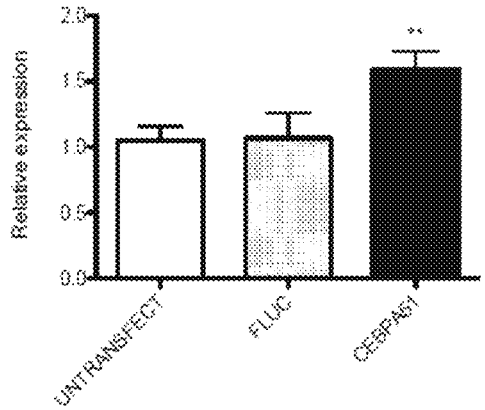
Figure 16D:
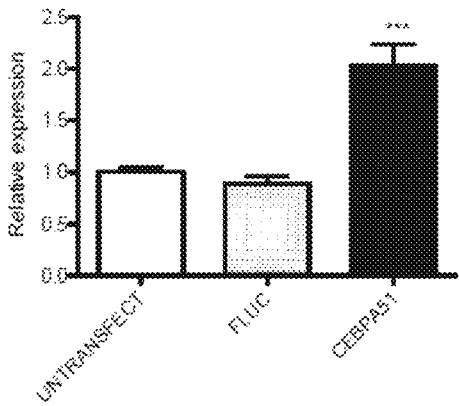
Figure 16E:
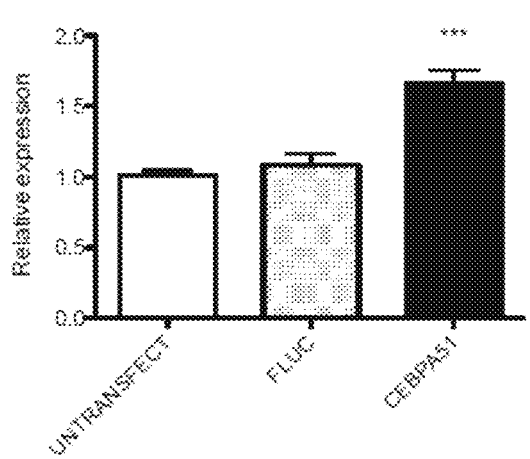
Figure 16F:
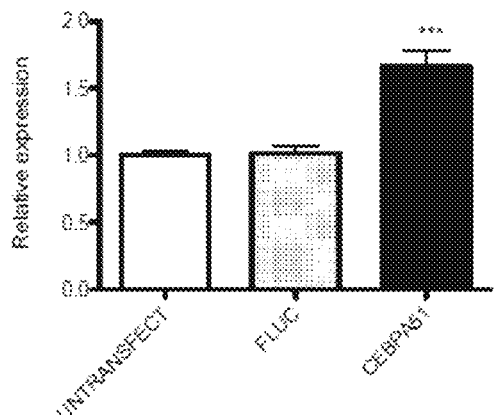

To assess if increased CEBPA and Albumin transcript levels also mirrored a positive regulation in factors important for liver function; the expression levels of the followed transcripts were assessed in the primary hepatocytes transfected with CEBPA-51: FIG. 16A Alanine-glyoxylate aminotransferase (AGXT) increased 1.4 fold; FIG. 16B albumin increased 1.5 fold; FIG. 16C Cytochrome P450 3A4 (CYP3A4) increased 1.5 fold; FIG. 16D Ornithine transcarbamylase (OTC) increased 2.3 fold; FIG. 16E Hepatocyte nuclear factor 4-alpha (HNF4A) increased 1.5 fold; and FIG. 16F CEBPA increased 1.6 fold.

Conclusion

CEBPA is recognised as an important liver enriched transcription factor. Its biological function becomes more evident in knock out and knock-in transgenic animal studies. This study demonstrates the transcriptional response of CEBPA-51 induced upregulation of CEBPA and its downstream effectors that were more relevant for hepatocyte function in normal human primary hepatocytes. It is found that normal primary hepatocytes respond favorably to CEBPA-51 transfection with a significant increase in albumin secretion and a significant upregulation of detoxification enzymes.

Example 8. CEBPA-saRNA saRNA Activity in Cynomogus Fibroblasts

Cell Lines

Primary cynomolgus hepatocytes were obtained from Primacyt Cell Culture Technology (Schwerin, Germany). CYNOM-K1 cynomolgus embryonic fibroblast cells (Public Health England, Salisbury, UK) were maintained in MEM medium supplemented with 10% Fetal Bovine Serum, 1% non-essential amino acids (Life Technologies), and 1× L-glutamine-penicillin-streptomycin solution (Sigma-Aldrich, St. Louis, Mo.) in an incubator maintained at 37° C. with 5% $CO_2$. The ability of CEBPA-51 to upregulate CEBPA mRNA in cynomolgus cells was assessed to confirm cross-reactivity. First, the cynomolgus genomic sequence at the CEBPA-51 target site was verified. The sequence was accessed from publically available databases as well as verified by direct sequencing of gDNA-derived PCR products. CEBPA51 target sequence was used as a query search on the *Macaca fascicularis* (cynomolgus monkey) genome using BLAST. The query mapped to the genomic location of CEBPA and there were no mismatches between the sequence of CEBPA-51 and the genomic target site. To verify this sequence information, gDNA was isolated from primary cynomolgus hepatocytes and a PCR product of the target site was generated for direct sequencing. The resulting sequence aligns with no mismatches to the published cynomolgus genomic sequence and the CEBPA-51 target site.

Figure 17:
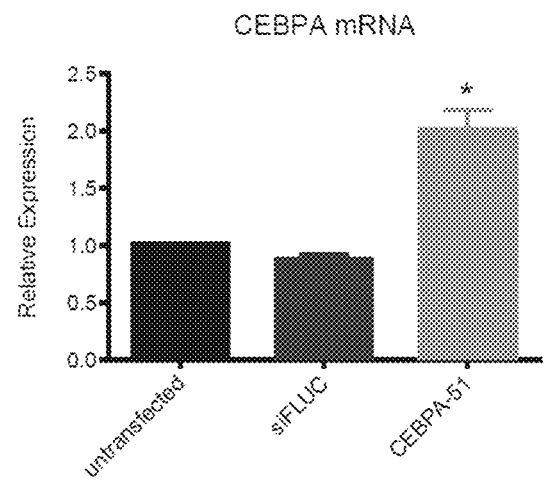
FIG. 17 shows CEBPA mRNA expression in cynomogus (CYNOM-K1) fibroblasts 24 hours after second transfection of CEBPA-51.

After confirming the cynomolgus genomic target sequence, CEBPA-51 was transfected into cynomolgus fibroblasts to determine if CEBPA-51 is cross-reactive and able to upregulate CEBPA mRNA in other cells than hepatocytes. mRNA levels in untransfected cells, siFLUC transfected cells and CEBPA51 transfected cells were measured. The experiment was performed in triplicate. CYNOM-K1 cells were seeded in 24-well dishes at 100,000 cells per well and were reverse transfected with 20 nM (f.c.) of each test item using Lipofectamine 2000. After an incubation period of 24 hours an additional forward transfection step was conducted with 20 nM (f.c.) of each test item using Lipofectamine 2000. Preliminary experiments determined that maximal saRNA activity is observed after a second transfection. Twenty-four hours after the second transfection, cells were lysed and collected to determine the CEBPA mRNA levels by quantitative reverse transcription-PCR (qRT-PCR). As shown in FIG. 17, compared to untransfected cells, a 2-fold CEBPA mRNA upregulation was observed 24 hours after cells were transfected the second time with CEBPA-51, while no upregulation was seen with siFLUC. This upregulation was statistically significant at $p<0.05$.

Therefore, cross-reactivity of CEBPA-saRNA was confirmed in cynomogus cell line. It was demonstrated that the genomic sequence of cynomolgus contains no mismatches with the CEBPA-51 target sequence according to the BLAST database. This was further verified by sequencing of primary cynomolgus gDNA. Cross-reactivity of CEBPA-51 was then confirmed by transfection in cynomolgus fibroblasts and the observation of CEBPA gene activation.

Example 9. In Vitro Stability Analysis in Rat, Cynomolgus Monkey and Human Serum This study is an in vitro stability analysis investigating the stability of CEBPA-51 and the liposomal-formulated MTL-CEBPA in rat, cynomolgus monkey and human plasma anticoagulated with EDTA-K2 over 120 min at 37° C.

3 μL of a 50 uM CEBPA-51 solution in PBS or 3 μL of the MTL-CEBPA solution were mixed with 30 μL of plasma and incubated in plasma for 0, 5, 10, 20, 30, 60 and 120 min at 37° C. Incubation of 3 μL CEBPA-51 solution in PBS or 3 μL MTL-CEBPA solution in 30 μL PBS served as control for unspecific degradation. Incubation was done in sealed 96-well PCR plates in an Eppendorf Mastercycler. Incubation was stopped at the indicated time points by a proteinase K treatment to digest all present nucleases in the plasma samples. After proteinse K treatment, CEBPA-51 is stable in the samples and in the lysis buffer containing SDS CEBPA-51 is released from the LNP formulation in MTL-CEBPA.

Samples were subsequently analysed by a generic AEX-HPLC method under denaturing conditions at elevated pH (11) and 40° C. on a ThermoFisher DNA Pac PA200 column (4×250 mm). A sodium bromide gradient from 250 to 620 mM in 18 min at a flow rate of 1 mL/min was used to separate and elute the RNA strands from the HPLC column. Detection was conducted with a UV detector at 260 nm.

Under these conditions the two single strands of the CEBPA-51 alone or CEBPA-51 released from MTL-CEBPA were separated from each other and from the degradation products and could be evaluated as distinct peaks. As no reference single strands were available and AEX-HPLC could not be combined with mass spectrometry, an assignment of the two single strands was not possible. Therefore, the two strands were labelled $1^{st}$ and $2^{nd}$ strand depended on the retention time during gradient elution. For data evaluation, only the peak area of the two single strands of CEBPA-51 alone and CEBPA-51 in MTL-CEBPA were evaluated. Peak area at T=0 was set to 100% and all other time points were normalized to peak area at T=0 for plasma of each species. The data were then reported as % intact strand normalized to T=0.

Results

Figure 18A:
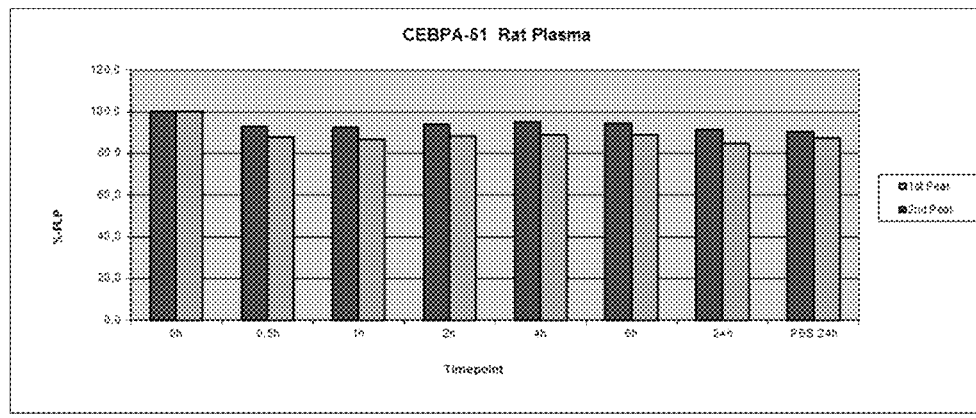
FIG. 18A-18C show stability of CEBPA-51 in rat plasma, human plasma and cynomolgus monkey plasma.
Figure 18B:
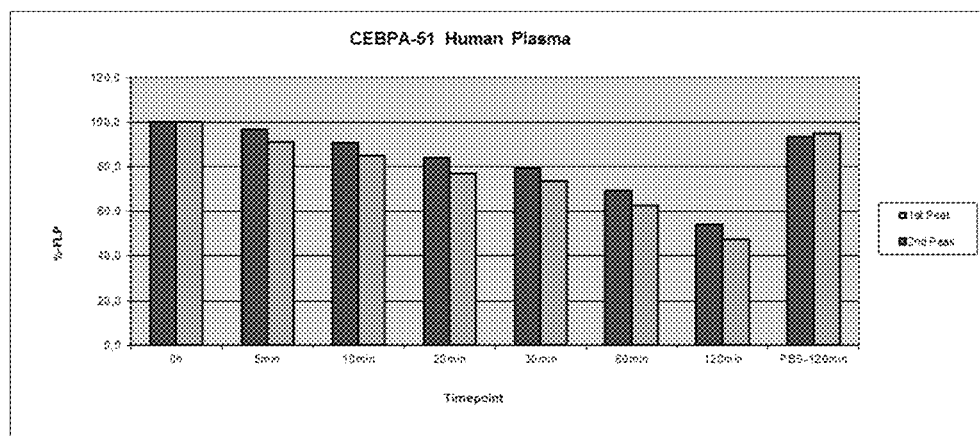
Figure 18C:
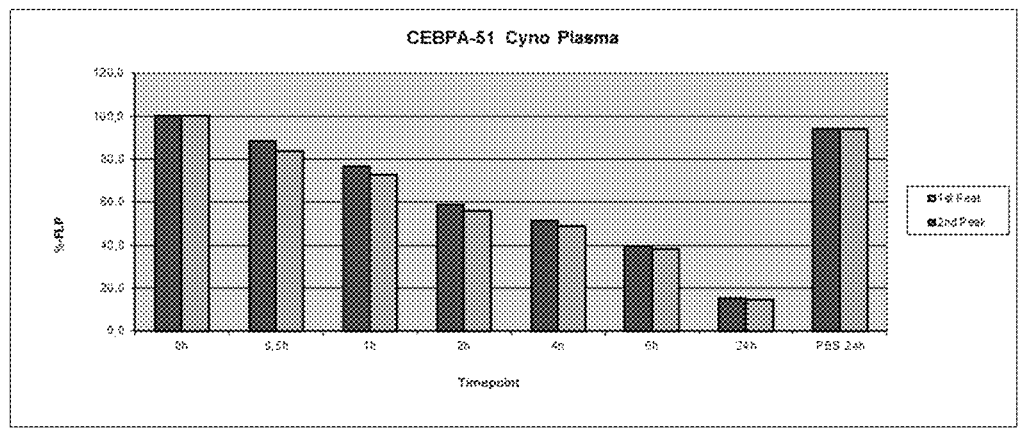

CEBPA-51 with No Formulation:

CEBPA-51 is relatively stable in rat plasma anticoagulated with EDTA and 15% degradation of the first and 8% of the second peak was observed (see FIG. 18A). CEBPA-51 is degraded by ~50% over 2 hours in human plasma (see FIG. 18B). CEBPA-51 is least stable in cynomolgus monkey plasma with ~85% of both strands degraded within 2 hours (see FIG. 18C).

Data demonstrate that CEBPA-51 alone was less stable in human and cynomolgus monkey plasma, but relatively stable over two hours in rat plasma. Not willing to be bound to any theory, in rat plasma, degradation of RNA is mainly induced by 3'-exonuclaese that depends on divalent cations. Therefore, the use of EDTA as anticoagulant blocks this degradation pathway efficiently and CEBPA-51 is relatively stable. In contrast, the main degradation pathway in human and cynomolgus monkey plasma is dependent on RNase A. The activity of this endonuclease is independent from divalent cations and therefore the CEBPA-51 without protection by liposomal formulation is degraded in plasma of these species.

Figure 19A:
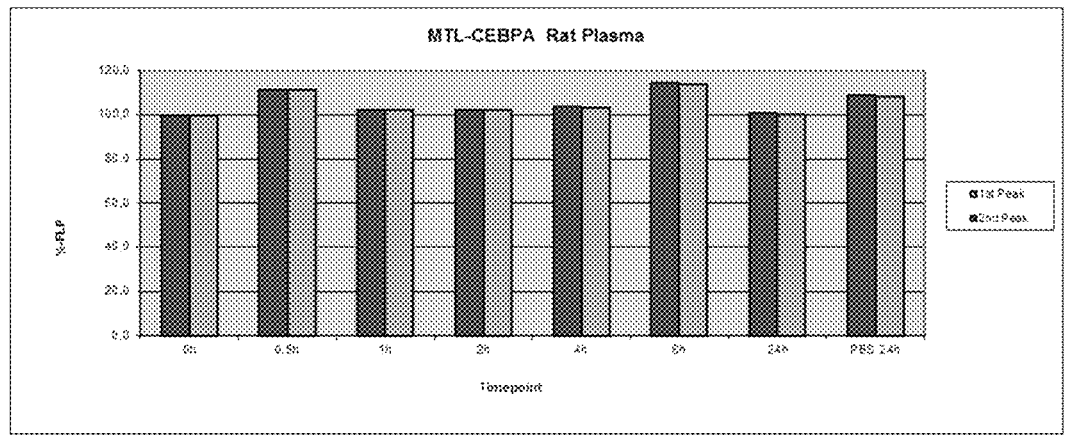
FIG. 19A-19C show stability of MTL-CEBPA in rat plasma, human plasma and cynomolgus monkey plasma.
Figure 19B:
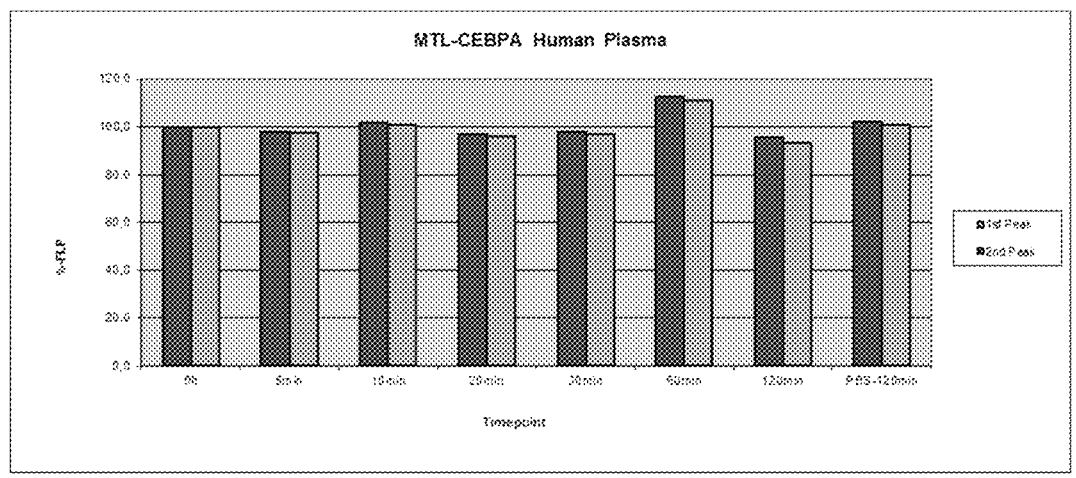
Figure 19C:
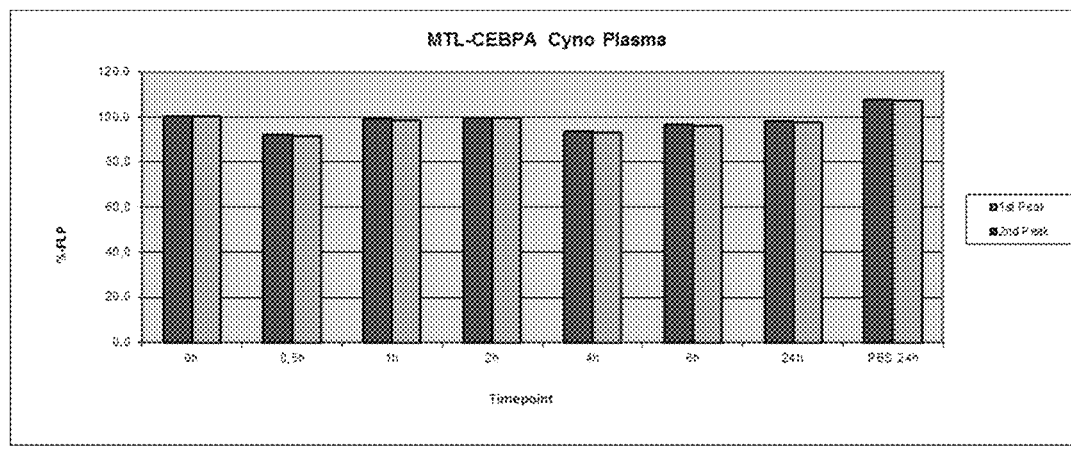

Liposomal Formulated CEBPA-51:

CEBPA-51 in MTL-CEBPA was stable over 2 hours in plasma of all species and no significant degradation was observed (see FIGS. 19A, 19B, and 19C). This indicates that the LNP formulation in MTL-CEBPA is stable over 2 hours and completely protects CEBPA-51 from degradation in plasma.

From the results, it can be concluded that MTL-CEBPA formulation is intact over at least 2 hours in plasma.

Example 10. In Vivo Pharmacokinetic Study in Rat

This study is a PK study investigating CEBPA-51 and the liposomal-formulated MTL-CEBPA in rat plasma samples after one single IV application of 2.175 mg/kg MTL-CEBPA in Group 1 and 1.5 mg/kg CEBPA-51 in Group 2. Each group comprised of 3 male rats. Blood was collected after 0.25, 0.5, 1, 2, 3, 6, 12, 24 and 48 hr for both groups.

An aliquot of the plasma was homogenized by a proteinase K treatment in an SDS containing buffer system. After proteinase K digestion, the SDS was precipitated with 3M KCl and removed by centrifugation. The supernatant was heated in presence of a complementary 15-mer fluorescently labelled peptide nucleic acid (PNA)-probe to specifically form stable duplexes between the PNA and the antisense strand of CEBPA-51 alone or CEBPA-51 released from liposomal formulated MTL-CEBPA. PNA formed duplexes between CEBPA-51 (referred to in this example as the parent compound), but also with metabolites or impurities from the synthesis. The formed duplexes were then analysed by non-denaturing Anion Exchange-High Performance Liquid Chromatography (AEX-HPLC) coupled to a fluorescence detector. The metabolites or synthetic impurities were separated from the main compound by AEX-HPLC.

The concentrations of CEBPA-51 were calculated using external calibration curves generated from known concentrations of the parent compound spiked into untreated plasma lysates. The total metabolite/synthetic impurity level for each sample was determined by subtraction of the peak area for the parent compound from the total peak area. The resulting peak area was then quantified against the external calibration curve.

Results

Figure 20A:
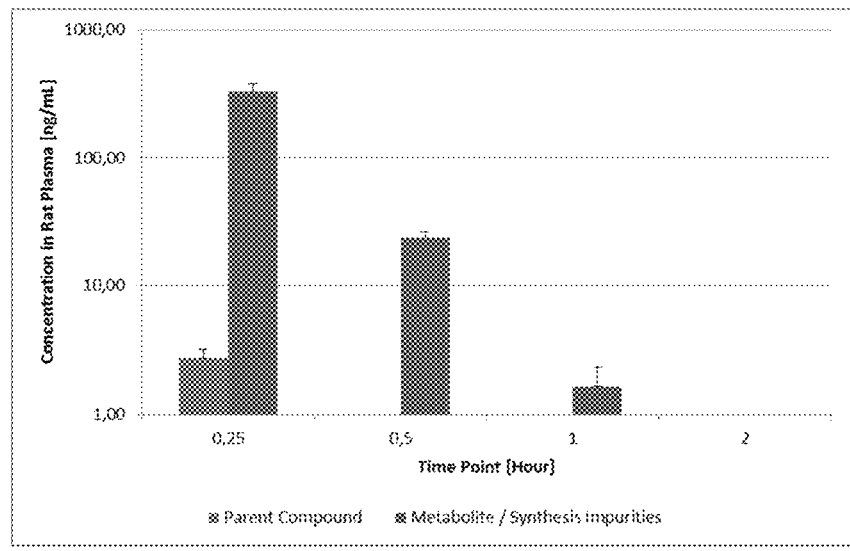
FIG. 20A shows mean concentration of CEBPA51 and metabolites/impurities after IV administration of 1.5 mg/kg CEBPA51 in rat plasma.
Figure 20B:
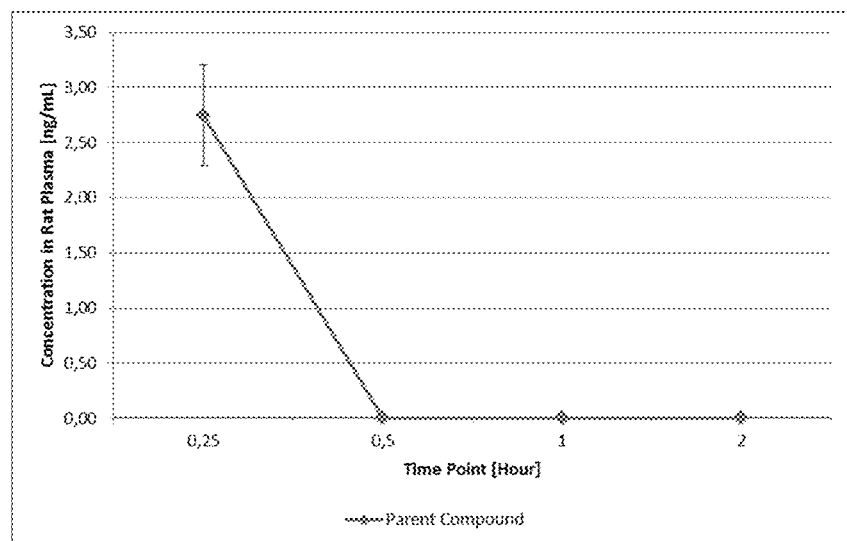
FIG. 20B shows mean concentration of intact CEBPA51 in rat plasma after IV administration of 1.5 mg/kg CEBPA51. 0.5 hours after administration the concentration of intact CEBPA51 is below detection limit.
Figure 21A:
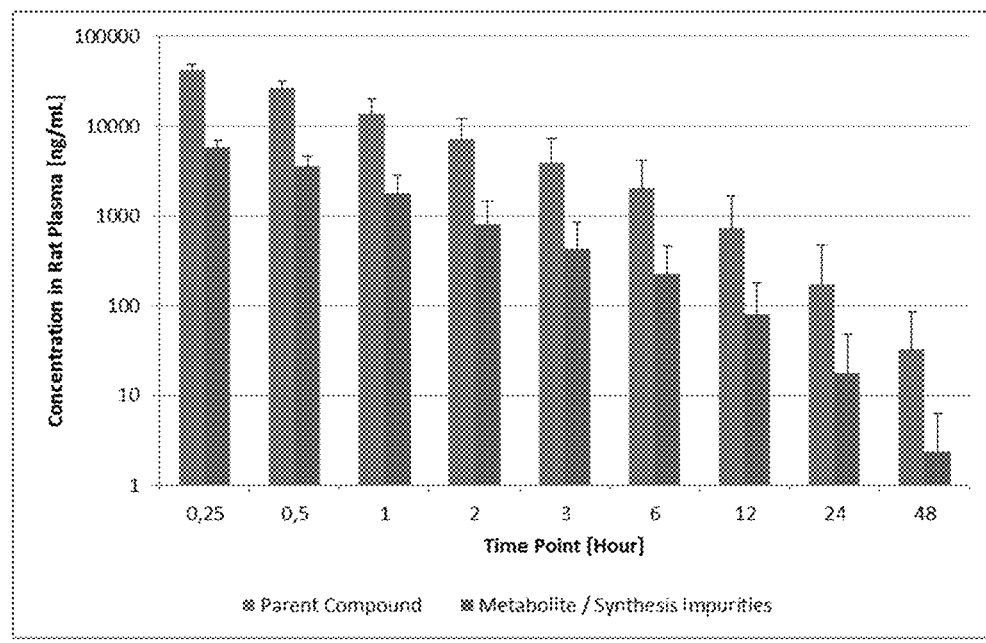
FIG. 21A shows mean concentration of CEBPA51 after IV administration of 2.175 mg/kg MTL-CEBPA in rat plasma. Comparison of intact parent compound to metabolites of CEBPA51 shows a high stability of MTL-CEBPA in plasma.
Figure 21B:
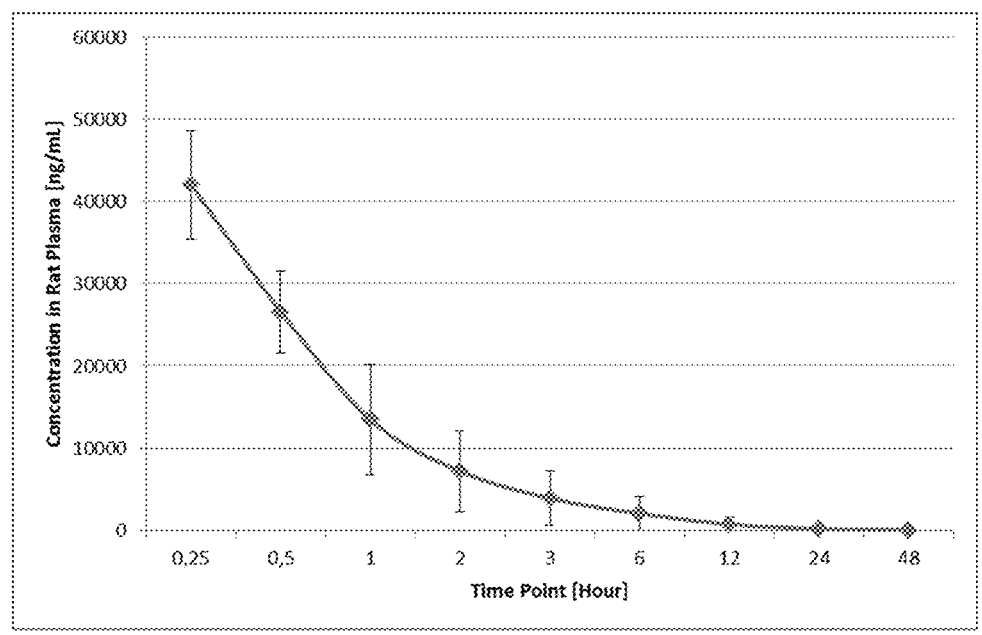
FIG. 21B shows mean concentration of intact CEBPA51 in rat plasma after IV administration of 2.175 mg/kg MTL-CEBPA. 48 hours after administration CEBPA51 is still found in plasma.

CEBPA-51 with No Formulation:

A high degradation of the parent compound was observed in plasma obtained from rats treated with CEBPA-51. The parent compound was only detected at the first sampling time-point (15 minutes post administration, see FIGS. 20A and 20B). Metabolites were detected up to 60 minutes, but below detection limit (BDL) 2 hours post administration.

of parent compound increased over the "metabolites/impurities", as the signals were below detection limit for most of the minor site peaks in the chromatograms (see FIG. 21A). 48 hours post administration CEBPA-51 was still detectable in rat plasma (see FIGS. 21A and 21B).

This study suggests that the observed metabolites after IV administration of MTL-CEBPA, which account for about 10% of detected RNA, might originate from the RNA synthesis process rather than from strong metabolism. However, as comparison to the un-encapsulated compound (CEBPA-51) is not feasible due to plasma instability and extremely fast clearance of the unformulated CEBPA-51, metabolic conversion of the dsRNA cannot be excluded.

Example 11. In Vivo Studies of CCL4 Induced Liver Failure/Fibrosis with CEBPA-saRNA Liver fibrosis is the pathologic result of chronic inflammatory liver diseases such as chronic viral hepatitis (e.g. hepatitis B and C), alcohol abuse, drug overload/toxicity, cholestatic liver injury, congenital abnormalities or autoimmune attack of hepatocytes. It is characterized by hepatic stellate cell (HSC) proliferation and differentiation into myofibroblast-like cells which results in the deposition of extracellular matrix (ECM) and collagen. Carbon tetrachloride (CCL4) induced hepatic fibrosis is a well-established and widely accepted experimental model in rodents for the study of liver fibrosis and cirrhosis. Chronic administration of carbon tetrachloride to rats induces severe disturbances of hepatic function together with histologically observable liver fibrosis.

A 10-week long study was carried out with CEBPA51 formulated with amphoteric liposomes (NOV340 Smarticle liposomes provided by Marina Biotech), referred to as MTL-CEBPA. CEBPA51 (XD-03934) has the same sequence as AW51, but with 2'O-Me and 5' inverted abasic modifications on sense strand. Lipids in NOV340 include Mochol, Chems, DOPE, and POPC. Liver failure in Sprague Dawley rats was induced by i.p. injection of carbon tetrachloride (CCL4) twice weekly. Male Sprague Dawley rats with a starting body weight of 120-150 g were used. The animals were administered intraperitoneal (i.p.) injection of CCL4: Olive oil (1:1 ratio) twice a week with 2 ml/kg for 2 weeks, followed by 1 ml/kg i.p, twice weekly for 8 weeks. The animals were weighed twice weekly and maintained in a controlled environment with 22±3° C. temperature, 50±20% humidity, a light/dark cycle of 12 hours each and 15-20 fresh air changes per hour. Animals were housed group wise (3 animals/cage), autoclaved corncob was used as a bedding material and were fed, ad libitum, with certified Irradiated Laboratory Rodent Diet (Nutrilab brand, Tetragon Chemie Pvt. Ltd, Bangalore) during the study period.

| CEBPA51 antisense (X11283) | GACCAGUGACAAUGACCGCuu | SEQ ID No. 109 |
|---|---|---|
| CEBPA51 sense (X11273) | (invabasic)gcGgUCAUUgUCAcUGGUCuu (lower case stands for 2'O-Me modifications) | SEQ ID No. 110 |

Liposomal Formulated CEBPA-51:

The MTL-CEBPA formulation showed a high stability in plasma. The parent compound was found in all plasma lysates obtained from rats treated with MTL-CEBPA. The ratio between parent compound and metabolites was about 9:1, i.e. approx. 88% of intact parent in the liposomal formulated groups. At later time points, the relative content The rats were randomized biased on bilirubin, body weight and AST. They were grouped into Group 1: Sham control; Group 2: Path control −1; Group 3: Path control −2; Group 4: Test compound −0.3 mg/kg; Group 5: Test compound −1 mg/kg; Group 6: Test compound −3 mg/kg. Test compound=MTL-CEBPA. Rats in Groups 4-6 were treated with Test compound starting from week 8 for 2 weeks via tail vein injection up to 3 mg/kg together with continued injection of CCL4. Rats in Group 3 were administered NOV340/siFLUC at 3 mg/kg. Test compound i.v. injections happened at week 8, week 8.5, week 9, and week 9.5.

| Gr. No | Group | Duration of CCL4 administration | Treatment | Route | Dosing Regimen | n | Euthanized at |
|---|---|---|---|---|---|---|---|
| 1 | Sham | — | — | — | — | 5 | week 10 |
| 2 | Path Control-1 | CCL4 administered for 8 weeks | — | — | — | 9 | week 10 |
| 3 | Path Control-2 | CCL4 administered for 10 weeks | Vehicle | i.v. | week 8, 8.5, 9 and 9.5 | 9 | week 10 |
| 4 | Test Compound | CCL4 administered for 10 weeks | 0.3 mg/kg | i.v. | week 8, 8.5, 9 and 9.5 | 9 | week 10 |
| 5 | Test Compound | CCL4 administered for 10 weeks | 1 mg/kg | i.v. | week 8, 8.5, 9 and 9.5 | 9 | week 10 |
| 6 | Test Compound | CCL4 administered for 10 weeks | 3 mg/kg | i.v. | week 8, 8.5, 9 and 9.5 | 9 | week 10 |

Figure 22A:
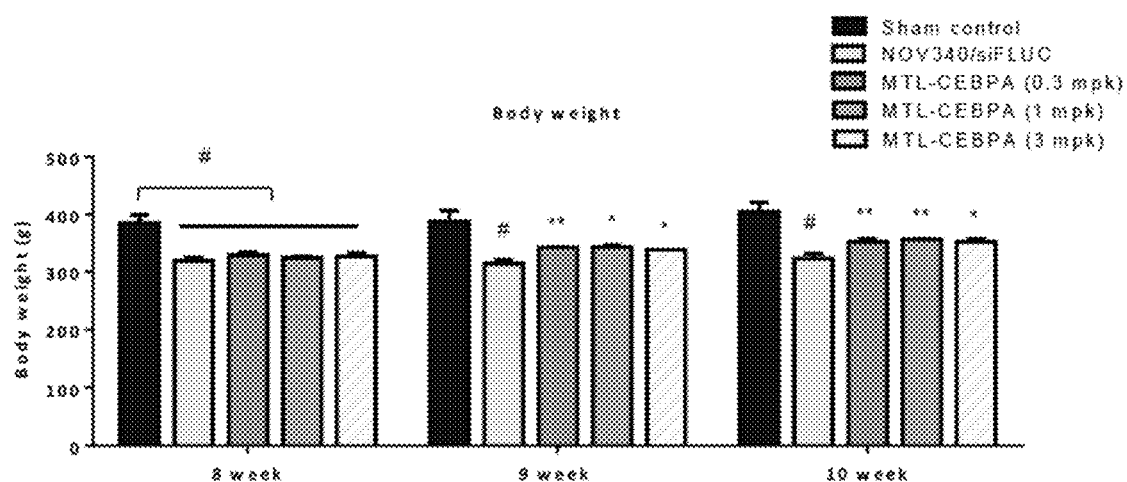
FIG. 22A-22K show body weight, ALT level, AST level, ALP level, GGT level, bilirubin level, total protein level, albumin level, prothrombin time, ammonia level, and hydroxyproline level changes in CCL4-treated rats after administration of different doses of MTL-CEBPA.
Figure 22B:
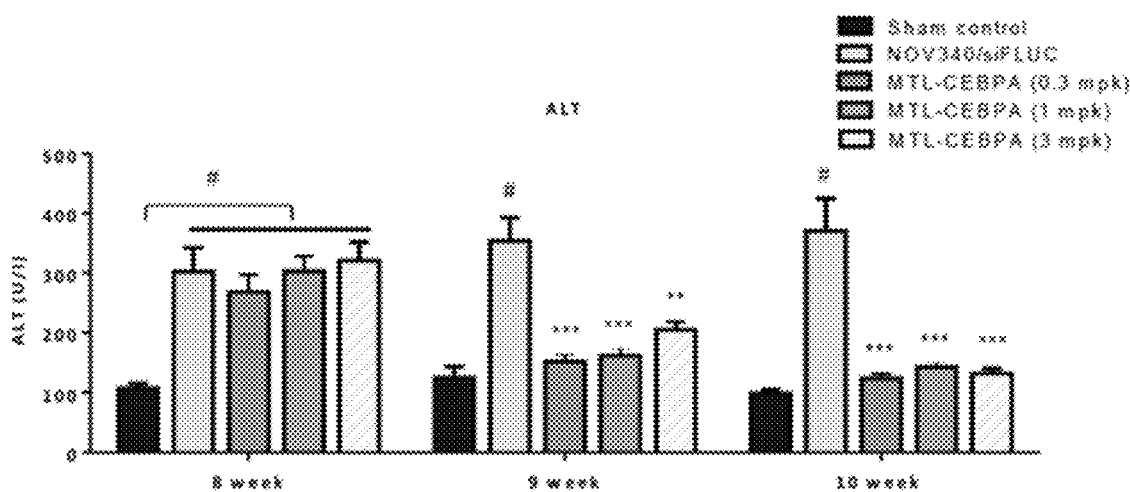
Figure 22C:
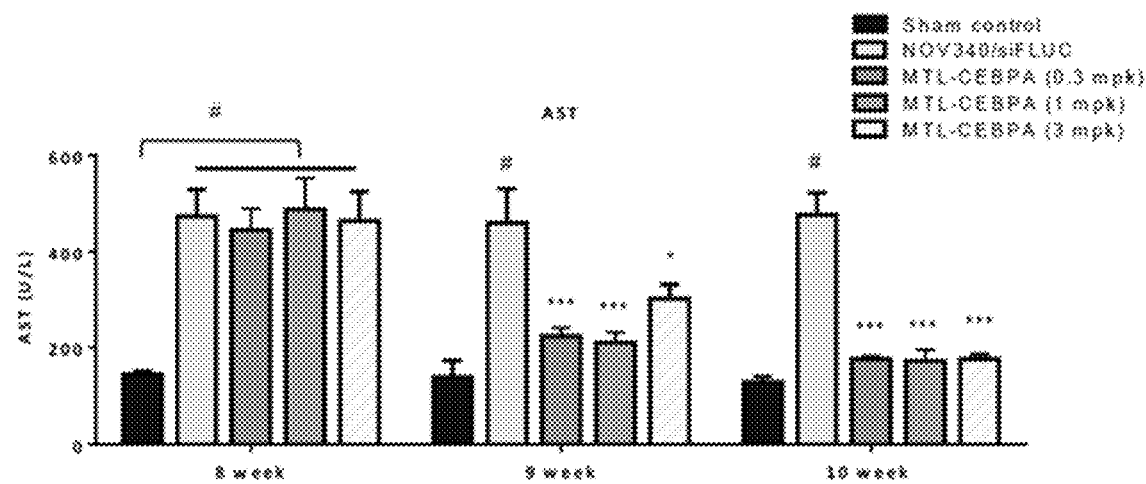
Figure 22D:
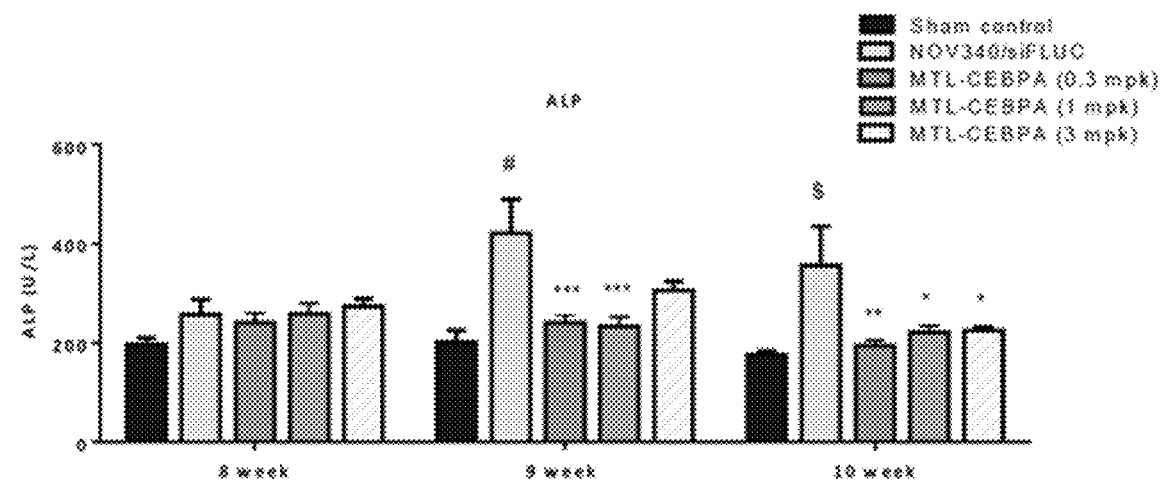
Figure 22E:
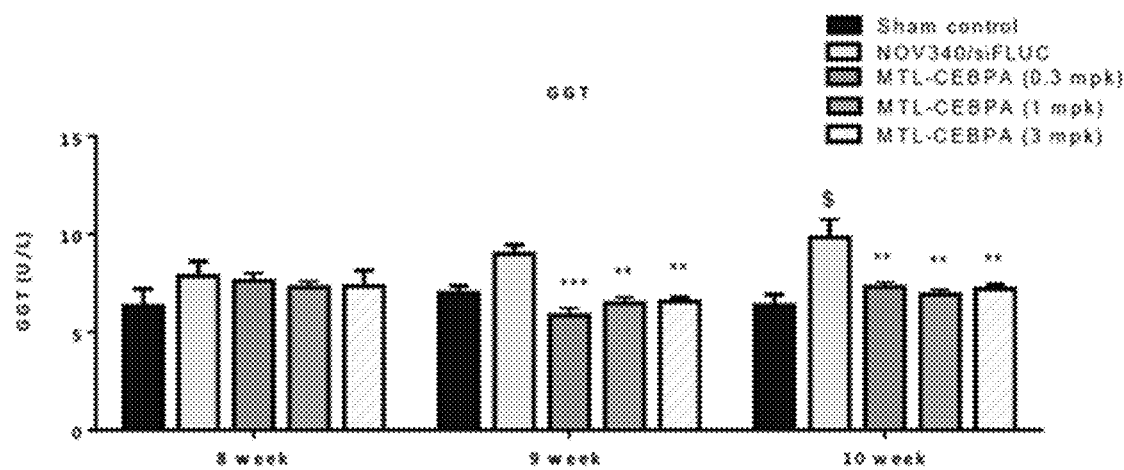
Figure 22F:
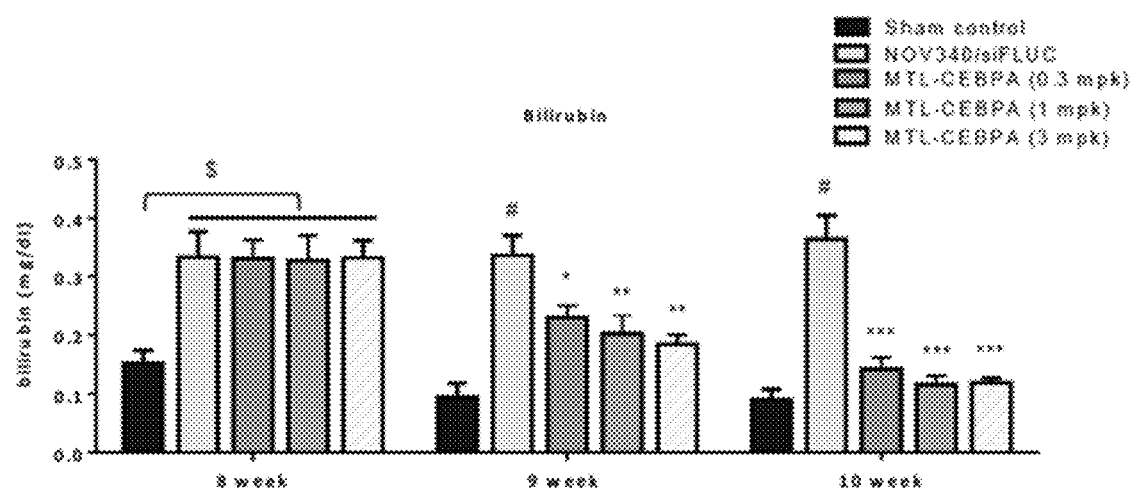
Figure 22G:
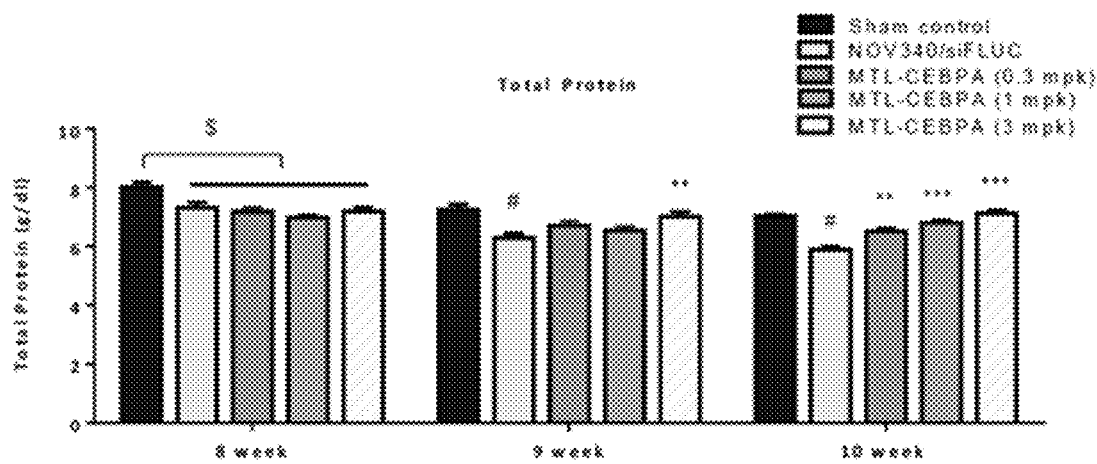
Figure 22H:
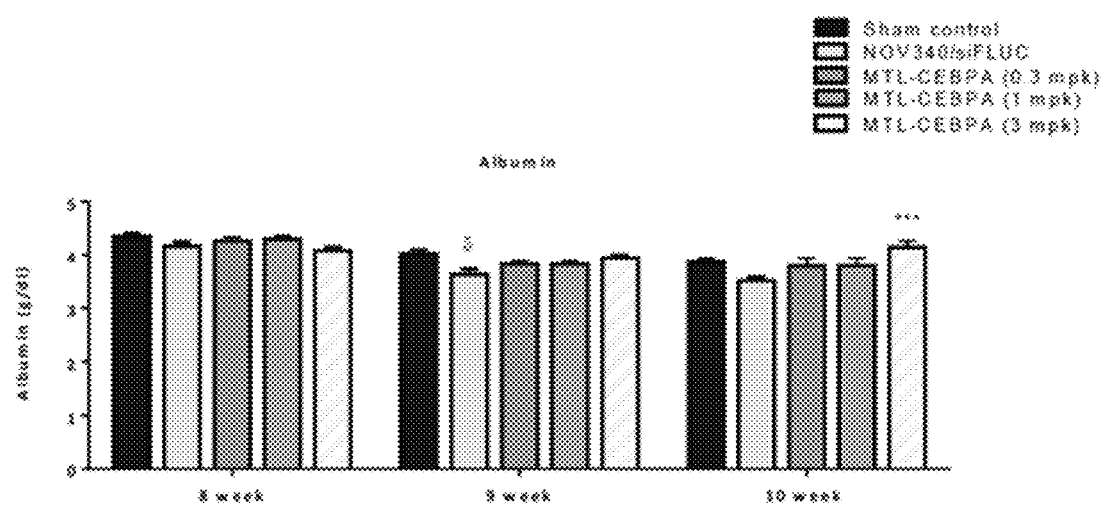
Figure 22I:
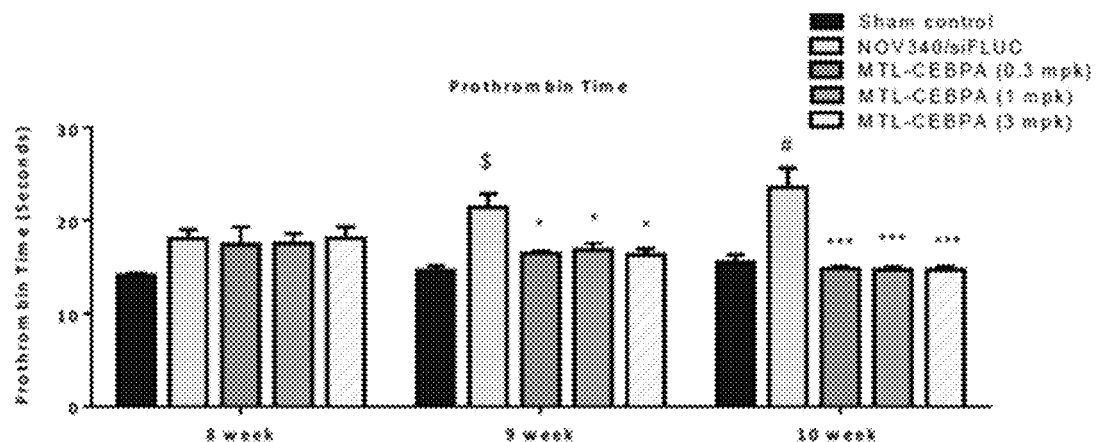
Figure 22J:
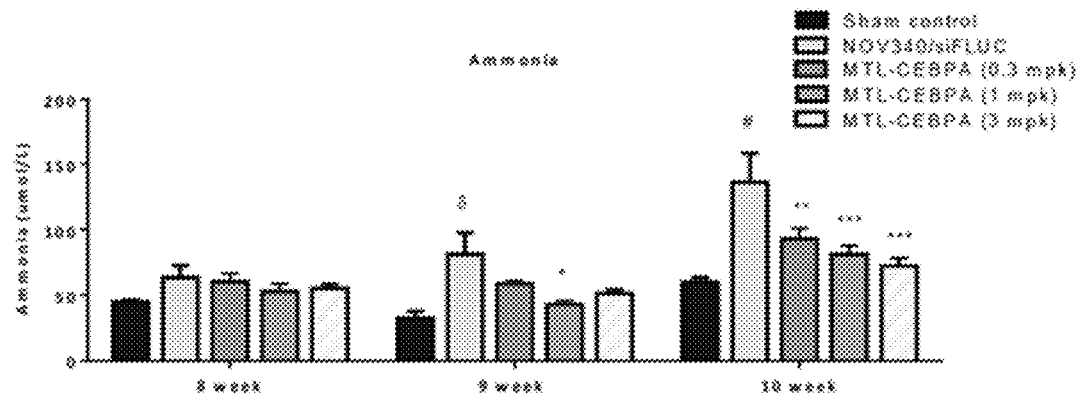
Figure 22K:
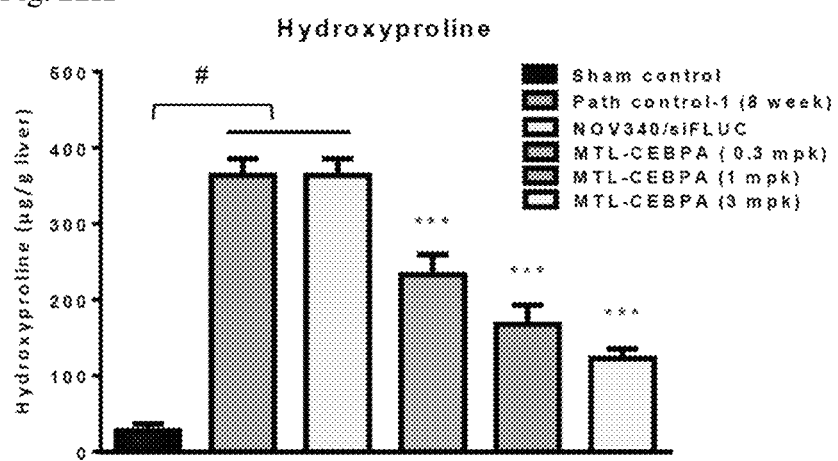

Liver function tests, hydroxyproline levels and histopathology in Path Control −1 group were done to assess fibrosis status after 8 weeks of CCL4 administration. Liver function tests, hydroxyproline levels and histopathology in Path Control −2 group were done to assess fibrosis status after 10 weeks of CCL4 administration. The efficacy of Test compounds was assessed by its ability to limit progression of disease or reverse fibrosis. Parameters assessed were body weight (once every three days), liver function test (day 0, day 42 (week 6), day 56 (week 8), day 63 (week 9) and day 70 (week 10)), histopathology at the end of the study and hydroxyl proline assay at the end of the study (week 8 for Path control −1 and week 10 for rest of the groups). Histopathology included H&E staining, Mason Trichrome staining, and Sirius red staining done for all the animals at the end of the study. Liver function test included Alanine aminotransferase (ALT), Aspartate aminotransferase (AST), Alkaline phosphatase (ALP), Gamma-glutamyl transfertase (GGT), total bilirubin (TBIL), Total protein (TP), Albumin, Globulin and Albumin/Globulin ratio measured at week 0, 4, 6, 8, 9 and 10. Parameters at week 8, week 9 and week 10 shown in FIG. 22A-22K demonstrated reversal and near normalisation of clinically relevant parameters including bilirubin (75% decrease, FIG. 22F), circulating alanine and aspartate aminotransferase (60% decreases, FIG. 22B and FIG. 22C) and prothrombin time (20% decrease, FIG. 22I). In addition, there were significant increases in serum albumin (FIG. 22H) and total protein (FIG. 22G) and significant decreases in alkaline phosphatase (ALP) (FIG. 22D) and gamma-glutamyl-transpeptidase (GGT) (FIG. 22E). Liver hydroxyproline was significantly decreased in a dose-dependent manner (FIG. 22K). A significant increase in body weight was observed with no associated toxicity (FIG. 22A).

Figure 23:
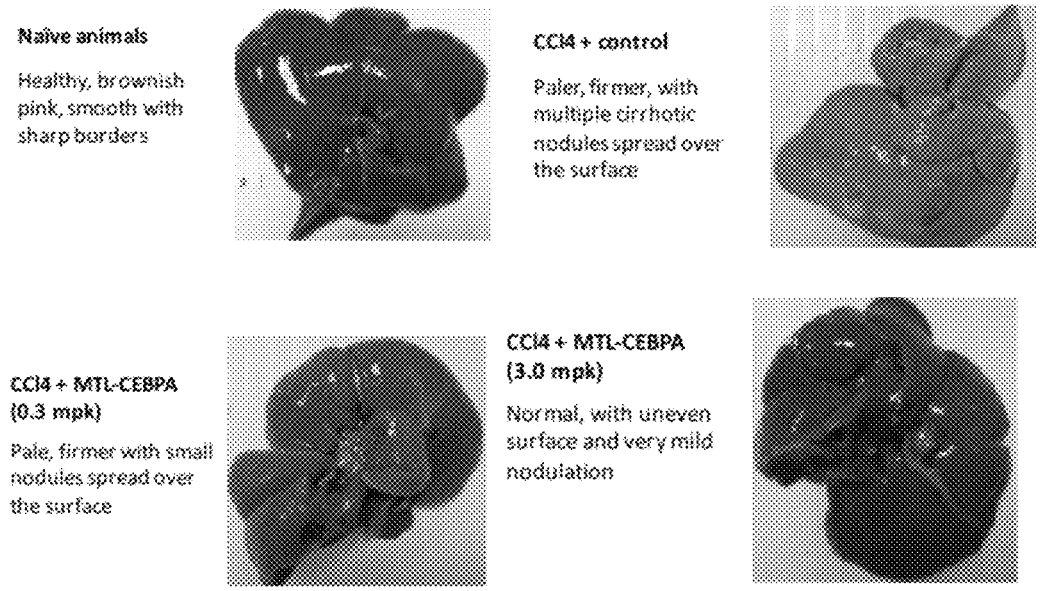
FIG. 23 is gross pathology of a healthy liver and livers treated with CCL4 and control, CCL4 and 0.3 mg/kg MTL-CEBPA, and CCL4 and 3.0 mg/kg MTL-CEBPA.

Pathology results were shown in FIG. 23. Naïve animals had healthy livers are brownish pink and are smooth with sharp borders. Livers of animals treated with CCL4 and vehicle control had paler firmer livers with multiple cirrhotic nodules spreading over the surface. Livers of animals treated with CCL4 and MTL-CEBPA (0.3 mg/kg) had pale firmer livers with small nodules spreading over the surface. The liver color was darker than the liver color of the CCL4 and vehicle control group. Livers of animals treated with CCL4 and MTL-CEBPA (3 mg/kg) had a normal brownish color with uneven surface and very mild nodulation.

Figure 24A:
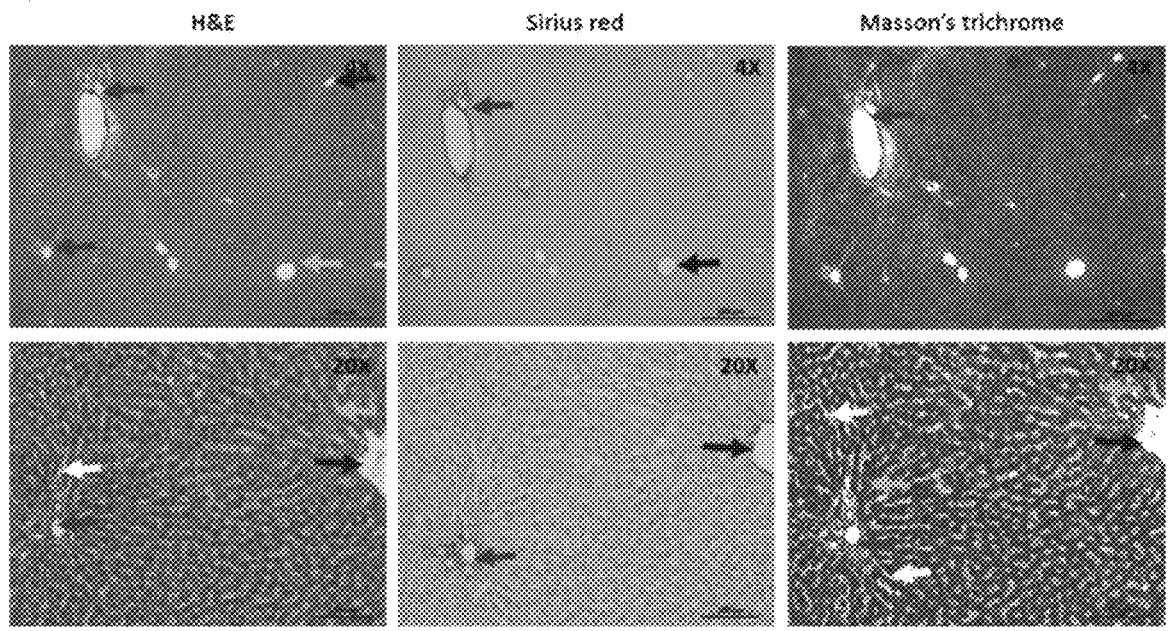
FIG. 24A-24C show histology staining including H&E staining, Mason Trichrome staining, and Sirius red staining for livers of naïve rats, rats treated with CCL4 and control, and rats treated with CCL4 and MTL-CEBPA.
Figure 24B:
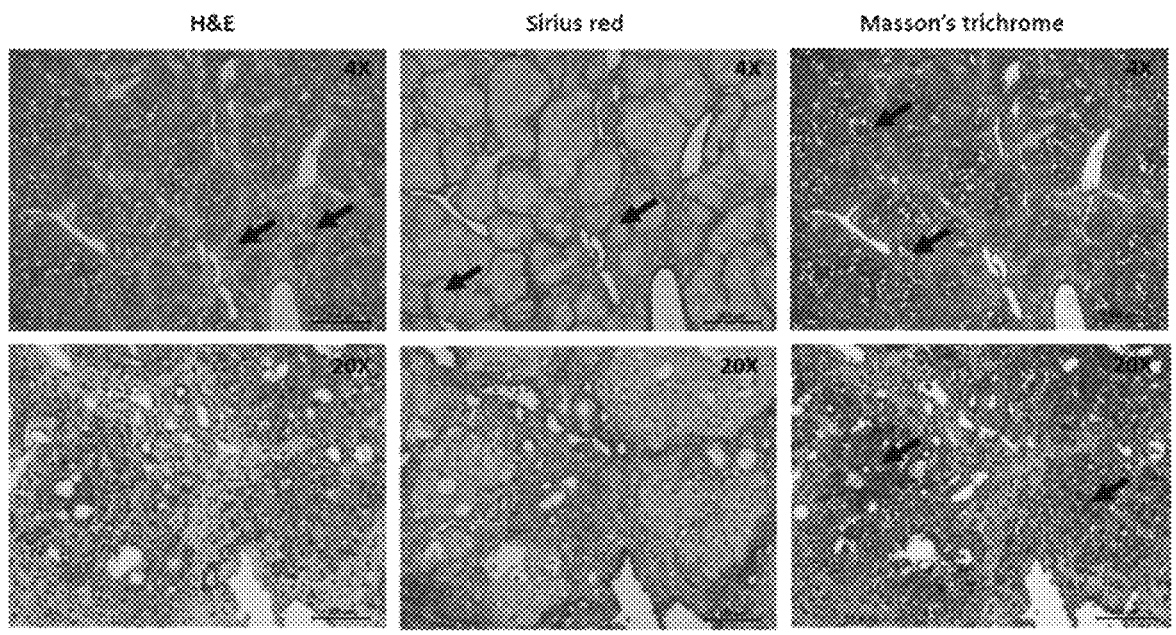
Figure 24C:
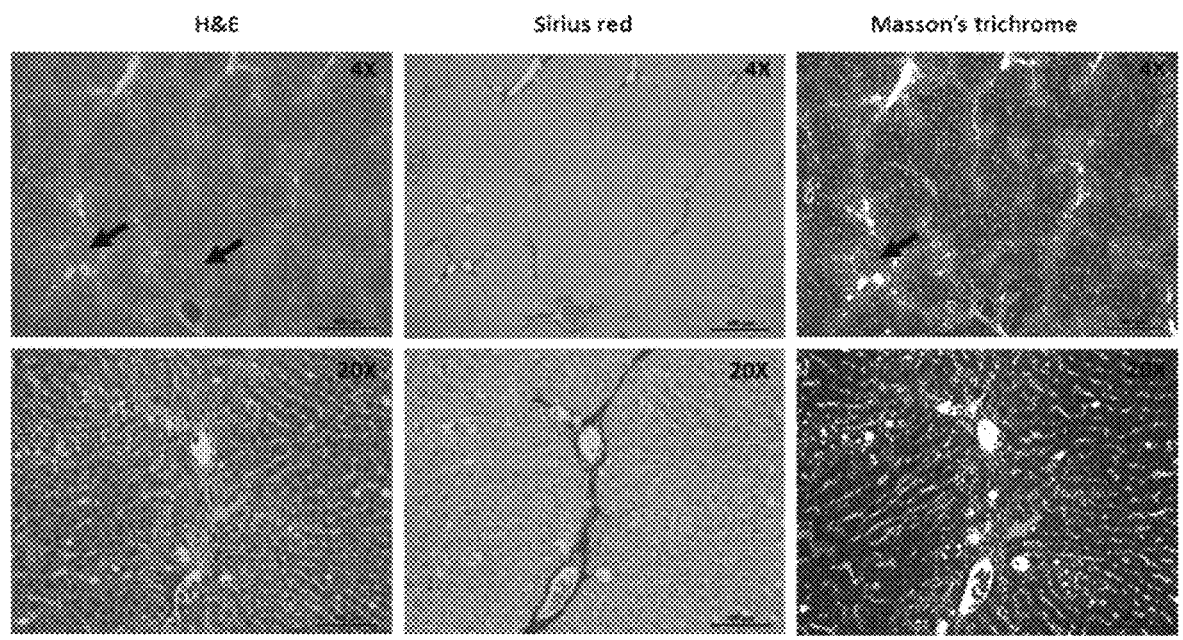
Figure 25A:
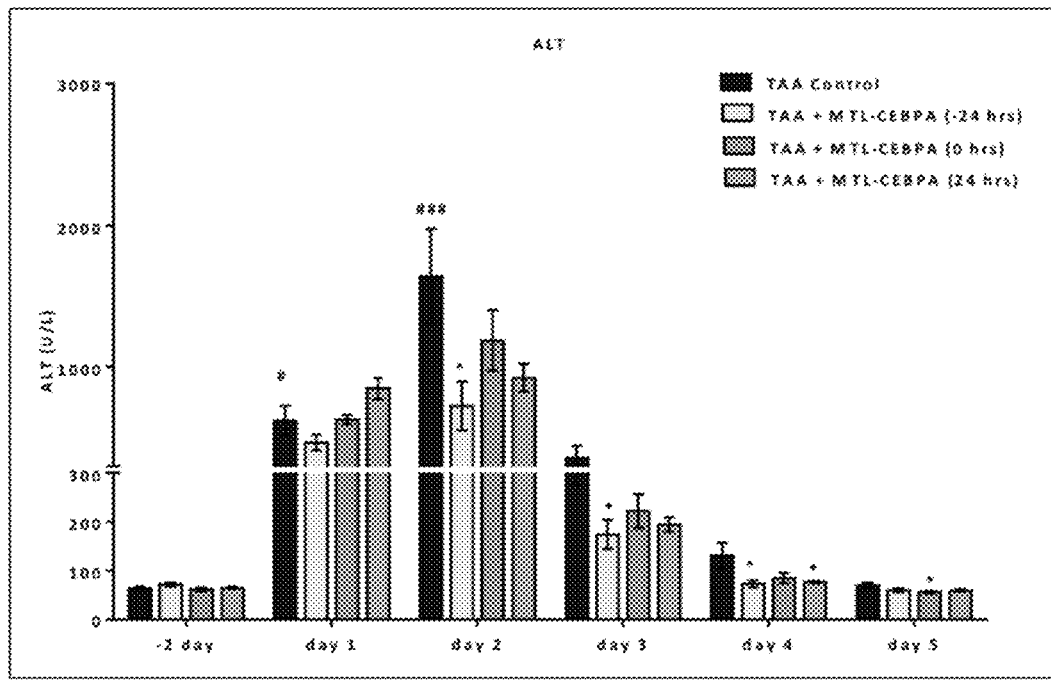
FIG. 25A-25H shows effect of TAA injection on liver function parameters such as ALT, AST, ALP, GGT, bilirubin, and other parameters such as total protein, albumin and ammonia.
Figure 25B:
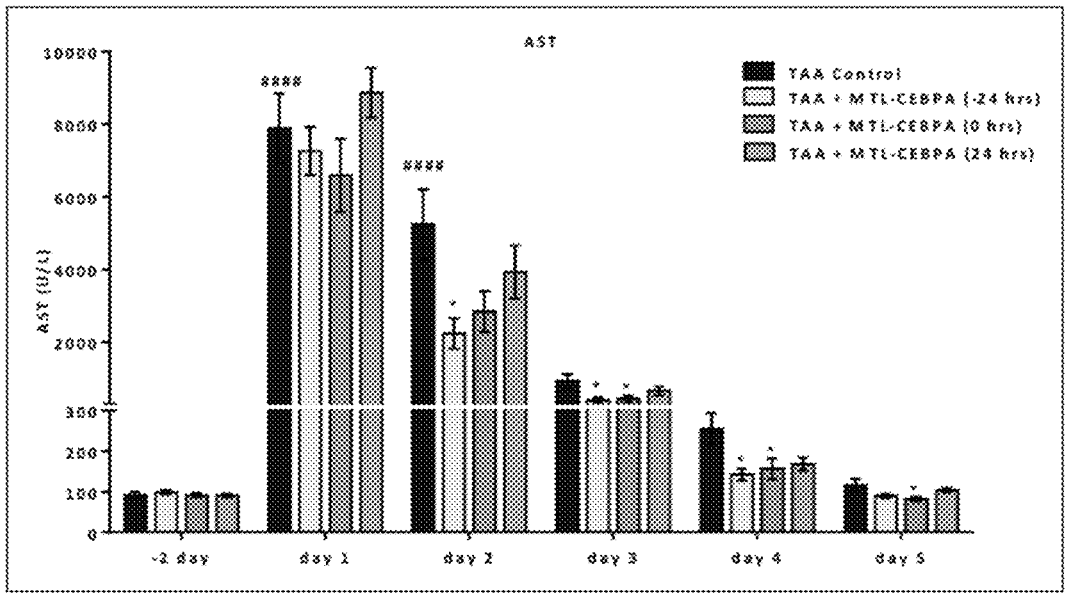
Figure 25C:
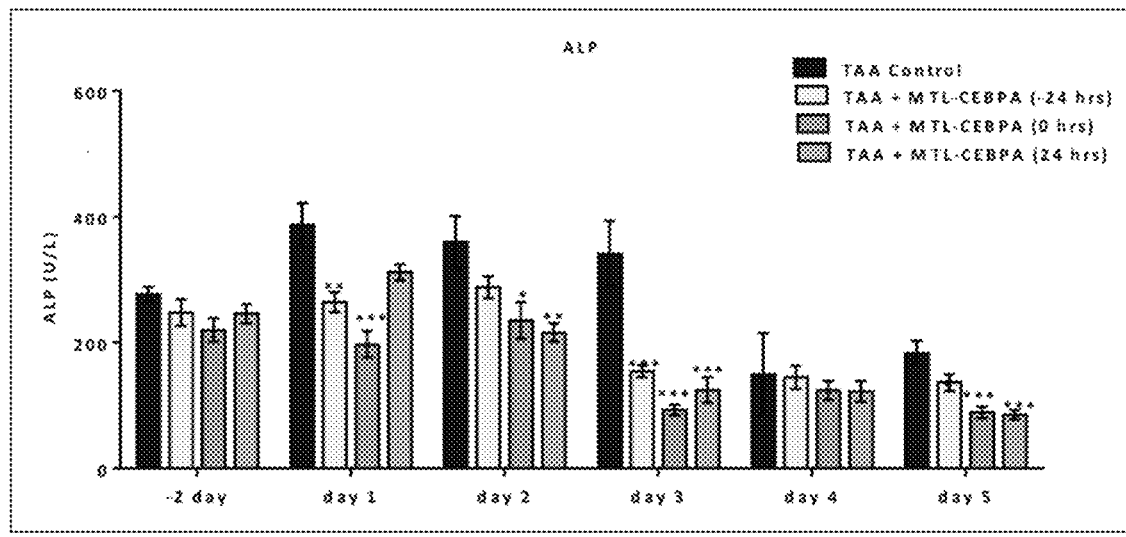
Figure 25D:
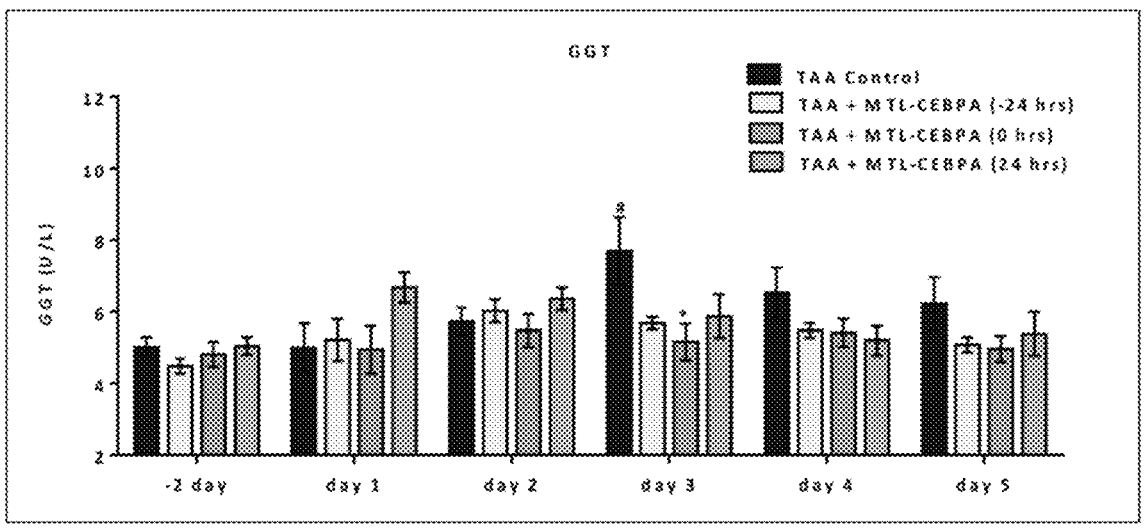
Figure 25E:
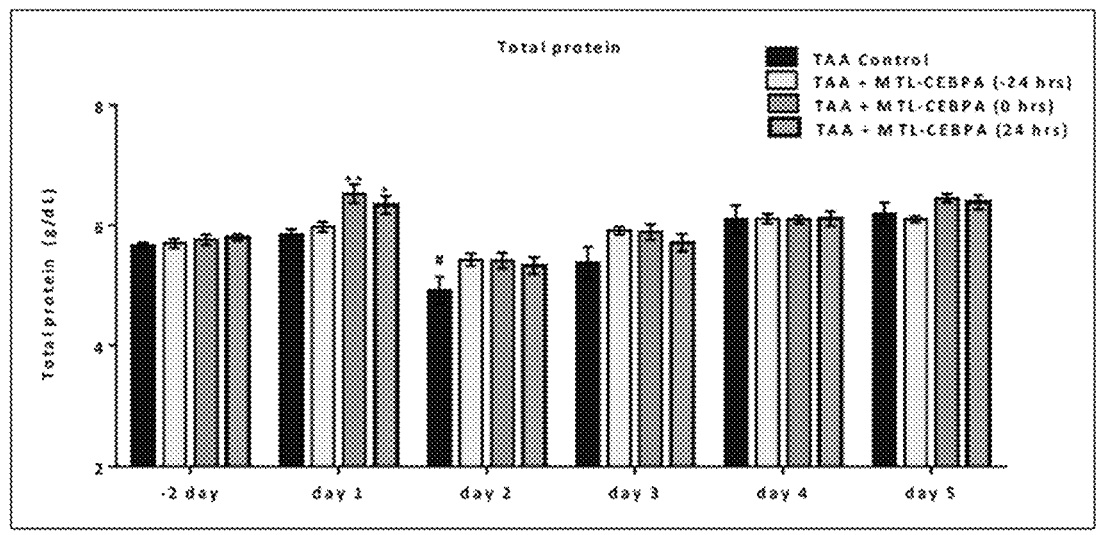
Figure 25F:
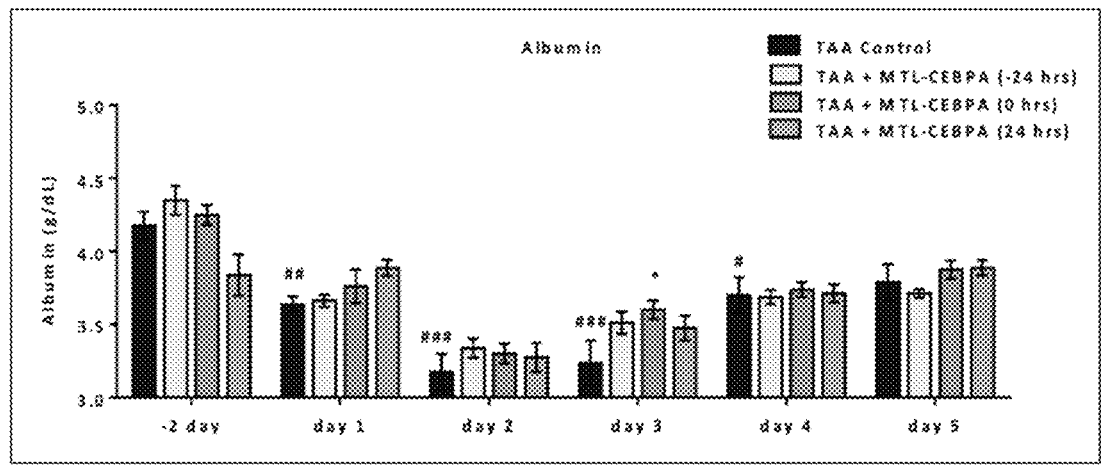
Figure 25G:
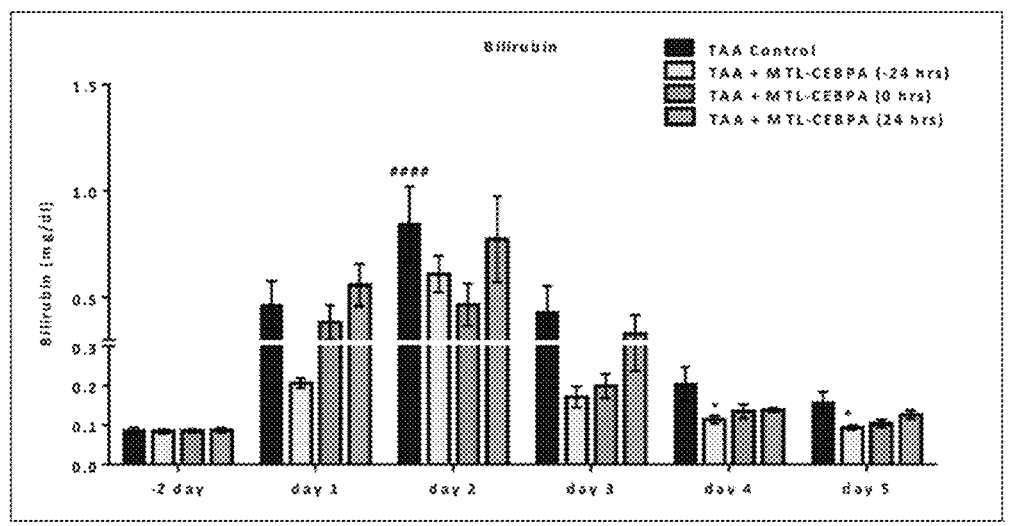
Figure 25H:
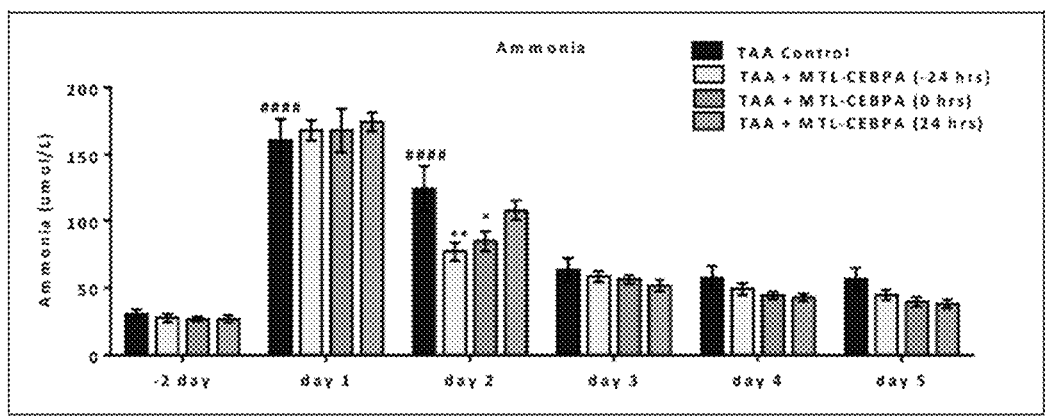

Histology staining results were shown in FIG. 24A-24C. FIG. 24A is sham control. FIG. 24B is CCL4-treated rats that received NOV340/siFluc treatment (negative control). FIG. 24C is CCL4-treated rats that received MTL-CEBPA treatment. MTL-CEBPA treated animals had reduced fibrous tissue and pseudolobule formation than the animals in the control groups.

Data discussed above showed that CEBPA-saRNA reversed liver failure across all clinical relevant parameters. Many parameters were reversed to normal. Serum albumin level was even better than normal.

Example 12. In Vivo Studies of Treating Acute Liver Failure

Acute liver failure (ALF) is a clinical condition with high mortality rate. Acute liver failure (ALF) is a condition characterized by rapid and severe deterioration of hepatocyte function in patients without known prior liver disease. Hepatotoxic drug thioacetamide (TAA) was used to induce ALF in this study. To establish thioacetamide (TAA) induced acute liver failure model in SD rats, the following parameters were measured: a) survival rate; b) liver function test (LFT) and biochemical parameters.

Test System
  Test species: *Rattus norvegicus*.
  Strain: Sprague Dawley rat (SD rats).
  Sex: Male.
  Boby weight/Age: 150-200 g/7-8 weeks.
  No. of groups: 4. No. of animals/group: 8.
  Source: Harlan Laboratories.
  Study period: 7 days.
  Male SD rats, 6-7 weeks of age were procured from Harlan. Animals were maintained in a controlled environment with 22±3° C. temperature, 50±20% humidity, a light/dark cycle of 12 h each and 15-20 fresh air changes per hour. Animals were housed group wise (3 animals per cage) and autoclaved corncob was used as bedding material. Upon receipt, animals were kept in quarantine for one week. The animals were assigned a temporary number at the base of tail using an indelible marker pen. After quarantine, animals were transferred to the experimental room and kept for acclimatization for a period of one week before initiation of the experiment.
  Equipments: EM-360 clinical chemistry analyzer (Erba Mannheim, Germany).
Disease Induction
  All animals were randomized into four groups based on basal body weight, bilirubin and AST on −2 day with consideration of less than 10% intergroup variation for basal parameters. Cages were identified by cage cards indicating the study number, study code, group number, sex, dose, cage number, number of animals and animal number details. Groups 1-4: All study animals were administered single intraperitoneal (i.p) injection of TAA in saline at the dose of 350 mg/kg (mpk), volume 5 ml/kg on day 0. Group 1 did not receive any treatment and served as pathological control. The MTL-CEBPA was injected intravenously to Group 2 at −24 h, Group 3 at 0 h and Group 4 at 24 h after TAA injection. Animals were assessed for LFT and biochemical parameters such as Alanine aminotransferase (ALT), Aspartate aminotransferase (AST), Alkaline phosphatase (ALP), Gamma-glutamyl transferase (GGT), total bilirubin (TBIL), Total protein (TP), Albumin (ALB) and ammonia at days 1, 2, 3, 4 and 5. At end of the study, all the available animals were euthanized by $CO_2$ asphyxiation and plasma was collected and stored at −80° C.

Experimental Groups:

| Groups | Description of groups | Induction | Treatment | No. of animals | Test dose |
|---|---|---|---|---|---|
| Group 1 (G1) | TAA control | TAA 350 mpk i.p. | NA | 8 | NA |
| Group 2 (G2) | MTL-CEBPA (−24 h) | TAA 350 mpk i.p. | MTL-CEBPA (24 h before TAA) | 8 | 3 mpk |
| Group 3 (G3) | MTL-CEBPA (0 h) | TAA 350 mpk i.p. | MTL-CEBPA (0 h before TAA) | 8 | 3 mpk |
| Group 4 (G4) | MTL-CEBPA (24 h) | TAA 350 mpk i.p. | MTL-CEBPA (24 h after TAA) | 8 | 3 mpk |

Administration of MTL-CEBPA

The test item MTL-CEBPA was administered intravenously through tail vein with appropriate disposable syringe and needle. The animals in group 2, 3 and 4 were administered with MTL-CEBPA. All the doses were administered at a dose volume of 1 ml/kg of animal body weight.

Observation

Body Weight and Animal Mortality

Initial body weight was recorded individually for all animals and daily once thereafter for the entire study period of 7 days. General health observation was done on a daily basis at the same time of the day. This includes alertness, hair texture, cage movement and presence of any discharge from nose, eyes, mouth and ears. All the group animals were monitored daily for mortality due to TAA administration.

Biochemical Analysis-LFT (for Randomization)

At day −2, blood samples were collected by retro-orbital puncture method under light isoflurane anesthesia and plasma was separated for estimating ALT, AST, ALP, GGT, TBIL, TP, ALB, and ammonia by fully automated random access clinical chemistry analyzer (EM-360, Make: Erba Mannheim, Germany). Animals were then randomized based on total bilirubin, body weight and AST.

Assessment of Biochemical Parameter, LFT after TAA Injection

Blood samples were collected by retro-orbital puncture method under light Isoflurane anesthesia from all the animals (from day 1 after TAA injection till end of study) and plasma was separated for estimating ALT, AST, ALP, GGT, TBIL, TP, ALB and ammonia.

Statistical Analysis

Statistical analysis was performed using one way or two way analysis of variance (ANOVA), followed by Dunnett's multiple comparison test wherever applicable. $p<0.05$ was considered to be statistically significant. Data expressed as Mean±SEM.

Results

Liver Functional Parameters and Body Weight

At day −2, all animals were randomized into four groups based on total bilirubin (TB), body weight and AST level for TAA injection to induce ALF and for MTL-CEBPA prophylactic, concurrent and preventive treatment.

Randomization of Groups Based on Bilirubin, Body Weight and AST:

| Groups | n | Total bilirubin (mg/dl) | Body weight (g) | AST (U/L) |
|---|---|---|---|---|
| 1. TAA control | 8 | 0.09 ± 0.01 | 263.8 ± 2.5 | 91.5 ± 7.6 |
| 2. MTL-CEBPA (−24 h) | 8 | 0.08 ± 0.01 | 267.0 ± 4.4 | 92.9 ± 4.0 |
| 3. MTL-CEBPA (0 h) | 8 | 0.09 ± 0.01 | 266.5 ± 4.2 | 91.2 ± 4.6 |
| 4. MTL-CEBPA (24 h) | 8 | 0.09 ± 0.01 | 266.5 ± 6.4 | 90.7 ± 4.6 |

Data Expressed as Mean±SEM

Pathological control (TAA control) group showed a significant reduction in body weight on days 2, 3, 4 ($p<0.01$) & 5 ($p<0.05$) compared to its basal body weight. Intravenous administration of MTL-CEBPA in Group 2, Group 3 and Group 4 at different time intervals showed no significant changes in body weight from day 1 to day 5 when compared with TAA control group at different days.

There was no mortality observed during the entire duration of study (7 days) in TAA and test item treatment groups. Animals were regularly monitored for local (site of injection) and general clinical signs. All animals were found lethargic on day 1 after TAA injection, and recovered to normal on subsequent days.

Daily Mean Body Weight of Animals:

| Gr. No. | n | Day −2 | Day 1 | Day 2 | Day 3 | Day 4 | Day 5 |
|---|---|---|---|---|---|---|---|
| 1. TAA control | 8 | 263.8 | 253.3 | 245.3 | 246.8 | 246.7 | 248.6 |
| 2. MTL-CEBPA (−24 h) | 8 | 267.0 | 254.6 | 248.6 | 253.3 | 257.1 | 266.4 |
| 3. MTL-CEBPA (0 h) | 8 | 266.5 | 249.7 | 244.6 | 248.6 | 252.7 | 260.1 |

-continued

| Gr. No. | n | Day −2 | Day 1 | Day 2 | Day 3 | Day 4 | Day 5 |
|---|---|---|---|---|---|---|---|
| 4. MTL-CEBPA (24 h) | 8 | 266.5 | 253.4 | 244.3 | 246.2 | 250.3 | 262.0 |

Biochemical Analysis

Single i.p. injection of TAA resulted insignificant increase in most of the liver function parameters such as ALT on day 1 ($p<0.05$) and day 2 ($p<0.001$), AST on day 1 and day 2 ($p<0.001$), GGT on day 3 ($p<0.05$), bilirubin on day 3 ($p<0.05$) and significant decrease in other parameters such as albumin on day 1 ($p<0.01$), day 2 ($p<0.001$), day 3 ($p<0.05$) and ammonia on day 1 and day 2 ($p<0.001$) when compared with its basal readings.

Prophylactic, concurrent but not preventive MTL-CEBPA injection showed significant improvement in the liver function parameters such as ALT ($p<0.05$), AST ($p<0.05$), ALP ($p<0.001$), GGT ($p<0.05$), bilirubin ($p<0.05$) and other parameters such as total protein ($p<0.01$), albumin ($p<0.01$) and ammonia ($p<0.01$) when compared with TAA control on different days after treatment (FIG. 25A-25H).

Discussion and Conclusion

In this study, acute liver failure model was established in SD rats by administration of TAA injection intraperitoneally. No mortality was observed in any of the groups after TAA injection. TAA injection resulted in significant changes in the liver biochemical parameters such as, AST, ALT, Bilirubin, GGT, Total Protein, Albumin, and Ammonia when compared to its basal levels as observed in pathological control (TAA control) animals. Significant decrease in body weight was also observed in TAA control animals. MTL-CEBPA treatment showed significant improvement in the LFT parameters and ammonia when it was injected prophylactically (−24 hrs) and concurrent (0 hrs) of TAA injection.

Example 13. In Vivo Studies of Treating Diabetes

Given the role of CEBPA in the regulation of glucose metabolism, a study was conducted in a rat model of diabetes to determine if CEBPA activation could improve clinically relevant blood parameters. Type II diabetes was induced in six wistar rats by high fat diet. The rats were then treated with a total of 4.35 mg/kg CEBPA-saRNA (AW1-50) or non-targeting FLUC siRNA formulated in a NOV340 liposome. 6 days after last treatment, blood was drawn and the animals were sacrificed to assess changes in serum chemistry and weight. Experimental Groups and Doses:

| Group | Test article | Dose |
|---|---|---|
| Control | NOV340-siFLUC | 1.45 mg/kg, 3 doses |
| Treatment | NOV340-CEBPA (i.e., MTL-CEBPA) | 1.45 mg/kg, 3 doses |

Figure 26A:
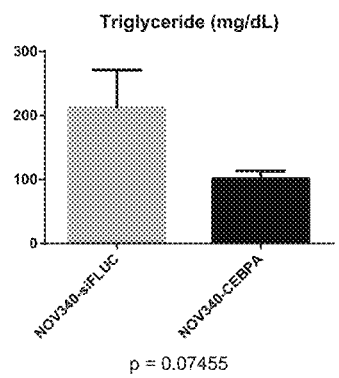
FIG. 26A: triglyceride levels.
Figure 26B:
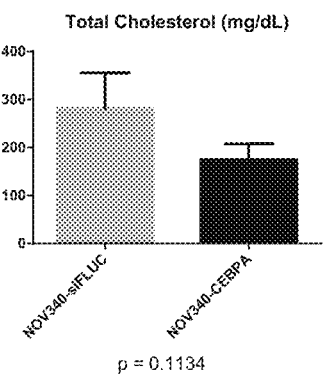
FIG. 26B: total cholesterol levels.
Figure 26C:
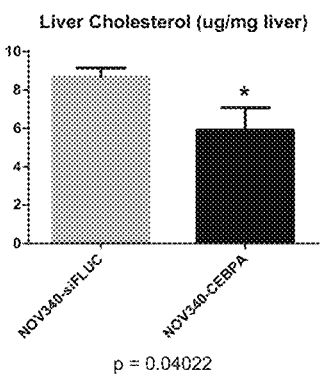
FIG. 26C: liver cholesterol levels.
Figure 26D:
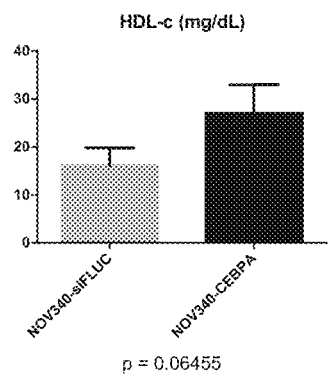
FIG. 26D: HDL-c levels.
Figure 26E:
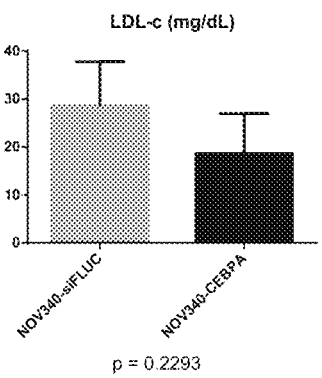
FIG. 26E: LDL-c levels.
Figure 26F:
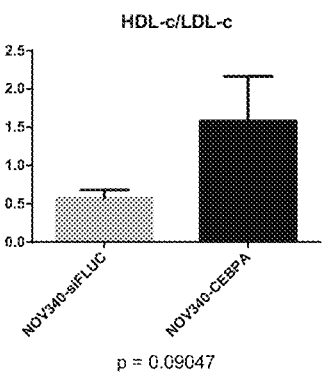
FIG. 26F: HDL-c/LDL-c ratios.
Figure 26G:
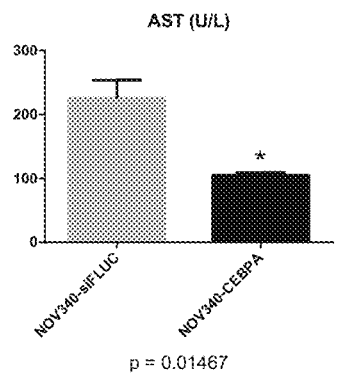
FIG. 26G: AST levels.
Figure 26H:
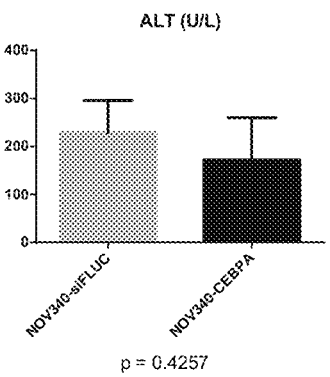
FIG. 26H: ALT levels.
Figure 26I:
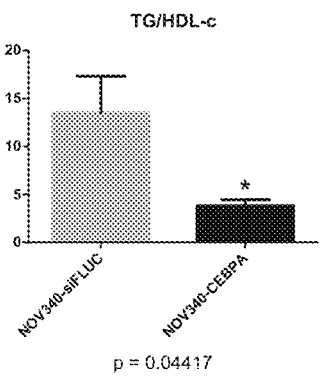
FIG. 26I: TG/HDL-c ratios.
Figure 26J:
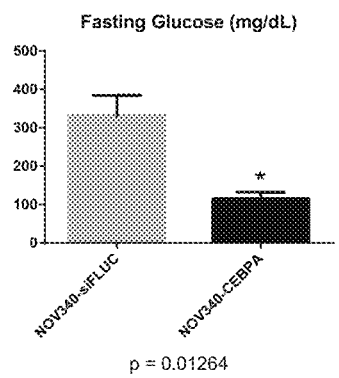
FIG. 26J: fasting glucose levels.
Figure 26K:
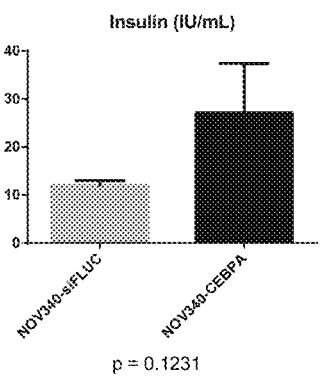
FIG. 26K: insulin levels.
Figure 26L:
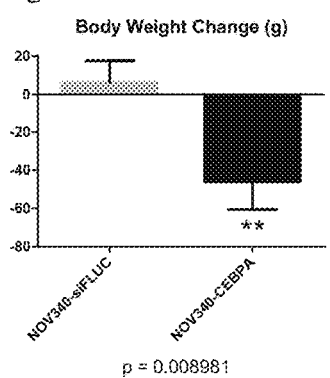
FIG. 26L: body weight changes.
Figure 26M:
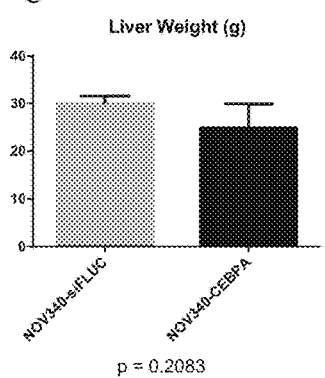
FIG. 26M: liver weight changes.
Figure 26N:
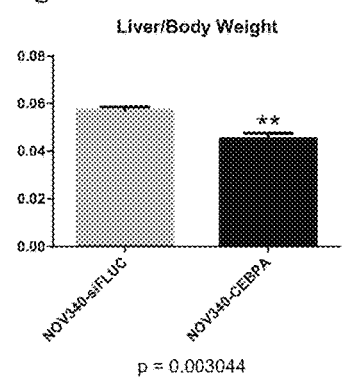
FIG. 26N: liver weight/body weight ratios.

As shown in FIG. 26A-26N, compared to control, rats treated with NOV340-CEBPA showed significant decreases in liver cholesterol, serum AST, fasting glucose, and the ratio of triglycerides to HDL-c. They also had a significant reduction in body weight as well as the ratio of liver to body weight (FIG. 26L and FIG. 26N). Insulin level increases with CEBPA-saRNA treatment (FIG. 26K). The results indicate that CEBPA upregulation with CEBPA-saRNA may be beneficial for the management of diabetes. CEBPA-saRNA may also be used for treating fatty liver disease and insulin resistance.

Example 14. In Vivo Studies of Treating NASH

Nonalcoholic steatohepatitis (NASH) is liver inflammation and damage that may be caused by a buildup of fat in the liver. It is part of a group of conditions called nonalcoholic fatty liver disease. NASH may cause scarring of the liver, which may lead to cirrhosis. The effect of MTL-CEBPA in treating NASH is studied using animals fed with methionine choline deficient (MCD) diet. The MCD diet results in liver injury similar to NASH.

In this study, CEBPA-saRNA was used to treat MCD-induced NASH in C57BL/6 mice. The length of the study was 6 weeks. Male 7-8 weeks-old C57B/L6 mice were randomized based on body weight on Day 0. Group 1 had normal diet for 4 weeks, and Group 2 for 6 weeks. Group 3 had MCD diet for 4 weeks, and Groups 4-8 for 6 weeks. At week 4, treatment groups (Groups 4-8) were randomized based bilirubin, body weight and ALT levels. Groups 4-8 received PBS treatment or therapeutic treatment via i.v. injection twice weekly (week 4, 4.5, 5 and 5.5).

At week 4, Group 1 and 3 were terminated. At week 6, Group 2 and Groups 4-8 were terminated. Liver function tests (LFT) (ALT, AST, ALP, albumin, total bilirubin & liver triglyceride (TG)) and histopathology of liver (H&E stain, oil red O staining, and Masson trichrome) were conducted. Serum cytokines/markers (IL1β, IL6 and TNF-α) & α2 Macroglobulin were measured.

Studies groups and description of treatment were summarized below:

| GroupNo. | Groups | No. of animals | Treatment | Dose Regimen/ROA |
|---|---|---|---|---|
| G1 | Normal diet control (4 weeks), terminated at week 4. | 5 | — | N/A |
| G2 | Normal diet control (6 weeks), terminated at week 6. | 5 | — | N/A |

-continued

| GroupNo. | Groups | No. of animals | Treatment | Dose Regimen/ROA |
|---|---|---|---|---|
| G3 | MCD diet control (4 weeks), terminated at week 4. | 10 | — | N/A |
| G4 | MCD diet control (6 weeks) + PBS treatment. | 10 | PBS Treatment | Twice weekly, i.v injection, from week 4 toweek 6 |
| G5 | MCD + NOV340/siFLUC control 3 mpk therapeutic. | 10 | NOV340/siFLUC 3 mpk | Twice weekly, i.v injection, from week 4 to week 6 |
| G6 | MCD + MTL-CEBPA 0.3 mpk Therapeutic. | 10 | MTL-CEBPA 0.3 mpk | Twice weekly, i.v injection, from week 4 to week 6 |
| G7 | MCD + MTL-CEBPA 1 mpk Therapeutic. | 10 | MTL-CEBPA 1 mpk | Twice weekly, i.v injection, from week 4 to week 6 |
| G8 | MCD + MTL-CEBPA 3 mpk Therapeutic. | 10 | MTL-CEBPA 3 mpk | Twice weekly, i.v injection, from week 4 to week 6 |

Figure 27A:
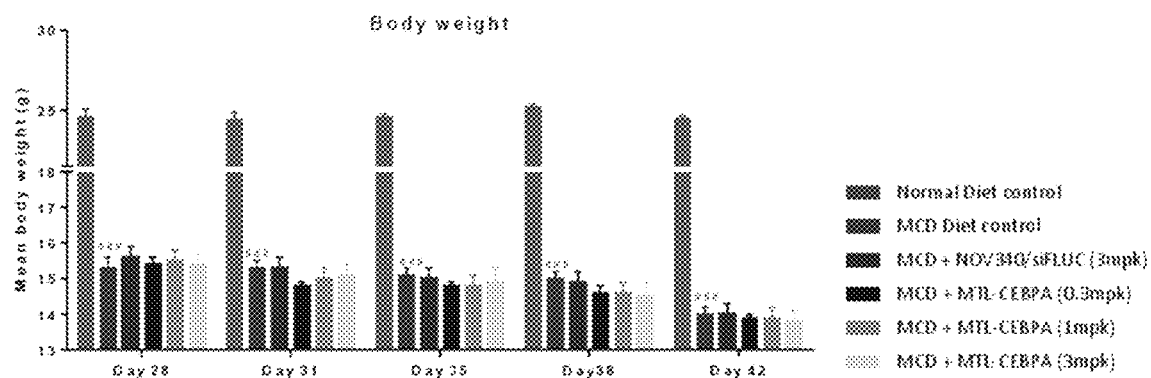
FIG. 27A-27B show body weight and feed consumption changes in an MCD-induced NASH study.
Figure 27B:
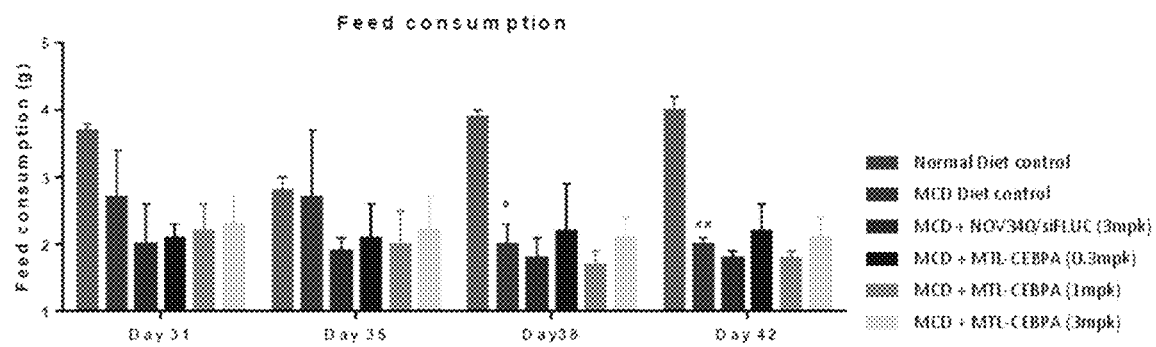
Figure 27C:
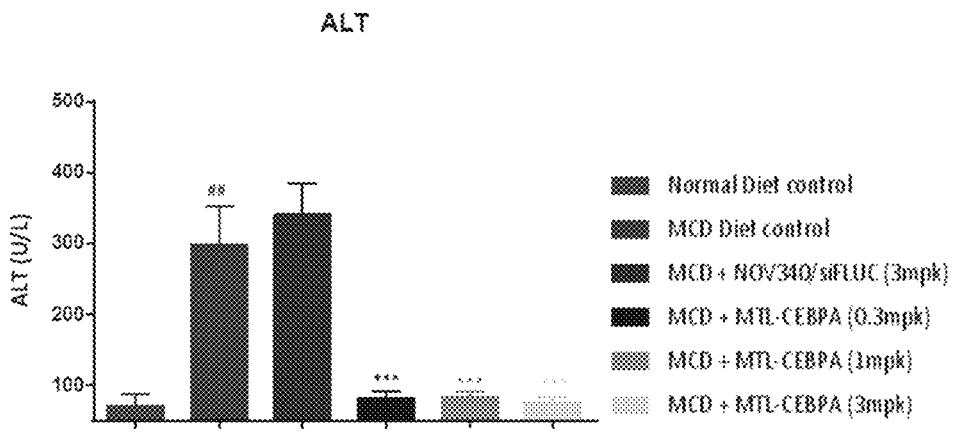
FIG. 27C-27H showed ALT, AST, ALP, bilirubin, albumin, and liver TG level changes in the study.
Figure 27D:
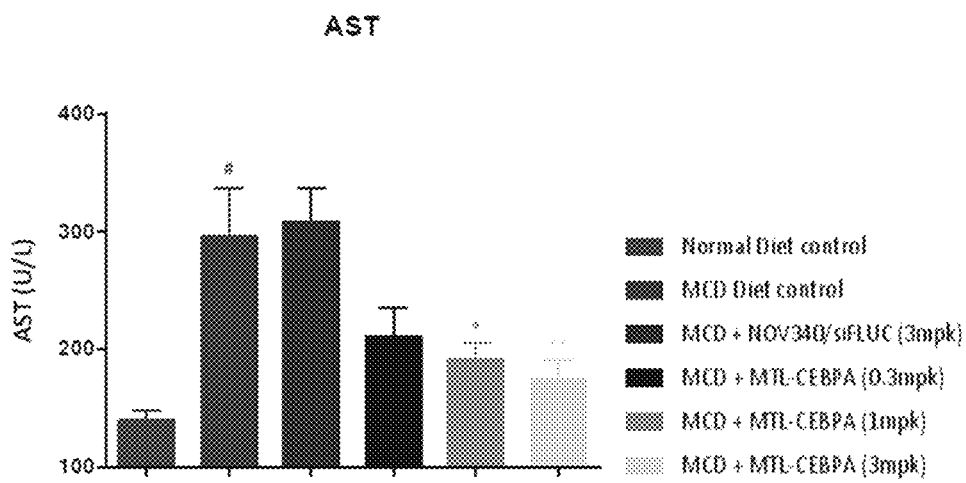
Figure 27E:
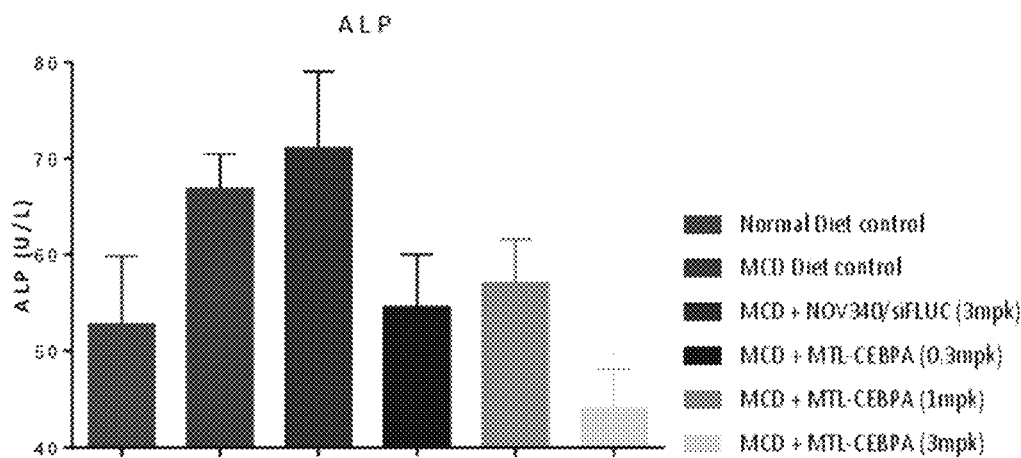
Figure 27F:
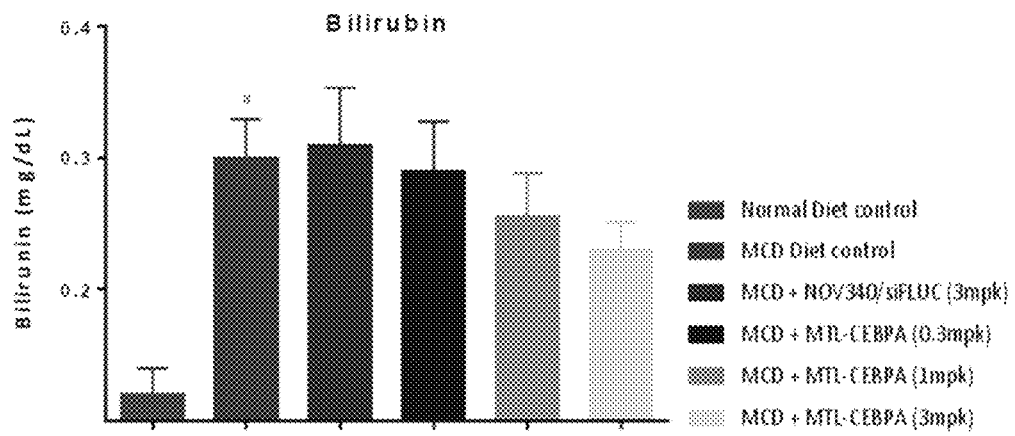
Figure 27G:
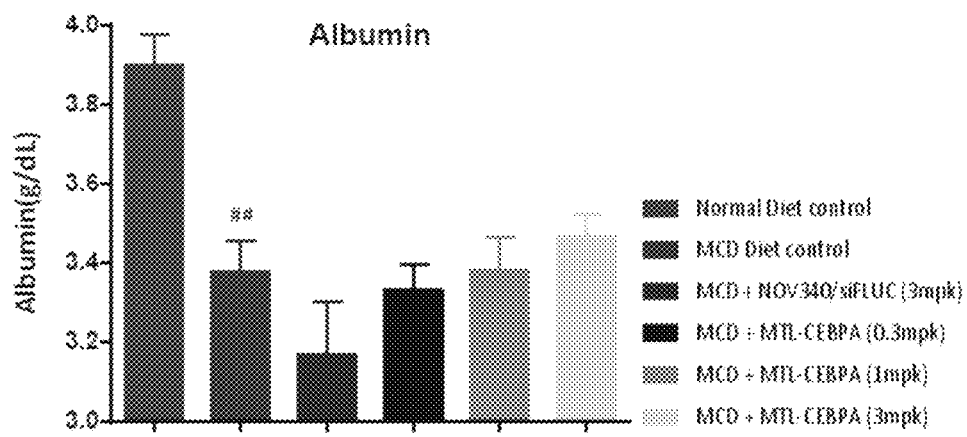
Figure 27H:
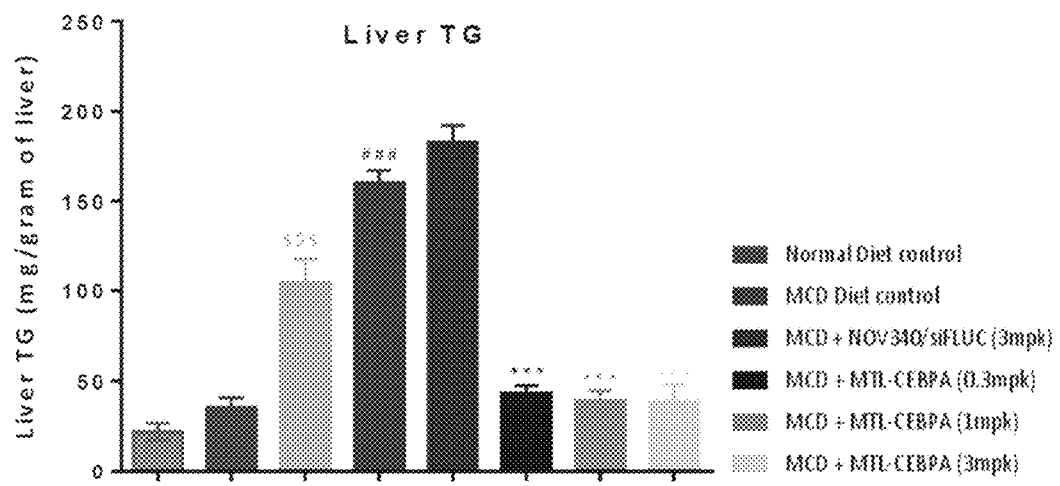

FIG. 27A-27B showed body weight and feed consumption changes. As expected, MCD diet treatment showed significant reduction in body weight and feed consumption throughout the study. Treatment groups (G5-G8) showed no significant changes in body weight and feed intake compared to MCD diet control. Hence, MTL-CEBPA treatment did not change body weight and feed consumption. FIG. 27C-27G showed LFT results including ALT, AST, ALP, bilirubin, and albumin level changes. Animals fed with MCD diet showed significant increase in LFT parameters such as ALT, AST, bilirubin and reduction in protein levels when compared with normal diet control. Treatment with MTL-CEBPA showed significant reduction in ALT and AST levels. Reduction was also observed in ALP & bilirubin with MTL-CEBPA treatment. FIG. 27H showed liver triglyceride (TG) level changes. Liver TG was significantly increased in the MCD diet control group. Treatment with MTL-CEBPA showed significant reduction in liver TG levels, reversing liver TGs to normal levels.

Therefore, CEBPA-saRNA treatment may be used to for treating NASH.

Example 15. Other In Vivo Studies with CEBPA-saRNA—Evaluation of MTL-CEBPA Efficacy in a Rat Model of DEN-Induced HCC The purpose of this study was to investigate if activation of CEBPA by treatment with MTL-CEBPA would improve clinical parameters in a rat model of HCC.

Experimental Design:

Male Wistar rats were treated with DEN to induce HCC. Briefly, the animals were treated for 9 weeks with DEN followed by 3 treatment-free weeks. Animals were then randomized into three groups according to body weight (6 to 7 males/group). Group 1 was sacrificed on Day 1 to serve as the pre-treatment control and groups 2 and 3 were treated i.v. 3 times (Day 1, 3, and 5) with either a non-targeting dsRNA formulated in NOV340 (siFLUC) or MTL-CEBPA at a dose of 4 mg/kg. On Day 12, blood was drawn and all animals were sacrificed. Tumour and liver weights were measured and sections of liver tissue were immediately flash-frozen for mRNA analysis. CEBPA and albumin mRNA levels were determined by qRT-PCR (housekeeping gene: GAPDH; measured in triplicates)

Figure 28:
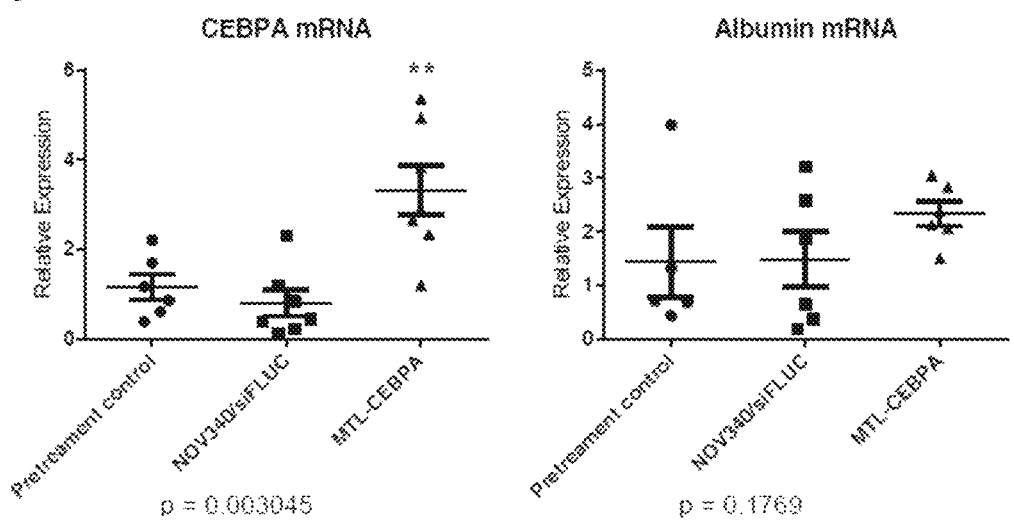
FIG. 28 shows CEBPA and Albumin mRNA expression in liver tissue. Expression values are relative to pretreatment control (DEN-induced HCC), **$p<0.01$ vs. NOV340/siFLUC.
Figure 29A:
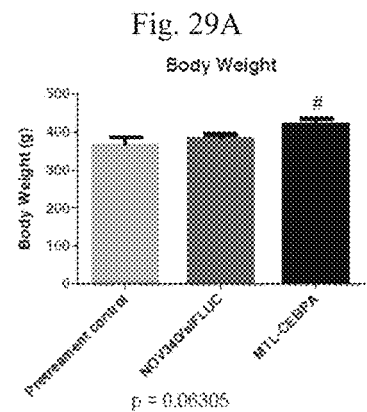
FIG. 29A-29I show physical and Serum Parameters in MTL-CEBPA-treated DEN-Rats. Values shown as mean±SEM; p-values shown for MTL-CEBPA: #$p<0.1$, *$p<0.05$ vs. NOV340/siFLUC; $$p<0.05$ vs. Pretreatment control.
Figure 29B:
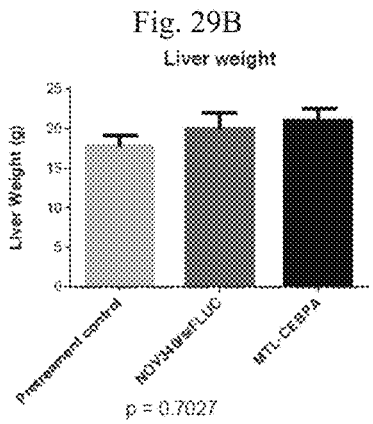
Figure 29C:
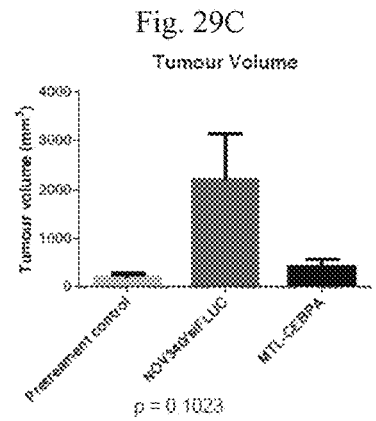
Figure 29D:
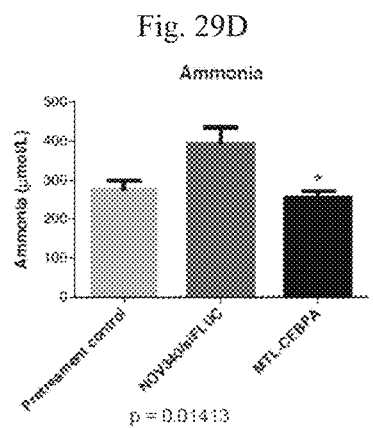
Figure 29E:
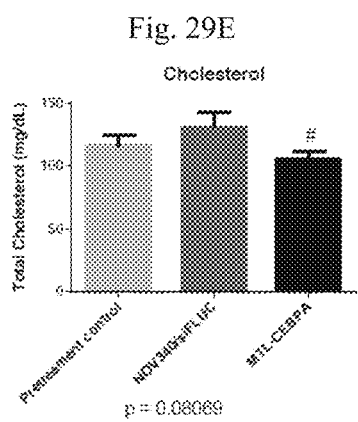
Figure 29F:
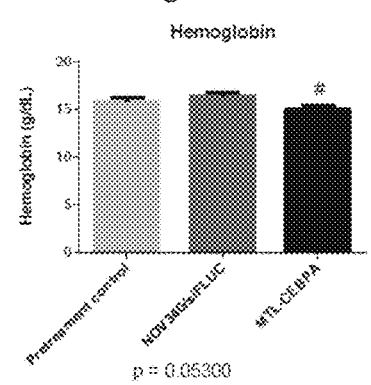
Figure 29G:
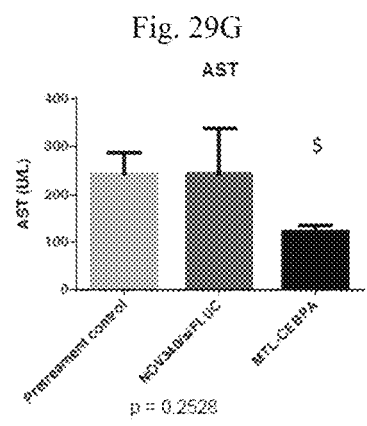
Figure 29H:
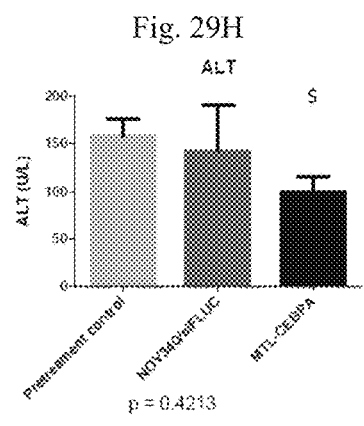
Figure 29I:
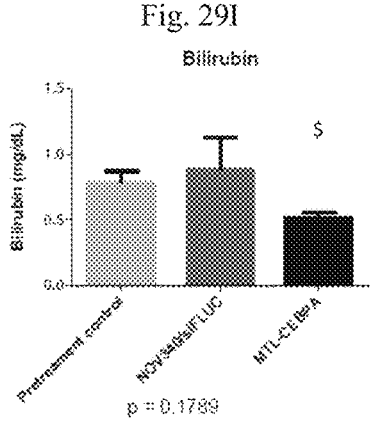

Results: As shown in FIG. 28, compared to NOV340/siFLUC (non-targeting liposome control, vehicle-control), animals treated with MTL-CEBPA showed a significant increase in CEBPA mRNA expression in the liver. A trend for increased albumin mRNA expression was observed, this was not statistically significant.

As shown in FIG. 29A-29I, compared to the NOV340/siFLUC control, rats treated with MTL-CEBPA showed a significant decrease in serum ammonia (p<0.05), as well as changes in body weight (bw), tumour volume, cholesterol, and haemoglobin that were trending towards statistical significance (bw: p=0.063; tumour volume: p=0.10; cholesterol: p=0.08; hemoglobin: p=0.05). Compared to pretreatment control, rats treated with MTL-CEBPA showed a significant decrease in AST, ALT, and bilirubin (p<0.05).

Conclusion:

In the DEN-induced rat model of HCC, MTL-CEBPA treatment resulted in target engagement (upregulation of CEBPA mRNA in the liver) and an improvement in several disease markers, including haemoglobin, ammonia, and cholesterol, when compared to NOV340/siFLUC control. Although not statistically significant due to small animal numbers, the group treated with MTL-CEBPA showed a trend toward tumour growth inhibition with a mean tumour size approximately 80% smaller than the NOV340/siFLUC control. As seen in comparison to the pretreatment disease control, MTL-CEBPA not only stabilized disease symptoms but reversed some liver toxicity serum markers, including AST, ALT and bilirubin, consistent with the benefits seen in these markers in the CCL4 fibrosis model. Taken together, these results indicate that MTL-CEBPA can improve liver function and reduce tumour growth in the widely used rat model of DEN-induced liver fibrosis and HCC.

Example 16. Studies of CEBPA-saRNA Interactions with Ago Proteins

HepG2 cells were transfected with Biotinylated antisense strand (AS) and sense strand (ss)-CEBPA51 and compared to untransfected or scramble-biotin control. At harvest point (72 hr) Biotinylated conjugates were cross-linked with 1% formaldehyde followed by immobilization on streptavidin agarose beads. Co-immunoprecipitation (Co-IP) with anti-Ago1, Ago2, Ago3 and Ago4 was then performed. Isotype IgG was used as a negative control. Co-immunoprecipitated conjugates were then immobilized with Dynabead-Protein-G. The pulldown immune complex was washed and eluted on a magnetic column. Samples were then separated on SDS-PAGE and transferred onto PVDF for Western blotting against the respective ARgonaute antibody.

Figure 30A:
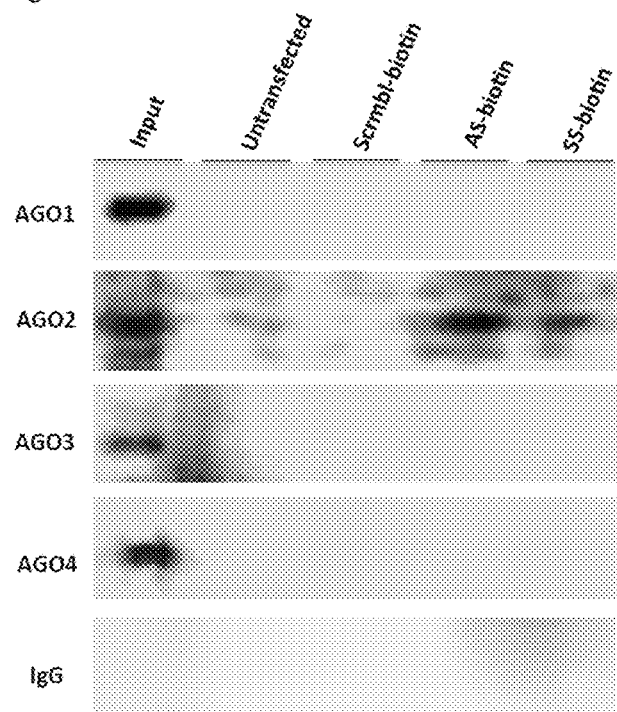
FIG. 30A shows co-immunoprecipitation results of Argonaute proteins with Biotinylated strands of CEBPA51.

As shown in FIG. 30A, Ago2 appears strongly on the AS-biotin strand compared to the SS-biotin strand. Ago1, 3 and 4 do not appear to be present on either strand. This indicates anti-sense strand of CEBPA-saRNA associates with Ago2 and not the other Argonautes.

Figure 30B:
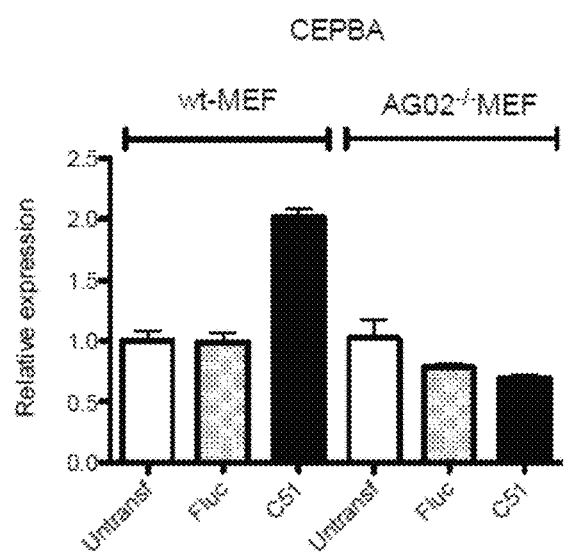
FIG. 30B shows CEBPA levels in wild type and Ago2 knock-out mouse embryonic fibroblasts (MEF) cells both transfected with CEBPA-saRNA.
Figure 30C:
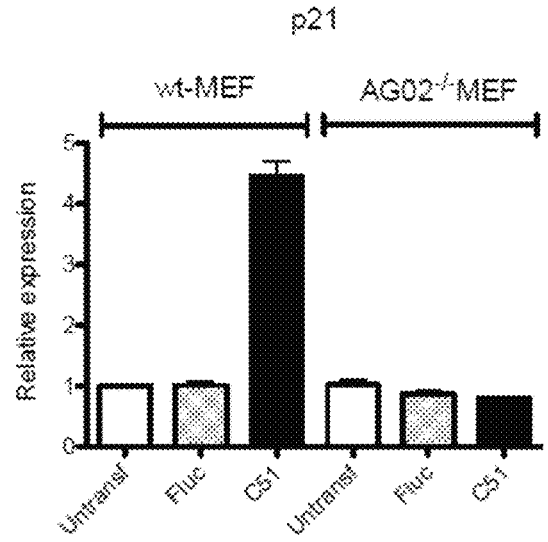
FIG. 30C shows p21 levels in wild type and Ago2 knock-out mouse embryonic fibroblasts (MEF) cells both transfected with CEBPA-saRNA.

In a further study, Ago2 was knocked out in mouse embryonic fibroblasts (MEF) cells. Wild-type and Ago2 knock-out cells were seeded in 24 well plates at $9.8 \times 10^5$ per well. 20 nM of CEBPA51 and Fluc were transfected as previously described (forward+reverse). RNA was harvested to determine activity of saRNA at 48 hour time point. As shown in FIG. 30B, CEBPA transcript levels increased 2-fold in CEBPA51 transfected wild type cells vs Fluc. FIG. 30C showed that p21 transcript levels increased 4-fold in CEBPA51 transfected wild type cells vs Fluc. However, no CEBPA or p21 induction was measured in Ago2 knock-out cells. It is demonstrated that Ago2 is required for gene activation by saRNA.

Example 17. Formulation of CEBPA-saRNA

CEBPA-51 saRNA is encapsulated into liposomes. The delivery technology used is the NOV340 SMARTICLES® technology owned by Marina Biotech. The lipid components of these nanoparticles are comprised of 1-palmitoyl-2-oleoyl-sn-glycero-3-phosphocholine (POPC), 1,2-dioleoyl-sn-glycero-3-phosphoethanolamine (DOPE), cholesteryl-hemisuccinate (CHEMS), and 4-(2-aminoethyl)-morpholino-cholesterol hemisuccinate (MOCHOL). NOV340 consists of POPC, DOPE, CHEMS and MOCHOL in the molar ratio of 6:24:23:47. The nanoparticles are anionic at physiological pH, and their specific lipid ratio imparts a "pH-tunable" character and a charge to the liposomes, which changes depending upon the surrounding pH of the microenvironment to facilitate movement across physiologic membranes. SMARTICLES® nanoparticles are sized to avoid extensive immediate hepatic sequestration, with an average diameter of approximately about 50-about 150 nm, or about 100-about 120 nm, facilitating more prolonged systemic distribution and improved serum stability after i.v. injection leading to broader tissue distribution with high levels in liver, spleen and bone marrow reported.

Sequence of CEBPA-51, Sense and Antisense (Also Shown in FIG. 39):

flow rate and pressure. The solid-phase approach enables efficient separation of reaction products as coupled to the solid phase from reagents in solution phase at each step in the synthesis by washing of the solid support with solvent.

Figure 40A:
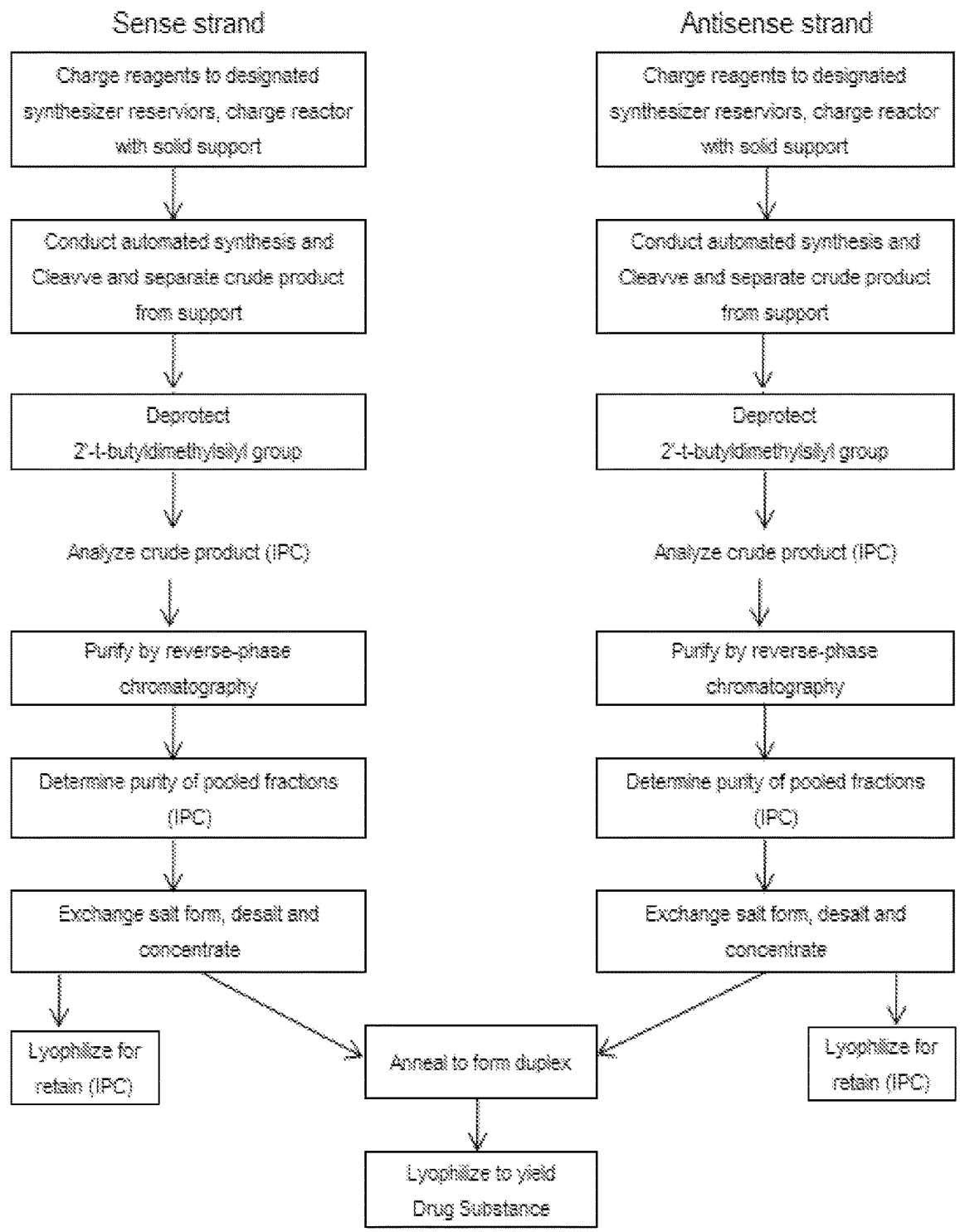
FIG. 40A is a general overview of CEBPA-51 synthesis.

General overview of CEBPA-51 synthesis is shown in FIG. 40A.

A detailed flow chart of CEBPA-51 synthesis is shown in FIG. 40B.

The general size and purity of CEBPA-51 present in solution is determined by size exclusion chromatography (SE-HPLC), mainly to differentiate between double and single strand versions. The melting point of the CEBPA-51 double strand is sequence specific. It is determined as the inflection point in the UV (at 260 nm) versus T (° C.) curve created during heat induced 'melting' (dehybridisation) of the duplex. This Tm value was determined to be at 81.3° C., in connection with the increased absorption at 260 nm (hyperchrome effect). Extinction coefficient has been determined in PBS at 260 nm and 25° C., based on ≥90% content oligonucleotide as sodium salt. Molecular mass is determined for both single strands by LC-MS during the manufacturing process. For the release test, the duplex was separated into single strands and each peak was analyzed by MS which is performed by a combination of IPRP-HPLC with ESI-MS.

Impurities

Product-Related Impurities:

Potential product-related impurities are multimers, aggregates, as well as extended or truncated/degraded forms. These are controlled by SE-HPLC.

Furthermore and as a result of incomplete or inefficient synthesis, polymeric by-products can occur which differ by lacking e.g. n-1 or n-2 nucleotides (with "n=21" i.e. 20-mers, or 19-mers instead of 21-mers for full chain length of sense and antisense strands). Also sequence extension by 1 or 2 nucleotides can occur, resulting in n+1 or n+2 oligonucleotides (22- or 23-mers). The latter however with lower probability. These variants cannot be identified by SE-HPLC due to limited resolution, but can be determined by IPRP-HPLC.

| saRNA name | CEBPA-51 Total base: 21 mer, including base modifications | | | | | | |
|---|---|---|---|---|---|---|---|
| mer | 3 | 6 | 9 | 12 | 15 | 18 | 21 |
| Sense strand 5' → 3' (SEQ ID No. 128) | bmGmCG | mGUC | AUU | mGUC | AmCU | GGU | CmUmU |
| Complementary antisense strand 3' → 5' (SEQ ID No. 129) | mUmUC | GCC | AGU AAC | | AGU | GAC | CAG |

Definition of symbols: A, U, G, C are 2'-OH ribonucleotides, mU, mG, mC are 2'-O-methyl ribonucleotides, b = inverted abasic sugar cap (additional modification).

Each strand of CEBPA-51 is synthesized on a solid support by coupling phosphoramidite monomers sequentially. The synthesis is performed on an automatic synthesizer such as an Akta Oligopilot 100 (GE Healthcare) and a Technikrom synthesizer (Asahi Kasei Bio) that delivers specified volumes of reagents and solvents to and from the synthesis reactor (column type) packed with solid support. The process begins with charging reagents to the designated reservoirs connected to the reactor and packing of the reactor vessel with the appropriate solid support. The flow of reagent and solvents is regulated by a series of computer-controlled valves and pumps with automatic recording of Furthermore, also mis-incorporation or modification of ribonucleotides may occur also leading to product-related impurities. The latter are either detected by ion pair reversed-phase high-pressure chromatography (IPRP-HPLC) MS or MS/MS-sequencing.

Process-Related Impurities:

Potential process-related impurities include residual reagents, reactants and solvents from chemical synthesis. Based on the given RNA synthesis on solid-phase and reagents used in the production process the following process related impurities can be expected (Table 14):

TABLE 14

Process-related Impurities of CEBPA-51 Production

| Residual Solvent | Origin | Actual Results |
|---|---|---|
| Acetonitrile (class 2) | synthesis | n.d.* (<410 ppm) |
| DMSO - Dimethylsulfoxide (class 3) | synthesis | n.d.* (<5000 ppm) |
| Toluene (class 2) | synthesis | n.d.* (<890 ppm) |
| TEA, Triethylamine | synthesis | (<320 ppm) |

*n.d. = "not detected" (below LoQ)

Formulations

The required amount of CEBPA-51 is dissolved at ambient temperature in sodium acetate/sucrose buffer pH 4.0 and the required amounts of lipids are dissolved in absolute ethanol at 55° C. Liposomes are prepared by crossflow ethanol injection technology. Immediately after liposome formation, the suspension is online diluted with sodium chloride/phosphate buffer pH 9.0. The collected intermediate product is extruded through polycarbonate membranes with a pore size of 0.2 µm. The target saRNA concentration is achieved by ultrafiltration. Non-encapsulated drug substance and residual ethanol is removed by subsequent diafiltration with sucrose/phosphate buffer pH 7.5. Thereafter, the concentrated liposome suspension is 0.2 µm filtrated and stored at 5±3° C. Finally, the bulk product is formulated, 0.2 µm filtrated and filled in 20 ml vials.

MTL-CEBPA is presented as a concentrate solution for infusion. Each vial contains 50 mg of CEBPA-51 (saRNA) in 20 ml of sucrose/phosphate buffer pH about 7.5.

The composition of MTL-CEBPA is provided in Table 15 below.

TABLE 15

Qualitative and quantitative composition of MTL-CEBPA (2.5 mg/ml)

| Name of Ingredient | Function | Reference | Quantity (per ml) |
|---|---|---|---|
| CEBPA-51 (saRNA) | Active pharmaceutical ingredient | Manufacturer's specifications | 2.5 mg/ml |
| 1-palmitoyl-2-oleoyl-sn-glycero-3-phosphocholine (POPC) | Membrane forming lipid | Manufacturer's specifications | 4.65 mg/ml |
| 1,2-dioleoyl-sn-glycero-3-phosphoethanolamine (DOPE) | Membrane forming fusogenic lipid | Manufacturer's specifications | 18.0 mg/ml |
| Cholesteryl hemisuccinate (CHEMS) | Anionic ampotheric lipid | Manufacturer's specifications | 11.3 mg/ml |
| Cholesteryl-4-[[2-(4-morpholinyl)ethyl]amino]-4-oxobutanoate (MOCHOL) | Cationic amphoteric lipid | Manufacturer's specifications | 27.0 mg/ml |
| Sucrose | Cryoprotectant, osmolality control | BP, JP, NF, EP | 92.4 mg/ml |
| Disodium hydrogen phosphate, dihydrate | Buffer pH adjustment | BP, USP, EP | 1.44 mg/ml |
| Potassium dihydrogen phosphate | Buffer pH adjustment | EP, BP, NF | 0.2 mg/ml |
| Potassium chloride (KCl) | Ionic strength adjuster | EP, BP, USP | 0.2 mg/ml |
| Water for injection (WFI) | Solvent | WFI (USP, EP) | qs 1 ml |

MTL-CEBPA is supplied in the form of a suspension and will be packaged in 2 U mL glass vials with stopper. To ensure that 20 ml can be withdrawn from the primary container by syringe, there is an overfill of 20.6 ml (equivalent to 21.4 g). There is no manufacturing overage. The formulation is:

|  | Quantity per mL | Quantity per vial |
|---|---|---|
| MTL-CEBPA | 2.5 mg | 50 mg |

Excipients

The excipients in MTL-CEBPA can be categorized into two groups: the liposome-forming lipid excipients (NOV340—Smarticles® technology owned by Marina Biotech) and the buffer forming excipients sucrose and phosphate-salts (also refer to Table 15). The development of the liposomes and their composition is described by Andreakos E. et al., *Arthritis Rheum*, vol. 60(4): 994-1005 (2009), the contents of which are incorporated herein by reference in their entirety. The used sucrose-phosphate-buffer, pH 7.5, is known to have good compatibility with the excipients and the drug substance.

The liposome-forming lipid excipients are comprised of 1-palmitoyl-2-oleoyl-sn-glycero-3-phosphocholine (POPC), 1,2-dioleoyl-sn-glycero-3-phosphoethanol-amine (DOPE), cholesteryl-hemisuccinate (CHEMS), and 4-(2-aminoethyl) morpholino-cholesterol hemisuccinate (MOCHOL) in a molar ratio of: 6:24:23:47 as shown in Table 16 below.

TABLE 16

Lipid Components of NOV340

| Abbr. Name | Chemical Name | Formula | Molecular Mass [g/mol] |
|---|---|---|---|
| POPC | 1-Palmitoyl-2-oleoyl-sn-glycero-3-phosphocholine | $C_{42}H_{82}NO_8P$ | 760.08 |
| DOPE | 1,2-Dioleoyl-sn-glycero-3-phosphoethanolamine | $C_{41}H_{78}NO_8P$ | 743.55 |

TABLE 16-continued

Lipid Components of NOV340

| Abbr. Name | Chemical Name | Formula | Molecular Mass [g/mol] |
|---|---|---|---|
| CHEMS | 3β-Hydroxy-5-cholestene3-hemisuccinale 5-cholesten·3β-ol 3-hemisuccinate | $C_{31}H_{50}O_4$ | 486.37 |

TABLE 16-continued

Lipid Components of NOV340

| Abbr. Name | Chemical Name | Formula | Molecular Mass [g/mol] |
|---|---|---|---|
| MOCHOL | 4-(2-Aminoethyl) morpholino-cholesterol hemisuccinate | $C_{37}H_{62}N_2O_4$ | 598.90 |

Solvent: Ethanol, lipid ratios: POPC:DOPE:CHEMS:MOCHOL in a molar ratio of: 6:24:23:47

Figure 31:
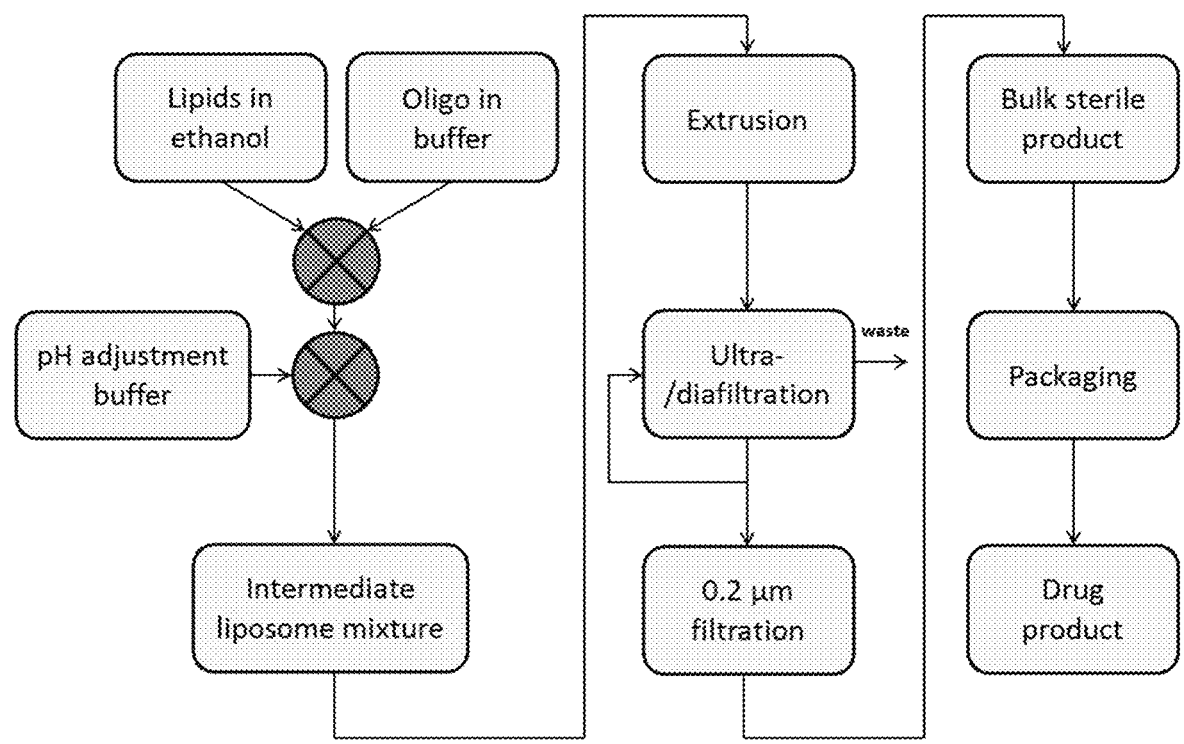
FIG. 31 is a general overview of MTL-CEBPA production process.
Figure 32A:
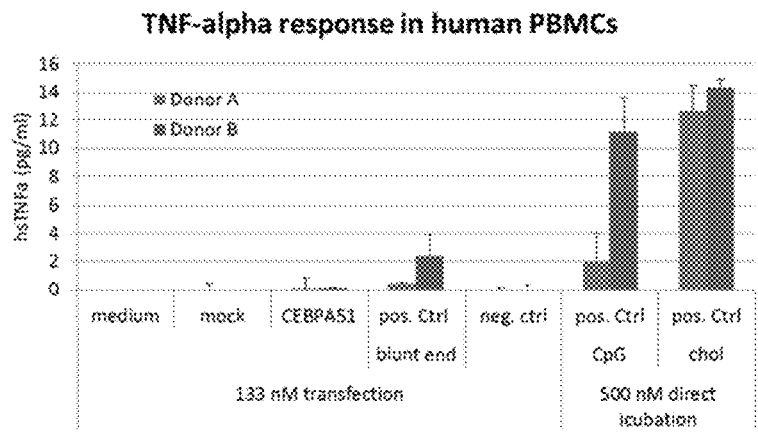
FIG. 32A and FIG. 32B show TNF-α and IFN-α secretion in huPBMCs after transfection with CEBPA-51 and control oligos.
Figure 32B:
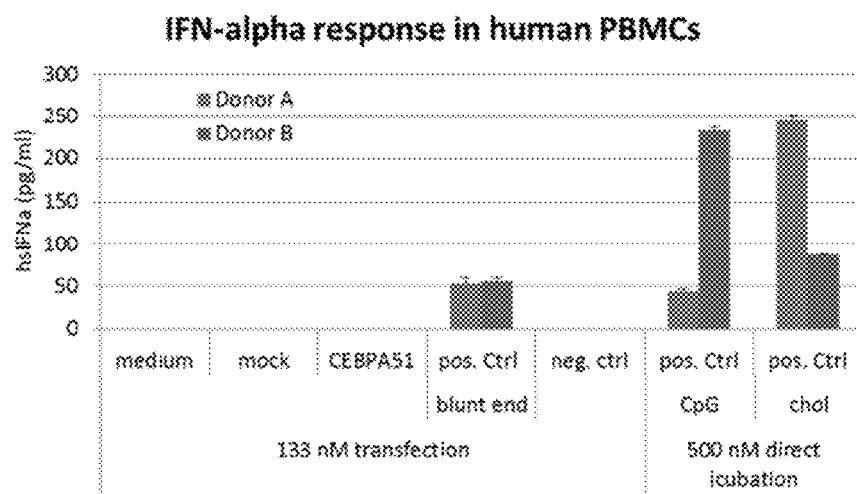

A general overview of MTL-CEBPA production process is shown in FIG. 31. A detailed process of MTL-CEBPA production (Steps 1-9) is shown in FIG. 41.

MTL-CEBPA was prepared by first dissolving the lipids in ethanol and dissolving CEBPA-51 separately in sodium acetate/sucrose buffer pH 4.0 (Step 1a and Step 1b).

The two solutions are then combined through an injection process to form the primary vesicles, after which the ethanol concentration is rapidly decreased and the pH rapidly increased by the addition of the pH adjustment buffer (sodium chloride/phosphate buffer pH 9.0) (Step 2).

The intermediate liposome mixture is then extruded through a polycarbonate membrane to reduce the size of large particles and aggregates (Step 3).

The bulk mixture is then concentrated by ultrafiltration, and the buffer is exchanged against at least 7 volumes of a sucrose/phosphate buffer pH 7.5 to reduce the concentration of ethanol and salts (Step 4). This bulk product is then passed through a 0.2 µm filter for bioburden reduction (Step 5). The product is adjusted to the final target concentration and sterilized by 0.2 µm sterile filtration (Step 6). Subsequently the bulk product is filled into sterile vials (Step 7). The filled vials are tested for final release (Step 8). Current in-process controls are depicted in the respective figures below. Final release of the drug product according to the specifications defined in this document is performed on the drug product.

After completion of the process, including final vialling and release, the entire DP vials are stored at or below −20° C. (Step 9).

Lipid to drug ratio at the point of liposome formation is of major importance for the encapsulation efficiency of RNA within liposomes, as CEBPA-51 solubilized in a pH 4.0 buffer interacts with MOCHOL, which is positively charged in this environment. To optimize the encapsulation yield, lipid concentration in the EtOH solution was kept constant and the concentration of CEBPA-51 in the solution was altered ranging from 1.06 up to 3.44 mg/ml. The obtained results clearly showed a trend indicating that by decreasing the CEBPA-51 concentration in the solution, there is a slight increase in the encapsulation efficiency.

Container Closure System

The container closure system selected for MTL-CEBPA is a standard 20 ml serum vial configuration with 20 mm closure. The glass vials are made from clear USP Type I borosilicate glass, which provides for good protection of the product with minimal potential for leaching. This type of glass also has good thermal stability, which is critical for storing frozen product. The stopper is made from a standard chlorobutyl rubber compound, and product-contacting surfaces are coated with a fluoropolymer which minimizes the potential for product adsorption. Finally, the aluminum crimp cap provides for a secure seal of the stopper to the vial, and protects the external interface of the rubber septum from potential contamination until the time of use.

Microbiological Attributes

MTL-CEBPA is provided as a sterile, single use vial. No preservative is added to inhibit microbial growth. The standard glass serum vial with rubber stopper and aluminum crimp cap provides a well-proven barrier to prevent microbial contamination.

The bioburden of MTL-CEBPA is reduced by filtration through a 0.2 µm filter. Immediately prior to filling into sterile vials, the product is sterilized by passing through a sterilization-grade 0.2 µm filter (Step 6, DP). All packaging components are provided sterile "ready to use". They are handled under aseptic conditions in an ISO class 5 environment without additional treatment.

MTL-CEBPA is stored frozen at −20° C.±5° C. and protected from light. Shipping is performed in a cooler packed with dry ice. MTL-CEBPA is stable when stored at −20° C. for up to 6 months, showing no trend for slight decrease or changes (within the range of analytical variability). A shelf life of 12 months for material stored at −20° C. is proposed since a rapid decrease of material quality under frozen conditions is considered very unlikely.

MTL-CEBPA is administered by i.v. infusion (250 mL). MTL-CEBPA at a concentration of 2.5 mg/mL saRNA is thawed at room temperature before diluting the suspension in 0.9% Normal Saline for Intravenous Use in order to obtain a volume of 250 mL regardless of the concentration.

The test item and diluent are mixed together by manual inversion of the infusion bag (to avoid foaming).

MTL-CEBPA is administered at a constant rate over 60 minutes into a vein (peripheral or central) using an infusion pump.

Storage of prepared solution: Room temperature (15 to 25° C.) with a maximum expected in-use shelf life of at least 6 hours.

The properties of CEBPA-51 saRNA and MTL-CEBPA are shown in Table 17-1 and Table 17-2: Generally, MTL-CEBPA is a milky white suspension. saRNA encapsulation measured by fluorescence detection is ≥75%. Particle size measured by dynamic light scattering is between about 50 nm to about 150 nm or about 100 to about 140 nm. Polydispersity index measured by dynamic light scattering is ≤0.200. Zeta potential measured by dynamic light scattering is ≤−30.0 mV at pH 7.2-7.8. pH value measured by potentiometry is between about 7.2 to about 7.8. Osmolality measured by freezing point depression is between about 280 to about 400 mOsmol/kg. Impurities saRNA measured by RP-HPLC is ≤15%.

saRNA encapsulation: The total and "external" free saRNA contents are quantitated by measuring fluorescence intensity from RiboGreen and saRNA complexation to determine the % encapsulation. The drug product sample solutions are analyzed under two different conditions, untreated samples for external saRNA and samples treated with Triton X-100 for total saRNA. The content of RNA is determined using a calibration curve generated from a standard with known concentration.

The percent content of encapsulated saRNA is calculated:

$$E\ (\%) = (C_T - C_F) \cdot 100 / C_T$$

E (%) % encapsulated saRNA
$C_T$ total content of saRNA
$C_F$ content free (external) saRNA Particle size and polydispersity index: The size of liposomes and PDI are determined by Photon Correlation Spectroscopy (PCS) using a Zetasizer Nano ZS instrument (Malvern).

Zeta potential: The surface potential is determined by Laser Doppler Velocity/Laser Doppler Anemometry (LDV/LDA) using a Zetasizer Nano ZS instrument (Malvern).

pH: The pH of liposomal drug product is measured at 20-25° C. using a glass electrode.

Osmolality: The determination of osmolality is based on the principle of freezing point depression in comparison to pure water using an Osmomat 030 (Gonotec).

Residual ethanol: Residual ethanol in liposomal curcumin drug product is quantified by head-space gas chromatography using a flame ionization detector (GC/FID).

Impurities saRNA: The content (area %) of saRNA impurities is quantified by ion pair-reversed phase (IPRP) HPLC using a Waters XBridge C18 column (4.6×100 mm, 3.5 particle size). Nanoparticles are disrupted with 2% Triton X-100 buffer and released saRNA is separated on the HPLC column using a a gradient of 100 mM hexafluoroisopropanol (HFIP)/7 mM triethylamine (TEA) in water and 100% methanol. RNA is detected at 260 nm. The content of impurities (area %) is determined by subtracting the peak areas (%) of the main strands (anti-sense, sense strand) from the total peak area (100 area %).

TABLE 17-1

Properties of CEBPA-51

| Analytical Tests | Single Strand | Specifications Duplex | Results |
|---|---|---|---|
| Appearance | | A white to pale yellow powder | Conforms |
| Identification (LC-MS) | | | |
| Sense | 6920 ± 3 Da | 6920 ± 3 Da | 6920 Da |
| Antisense | 6723 ± 3 Da | 6723 ± 3 Da | 6722 Da |
| Purity (RP-IP HPLC, area %) | | | |
| Sense | NLT 90% | | 96.90% |
| Antisense | NLT 90% | | 90.50% |
| Duplex | | NLT 90% | 92.60% |
| Purity (/EX HPLC, are %) | | | |
| Sense | NLT 85% | 85% | 94.60% |
| Antisense | NLT 85% | | 92.20% |
| Duplex | | NLT 90% | 94.30% |
| Purity (SEC HPLC, area %) | | NLT 90% | 99.5% |
| Bio burden | | NMT 100 CFU/g | 30 CFU/g |
| Bacterial Endotoxins | | NMT 1 EU/mg | <0.25 EU/mg |
| Water contents (Karl-Fisher) | | NMT 10% | 5% |
| Sodium content (/GP-MS) (Anhydrous Basis) | | Report | 5.6% w/w |
| Oligonucleotide Content by UV (Anhydrous Basis) | | Report | 1040 µg/mg |

TABLE 17-2

Properties of MTL-CEBPA

| Test Method | Result |
|---|---|
| Appearance | milky, white |
| Total saRNA | 2.50-2.56 mg/ml |
| saRNA encapsulation | 83%-85% |

TABLE 17-2-continued

Properties of MTL-CEBPA

| Test Method | Result |
|---|---|
| Content MoChol | 24.9-26.9 mg/ml |
| Content DOPE | 17.3-18.4 mg/ml |
| Content CHEMS | 11.0-11.5 mg/ml |
| Content POPC | 4.7-4.8 mg/ml |
| Content cholesterol | 0.9-1.0 mg/ml |
| Particle size (z-average) | 107 nm-112 nm |
| Polydispersity index | 0.160-0.169 |
| Zeta potential | −35.6-−39.1 mV |
| saRNA impurities | 5.9%-6% |
| Residual ethanol | ≤0.5% w/v |
| PH | 7.4-7.6 |
| Osmolality | 349 mOsmol/kg |
| Subvisible particles | ≥10 µm: 2 particles/container ≥25 µm: <1 particle/container |
| Extractable volume | pass |
| Endotoxin | <0.5 EU/ml |
| Sterility | Pass/no growth |

Example 18. Immunosafety Study of CEBPA-51 in Primary Human PBMCs

Aim of Study:

The objective of this study was to assess the immunosafety of CEBPA-51, as measured by the activation of TLR pathways ex vivo in human blood cells.

Experimental Design:

The induction of cytokines by CEBPA-51 was tested with peripheral blood mononuclear cells isolated from two human donors (huPBMCs).

TNF-α:

The huPBMCs were transfected in triplicates with 133 nM of CEBPA-51 or control sequence RD-01010 (positive control) and RD-01011 (negative control) using Dotap as a transfection reagent. Transfection reagent alone was used as mock control. In addition, controls ODN2216 (CpG-oligonucleotide) and RD-01002 (cholesterol-conjugated siRNA) were added directly at a concentration of 500 nM without transfection. After 20 hours of incubation the supernatants from the triplicate transfections were pooled and TNF-α secretion was measured using a commercial human TNF-α ELISA assay (samples measured in duplicates).

IFN-α: HuPBMCs were transfected in triplicates with 133 nM CEBPA-51 or control sequences RD-01010 (positive control) and RD-01011 (negative control) using Geneporter-2 as a transfection reagent. Transfection reagent alone was used as mock control. In addition, controls ODN2216 (CpG-oligonucleotide) and RD-01002 (cholesterol-conjugated siRNA) were added directly at a concentration of 500 nM without transfection. After 20 hours of incubation the supernatants from the triplicate transfections were pooled and IFN-α secretion was measured using a commercial human IFN-α ELISA assay (sample measured in duplicate.

Results:

The secretion of cytokines TNF-α and IFN-α by human PBMCs was measured after transfection with CEBPA-51 or control oligos. CEBPA-51 elicited no significant secretion of either cytokine into the cell culture media after incubation for 20 hours whereas the positive controls triggered the expected cytokine release (see F. 32A and 32B).

Conclusion:

The CEBPA-51 did not trigger activation of the TLR-8 or TLR7/9 pathways in human PBMCs, as indicated by the lack of cytokine TNF-α and IFN-α release following transfection of CEBPA-51. These results suggest that the chemically modified saRNA does not have immune-stimulatory activity.

Example 19. Phase I Study and Selection of a Safe Starting Dose

Proposed First-in-Human Clinical Trial

The FIH study will be a multi-centre, open-label, Phase 1 clinical study with RNA oligonucleotide MTL-CEBPA to investigate its safety and tolerability in patients with advanced liver cancer.

Indication

Treatment of patients with histologically advanced cancer characterised by hepatocellular carcinoma or advanced stage cancer presenting with secondary liver tumours derived from extra hepatic primary cancer types who are considered unfit for any therapy or surgery, or are progressing following loco-regional therapy and sorafenib.

Study Objectives

Primary Objective:

To determine the safety and tolerability of weekly administration of MTL-CEBPA for 3 weeks to participants with histologically advanced cancer characterised by hepatocellular carcinoma or advanced stage cancer presenting with secondary liver tumours derived from extra hepatic primary cancer types.

Secondary Objectives:

To determine the Recommended Phase 2 Dose (RP2D) of MTL-CEBPA; to characterise the pharmacokinetics (PK) parameters of MTL-CEBPA; to assess the pharmacodynamic (PD) process of MTL-CEBPA notably the characterisation of MTL-CEBPA effect on serum albumin and bilirubin; to assess changes in health-related quality of life in HCC patients following administration of MTL-CEBPA.

Biomarkers

Biomarker Strategy

Predictive biomarkers

Inclusion/Exclusion Biomarkers

To date, no predictive biomarkers or gene signatures have been identified for MTL-CEBPA. Therefore, patient eligibility criteria for the study do not include such biomarkers.

Exploratory Predictive Biomarker

Preclinical data with CEBPA-51 and tool compounds and the scientific literature suggest multiple biomarker hypotheses for HCC response to saRNA against CEBPA. For instance, tumour cell growth arrest in response to CEBPA saRNA may depend on the basal level of CEBPA expression. Certain regulatory mechanisms that inactivate C/EBP-α protein may result in resistance to CEBPA saRNA, including for instance dephosphorylation of Ser193 as a consequence of PI3K-AKT pathway activation or overexpression of dominant-negative forms of C/EBP-β.

The study does not include prospective exploratory biomarkers of tumour response. However, retrospective analyses of biomarkers of tumour sensitivity/resistance may be conducted based on archived biopsies.

No definitive biomarker hypotheses have been formulated to date for responsiveness of fibrotic or cirrhotic liver to MTL-CEBPA, although certain endocrine loops, e.g. via insulin and TNF-α, are known to modulate CEBPA activity. No prospective analyses of predictive biomarkers are currently envisioned; however, retrospective analyses may be conducted on archived tissues.

Response Biomarkers

Target Engagement

The molecular target of CEBPA-51 saRNA is the CEBPA promoter. Upregulation of CEBPA transcription can be measured in tissue samples via qRT-PCR of CEBPA mRNA or via immunostaining for C/EBP-α protein.

Several exploratory approaches will be pursued to measure changes in CEBPA expression and establish proof-of-mechanism. During the expansion phase, circulating tumour cells (CTC) will be collected pre/post-treatment for immunostaining of C/EBP-α protein levels. If we obtain sufficient tissue from any matched pre/post-treatment biopsies we would aim to look at CEBPA mRNA levels by the qRT-PCR method used in the preclinical models, as well as at C/EBP-α protein levels by immunostaining. The use of surrogate tissues such as WBCs has not been validated to date but will be explored as another potential option for demonstrating target engagement that may be introduced once the MTD is established.

PD Biomarkers

PD biomarkers include liver-specific genes, and their respective protein products, that are under direct transcriptional control of C/EBP-α (proximal biomarkers), as well as downstream gene targets and proteins that are markers of C/EBP-α-dependent differentiation or proliferation programs (distal biomarkers). Several proximal biomarkers of C/EBP-α are secreted proteins that can be monitored in serum including, for instance, albumin, AFP, transferrin, and coagulation factors.

Serum albumin was selected as the primary liver-specific PD biomarker because of the ease of sampling and the availability of validated clinical assays. Other serum-based biomarkers are under investigation as additional exploratory PD biomarkers.

Depending on availability of pre/post-treatment tumour biopsies, changes in the cell cycle regulatory protein p21 will be assessed in tumour sections by IHC, as a marker of tumour cell growth arrest.

Surrogate Efficacy Biomarkers

Serum albumin and total bilirubin levels are secondary endpoints in this study. Albumin and bilirubin are validated biomarkers of overall liver function status. In addition, a combined measure of albumin and bilirubin serum levels (ALBI grade) has been shown to correlate with survival in patients with advanced HCC and liver disease. Both, serum albumin and bilirubin have been shown to respond to MTL-CEBPA treatment in preclinical models of liver disease, with improvements in albumin compared to control groups and near normalization of bilirubin levels.

CTCs and circulating DNA will be collected during the expansion phase as exploratory biomarker of tumour response. Serum alpha-fetoprotein (AFP) is a validated marker of HCC burden. However, the AFP gene is also under the control of C/EBP-α in normal liver, with MTL-CEBPA treatment expected to increase AFP serum levels. Because of this opposite response in liver and tumour, AFP levels will need to be interpreted with caution.

Efficacy Biomarkers

Liver function status will be assessed by serum chemistry including, albumin, total protein, bilirubin, ALP, GGT, ALT, AST and ammonia levels. Tumour responses to MTL-CEBPA treatment will be monitored by CT or MRI and assessed using standard criteria (RECIST).

Drug PK and Biodistribution

ADME monitoring of MTL-CEBPA will be limited to determination of total API levels in plasma. Because of the rapid metabolism and clearance of free dsRNA, total API levels will primarily represent encapsulated CEBPA-51. The nanoparticle and its lipid components will not be monitored separately. It is assumed that the levels of intact nanoparticles in circulation are proportional to the levels of total API. Tissue biodistribution and metabolites of CEBPA-51 will not be measured.

Biomarker Assays

All serum biomarkers will be assessed by local accredited laboratories. Gene expression in biopsies will be measured by validated Immunohistochemistry (IHC) assay.

A program-specific PK assay was developed to measure the total API in plasma of participants. The assay is based on heat-denaturing of CEBPA-51 to separate the two RNA strands, followed by hybridization of the antisense strand to an immobilized complementary PNA probe. As such the assay measures the concentration of the antisense strand (and any of its metabolites capable of hybridizing to the PNA probe), rather than the RNA duplex itself. The assay was developed and validated for non-clinical and clinical use by Axolabs GmbH, Germany.

Study Outcome Measures

Primary Outcome Measures

Continuous measurement of vital signs (incl. blood pressure, pulse, body temperature, respiratory rate), ECG (12 lead) and, safety laboratory data (incl. haematology, coagulation, clinical chemistry, clotting and activation fragment of complement factor B (Bb) and complement component 3a (C3a)) as well as the description of both participant and investigator assessment of tolerability will be collected.

All adverse events documented following the first MTL-CEBPA infusion will be graded for seriousness, expectedness and relationship to study drug as 'unrelated', 'possible', 'probable' or 'definite'.

Safety and tolerability of MTL-CEBPA will be evaluated in terms of frequency of adverse events graded according to toxicity criteria (NCI CTCAE v 4.03) and categorised by body system and diagnosis.

Secondary Outcome Measures

The plasma concentration of MTL-CEBPA will be analysed at defined time points using hybridization-based HPLC-assay in order to determine the Pharmacokinetic (PK) properties of MTL-CEBPA in plasma after intravenous administration.

This protocol plans to collect measurements of surrogate PD biomarkers including albumin, bilirubin, liver enzyme levels, chemokines and tumour markers. Gene and protein expression levels in tumour tissue will also support the determination of the pharmacodynamics characteristics of MTL-CEBPA in participants with liver tumours after intravenous administration.

Health-related quality of life questionnaire data will be collected on Day 1, Day 15, week 8 and at EOS of part 1b using the self-administered FACT-Hep questionnaire.

Study Design

This study is a multi-centre, open-label, first-in-human, phase 1 clinical study in two parts: dose escalation followed by dose expansion.

Part 1a—Dose Escalation

The dose escalation part of the study follows a standard 3+3 design. Doses are between about 20 to about 160 mg/m$^2$. Participants with advanced HCC or participants with secondary liver tumours who meet the eligibility criteria will be recruited into 6 cohorts of 3 participants each at the following doses: 28, 47, 70, 98, 130, 160 mg/m$^2$ until there is either development of drug related Grade 3 toxicities (NCI-CTCAE version 4.03) or the maximum improvement in serum albumin has been observed as defined above. Dose escalation procedure is described above. Dose and schedule might be modified depending on data arising from the study.

In the first dose cohort the first participant receives MTL-CEBPA treatment at the study's starting dose. MTL-CEBPA is administered by intravenous infusion over 60 minutes once a week for 3 weeks followed by a rest period of 1 week; this defines a 4-week cycle. The determination of the starting dose of MTL-CEBPA was based on GLP toxicity studies in rodents and cynomolgus monkeys. Based on these data, a starting dose of MTL-CEBPA 28 mg/m$^2$ was considered to be the safe starting dose in humans.

Participants in Part 1a of the study who obtain clinical benefit will be offered further cycles. Participants may also continue to receive MTL-CEBPA on compassionate grounds; the investigator must discuss with the sponsor on case by case basis before the participant can continue on treatment.

An additional cohort of three HCC only participants may be added after completion of Part 1a and before commencing Part 1b to confirm the RP2D in this group of patients. The cohort will only be considered if deemed appropriate by the PIs and Sponsor's Safety Committee after review of clinical data and recruitment of HCC participants to Part 1a of the study.

The RP2D will be defined by the safety review committee (SRC) as the most appropriate dose to maximise a favourable risk/benefit reward for the participant population in the dose expansion part of the study.

Part 1b—Dose Expansion

Once the RP2D is obtained, an additional group of 12-15 eligible participants with advanced HCC will be recruited sequentially. Each participant will be enrolled for 2 cycles and administered with MTL-CEBPA at the RP2D until the participant withdraw from the study.

Participants in Part 1b of the study who obtain clinical benefit will be offered further cycles. Participants may also continue to receive MTL-CEBPA on compassionate grounds. The investigator must discuss this with the sponsor on case by case basis before the participant can continue on treatment.

Study Endpoints

Primary Endpoint

In Part 1a, the primary endpoint will be dose limiting toxicity (DLT) defined as: Any drug related toxicity grade greater than or equal to 3 according to the Common Terminology Criteria for Adverse Events (CTCAE) v4.03, including: Grade≥3 nausea, vomiting and diarrhoea despite adequate treatment for more than 3 days; Decrease in the participant's performance status≥2 points compared to baseline; Grade≥3 fatigue for more than 7 days; Grade≥3 haemoglobin, platelets or neutrophils abnormal laboratory value, myelosuppression for more than 5 days; Grade≥3 bilirubin abnormal laboratory value (>3.0×ULN); Grade 4 AST and/or AST abnormal laboratory value (>20.0×ULN).

Evaluation of any potential DLT will be performed during the first 28 days (i.e. first cycle). All patients on the cohort should clear the DLT period before any dose escalation can take place; to this end an interval of not less than 7 days after the third dose administered to the final participant in the previous cohort during Part 1a of the study to assess for possible treatment related side-effects is mandatory.

In Part 1b, safety and tolerability of MTL-CEBPA will be evaluated in terms of frequency of adverse events graded according to toxicity criteria (NCI CTCAE v 4.03) and categorised by body system and diagnosis.

Secondary Endpoints

PK parameters will be defined by the maximum plasma concentration (Cmax), time to maximum plasma concentration (Tmax), area under the plasma concentration curve (AUC) and the half-life (t½) of MTL-CEBPA after intravenous administration.

This protocol plans to evaluate the clinical efficacy (PD) of MTL-CEBPA in participants with advanced HCC or participants presenting with secondary liver tumours using descriptive analysis of changes from baseline of surrogate biomarkers including albumin, bilirubin, liver enzyme levels, chemokines, CTCs, tumour markers and gene and protein expression levels in tumour tissue. Health-related quality of life will be assessed in participants with advanced HCC using descriptive analysis of changes from baseline of FACT-Hep score.

Study Enrolment and Withdrawal

During the screening phase, after the participant has signed the ICF, the following criteria will be assessed; each participant should meet all of the inclusion criteria and none of the exclusion criteria for this study. Under no circumstances can there be exceptions to this rule and no waiver will be approved by the sponsor as it is considered to be inappropriate and non-compliant to GCP.

Participants will be assigned with a unique participant trial ID sequentially in order of their recruitment (e.g. 001, 002, etc.)

Inclusion Criteria

Participants should meet all of the following inclusion to be eligible to participate in the study.

Inclusion Criteria for Dose Escalation (Part 1a)

The dose escalation part of the study will focus on recruiting patients with either advanced HCC or with secondary liver tumours. Recruitment will depend on observed toxicity. Nevertheless, the protocol aims to recruit a maximum of 30 participants in Part 1a.

Inclusion Criteria for Patients with Advanced HCC: Histologically confirmed advanced HCC; Patients who are considered ineligible for surgery, or any other treatment, who are progressing following loco-regional therapy and/or sorafenib (naïve sorafenib patients are eligible); At least one measurable lesion with target lesion size≥1.0 cm as measured by MRI or CT; Child-Pugh A or Class B7 disease; Platelets≥75×10$^9$/L; Serum albumin>28 g/L and <35 g/L; ALT and AST≤5×ULN Inclusion Criteria for Patients with Secondary Liver Cancer: Histologically confirmed advanced extra-hepatic solid tumour and incurable liver tumours refractory to prior standard therapies or for whom no standard therapy exists; At least one measurable lesion with target lesion size≥1.0 cm as measured by MRI or CT located in the liver; Platelets≥100×109/L; Serum albumin>25 g/L; ALT and AST≤3× ULN.

Other Inclusion Criteria: Written informed consent obtained prior to any trial specific procedure; Male or female aged≥16 years; ECOG performance status 0 and 1; Available archival tumour tissue or ability and willingness to perform a pre-treatment tumour biopsy; Acceptable laboratory parameters, as demonstrated by: Bilirubin≤50 μmol/L, WBC≥2.0×10$^9$/L, Absolute neutrophil count≥1.5×10$^9$/L, Haemoglobin≥9.0 g/dL or Prothrombin time (PT)<20 seconds; Acceptable renal function as demonstrated by: Serum creatinine≤1.5×ULN or Calculated creatinine clearance≥60 mL/min/1.73 m2 (estimated using the CKD-EPI formula); Negative blood pregnancy test for women of childbearing potential; Safe contraception in females of childbearing potential during the entire study, using an established treatment with hormonal contraceptives for at least 2 months prior to start of screening: For females of child bearing potential (without using hormonal contraceptives for at least 2 months prior to start of screening) a double contraception method is required during the entire study meeting the criteria for an effective method of birth control, i.e. at least two effective birth control methods such as condoms, diaphragms or intra-uterine devices must be used; Male participants with partners of child bearing potential are required to use barrier contraception in addition to having their partner use another method of contraception during the trial and for 3 months after the last dose. Male participants will also be advised to abstain from sexual intercourse with pregnant or lactating women, or to use condoms; Willingness and ability to comply with all protocol requirements including scheduled visits, treatment plans, laboratory tests and other study procedures.

Inclusion Criteria for Dose Expansion (Part 1b)

This protocol aims to recruit 12 to 15 participants with advanced HCC:

Histologically proven advanced HCC; Patients who are considered not eligible for surgery, or any other treatment, who are progressing following loco-regional therapy and sorafenib (naïve sorafenib patients are eligible); At least one measurable lesion with target lesion(s) size≥1.0 cm as measured by MRI or CT; Child-Pugh A or B7 disease; Platelets≥75×10$^9$/L; Liver dysfunction with serum albumin>28 g/L and <35 g/L; ALT and AST≤5 times upper limit of normal range; Bilirubin≤50 μmol/L; Written informed consent obtained prior to any trial specific procedure; Male or female aged≥16 years; ECOG performance status 0 and 1; Available archival tumour tissue or ability and willingness to perform a pre-treatment tumour biopsy; Acceptable laboratory parameters, as demonstrated by: WBC≥2.0×10$^9$/L, Absolute neutrophil count≥1.5×10$^9$/L, Haemoglobin≥9.0 g/dL, or Prothrombin time (PT)<20 seconds; Acceptable renal function as demonstrated by:Serum creatinine≤1.5× ULN, Calculated creatinine clearance≥60 mL/min/1.73 m2 (CKD-EPI formula), or Negative blood pregnancy test for women of childbearing potential; Safe contraception in females of childbearing potential during the entire study, using an established treatment with hormonal contraceptives for at least 2 months prior to start of screening: For females of child bearing potential (without using hormonal contraceptives for at least 2 months prior to start of screening) a double contraception method is requested during the entire study meeting the criteria for an effective method of birth control, i.e. at least two effective birth control methods such as condoms, diaphragms or intra-uterine devices must be used. Male participants with partners of child bearing potential are requested to use barrier contraception in addition to having their partner use another method of contraception during the trial and for 3 months after the last dose. Male participants will also be advised to abstain from sexual intercourse with pregnant or lactating women, or to use condoms; Willingness and ability to comply with all protocol requirements including scheduled visits, treatment plans, laboratory tests and other study procedures.

Participant Exclusion Criteria

Patients should not enter the study if any of the following exclusion criteria are fulfilled.

Exclusion Criteria for Advanced HCC Patients: Child-Pugh classes B8, B9 or C;

Patients who have been treated with TACE, sorafenib or chemotherapy within the last 28 days Other Exclusion Criteria: Prior systemic cancer-directed treatments within 15 days or investigational drugs within the last 30 days; Grade>1 treatment-related toxicities (excluding alopaecia) at the time of screening; Patients with clinically significant cancer ascites; Any episode of bleeding from oesophageal varices or other uncontrolled bleeding within the last 3 months; Patients administered with serum albumin within the last 7 days prior to the first MTL-CEBPA injection; Known infection with human immunodeficiency virus (HIV); Patient with central nervous system (CNS) metastasis; Signs and symptoms of heart failure characterised as greater than the New York Heart Association (NYHA) Class I; Patient presenting with a prolonged corrected QT (QTc) interval defined as ≥450 ms (males) and ≥460 ms (females) using Fridericia's correction formula; or other clinically significant cardiac abnormalities; Major surgery within the last 30 days; Patients with sepsis, obstructive jaundice or encephalopathy; Evidence of spontaneous bacterial peritonitis or renal failure or allergic reactions to the agent or excipient; Pregnant or lactating women; Any other condition (e.g., known or suspected poor compliance, etc.) that, in the judgment of the investigator, may affect the participant's ability to follow the protocol specific procedures.

Treatment Assignment Procedures

Part 1a—Dose Escalation

Figure 33:
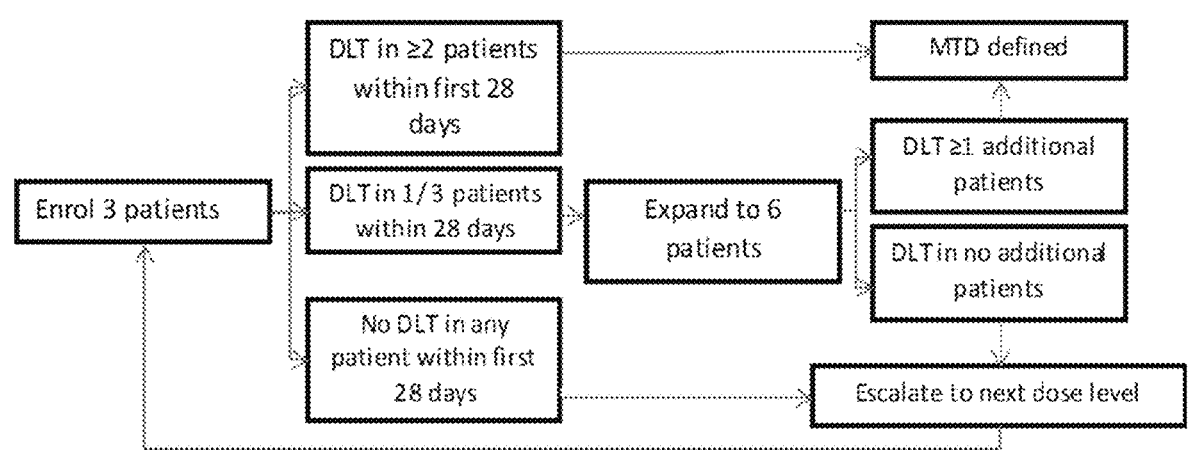
FIG. 33 is a dose escalation flowchart.

Participants will be enrolled for 2 cycles. The dose escalation phase of the study will follow a standard 3+3 design as shown in FIG. 33. Six cohorts of 3 eligible participants are planned at the following doses: 28, 47, 70, 98, 130, 160 mg/m². Individual dose will be based on the participant's most recent height and weight using the DuBois & DuBois (133) body surface area (BSA) calculation.

At each dose cohort the first participant receives MTL-CEBPA treatment at the study starting dose. MTL-CEBPA is administered once a week for 3 weeks on Day 1, Day 8 and Day 15 by intravenous infusion over 60 minutes followed by a week of rest. This defines a cycle.

Subsequent participants will be recruited not less than 7 days after the first dose of the first participant in order allow the assessment of treatment related side-effects.

Evaluation of any potential DLT as defined in above will be performed during the first 28 days (i.e. first cycle).

A gap of not less than 7 days should lapse between the last dose of the final participant in the previous cohort to allow for adverse events or toxicities to become apparent. A decision to progress to the next cohort will require a review of the previous cohort safety and clinical data for all Participants by the SRC. Following the review, the next cohort may be initiated. The decision will be documented in writing, and a record will be retained in the Trial Master File (TMF).

If there is no occurrence of toxicities qualifying as DLT in 3 participants of a dose cohort, dose escalation to the next dose level may be performed. If there is a DLT in one of three participants in a dose cohort, a further 3 participants will be enrolled at this dose. If there are no further DLT occurrences in these additional 3 participants, escalation to the next dose level may be performed. If, however, 2 or more of those 6 participants (3+3) present with a DLT there will no further dose escalation step and the dose level will be considered as the maximum tolerated dose (MTD). Additionally, if 2 participants present with a DLT in a single cohort then there will be no further dose escalation step and the dose level will be considered as the MTD. All dose escalation decisions will be based on the judgement of the SRC.

An additional cohort of three HCC only participants may be added after completion of Part 1a and before commencing Part 1b and may be administered with an intermediate dose of MTL-CEBPA using the same dosing regimen as in Part 1a. The cohort will only be considered if deemed appropriate by the PIs and Sponsor s Safety Committee after review of clinical data and recruitment of HCC participants to Part 1a of the study.

The RP2D will be defined by the SRC as the most appropriate dose to maximise a favourable risk/benefit reward for the participant population in the dose expansion part of the study. FIG. 33 is a flowchart for dose escalation.

Part 1b—Dose Expansion

Following completion of the escalation part of the study, 12-15 eligible participants presenting with advanced HCC will be enrolled for 2 cycles sequentially onto the dose expansion part of the study and will be administered MTL-CEBPA at the RP2D.

Reasons for Withdrawal

A participant may be discontinued from the study for the following reasons:

Patient decision: The participant is at any time free to withdraw his/her participation in the study, without prejudice; Grade≥3 infusion related allergic reaction to the study medication not controlled with prophylactic procedure as described); Any clinical adverse event (AE), laboratory abnormality, intercurrent illness, or other medical condition or situation occurs or worsens such that continued participation in the study would not be in the best interest of the participants; Confirmed disease progression, unless the participant is receiving clinical benefit in the opinion of the investigator; Severe non-compliance to this protocol as judged by the investigator; The participant becomes pregnant; The participant dies.

Study-specific discontinuation criteria: Presence of benefit with an increase in serum albumin≥45 mg/L; the participant may be advised by the investigator to discontinue from the study medication if this is in the participant's best interest, or if the participant's response is positive and allows the participant to receive another conventional therapy that was inappropriate at the start of the study (i.e. stage migration), such as surgery, RFA, TACE or sorafenib.

Termination of Study

Patients are free at any time to withdraw from the study (IP and assessments), without prejudice to further treatment (withdrawal of consent). Such participants will always be asked for the reason(s) and the presence of any AEs. If possible, they will be seen and assessed by an Investigator. AEs will be followed up.

Survival, based on publicly available sources or contact with the participant medical care may be investigated at the scheduled study end and in cases where participants have withdrawn consent. These data will be collected in the eCRF.

To prevent participants being lost to follow-up, their contact details, including next of kin contacts should be collected initially and updated regularly by the site staff or representative.

Dosing Scheme

Administration of MTL-CEBPA will be once a week for 3 weeks followed by a rest period of 1 week [3 plus 1 week=4 weeks=one cycle]. Other schedules and dosage may be explored depending on the results of ongoing preclinical experiments or from data arising from the study.

Six cohorts of 3 eligible participants are planned at the following doses: 28, 47, 70, 98, 130, 160 mg/m².

An extended treatment is allowed for those patients who clinically benefit from treatment in the planned FIH Phase 1 study in patients with primary or secondary liver tumours for whom no further approved treatment options exist, i.e., treatment may continue as long as the clinical benefit persists.

Considerations on Calculation of Human Starting Dose

MTL-CEBPA was efficacious in two liver disease models. In the CCL4 model, biweekly doses as low as 0.3 mg/kg showed reduction or reversal of a subset of disease symptoms. However, the highest dose of 3 mg/kg was required for maximal impact on some biomarkers considered disease relevant, including serum albumin and liver hydroxyproline. Therefore, the maximally effective dose in this model is likely 3 mg/kg or higher, for a 2-week biw regimen. Only a single dose level (3 doses of 4 mg/kg) was evaluated in the DEN model. It is therefore not clear if lower doses would have activity or whether higher doses would further improve the observed impact on tumours and other disease metrics. The effective dose for a single week of treatment is therefore estimated at 4 mg/kg.

Based on the rat PK data with MTL-CEBPA, the biw and tiw schedules in the CCL4 and DEN models should not have led to drug accumulation in circulation, thus allowing human dose estimations based on single doses. Taken together, and considering the very short treatment period in the DEN model, repeat doses of 3-4 mg/kg may be sufficient for meaningful anti-tumour efficacy and doses of 0.3 to 3 mg/kg for improvement in liver function.

The non-clinical toxicity program included repeat-dose toxicity testing in rats and cynomolgus monkeys, including toxicokinetic profiling and local tolerance evaluation.

MTL-CEBPA, given daily for 3 consecutive days by the intravenous route (1-hour infusion) at 7.5 mg/kg for 4 weeks (total of 12 administrations) to cynomologus monkeys was clinically well-tolerated and only induced transient non-adverse changes in body weight, food consumption, clinical laboratory parameters as well as decreases in platelet count and activation of the alternative and common complement pathways. The 7.5 mg/kg administered 3 times weekly for the duration of the 1 month study was defined as a NOAEL in cynomologus monkeys. MTL-CEBPA administered to rats given daily for 3 consecutive days by the intravenous route (1-hour infusion) at 7.5 mg/kg for 4 weeks (total of 12 administrations) induced lower body weight gain and food intake, clinical signs in a few animals, various changes in haematological, coagulation and serum clinical chemistry parameters as well as local reactions at the infusion sites. Because of their small magnitude and reversibility, these clinical pathology changes were not considered adverse. Histologically, the main finding was macrophage vacuolation in several organs or tissues, which could reflect clearance of the particulate test item and this was not considered adverse. The 7.5 mg/kg administered 3 times weekly for the duration of the 1 month study was defined as a HNSTD in rats.

There were no MTL-CEBPA-related ophthalmological or cardiovascular findings in monkeys or rats at the end of the treatment period.

An in vitro immunogenicity assay was performed with primary human peripheral blood mononuclear cells (PBMCs) transfected CEBPA-51. The assessment of TNF-α and IFN-α showed no induction and thus no immune-stimulatory activity in terms of toll-like receptor (TLR) pathway induction.

As above 7.5 mg/kg administered 3 times weekly for the duration of the 1 month study was defined as a HNSTD in rats and a NOAEL for MTL-CEBPA in monkeys. Although dose extrapolation from animals to humans has traditionally been based on body surface area (BSA)-related scaling or similar mathematical paradigms, these conventions were derived from studies performed with small-molecule anti-cancer agents and are very unlikely to be relevant for dose extrapolation with a product that consists of an RNA in liposomal or other lipid particle delivery system, such as MTL-CEBPA. The original impetus for BSA-based cross-species scaling stemmed from reports that direct extrapolation from the body weight-relative MTD under-predicted human sensitivity to cytotoxic anticancer agents, and better correlation of the MTD across species was obtained when doses were expressed per body surface area. The primary reason for the lesser sensitivity of smaller species such as rodents vs. larger species to small-molecule anticancer agents is that smaller species tend to metabolize such molecules via the hepatic cytochrome P450 system faster than higher species and/or exhibit faster clearance from the blood compartment, which collectively contributes to more rapid or more extensive detoxification than in higher species, including humans.

For many of the lipid-formulated oligonucleotides advanced through nonclinical development, the MTDs in rodents tend to be similar to or lower than in monkeys or other non-rodent species, which is the case for MTL-CEBPA. This pattern is not consistent with the fundamental principle of BSA-based scaling, which would predict a higher MTD in rodents vs. a larger species like monkey. It is not surprising that formulated oligonucleotide products behave differently than small-molecule anticancer drugs, as neither the nucleic acid payload nor the excipients have been shown to (or would be expected to) interact significantly with the hepatic cytochrome P450 system, and the formulation traverses the bloodstream in particulate form, exhibiting unique pharmacokinetics and clearance pathways unlike small-molecule drugs.

Although the plasma AUC for the active saRNA ingredient (CEBPA-51) was substantially lower in rats than in monkeys at similar dose levels, the toxicity produced by MTL-CEBPA is unrelated to the amount of drug in circulation, as none of the toxicities stem from interaction with blood components, and the primary effect observed (i.e., vacuolation of macrophages in various tissues) would be expected to correlate with tissue, not blood, concentrations. In fact, the faster clearance of MTL-CEBPA (CEBPA-51) from circulation in rats very likely reflects more rapid uptake by macrophages, which could result in greater activation of those cells and more pronounced downstream sequelae from such activation, which would account for the greater severity of toxicity in rats vs. monkeys. Thus, although the lesser plasma exposure in rats vs. monkeys at the same mg/kg dose levels may appear to be consistent with conventional BSA-based scaling, this difference certainly does not correlate with a lesser degree of toxicity in rats, and the faster clearance of the particles from the blood compartment in rats may actually underlie the greater toxicity. In other words, for this type of drug product, when comparing exposure across species, faster clearance, reflected by lower AUC values, should not be construed to imply lesser sensitivity, as has been seen with cytotoxic anticancer agents.

Therefore, BSA-based scaling is not applicable to calculation of the human-equivalent dose (HED) from the cynomolgus monkey NOAEL and the rat HNSTD. It is also viewed that that monkey may be a better predictor of human sensitivity for MTL-CEBPA, but this cannot be proven at this time. Thus, in the interest of trying to identify an appropriate starting dose level for the initial clinical trial that achieves a sufficient safety margin, while not falling so conservatively low that pharmacologic activity and clinical efficacy is undermined, it is believed that a dose level 10-fold below the HNSTD of 7.5 mg/kg/adm. (3× weekly dosing for 4 weeks) in rats and a NOAEL in monkeys i.e., 0.75 mg/kg, is an appropriate choice. This proposed starting dose level is even more conservative when one considers that, at the HNSTD in the 4-week rat abd minkey studies, doses were given for 3 consecutive days each week, as opposed to the once-weekly dosing intended for the initial trial. Thus it is concluded that MTL-CEBPA is expected to be safe and well-tolerated with no unusual or alarming signs of toxicity that would preclude the use in humans at the intended initial dose of 0.75 mg/kg (28 mg/m$^2$) administered as a 60-minute intravenous (i.v.) infusion once weekly. Based on the pharmacology we might expect to see liver function benefits from 0.3-3.0 mg/kg and tumour benefit at approximately 4 mg/kg. Starting at a dose of 0.75 mg/kg thus gives the initial patients the potential opportunity to benefit from liver improvements although dose escalation may be required to achieve direct anti-tumour activity.

Dosage, Preparation and Administration of Investigational Product

During the dose escalation and dose expansion, the dosage will follow the schedule. The dose will be based on the participant's most recent height and weight using the DuBois & DuBois (133) body surface area (BSA) calculation:

$$BSA\ (m2) = 0.007184 \times Height\ (cm)^{0.725} \times Weight\ (kg)^{0.425}$$

MTL-CEBPA is thawed at room temperature before diluting the drug product suspension in 0.9% Normal Saline for Intravenous Use. The volume of the prepared infusion bag should be 250 mL regardless of the concentration and administered at a constant rate over 60 minutes into a vein (peripheral or central) using an infusion pump with no filter (refer to the Pharmacy manual for more details on instruction for handling IMP).

The preparation should be kept at room temperature (25° C.) with a maximum in-use shelf-life of 6 h.

Compatibility issue between the IMP and diluent and/or infusion devices is not expected.

Modification of Investigational Product Dosing for a Participant

Other schedules and dosage may be explored depending on the results of ongoing preclinical experiments or from data arising from the study.

In the event of a grade≥3 infusion reaction (e.g. drop in blood pressure, facial flushing, chest tightness, back or abdominal pain, elevated heart rate, sweating), the infusion should be stopped immediately until the symptoms subside; then the infusion can be restarted. If the symptoms reappear the investigator should stop the infusion. The volume of infusion administered at this point will be capture in the CRF. The investigator should discuss with the medical monitor any dose modification plan prior implementation. This may result in dividing the remaining weekly dose equally over the two following days. The following administration would follow a 3 days administration schedule as described.

If, despite modification of dosing, the symptoms persist the treatment should be discontinued and the participant advised to withdraw from the study.

Concomitant Medications/Treatments

Information on any treatment in the 4 weeks prior to starting study treatment and all concomitant treatments given during the study, with reasons for the treatment, will be recorded in the eCRF.

Prohibited Medications and Procedures

The following medications are prohibited during the participants' participation in the trial: Other investigational agents; Anti-neoplastic agents.

Prophylactic Medications and Procedures

All participants will be premedicated (unless contraindication) prior to dosing with MTL-CEBPA to reduce the potential for an infusion reaction. Premedication should be administered 30 to 60 minutes prior to the start of the infusion as follow: Steroid single dose (i.e. dexamethasone oral 8 mg or intravenous 10 mg); Oral H2 blocker single dose (i.e. Ranitidine 150 mg or famotidine 20 mg or equivalent other H2 blocker dose); Oral H1 blocker single dose, 10 mg cetirizine (hydroxyzine 25 mg or fexofenadine may be substituted if participant dose not tolerate cetirizine).

Overdose of Investigational Medicinal Product

MTL-CEBPA is an investigational agent and is contraindicated for all conditions other than those mentioned in this protocol.

Should an overdose occur, there is no known antidote. Symptoms and signs attributed to the overdose should be treated symptomatically. Any participant who inadvertently receives a higher dose than intended should be monitored closely, managed with appropriate supportive care until recovery and followed up expectantly.

Such overdoses should be recorded as follows: An overdose with associated AEs/SAEs is recorded as the AE diagnosis/symptoms on the relevant AE/SAE modules in the eCRF and on the overdose eCRF module; An overdose with no associated symptoms is only reported on the overdose eCRF module.

If an overdose occurs in the course of the study, site personnel must inform the PI within one day, i.e. immediately, but no later than the end of the next business day of when he or she becomes aware of it. An overdose will be reported by the PI to the sponsor.

For overdoses associated with an SAE, standard reporting timelines apply. For other overdoses, reporting should be done within 30 days.

Pregnancy and Maternal Exposure

As MTL-CEBPA is an investigational agent it is contraindicated for pregnant women and as such they are excluded from participating in this study. For all women of child bearing potential, barrier contraception should be used and should be continued for at least three months following the end of treatment with MTL-CEBPA. However, should a participant become pregnant whilst on study, despite using barrier contraception as mandated, immediate discontinuation of study is required.

It is not known if the study medicine will affect sperm or semen and therefore men are advised to use a reliable barrier form of contraception during the treatment phase and for at least three months following the final treatment.

Study Schedule

The study schedule applies to Part 1a and Part 1b of the study. Each treatment cycle consists of 3 weeks of treatment on Days 1, 8, and 15 followed by 1 week of rest.

Screening Visit (Day −21-Day −1):

The following data will be collected at enrolment and recorded in the appropriate sections of the CRF: Date of signed ICF; Demographic data, full medical history, physical examination, recording of vital signs, performance score, weight (kg), height (cm) and girth measurement (cm). Evaluation against inclusion and exclusion criteria. Recording of baseline symptoms and causality. Prior and concomitant medication. Blood pregnancy test for women of childbearing potential. 6-hour fasting blood sampling for assessment of haematology, clotting profile, clinical biochemistry (including LFT, renal profile), lipid profile, appropriate tumour marker(s), cytokine profile and complement activation factors Bb and C3a. 12 lead ECG. Chest X-Ray. MRI or CT scan of liver and abdomen with RECIST report. (Note: Scan should not be repeated if a previous scan available within 1 month prior to the start of study treatment). Fibroscan will be performed in HCC participants only. FDG-PET scan (Part 1b only). Radiological guided liver biopsy of tumour tissue will be performed in participants in whom archival material is unavailable. The tumour tissue will be a formalin-fixed, paraffin-embedded (FFPE) sample.

Participants who fail their first screening visit due to serum albumin level being outside the inclusion range can be re-screened 14 days later. A third screening is not acceptable.

Days 1, 8 and 15 Visit (+\−2 days):

Unless otherwise specified, procedures and assessments should be undertaken pre-dose. Standard physical examination, weight and girth measurements. Recording of new symptoms and new medications since previous visit, performance score, 12 lead ECG. FACT-Hep quality of life questionnaire administration at day 1 pre-dose and post-dose at Day 15, week 8 and at the end of study visit (participant in Part 1b only). Place cannula into a vein (peripheral or central). 6-hour fasting blood sampling assessment of haematology, clotting profile and clinical biochemistry (including LFT and renal function tests) and complement activation factors Bb and C3a. Day 8 and 15 only: Blood sampling for appropriate tumour markers and cytokine profile. If required administer pre-medication via the cannula 30 minutes pre MTL-CEBPA infusion. Administer MTL-CEBPA intravenously via the cannula over 60 minutes as per dosing schedule. Vital signs (other than weight and girth measurement) recording pre-dose, and at 15 minute, 30 minute, 1 hour and 2 hour time points post administration. PK samples pre and post infusion (Part 1a participants on Days 1 and 8 only) at the following time points: pre-dose, immediately post infusion, 0.25 hour, 1 hour, 3 hours and 6 hours timed from the completion of the infusion. FDG-PET scan at Day 15 post-dose (participants in Part 1b only) (Note: All pretreatment blood samples, except for PK, may be taken and analysed the day prior to administration of MTL-CEBPA.)

Days 2, 9 and 16 Visit:

Recording of new symptoms and medications, vital signs and performance score. 6-hour fasting blood sampling assessment of haematology, clotting profile and clinical biochemistry (including LFT and renal function tests) and complement activation factors Bb and C3a. PK (Part 1a participants on Days 2 and 9 only) at 24 hours after completion of the infusion.

Days 3 and 10 Visit:

48 hour PK sampling for participants in Part 1a only

Days 4 and 11 Visit:

72 hour PK sampling for participants in Part 1a only

Day 22 Visit (+\−2 Days):

Standard physical examination. Recording of new symptoms and medications, vital signs and performance score. Blood pregnancy test for women of childbearing potential. 6-hour fasting blood sampling for assessment of haematology, clotting profile, clinical biochemistry (including LFT, renal profile), lipid profile, appropriate tumour marker(s), cytokine profile and complement activation factors Bb and C3a. FACT-Hep quality of life questionnaire administration (Part 1b only). Chest X-Ray.

Week 8-Day 22 of Cycle 2 Visit (+\−2 Days):

In addition to the Day 22 investigations and procedures listed above, the following imaging procedures should be carried out: MRI/CT scan will be performed and every 8 weeks thereafter; FDG-PET scan will be performed at week 8 only for participants in Part 1b and will not be repeated thereafter.

End of Study Visit (Day 29 or 14 Days +/−7 Days after Last Dose):

Standard physical examination, weight and girth measurement. Recording of new symptoms and new medications since previous visit, vital signs and performance score. FACT-Hep quality of life questionnaire administration (Part 1b only). Blood pregnancy test for women of childbearing potential. 6-hour fasting blood sampling assessment of haematology, clotting profile and clinical biochemistry (including LFT and renal function tests) and complement activation factors Bb and C3a. For premature withdrawal participants only (i.e. if not done at Day 22) blood sampling for fasting lipid profile, appropriate tumour marker(s) and cytokine profile. Fibroscan (in participants with HCC only). Tumour biopsy; a post treatment biopsy is highly desirable and will be performed on investigator judgement.

Early Termination Visit:

Should the participant withdraw from the study the assessments described above should be undertaken.

Unscheduled Visit:

Unscheduled visits or phone contacts may be performed for adverse event follow-up.

Pregnancy Visit:

In the event of a participant becoming pregnant during the study, the participant should be advised to stop study treatment immediately. The reason for withdrawal will be recorded in the eCRF and the participant will be seen and assessed by an Investigator(s) in order to complete all assessments for an End of Study Visit to assess the safety of the study drug as described above.

Treatment Plan for Responders:

Participants in Part 1a and Part 1b are initially enrolled for 2 cycles. At the end of the first cycle, participants may receive additional cycle(s) of MTL-CEBPA on the same treatment regimen basis (excluding PK sampling) should participants display clinical benefits (e.g. improvements in liver function) and agree to continue in the study. At the end of the second cycle, tumour response will be assessed; participants who do not show tumour progression will be offered a further 2 additional treatment cycles.

At this point participants may be advised by the investigator to exit from the study if this is in the participant's best interest, or if the participant's response is positive, which allows the participant to receive another conventional therapy that was inappropriate at the start of the study (i.e. stage migration), such as surgery, RFA, TACE or sorafenib.

Participants will be given the opportunity to receive further cycles of MTL-CEBPA as long as the response to treatment lasts.

Study Procedures/Evaluations—Patient Reported Outcome

The Functional Assessment of Cancer Therapy-Hepatobilliary (FACT-Hep) version 4 questionnaire will be used to assess changes in health-related quality of life for participants following the administration of MTL-CEBPA at the RP2D level (Part 1b) on, Day 1 and 15 and week 8.

FACT-Hep Questionnaire

The Functional Assessment of Cancer Therapy-Hepatobilliary (FACT-Hep) is a validated health-related quality of life questionnaire and is a combination of the FACT-General and the 18-item module specifically designed to measure symptoms and side effects of treatment associated with hepatobiliary carcinoma. The FACT-G is a multidimensional 27-item instrument that measures four dimensions of quality of life including physical, social/family, emotional, and functional well-being. The FACT-Hep also includes an 18-item module assessing the symptoms of hepatobiliary carcinoma and side effects of treatment (Additional Concerns).

Method of Assessment

The FACTHep will be self-administered using a paper version of the questionnaire at scheduled visits. The questionnaire will be assessed at Day 1 pre-dose and post dose at Day 15 and then at Day 22 (week 8).

Administration of PRO Questionnaires

The FACIT scales are designed for participant self-administration, but can also be administered by interview format. For self-administration, participants should be instructed to read the brief directions at the top of the page. After the participant's correct understanding has been confirmed, he/she should be encouraged to complete every item in order without skipping any. Patients should be encouraged to circle the response that is most applicable. If, for example, a participant is not currently receiving any treatment, the participant should circle "not at all" to the question "I am bothered by side effects of treatment." Interview administration is considered appropriate given adequate training of interviewers so as to elicit non-biased participant responses.

Scoring

The FACT-Hep includes 5 dimensions: "physical well-being", "Social/family well-being, "emotional well-being", "Functional well-being" and "Additional concerns". Each dimension has 5 levels: "Not at all", "A little bit", "Somewhat", "Quite a bit" and "Very much". The participant rates his/her current health state on the FACT-Hep by circling or marking one number per line to indicate his/her response as it applies to the past 7 days to the statement on the FACT-Hep. This is the FACT-Hep score.

Laboratory Safety Evaluations

Sample collection times are included in the study schedule of event. Details of methodology and reference ranges will be stored in the TMF. Laboratory values that have changed significantly from baseline and are considered to be of clinical concern must be recorded as an adverse event and followed up as appropriate.

The estimated blood volumes to be collected from each participant over 1 cycle are presented below:

| Assessment | Sample volume (mL) | No. of Samples | Total volume (mL) |
|---|---|---|---|
| Safety | | | |
| Biochemistry [a] | 3.5 | 9 | 31.5 |
| Plasma ammonia [a] | 4 | 9 | 36 |
| Tumour markers [a] | 2.5 | 5 | 12.5 |
| Fasting glucose | 2 | 9 | 18 |
| Haematology | 3 | 9 | 27 |
| Coagulation | 4 | 9 | 36 |
| Complement (C3a and Bb) | 2 | 9 | 18 |
| Serum pregnancy test [b] | 2 | 2 | 4 |
| Pharmacokinetic | | | |
| Plasma MTL-CEBPA | 5 | 18 | 90 |
| Pharmacodynamics | | | |
| Cytokines | 3 | 6 | 18 |
| Total: | | | |
| Male | | | 287 |
| Female | | | 291 |

[a] Total protein, albumin, total bilirubin, ALT, AST, plasma ammonia, tumour markers total cholesterol, HDL-C and triglycerides will be assessed to allow review of PD biomarkers.
[b] For women of childbearing potential.

Less than 50 mL will be taken from each participant on each visit and a total of less than 300 mL per 4-week cycle.

Local Laboratory Tests

All samples for laboratory safety assessment will be collected at each investigational site according to local practices and analysed at the local laboratory using standard methods for routine tests. All blood samples should be collected pre-MTL-CEBPA infusion at screening and on Days 1, 2, 8, 9, 15, 16, 22 and EOS (with the exception of lipid profile).

Clinical biochemistry and haematology parameters will be measured. Clinical biochemistry samples including liver function, ammonia and glucose as well as the lipid profile should be collected in a fasting state (6 hours before blood sample).

| Serum Biochemistry Parameters | |
|---|---|
| Sodium | Total bilirubin [a] |
| Potassium | ALP [a] |
| Calcium | Alanine transaminase (ALT) [a] |
| Phosphate | Aspartate transaminase (AST) [a] |
| Urea (BUN) | Gamma glutamyl transferase (GGT) [a] |
| Fasting glucose | Plasma ammonia [a] |
| Total protein [a] | Total cholesterol [b] |
| Creatinine | HDL-C [b] |
| Albumin [a] | Triglycerides [b] |

[a] Total protein, albumin, total bilirubin, ALT, AST and plasma ammonia will be assessed to allow review of eligibility at screening and allow for review of PD biomarkers.
[b] Total cholesterol, HDL-C and triglycerides will be assessed at screening, at the end of each cycle (day 22) and EOS (for premature withdrawal participants) to allow review of exploratory PD biomarkers.

| Haematology Parameters | |
|---|---|
| White blood cells (WBC) | Lymphocytes absolute and % |
| Red blood cells (RBC) | Monocytes absolute and % |
| Haemoglobin (Hb) | Eosinophils absolute and % |
| Glycosylated haemoglobin (HbA1c) | Basophils absolute and % |
| Neutrophils absolute and % | Platelets |

| Coagulation Parameters | |
|---|---|
| International normalised ratio (INR) | Prothrombin time (PT) |
| Activated partial thromboplastin time (aPTT) | |

| Complement Activation Parameters |
|---|
| Activation fragment of complement factor B (Bb) |
| Complement component 3a (C3a) |

Pregnancy Test (Blood)

Human chorionic gonadotrophin (hCG) will be measured for women of childbearing potential at screening, Day 22 and every 8 weeks thereafter (if the participant is receiving further cycles of treatment).

Tumour Marker(s)

The most suitable marker(s) among the list below will be selected on the basis of the cancer history and will be performed at screening and on Days 8, 15, 22 and EOS (for premature withdrawal participants).

| Tumour Markers | |
|---|---|
| Alpha-fetoprotein (AFP) | Carcinoembryonic antigen (CEA) |
| Cancer antigen 125 (CA125) | Cancer Antigen 15-3 |
| Carbohydrate antigen 19-9 (CA 19-9) | (CA15-3) |

Imaging

Chest X-ray: Chest X-ray will be performed during screening and Week 4. A further X-ray will be performed at Week 12 and thereafter according to standard of care if the participant is receiving further cycles of MTL-CEBPA.

MRI or CT Scans: MRI or CT scan of the chest and abdomen will be performed during screening (within 1 month prior to the first dose of the study drug) and at week 8. MRI is the preferred method, but CT scans are allowed; whether MRI or CT scan is used, it is important to maintain consistency of assessment method for each participant.

MRI/CT scans will then be performed every 8 weeks.

Fibroscan: Fibroscan will be performed only in participants with HCC at screening and at the end of the study in order to assess the fibrotic characteristics of the liver prior and post treatment with MTL-CEBPA.

FDG-PET Scan: Metabolism of the liver and the tumour will be assessed using FDG-PET scan in participants enrolled in Part 1b only. FDG-PET scan will be performed during screening, at Day 15 post MTL-CEBPA infusion and at the time of restaging CT (i.e week 8).

Patients are not allowed to consume any food or sugar for at least 6 h prior to the start of the PET study (i.e. with respect to time of injection of FDG). In practice, this means that patients scheduled to undergo the PET study in the morning should not eat after midnight and preferably have a light meal (no alcohol) during the evening prior to the PET study. Those scheduled for an afternoon PET study may have a light breakfast before 8.00 a.m. (i.e. up to two sandwiches, no sugars or sugar containing sandwich filling). Medication can be taken as prescribed.

Liver Biopsy

If available, an archival tissue sample in the form of a formalin fixed paraffin embedded (FFPE) tumour block will be collected for each participant. If it is not possible to obtain the tumour block or it does not exist, the participant must have agreed to a biopsy at screening as part of the informed consent process.

Archival tumour tissue should be requested by the research team and should be sent as described. Archival tumour blocks will be returned to source at the end of the study or, upon request, earlier if required.

A post treatment liver tumour biopsy is highly desirable at the EOS visit.

Administration of fresh frozen plasma and platelets to correct any coagulation abnormalities should be administered as necessary.

Pharmacokinetics (PK)

PK blood samples, 5 mL of whole blood, be will be collected in an EDTA tube from each participant in each of the 6 cohorts of the dose escalation part of the study on Days 1, 2, 3 and 4, 8, 9, 10 11 of the first cycle and at the following time points: pre-dose of study drug, immediately after completion of the infusion, then at 0.25 hour, 1 hour, 3 hours, 6 hours, 24 hours, 48 hours and 72 hours time points from completion of the infusion.

Clinical staff is encouraged to take the blood samples for PK analysis at the scheduled time point. However, deviations from the scheduled sample times are not considered protocol deviations. The exact time and date of the blood draw must be recorded using an unambiguous format.

Plasma concentration of MTL-CEBPA will be analysed centrally at the defined time points using a hybridization-based HPLC-assay.

Instructions for specimen preparation, handling, and storage are described below.

Pharmacodynamics (PD)

Liver function tests, AFP tumour marker (for HCC participants), cytokine profile and CEBPA gene expression have been identified as surrogate biomarkers of the pharmacological effect of MTL-CEBPA.

Liver function tests: alanine transaminase (ALT), serum albumin, plasma ammonia, aspartate transaminase (AST), and total bilirubin will be taken on Day 1 (pre-dose), Day 2, Day 8 (pre-dose), Day 15 (pre-dose), Day 22 and at EOS visits. These samples will be analysed at the local laboratory.

AFP tumour marker: AFP will be tested on Day 1 (pre-dose), Day 8 (pre-dose) Day 15 (pre-dose), Day 22 and at EOS visits (for premature withdrawal participants). These samples will be analysed at the local laboratory.

Lipid profile: Total cholesterol, HDL-C and triglycerides will be assessed on days 1, 8, 15, 22 of each cycle and EOS (for premature withdrawal participants) to allow review of exploratory PD biomarkers Cytokine profile: IL-2, IL-6, TNF-a, IFN-g, IL-4, IL-17a, IL-10 will be tested at screening, Day 8 (pre-dose), Day 15 (pre-dose), Day 22 visits and at EOS visits (for premature withdrawal participants). Samples will be analysed at a central laboratory.

Gene expression: CEBPA gene expression will be studied using CEBPα and p21 protein expression using immunochemistry staining assay on formalin-fixed, paraffin-embedded (FFPE) tumour biopsy samples obtained from archival tumour tissue and/or from new biopsy tissue at screening visit and EOS visit.

Specimen Preparation, Handling, and Shipping

Instructions for Specimen Preparation, Handling, and Storage

All samples with the exception of PK samples and cytokine profile samples will be collected by the sites according to local practices and analysed at the local laboratory using standard methods for routine tests.

A Laboratory Manual for Investigators giving detailed instructions will be provided to each study site prior to the start of the study. The investigator and delegated site personnel should follow the procedures defined in the Laboratory Manual.

For PK samples, 5 mL of whole blood is collected into EDTA-treated tubes. The EDTA tube will be processed and centrifuged using a refrigerated centrifuge (4° C.) immediately after sampling to generate plasma. Once obtained, the plasma will be divided into at least two aliquots of 100 μL while on ice. Aliquots will be centrifuged following the same protocol mentioned above and snap frozen using liquid nitrogen or dry ice before storage at −80° C. The recommended time from blood collection to plasma storage is 30 min.

For the cytokines profile, 3 mL will be collected into EDTA-treated tubes. The tubes will be centrifuged in order to generate plasma. The samples will be stored frozen at −80° C. on site before to be sent to the central laboratory (see section below).

An archival tumour block, if available, should be requested from the relevant pathology department. Newly obtain tumour tissue samples should be formalin fixed paraffin embedded (FFPE). Block (preferably) or slides will be sent to the central laboratory contracted to undertake IHC staining testing (see section below).

Adverse Events (AE)

An adverse event (AE) is defined as any untoward medical occurrence (including deterioration of a pre-existing medical condition) in a participant or clinical investigation participants administered a pharmaceutical product regardless of its causal relationship to the study treatment. An AE can therefore be any unfavourable and unintended sign including abnormal results of an investigation (e.g. laboratory finding, electrocardiogram), symptom(s) (e.g. nausea, chest pain), signs (e.g. tachycardia, enlarged liver) or disease temporally associated with the use of the investigational medicinal product (IMP).

AEs will be collected throughout the study, from informed consent until the end of study visit. All AEs including local and systemic reactions not meeting the criteria for "serious adverse events" should be captured on the appropriate eCRF.

All AEs spontaneously reported by the participant or reported in response to the open question from the study personnel or revealed by observation will be collected and recorded in the CRF. When collecting AEs, recording a diagnosis is preferred (when possible) to recording a list of signs and symptoms. However, if a diagnosis is known and there are other signs or symptoms that are not generally part of the diagnosis, the diagnosis and each sign or symptom will be recorded separately.

Any medical condition that is present at the time when the informed consent is signed should be considered as medical history and not reported as an AE. However, if it deteriorates at any time after the signed ICF, it should be recorded as an AE.

AE Variables

The following variables will be collected for each AE: Diagnosis/symptoms (verbatim). Date when the AE started (date of onset) and stopped (date of resolution). NCI-CTCAE maximum severity. Whether or not the AE is serious (seriousness). Investigator causality rating against the investigational product. Action taken with regard to the IMP. Whether or not AE caused participant's withdrawal from IP. Outcome.

In addition, the following variables will be collected for SAEs: Date AE met criteria for serious AE. Date Investigator became aware of serious AE. Reason for classification as serious. Date of hospitalisation. Date of discharge. Reason for hospitalisation. Probable cause of death. Date of death. Post mortem performed. Causality assessment in relation to study procedure(s). Causality assessment in relation to other medication. Causality assessment in relation to additional study drug. Description of AE.

All AEs occurring while on study must be documented appropriately regardless of relationship. All AEs will be followed up according to local practice until the event has stabilised or adequate resolution.

All AEs must be graded for severity and relationship to study drug.

Modification of MTL-CEBPA Administration for a Participant

Alternative or intermediate doses and schedules maybe required depending on arising clinical data from the study. This may include rescheduling, dividing, reducing or de-escalating the required dose.

Schedule Modification for a Participant

Dosing visits should be planned within the allowable time window as specified in this protocol. However, in the event of the participant not being able to attend the scheduled dosing day (e.g. participant feeling unwell), the dosing may be rescheduled and the timing of subsequent study visits should be altered accordingly.

Administration of MTL-CEBPA may be delayed up to 1 week. Should the participant not be able to attend the next dosing date, the participant should be withdrawn from the study and an EOS study visit should be schedule.

Dose and Schedule Modifications for a Participant

In the event of grade≥3 infusion reaction the procedure mentioned above should be followed. Following this procedure the initial dose may be divided over 3 consecutive days.

An example of divided dose schedule is shown below.

| Starting Dose | 28 mg/m$^2$ days 1, 8, 15 |
| Divided dosing over 3 consecutive days | 14 mg/m$^2$ days 1, 2, 3, 8, 9 10, 15, 16, 17 |

In the event of divided dosing over three days, the PK samples should be taken as planned at Day 1 and Day 8 and then pre-dose at Day 2, 3 and at Day 9, 10.

In any case, a dose and schedule modification should be discussed with the medical monitor prior implementation.

Dose Modifications for a Participant Decision to de-escalate (e.g. if the starting dose on a particular schedule results in toxicities such that the MTD is exceeded) or to reduce the dose will be advised by the SRC.

Example 20. Formulation Optimization Study

NOV340 is a well-established liposomal formulation used for encapsulation of oligonucleotides. Table 18 shows the lipid composition of the formulation in molar ratio.

TABLE 18

Compositoin of NOV340

| Lipid | Molar ratio |
|---|---|
| POPC (1-palmitoyl-2-oleoyl-sn-glycero-3-phosphocholine) | 6 |
| DOPE (1,2-dioleoyl-sn-glycero-3-phosphoethanolamine) | 24 |
| Chems (cholesteryl hemisuccinate) | 23 |
| MoChol (Cholesteryl-4-[[2-(4-morpholinyl)ethyl]amino]-4-oxobutanoate) | 47 |

The present optimization study was done to improve the encapsulation efficiency of CEBPA-51 into liposomes. Based on the in-house experience in process development and optimization of oligonucleotides formulated in NOV340 liposomes, the most critical parameter to be optimized for CEBPA-51 is the encapsulation efficiency. Encapsulation efficiency (%) is the amount of the liposome-associated oligonucleotide (encapsulated and membrane bound) divided by the total amount dissolved in the API solution intended for encapsulation, excluding water content and impurities. High process losses when preparing at small scale, should be also taken under consideration when encapsulation efficiency is calculated. Those losses are due to sampling and dead volumes in filter units and tubing. Process losses will be reduced when the production scale is increasing. Therefore, encapsulation efficiency based on lipid recovery is also calculated. To improve encapsulation efficiency, maximization of the interaction between RNA and lipid was the most reasonable direction to go for. To achieve this, two different parameters were varied and evaluated. The first was lipid to drug ratio at the point of liposome formation and the second was the pH of the buffer used to dissolve the CEBPA-51. The interaction between RNA and lipid formulation occurs primarily between MoChol and the oligonucleotide. MoChol is an amphiphilic lipid with a pKa of 6.5 which is positively charged in acidic medium. The interaction between the positively charged MoChol with the negatively charged RNA results in increased encapsulation of RNA into liposomes. Therefore, our hypothesis was that decreasing the pH of the API buffer would result to an increased MoChol charge, thus leading to increased interaction between MoChol and CEBPA-51 and increased encapsulation efficiency. The second option was to identify the optimal lipid to drug ratio, or simpler the "saturation point" (maximum amount of CEBPA-51 that can interact with MoChol). Therefore, various lipid to drug ratios were tested in the course of liposome preparation experiments. Lipid to drug ratio was changed by decreasing the concentration of CEBPA-51 in the API solution. Seven different CEBPA-51 concentrations were tested.

Methods

Liposome Preparation

Liposomes were prepared by crossflow ethanol injection method. In brief, lipids (POPC, Chems and DOPE) are dissolved in absolute EtOH at 55° C. After complete solubilisation, the solution is quantitatively transferred into another bottle containing pre-weighed MoChol. Selection of absolute EtOH and solubilization of lipids in two steps have been identified to be necessary to minimize the degradation of MoChol to Chol. After complete dissolution of the lipids, the ethanolic lipid solution is filtered through a 0.2 μm filter and transferred quantitatively in the injector which is as tempered at 55° C. in a heating cabinet. In the meantime, the oligonucleotide is dissolved in Na-Acetate/Sucrose buffer and filtered through a 0.2 μm filter into the API buffer bottle at RT. The standard pH of the API buffer for NOV340 formulations is at pH 4 but in the present optimization study buffers with pH 3.5 and pH 4.0 were used. Liposomes are forming when lipid solution is mixed with the API buffer in the injection module. Immediately after liposome formation there is an online dilution step with the dilution buffer (NaCl/Na$_2$HPO$_4$ pH 9.0 at RT) in order to neutralize the pH of the liposomal formulation. The liposome formulated oligonucleotide is collected in the IV bottle and stirred at room temperature for 30 minutes before extrusion. This intermediate suspension is then extruded through 0.2 μm polycarbonate membrane to refine the size and PdI of liposomes. After extrusion, free RNA and EtOH are removed by diafiltration and concentrated to the target saRNA concentration by ultrafiltration. Before filling into vials, the liposomal product is sterile filtered through a 0.2 μm filter.

Size Measurements of Liposomes

Measurements for the determination of liposome size were performed by Dynamic-Laser-Light-Scattering (DLS) using a Malvern Nano ZS (224/SOP/002). This system is equipped with a 4 mW Helium/Neon Laser at 633 nm wavelength and measures the liposome samples with the non-invasive backscatter technology at a detection angle of 173°. Liposomes were diluted in aqueous phase to reach optimal liposome concentration and the experiments were carried out at 25° C. The results are presented in an average diameter of the liposome suspension (z-average mean) with the polydispersity index to determine liposome homogeneity.

Zeta Potential Measurement of Liposomes

Zeta potential of liposomes was measured from the final bulk product using a Malvern Nano ZS according to 224/SOP/012.

Quantification of RNA-Extinction Coefficient

Quantification of RNA was done by spectrophotometer at OD 260 nm according to 221/SOP/012. RNA was quantified in API solution and in the final bulk product. In the very early stage of CEBPA-51 formulation development, the extinction coefficient of each single strand of saRNA was measured. Therefore, quantification of the saRNA was done using the average of extinction coefficient values of each single strand. Due to hyperchromicity effect, quantification of saRNA using the average extinction coefficient resulted in decreased encapsulation efficiency values in the low 30 percent range. During development phase, the correct extinction coefficient value was determined by STPharm resulted in the correct saRNA quantification and in optimized encapsulation efficiency. The first extinction coefficient used for quantification of CEBPA-51 was: 30.17 (L/(mole·cm)) and the updated value was: 20.68 (L/(mole·cm)).

Quantification of Lipids

Lipid concentration in the samples was measured from the bulk volume using HPLC according to 222/SOP/004.

Results & Discussion

Comparison Between Old and New Extinction Coefficient

Table 19 lists the derived encapsulation efficiencies as calculated by both extinction coefficient values for the samples prepared before starting process optimization of the formulation. From the derived values it is clear that the updated extinction coefficient improves markedly the encapsulation efficiency of CEBPA-51 into liposomes. However, further optimization studies were conducted to maximize the yield of the saRNA in the final formulation. Indeed, from an initial encapsulation efficiency of almost 30% the optimized formulation resulted in encapsulation efficiency of almost 60%.

TABLE 19

Encapsulation efficiency of CEBPA-51 into liposomes calculated by old and new extinction coefficient values

| | Encapsulation efficiency (%) | |
|---|---|---|
| Sample name | Calculated with old Ext. coef. 30.17 (L/(mole · cm)) | Calculated with new Ext. coef. 20.68 (L/(mole · cm)) |
| IV/MIT/120315/1 | 24.7 | 36.0 |
| IV/MIT/120315/2 | 33.7 | 49.1 |
| IV/MIT/120315/3 | 27.3 | 39.8 |
| IV/MIT/250315/1 | 39.2 | 57.3 |
| IV/MIT/250315/2 | 24.6 | 35.9 |
| IV/MIT/250315/3 | 27.8 | 40.5 |
| IVMIT/300315/1 | 29.7 | 43.3 |
| IV/MIT/300315/2 | 23.5 | 34.2 |

Liposome Preparation with API Solubilized in pH 3.5 Buffer

Figure 34:
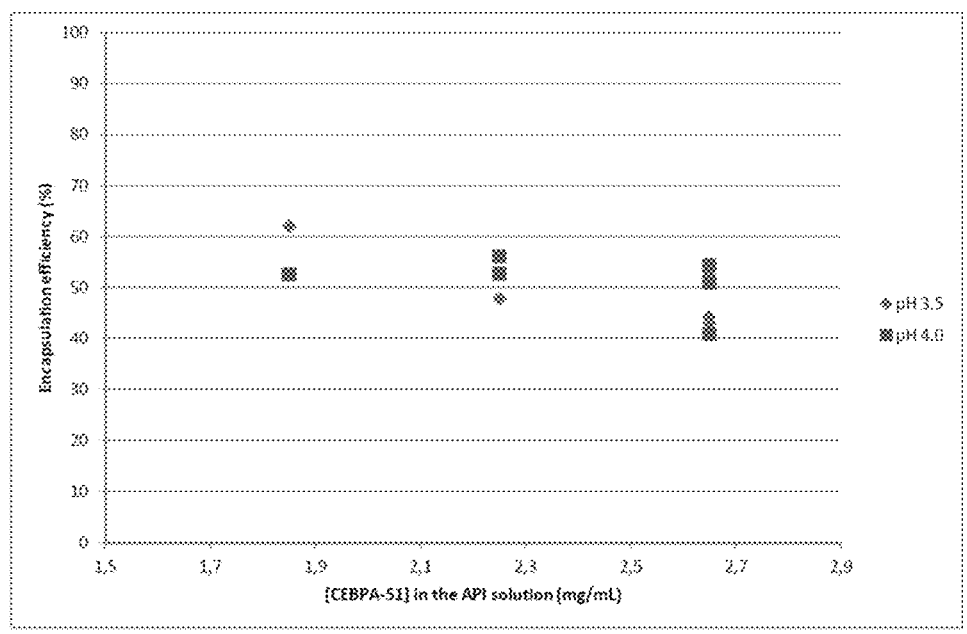
FIG. 34 shows encapsulation efficiency of CEBPA-51 into liposomes versus API concentration in the injection buffer for two different pH values of the API solution.

To study the effect of API solution's pH on the encapsulation efficiency, the pH of the API solution was reduced from pH 4.0 to pH 3.5. In addition, three different CEBPA-51 concentrations in the API solution were used, to study the effect of lipid to drug ratio on the encapsulation efficiency. Table 20 lists all the formulations prepared with API solution of pH 3.5 and their characteristics. Tables 21, 22 and 23 show the formulations prepared with API solution of pH 3.5 in comparison with their respective formulations prepared with API solution of pH 4.0. FIG. 34 presents the results shown in Tables 22, 23 and 24 as graph. From the obtained results, it is obvious that changing the pH of the API buffer results in slightly increased encapsulation efficiency just at low concentration of RNA in the API solution (1.85 mg/mL). With regard to the other two tested concentrations (2.25 and 2.65 mg/mL), no obvious trend towards this direction could be observed. Additionally, reduction of the pH resulted in the formation of liposomes with increased size and PdI. Such an increase in size and PdI would require an additional extrusion cycle, which is not recommended as it would increase RNA losses and process duration. Consequently, reduction of the injection buffer pH from 4.0 to 3.5 is not an option. With regard to alteration of the lipid to drug ratio, it was noticed that by decreasing the RNA concentration in the API buffer, there is an increase on the encapsulation efficiency. This trend seems to be similar for both pH values of the API solution.

TABLE 20

Prepared liposomal samples using buffer with pH 3.5

| Sample name | IV/MIT/ 250315/3 | IV/MIT/ 150415/1 | IV/MIT/ 150415/4 | IV/MIT/ 150415/3 | IV/MIT/ 150415/2 |
|---|---|---|---|---|---|
| [CEBPA-51] in the API solution (mg/mL) | 2.65 | 2.65 | 2.65 | 2.25 | 1.85 |
| [CEBPA-51] in the final product (mg/mL) | 1.014 | 1.667 | 1.981 | 1.791 | 2.009 |
| Encapsulation efficiency (%) | 40.53 | 32.72 | 37.8 | 41.47 | 56 |
| [POPC] in the final product (mg/mL) | 1.67 | 3.36 | 4.21 | 3.82 | 4.01 |
| [DOPE] in the final product (mg/mL) | 6.68 | 13.38 | 16.5 | 14.96 | 16.10 |
| [Chems] in the final product (mg/mL) | 4.05 | 8.30 | 10.25 | 9.34 | 9.90 |
| [MoChol] in the final product (mg/mL) | 10.42 | 20.13 | 24.13 | 22.96 | 23.87 |
| Total [lipid] in the final product (mg/mL) | 22.82 | 45.17 | 55.09 | 51.08 | 53.88 |
| Encapsulation efficiency based on lipid recovery (%) | 52.47 | 42.91 | 41.38 | 47.87 | 62.03 |
| Size/PdI of the final product (nm/PdI) | 125.5/0.176 | 124.7/0.184 | 125.6/0.185 | 116.1/0.190 | 109.6/0.195 |
| Maximum feasible concentration of CEBPA-51 in the final product (mg/mL) | 2.65 | 2.28 | 2.36 | 2.22 | 2.42 |

TABLE 21

Comparison between samples prepared with pH 3.5 and pH 4.0 buffer. CEBPA-51 concentration in the injection buffer is 2.65 mg/mL.

| pH of API solution | pH 3.5 | | | | pH 4.0 | | |
|---|---|---|---|---|---|---|---|
| [CEBPA-51] in the API solution (mg/mL) | 2.65 | | | | | | |
| Sample name | IV/MIT/ 250315/3 | IV/MIT/ 300315/2 | IV/MIT/ 150415/1 | IV/MIT/ 150415/4 | IV/MIT/ 120315/1 | IV/MIT/ 300315/1 | IV/MIT/ 160415/1 |
| [CEBPA-51] in the final product (mg/mL) | 1.017 | 1 | 1.667 | 1.981 | 1.104 | 1.486 | 2.03 |
| Encapsulation efficiency (%) | 40.53 | 34.2 | 32.72 | 37.80 | 36.0 | 43.3 | 41.89 |
| Encapsulation efficiency based on lipid recovery (%) | 52.47 | 44.33 | 42.91 | 41.38 | 40.80 | 54.31 | 51.02 |
| Size and PdI of the IV liposomes (nm/PdI) | 159.0/0.321 | 144.4/0.372 | 158.8/0.511 | 128.2/0.398 | 136.8/0.220 | 148.5/0.250 | 151.1/0.259 |
| Size and PdI of the final product (nm/PdI) | 124.7/0.184 | 128.2/0.207 | 125.6/0.185 | 116.1/0.190 | 128.0/0.149 | 132/0.154 | n.a. |

TABLE 22

Comparison between samples prepared with pH 3.5 and pH 4.0 buffer. CEBPA-51 concentration in the injection buffer is 2.25 mg/mL.

| pH of API solution | pH 3.5 | pH 4.0 | |
|---|---|---|---|
| [CEBPA-51] in the API solution (mg/mL) | | 2.25 | |
| Sample name | IV/MIT/ 250315/3 | IV/MIT/ 140415/2 | IV/MIT/ 050515/2 |

TABLE 22-continued

Comparison between samples prepared with pH 3.5 and pH 4.0 buffer.
CEBPA-51 concentration in the injection buffer is 2.25 mg/mL.

| pH of API solution | pH 3.5 | pH 4.0 | |
|---|---|---|---|
| [CEBPA-51] in the final product (mg/mL) | 1.79 | 2.23 | 2.62 |
| Encapsulation efficiency (%) | 41.47 | 51.65 | 47.66 |
| Encapsulation efficiency based on lipid recovery (%) | 47.87 | 56.12 | 52.71 |
| Size and PdI of the IV liposomes (nm/PdI) | 128.2/0.398 | 130.6/0.220 | 140.5/0.249 |
| Size and PdI of the final product (nm/PdI) | 116.1/0.190 | 127/0.152 | 131.3/0.166 |

TABLE 23

Comparison between samples prepared with pH 3.5 and pH 4.0 buffer.
CEBPA-51 concentration in the injection buffer is 1.85 mg/mL.

| pH of API solution | pH 3.5 | pH 4.0 |
|---|---|---|
| [CEBPA-51] in the API solution (mg/mL) | 1.85 | |
| Sample name | IV/MIT/150415/2 | IV/MIT/120315/2 |
| [CEBPA-51] in the final product (mg/mL) | 2.01 | 1.13 |
| Encapsulation efficiency (%) | 56.01 | 49.14 |
| Encapsulation efficiency based on lipid recovery (%) | 62.03 | 52.64 |
| Size and PdI of the IV liposomes (nm/PdI) | 112.2/0.294 | 132.9/0.233 |
| Size and PdI of the final product (nm/PdI) | 109.6/0.195 | 124.6/0.150 |

Optimization of Lipid to Drug Ratio.

Figure 35:
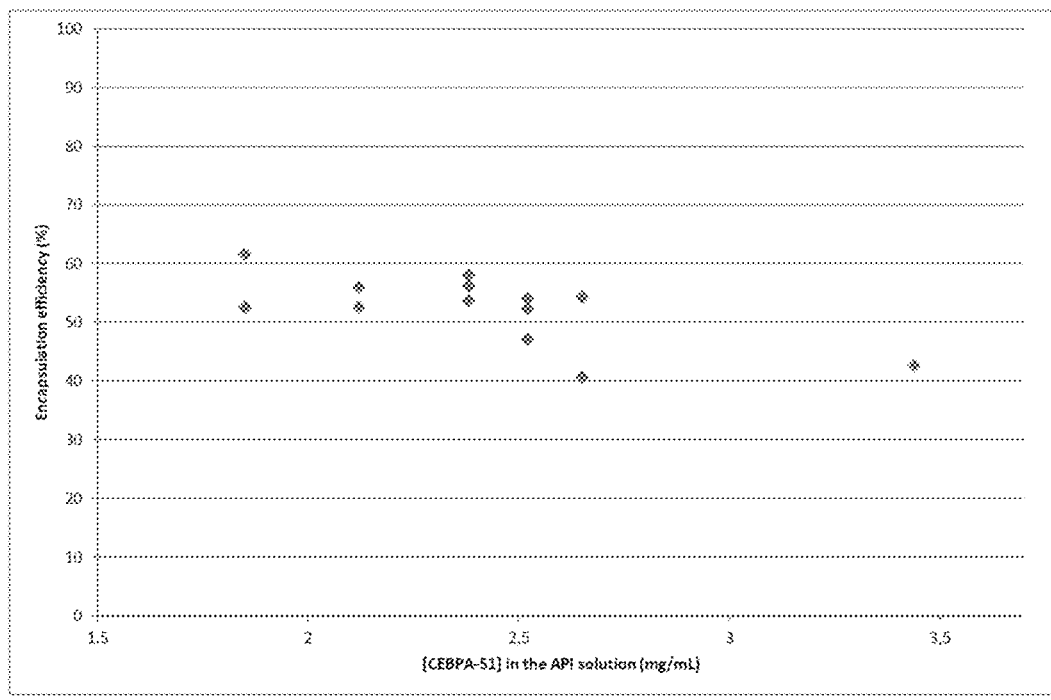
FIG. 35 shows encapsulation efficiency of CEBPA-51 into liposomes versus API concentration in the injection buffer.

Lipid to drug ratio at the point of liposome formation is of major importance for the encapsulation efficiency of RNA within liposomes. To optimize this, lipid concentration in the EtOH solution was kept the same and the concentration of CEBPA-51 in the API solution was altered ranging from 1.06 up to 3.44 mg/mL. All other process parameters remained constant and the pH of the API solution was maintained at pH 4.0. Table 24 lists all the formulations prepared and their characteristics. In FIG. 35 the same results are plotted as graph. From the obtained results it is clear that there is a slight trend indicating that by decreasing the CEBPA-51 concentration in the API solution, there is a slight increase in the encapsulation efficiency. At this point it is important to mention that lipid concentration in the final product is a key result which should be taken under consideration when trying to achieve the maximum yield of saRNA. On the other hand, increased lipid concentration in the final product can become critical at the final 0.2 μm filtration, as at some point, the filter membranes might block upon too much lipids exposed to filter membrane area. Consequently, the aim is not solely to minimize RNA losses, but also to achieve the optimal lipid concentration which would allow increased CEBPA-51 concentration in the final product.

TABLE 24

Prepared liposomal samples using buffer with pH 4.0.

| Sample name | IV/MIT/120315/3 | IV/MIT/120315/1 | IV/MIT/300315/1 | IV/MIT/290415/1 | IV/MIT/290415/2 | IV/MIT/170415/1 |
|---|---|---|---|---|---|---|
| [CEBPA-51] in the API solution (mg/mL) | 3.44 | 2.65 | 2.65 | 2.52 | 2.52 | 2.38 |
| [CEBPA-51] in the final product (mg/mL) | 1.781 | 1.10 | 1.486 | 2.27 | 1.94 | 1.69 |
| Encapsulation efficiency (%) | 39.76 | 35.99 | 43.28 | 46.74 | 45.41 | 50.37 |
| [POPC] in the final product (mg/mL) | 2.75 | 2.27 | 2.30 | 3.88 | 3.43 | 2.75 |
| [DOP7.06E] in the final product (mg/mL) | 11.39 | 9.48 | 9.35 | 15.30 | 13.28 | 10.96 |
| [Chems] in the final product (mg/mL) | 6.61 | 5.61 | 5.47 | 9.55 | 8.47 | 7.06 |
| [MoChol] in the final product (mg/mL) | 17.17 | 14.55 | 15.16 | 22.92 | 19.92 | 16.72 |
| Total [lipid] in the final product (mg/mL) | 37.94 | 31.92 | 32.27 | 51.66 | 45.10 | 37.49 |
| Encapsulation efficiency based on lipid recovery (%) | 42.71 | 40.80 | 54.31 | 54.10 | 52.38 | 58.17 |
| Size/PdI of the final product (nm/PdI) | 139.2/0.135 | 128.0/0.149 | 132.0/0.154 | 128.1/0.149 | 130.8/0.155 | 127.2/0.150 |
| Maximum feasible concentration of CEBPA-51 in the final product (mg/mL) | 3.17 | 2.25 | 2.70 | 2.76 | 2.72 | 2.80 |

Confirmation of the Optimization Study.

After conducting all the experiments towards optimization of encapsulation efficiency of saRNA into liposomes, two final batches of larger volume were prepared to confirm the results. Table 25 shows the derived data, which is also graphically presented together with the results of all other prepared batches in FIG. 35. The obtained data, clearly confirms the decision made to set the concentration of CEBPA-51 in the injection buffer to 2.38 mg/mL as it results both in higher encapsulation efficiency of saRNA and in higher concentration of CEBPA-51 in the final liposomal product.

TABLE 25

Liposomal samples prepared for confirmation of the derived results.

| Sample name | IV/MIT/ 270515/1 | IV/MIT/ 280515/1 |
|---|---|---|
| [CEBPA-51] in the API solution (mg/mL) | 2.52 | 2.38 |
| [CEBPA-51] in the final product (mg/mL) | 2.29 | 2.65 |
| Encapsulation efficiency (%) | 44.62 | 51.0 |
| [POPC] in the final product (mg/mL) | 4.53 | 4.79 |
| [DOP7.06E] in the final product (mg/mL) | 17.38 | 18.46 |
| [Chems] in the final product (mg/mL) | 11.00 | 11.71 |
| [MoChol] in the final product (mg/mL) | 25.88 | 27.91 |
| Total [lipid] in the final product (mg/mL) | 58.79 | 62.88 |
| Encapsulation efficiency based on lipid recovery (%) | 47.18 | 53.81 |
| Size/PdI of the final product (nm/PdI) | 130.8/0.143 | 124.6/0.141 |
| Maximum feasible concentration of CEBPA-51 in the final product (mg/mL) | 2.59 | 2.80 |

Conclusion

This study optimized encapsulation efficiency of CEBPA-51 into liposomes. The results derived indicate that production of liposomes should be done with API buffer of pH 4.0 and CEBPA-51 concentration in the API solution should be set at around 2.38 mg/mL. Those settings should result in a liposomal formulation with a yield in the area of higher 50 percent which is the typical yield derived when formulating oligonucleotides with NOV340.

Example 21. In-Use Stability Study 51.80 to 296.00 mg MTL-CEBPA was diluted to a total infusion volume of 250 ml resulting in a final concentration of 0.21 to 1.18 mg/ml in infusion bags. One type of infusion bag was used (Baxter VIAFLO 250 ml Sodium Chloride 0.9% Intravenous Infusion BP) and 2 representative, typical space lines (PVC and PVC-free) were selected for evaluation. The lowest dose of 0.21 mg/ml (corresponding to a clinical dose level of 28 mg/m$^2$) was selected for this in-use study as worst case scenario.

Material 5 vials MTL-CEBPA drug product, lot MIT1215-A, saRNA content: 2.5 mg/ml; nominal volume 20 ml; Infusion bags: 4×Baxter VIAFLO 250 ml Sodium Chloride 0.9% Intravenous Infusion BP (ref: FE1322); Infusion space lines: 1). 2×Braun Infusomat® Space line—Neutrapur (polyurethane) PVC-free (ref: 8700110SP); 2). 2×Braun Infusomat® Space line—PVC (DEHP-free) (ref: 8700036SP); Needles: e.g. BD Mirolance (ref: 301300); Syringes: e.g. BD Syringe (ref: 309658); Incubator QC-GTBS01MM (23-27° C.).

Preparation of Dosing Solutions, Sampling and Storage

MIT1215-A (2.5 mg/ml) was diluted in infusion bags by removal of approximately 21 ml 0.9% normal saline and replacement with approximately 21 ml of drug product. Duplicate bags were prepared for each space line resulting in a total of 4 infusion bags. Bags were weighed before and after removal of saline and after addition of drug product. A density of 1.04 g/ml was used for calculation of added amount of drug product. Two bags (#1 and #2) were connected with PVC-free space lines, the remaining two bags (#3 and #4) with PVC space lines. Bags were stored at 25±2° C. for 24 hours.

TABLE 26

Preparation of dosing solutions

| Bag ID | Weight bag before saline removal [g] | Weight bag after saline removal [g] | Removed saline volume (calculated) [ml]$^1$ | Weight after drug product addition [g] | Added drug product (calculated) [ml]$^2$ |
|---|---|---|---|---|---|
| #1 | 285.47 | 264.47 | 21.00 | 285.71 | 20.42 |
| #2 | 285.21 | 264.83 | 20.38 | 286.26 | 20.61 |
| #3 | 281.36 | 260.73 | 20.63 | 282.47 | 20.90 |
| #4 | 284.43 | 263.44 | 20.99 | 285.02 | 20.75 |

$^1$density saline: 1.00 g/ml
$^2$density DP: 1.04 g/ml

Samples (4×0.5 ml per time point and bag) were collected via space lines immediately after bag preparation (time point 0 hours), after 8 hours and 24 hours and stored at −20±5° C. At time points 8 and 24 hours the lines were purged with approximately 30 ml before sampling to ensure that sample material from infusion bags was collected rather than material incubated in the space lines. The analyses of all samples were performed within a single analytical run of SEC-HPLC (content) and RP-HPLC (lipids).

Tests and Acceptance Criteria
Overview

| Test/Analysis | Method | Acceptance criterion DP (prior to dilution) | Acceptance criterion DP (post-dilution; target concentration) |
|---|---|---|---|
| Content total saRNA | SEC-HPLC 222/SOP/013 | 2.5 ± 0.5 mg/ml | 0.21 ± 0.04 mg/ml |

-continued

| Test/Analysis | Method | Acceptance criterion DP (prior to dilution) | Acceptance criterion DP (post-dilution; target concentration) |
|---|---|---|---|
| Content POPC | RP-HPLC 222/SOP/018 | 3.5-5.8 mg/ml | 0.29-0.49 mg/ml |
| Content DOPE | RP-HPLC 222/SOP/018 | 13.5-22.6 mg/ml | 1.13-1.90 mg/ml |
| Content CHEMS | RP-HPLC 222/SOP/018 | 8.5-14.1 mg/ml | 0.71-1.18 mg/ml |
| Content MoChol | RP-HPLC 222/SOP/018 | 20.3-33.8 mg/ml | 1.71-2.84 mg/ml |
| Content cholesterol | RP-HPLC 222/SOP/018 | ≤2.0 mg/ml | ≤0.17 mg/ml |

Acceptance criteria were applied based on Drug Product (DP) specifications under consideration of respective dilution factor of about 12-fold upon preparation of the suspension for infusion. i.e. diluting saRNA content from 2.5±0.5 mg/ml to 0.21±0.04 mg/ml.

Results

Content saRNA

The content of total saRNA was measured by RP-HPLC with UV detection according 222/SOP/013. All samples were analysed within the same HPLC sequence. Results are listed in Table 27. All bags contained saRNA concentrations close to the target value and met the acceptance criterion of 0.21±0.04 mg/ml throughout the observation period.

TABLE 27 saRNA contents (mg/ml) in infusion bags

| Time point | Bag #1 (PVC free) | Bag #2 (PVC free) | Bag #3 (PVC) | Bag #4 (PVC) |
|---|---|---|---|---|
| 0 hours | 0.20 | 0.20 | 0.20 | 0.20 |
| 8 hours | 0.19 | 0.19 | 0.20 | 0.20 |
| 24 hours | 0.20 | 0.19 | 0.20 | 0.20 |
| Acceptance criterion 0.21 ± 0.04 mg/ml | met | met | met | met |

Content POPC

The content of total POPC was measured by RP-HPLC with CAD detection according 222/SOP/018. All samples were analysed within the same HPLC sequence. Results are listed in Table 28. All bags contained POPC concentrations close to the target value and met the acceptance criterion of 0.29-0.49 mg/ml throughout the observation period.

TABLE 28

POPC contents (mg/ml) in infusion bags

| Time point | Bag #1 (PVC free) | Bag #2 (PVC free) | Bag #3 (PVC) | Bag #4 (PVC) |
|---|---|---|---|---|
| 0 hours | 0.32 | 0.40 | 0.40 | 0.37 |
| 8 hours | 0.39 | 0.36 | 0.36 | 0.36 |
| 24 hours | 0.34 | 0.30 | 0.34 | 0.32 |
| Acceptance criterion 0.29-0.49 mg/ml | met | met | met | met |

Content DOPE

The content of total DOPE was measured by RP-HPLC with CAD detection according 222/SOP/018. All samples were analysed within the same HPLC sequence. Results are listed in Table 29. All bags contained DOPE concentrations close to the target value and met the acceptance criterion of 1.13-1.90 mg/ml throughout the observation period.

TABLE 29

DOPE contents (mg/ml) in infusion bags

| Time point | Bag #1 (PVC free) | Bag #2 (PVC free) | Bag #3 (PVC) | Bag #4 (PVC) |
|---|---|---|---|---|
| 0 hours | 1.27 | 1.51 | 1.52 | 1.45 |
| 8 hours | 1.50 | 1.40 | 1.38 | 1.41 |
| 24 hours | 1.31 | 1.17 | 1.30 | 1.24 |
| Acceptance criterion 1.13-1.90 mg/ml | met | met | met | met |

Content CHEMS

The content of total CHEMS was measured by RP-HPLC with CAD detection according 222/SOP/018. All samples were analysed within the same HPLC sequence. Results are listed in Table 30.

TABLE 30

CHEMS contents (mg/ml) in infusion bags

| Time point | Bag #1 (PVC free) | Bag #2 (PVC free) | Bag #3 (PVC) | Bag #4 (PVC) |
|---|---|---|---|---|
| 0 hours | 0.73 | 0.81 | 0.86 | 0.81 |
| 8 hours | 0.83 | 0.77 | 0.75 | 0.78 |
| 24 hours | 0.72 | 0.66 | 0.73 | 0.70 |
| Acceptance criterion 0.71-1.18 mg/ml | met | met at 0, 8 h failed at 24 h | met | met at 0, 8 h failed at 24 h |

Content MoChol

The content of total MoChol was measured by RP-HPLC with CAD detection according 222/SOP/018. All samples were analysed within the same HPLC sequence. Results are listed in Table 31. All bags contained MoChol concentrations close to the target value and met the acceptance criterion of 1.71-2.84 mg/ml throughout the observation period.

TABLE 31

MoChol contents (mg/ml) in infusion bags

| Time point | Bag #1 (PVC free) | Bag #2 (PVC free) | Bag #3 (PVC) | Bag #4 (PVC) |
|---|---|---|---|---|
| 0 hours | 1.75 | 2.02 | 2.06 | 1.95 |
| 8 hours | 2.00 | 1.86 | 1.84 | 1.89 |
| 24 hours | 1.72 | 1.55 | 1.75 | 1.64 |
| Acceptance criterion 1.71-2.84 mg/ml | met | met at 0, 8 h failed at 24 h | met | met at 0, 8 h failed at 24 h |

Content Cholesterol

The content of total cholesterol was measured by RP-HPLC with CAD detection according 222/SOP/018. All samples were analysed within the same HPLC sequence. Results are listed in Table 32. All bags contained cholesterol concentrations lower than the maximally allowed limit and met the acceptance criterion of ≤0.17 mg/ml throughout the observation period.

TABLE 32

Cholesterol contents (mg/ml) in infusion bags

| Time point | Bag #1 (PVC free) | Bag #2 (PVC free) | Bag #3 (PVC) | Bag #4 (PVC) |
|---|---|---|---|---|
| 0 hours | 0.06 | 0.08 | 0.08 | 0.08 |
| 8 hours | 0.09 | 0.08 | 0.08 | 0.09 |
| 24 hours | 0.09 | 0.09 | 0.10 | 0.09 |
| Acceptance criterion ≤0.17 mg/ml | met | met | met | met |

Conclusions

The in-use study was conducted to confirm stability of MTL-CEBPA in infusion bags at room temperature over a 24 hour period and compatibility with the intended infusion lines.

Results confirm that the drug product is stable and compatible over at least 8 hours at the lowest intended clinical dose of 0.21 mg/ml.

Thus it can be concluded that the selected materials (infusion bags and space lines) are compatible with the drug product and can be used in clinical studies of MTL-CEBPA within a time period of at least 8 hours.

Example 22. Stability Studies for MTL-CEBPA

Long term storage was performed at −20±5° C. Stability under accelerated conditions was investigated at 2-8° C. Stress test studies for identification of stability indicating parameters were performed by storage at 25±2° C. and 40±2° C. Table 33 provides an overview of batches tested in those stability studies including duration, condition and currently available data.

The analytical procedures used in the stability programme included tests for appearance, pH, assay, purity, lipid content and particle characteristics.

TABLE 33

Stability Studies for MTL-CEBPA Drug Product

| Batches Tested | Date of Manufacture | Stability Study Start | Duration | Conditions | Available Data |
|---|---|---|---|---|---|
| MIT0615-A | June 2015 | 25 Jun. 2015 | 0-36 M | −20 ± 5° C. | 0-3 months |
|  |  | 2 Nov. 2015 | 0-72 h | 25 ± 2° C. | 0-72 hours |
|  |  | 2 Nov. 2015 | 0-72 h | 40 ± 2° C. | 0-72 hours |
| MIT1215-A | December 2015 | 3 Dec. 2015 | 0-24 M | −20 ± 5° C. | 0-1 month |
|  |  | 3 Dec. 2015 | 0-6 M | 5 ± 3° C. | 0-1 month |
|  |  | 18 Jan. 2016 | 0-24 h | 25 ± 2° C. | 0-24 hours |

Stability Summary and Conclusion

Stability data were available for one batch of MTL-CEBPA (MIT0615-A) stored at long-term storage conditions (−20±5° C.). Stress test data were available for the same batch stored at 25±2° C. and 40±2° C.

No change was observed for MIT0615-A stored at −20±5° C. for up to 6 months. Samples stored under stress conditions (25±2° C. and 40±2° C.) showed a decrease in MOCHOL by degradation of MOCHOL and conversion into cholesterol upon storage. This degradation was more pronounced at 40±2° C. compared to 25±2° C.

Under stress testing at 25° C. for three days (72 h), content of the key lipid, morpholinoethaneamine cholesterol (MOCHOL) decreased from 33.2 to 27.8 mg/ml (a 16% decrease), while after three days at 40° C. the content of MOCHOL decreased from 30.1 to 22.5 mg/ml (a decrease of 25%). This reduction in MOCHOL corresponds to the formation of the degradation product cholesterol, which increased from 1.1 to 2.2 mg/ml after three days at 25° C. and from 1.0 to 8.2 mg/ml after three days at 40° C. The other lipid excipients did not exhibit significant changes under accelerated conditions. No significant changes were observed for the other lipids, total saRNA content and its impurity. Tables 35-38 shows stability and stress test results of MTL-CEBPA at different conditions.

TABLE 34

Long-term Stability at −20 ± 5° C. Batch MIT1215-A (long-term, −20 ± 5° C.)

| Parameter | Acceptance Criterion | 0 month | 1 month | 3 months | 6 months |
|---|---|---|---|---|---|
| Appearance | milky white suspension | pass | pass | pass | pass |
| Content total saRNA | 2.5 ± 0.5 mg/ml | 2.6 | 2.6 | 2.6 | 2.6 |

TABLE 34-continued

Long-term Stability at −20 ± 5° C. Batch MIT1215-A (long-term, −20 ± 5° C.)

| Parameter | Acceptance Criterion | 0 month | 1 month | 3 months | 6 months |
|---|---|---|---|---|---|
| saRNA encapsulation | ≥75% | 83 | 81 | 80 | 78 |
| Content POPC | 3.5-5.80 mg/ml | 4.8 | 4.2 | 4.8 | 4.6 |
| Content DOPE | 13.5-22.6 mg/ml | 18.4 | 17.0 | 18.9 | 16.9 |
| Content CHEMS | 8.5-14.1 mg/ml | 11.5 | 10.4 | 11.6 | 10.8 |
| Content MOCHOL | 20.3-33.8 mg/ml | 26.9 | 24.6 | 27.2 | 24.2 |
| Content Cholesterol | ≤2.0 mg/ml | 1.0 | 0.8 | 1.0 | 1.1 |
| Particle size | 100-140 nm | 107 | 108 | 108 | 108 |
| Polydispersity index | ≤0.200 | 0.169 | 0.159 | 0.163 | 0.167 |
| Zeta potential | ≤−30.0 mV at pH 7.2-7.8 | −39.1 | −38.5 | −36.6 | −35.2 |
| pH | 7.2-7.8 | 7.4 | — | — | — |
| Osmolality | 280-400 mOsmol/kg | 349 | — | — | — |
| Impurities saRNA | ≤15% | 6 | 7 | 5 | 7 |
| Sub-visible particles | part. ≥10 μm: ≤3000/vial | 2 | — | — | — |
| | part. ≥25 μm: ≤300/vial | <1 | — | — | — |
| Endotoxin | ≤5.0 EU/ml | <0.5 | — | — | — |
| Sterility | no growth | pass | — | — | — |

TABLE 35

Accelerated Stability at 5 ± 3° C. of Batch MIT1215-A

| Parameter | Acceptance Criterion | 0 month | 1 month |
|---|---|---|---|
| Appearance | milky white suspension | pass | pass |
| Total saRNA | 2.5 ± 0.5 mg/ml | 2.5 | 2.6 |
| saRNA encapsulation | ≥75% | 85 | 82 |
| Content POPC | 3.5-5.80 mg/ml | 4.7 | 4.4 |
| Content DOPE | 13.5-22.6 mg/ml | 17.3 | 16.0 |
| Content CHEMS | 8.5-14.1 mg/ml | 11.0 | 10.2 |
| Content MOCHOL | 20.3-33.8 mg/ml | 24.9 | 22.3 |
| Content Cholesterol | ≤2.0 mg/ml | 0.9 | 1.9 |
| Particle size | 100-140 nm | 112 | 113 |
| Polydispersity index | ≤0.200 | 0.160 | 0.140 |
| Zeta potential | ≤−30.0 mV at pH 7.2-7.8 | −35.6 | −36.1 |
| pH | 7.2-7.8 | 7.6 | 7.4 |
| Osmolality | 280-400 mOsmol/kg | 334 | 341 |
| Impurities saRNA | ≤15% | 6 | 7 |

TABLE 36

Stress test data at 25 ± 2° C. of Batch MIT0615-A

| Parameter | Acceptance Criterion | Time points [hours] | | | | | |
|---|---|---|---|---|---|---|---|
| | | 0 | 8 | 16 | 24 | 48 | 72 |
| Total saRNA | report result - [mg/ml] | 2.6 | 2.6 | 2.7 | 2.6 | 2.6 | 2.6 |
| Content POPC | report result - [mg/ml] | 5.5 | 5.2 | 5.5 | 5.3 | 5.3 | 4.9 |
| Content DOPE | report result - [mg/ml] | 22.6 | 21.2 | 22.4 | 21.8 | 21.7 | 20.3 |
| Content CHEMS | report result - [mg/ml] | 13.8 | 13.7 | 13.1 | 13.3 | 13.4 | 12.7 |
| Content MOCHOL | report result - [mg/ml] | 33.2 | 31.0 | 32.4 | 31.5 | 30.4 | 27.8 |
| Content Cholesterol | report result - [mg/ml] | 1.1 | 1.2 | 1.4 | 1.5 | 1.9 | 2.2 |
| Impurities saRNA | report result - [%] | 8 | 8 | 8 | 8 | 7 | 5 |

TABLE 37

Stress test data at 40 ± 2° C. of Batch MIT0615-A

| Parameter | Acceptance Criterion | Time points [hours] | | | | | |
|---|---|---|---|---|---|---|---|
| | | 0 | 8 | 16 | 24 | 48 | 72 |
| Total saRNA | report result - [mg/ml] | 2.6 | 2.6 | 2.7 | 2.6 | 2.5 | 2.6 |
| Content POPC | report result - [mg/ml] | 5.0 | 5.4 | 5.3 | 4.3 | 5.6 | 5.8 |
| Content DOPE | report result - [mg/ml] | 20.6 | 22.1 | 21.5 | 17.7 | 22.5 | 23.3 |
| Content CHEMS | report result - [mg/ml] | 12.5 | 13.6 | 12.8 | 10.7 | 13.7 | 14.2 |
| Content MOCHOL | report result - [mg/ml] | 30.1 | 31.1 | 28.0 | 22.1 | 24.4 | 22.5 |

TABLE 37-continued

Stress test data at 40 ± 2° C. of Batch MIT0615-A

| Parameter | Acceptance Criterion | Time points [hours] | | | | | |
|---|---|---|---|---|---|---|---|
| | | 0 | 8 | 16 | 24 | 48 | 72 |
| Content Cholesterol | report result - [mg/ml] | 1.0 | 1.9 | 2.6 | 2.8 | 5.8 | 8.2 |
| Impurities saRNA | report result - [%] | 6 | 7 | 7 | 7 | 5 | 6 |

MTL-CEBPA is stable when stored at long-term storage condition (−20±5° C.) for at least 6 months, showing no trend for decrease or changes other than derived from analytical variability. It is stable for at least 1 month under accelerated conditions at 2-8° C. (5±3° C.).

Example 23. In Vivo Studies of CCL4 Induced Liver Cirrhosis with CEBPA-saRNA This study was a repeat of Example 11 with ascites and survival exploring delayed administration. Carbon tetrachloride (CCL4) induced hepatic fibrosis is a well-established and widely accepted experimental model in rodents for the study of liver fibrosis and cirrhosis. Chronic administration of carbon tetrachloride to rats induces severe disturbances of hepatic function together with histologically observable liver fibrosis.

Liver cirrhosis in Sprague Dawley rats was induced by i.p. injection of CCL4. Male Sprague Dawley rats with a starting body weight of 120-150 g were used. CCL4 treated animals showed significant reduction in body weight throughout the study. CCL4 treated animals showed significant increase in liver function test (LFT) parameters such as Aspartate aminotransferase (AST), Alanine aminotransferase (ALT), Alkaline phosphatase (ALP), Prothrombin time (PT), and Bilirubin, but not GGT up to 8 weeks (first randomization). A significant increase in Ammonia and a significant reduction in total protein and in path control animals up to 8 weeks.

Figure 36:
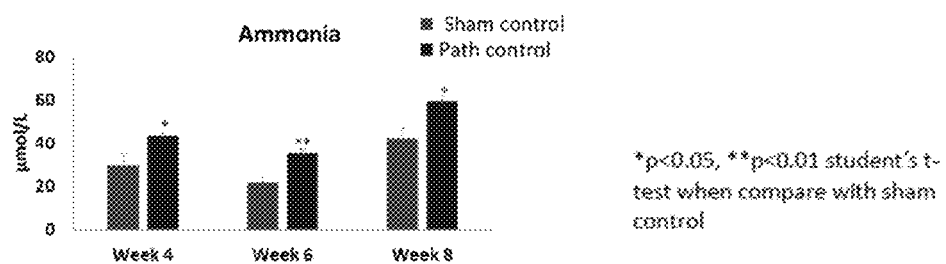
FIG. 36 shows ammonia levels after MTL-CEBPA treatment at week 8 or week 11.
Figure 36:
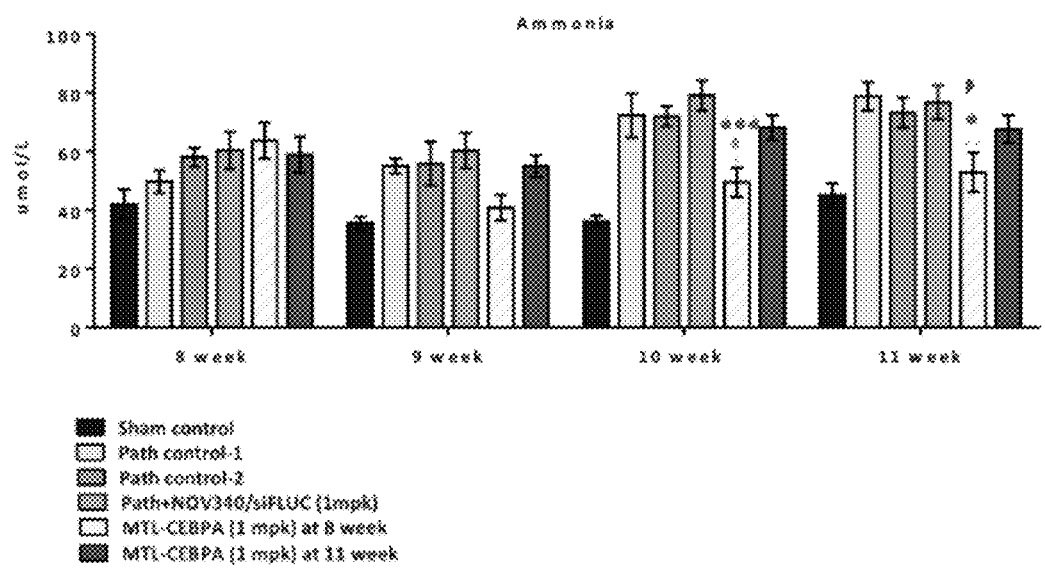

Treatment with MTL-CEBPA (1 mpk) at week 8 showed significant improvement in body weight of animals. LFT and ammonia levels were significantly reversed till 13 weeks. Total protein levels were significantly increased. Treatment with MTL-CEBPA (1 mpk) at week 11 also showed significant reversal in LFT and ammonia levels till 13 weeks. FIG. 36 showed that MTL-CEBPA treatment from week 8 reversed hyper-ammonaemia.

Figure 37A:
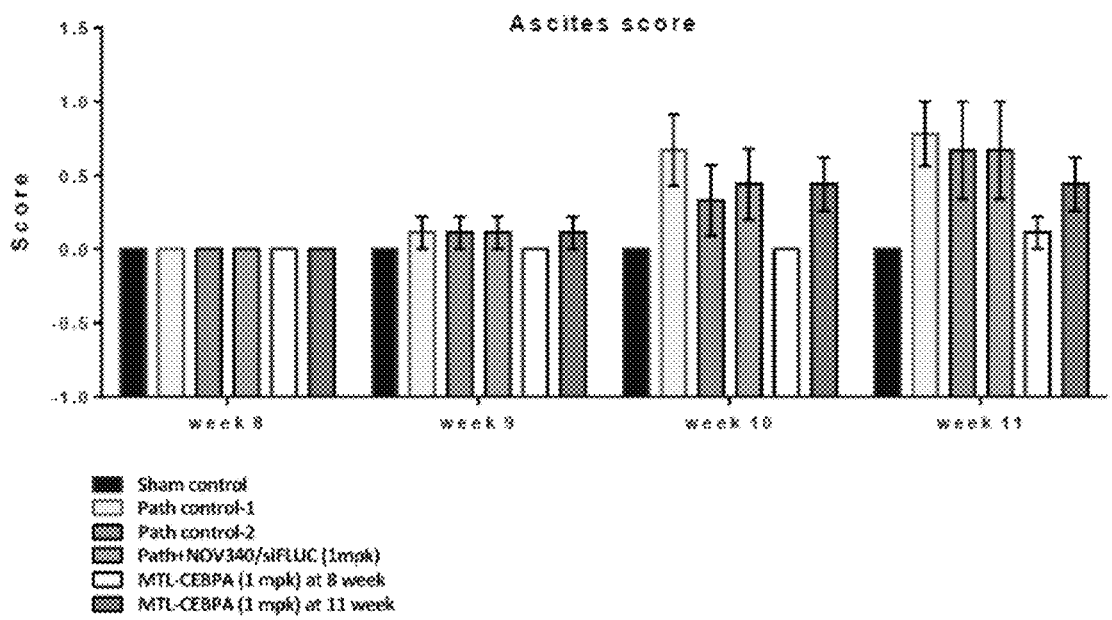
FIG. 37A and FIG. 37B show ascites scores after MTL-CEBPA treatment at week 8 or week 11.
Figure 37B:
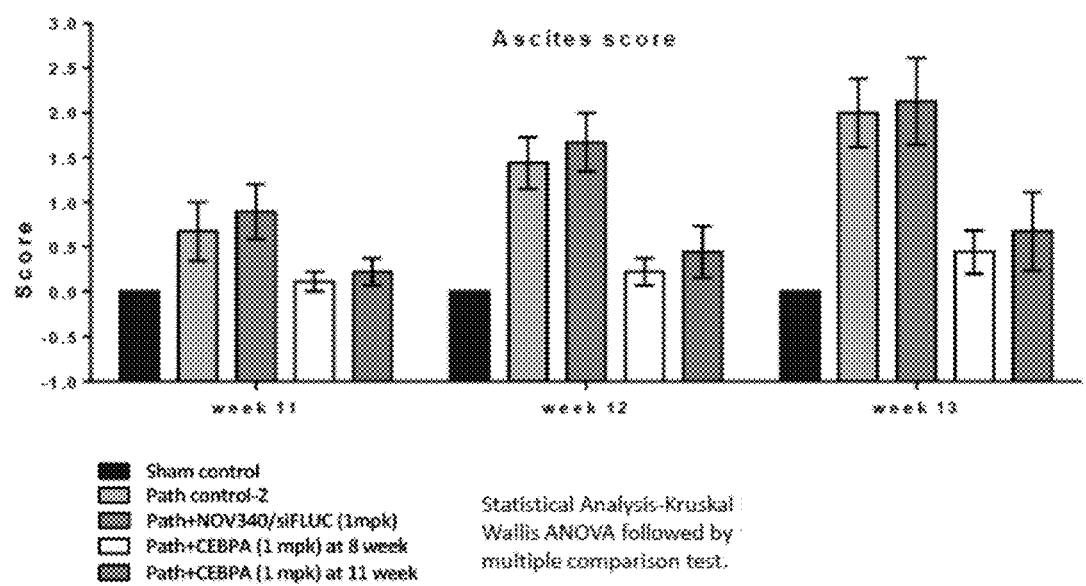

FIG. 37A and FIG. 37B showed that MTL-CEBPA treatment attenuated ascites. Ascites was assessed on a scale from 0 to 3 based on visual/physical examination. Absence of ascites was recorded as 0; barely palpable ascites as 1; gross ascites with expansion of the flanks as 2 and tense ascites at 3. Ascites was noticeable from week 9 onwards and attained high score at week 13.

Figure 38A:
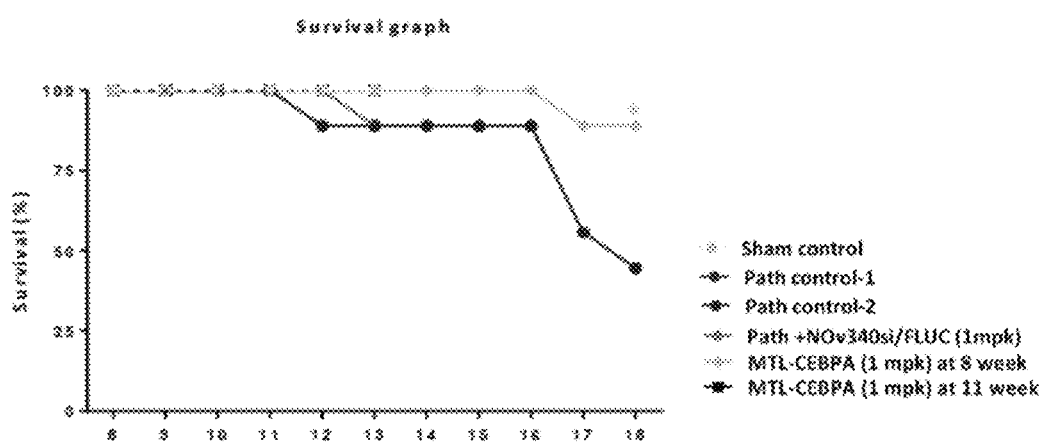
FIG. 38A and FIG. 38B show survival graphs after MTL-CEBPA treatment at week 8 or week 11.
Figure 38B:
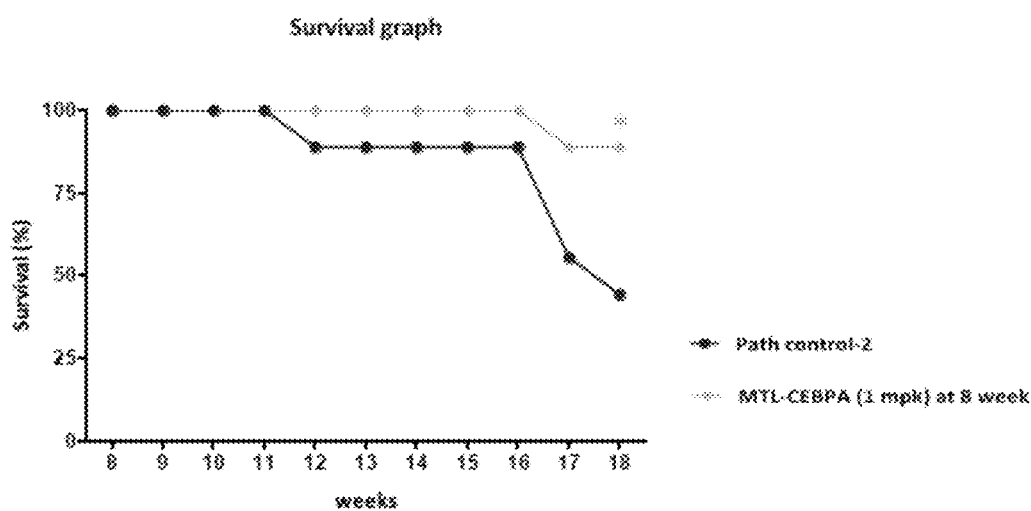

MTL-CEBPA treatment resulted in significant improvement in survival as shown in survival graphs in FIG. 38A and FIG. 38B.

Example 24. CEBPA-51 Cross-Reactivity in Mouse and Rat

Aim of Study:

The purpose of this study was to investigate if rat and mouse are appropriate rodent species for preclinical liver disease models and for non-clinical toxicology studies with MTL-CEBPA/CEBPA-51.

Experimental Design:

The study comprised 3 parts, 1) sequence match from database searches, 2) sequencing of rat and mouse genomic DNA (gDNA), and 3) confirming upregulation of CEBPA in rat and mouse cell lines.

First, the sequence homology of CEBPA was assessed with publically available databases (BLAST search). The CEBPA-51 target sequence was used as a query search on the *Rattus norvegicus* (Wistar strain) and *Mus musculus* (C57BL/6J strain) genomes using BLAST.

Additionally, genomic DNA was isolated from rat and mouse liver lobes and PCR products of the target sites were generated for direct sequencing. The resulting sequences were then compared with the published rat and mouse genome sequences via BLAST.

Functional cross-reactivity was then assessed by transfecting CEBPA-51 into rat liver clone-9 cells and mouse liver AML12 cells and measuring upregulation of CEBPA mRNA. Cells were reverse transfected with 20 nM (f.c.) of each test item (CEBPA-51 or siFLUC, an untargeted siRNA) using Lipofectamine 2000, followed by an additional forward transfection step (20 nM f.c.) of each test item using Lipofectamine 2000. 24 hours after the second transfection CEBPA mRNA levels were determined by qRT-PCR (housekeeping gene: GAPDH; measured in triplicates).

Results:

The BLAST search confirmed the absence of mismatches between the sequence of CEBPA-51 and the rat and mouse target sites (genomic location of the CEBPA gene). In addition, no mismatches were found comparing CEBPA-51 and the amplified sequence derived from gDNA from rat and mouse liver.

Transfection of CEBPA-51 into rat clone-9 cells and mouse AML12 cells resulted in a 2-fold (n=1) and 1.7-fold (n=2) CEBPA mRNA upregulation, respectively, while no upregulation was observed with the untargeted control RNA duplex (siFLUC).

Conclusion:

The genomic sequences of rat and mouse CEBPA are identical to the CEBPA-51 target sequence according to the BLAST database. This was further verified by sequencing of rat and mouse liver gDNA. Functional cross-reactivity of CEBPA-51 was verified by demonstration of CEBPA gene upregulation in initial studies in rat and mouse liver cell lines. Rat and mouse models of liver cancer and disease are therefore considered appropriate for preclinical assessment of MTL-CEBPA activity, and rat is considered an appropriate rodent species for non-clinical toxicology testing of MTL-CEBPA.

OTHER EMBODIMENTS

It is to be understood that while the present disclosure has been described in conjunction with the detailed description thereof, the foregoing description is intended to illustrate and not limit the scope of the present disclosure, which is defined by the scope of the appended claims. Other aspects, advantages, and modifications are within the scope of the following claims.

The invention claimed is:

1. A pharmaceutical composition comprising a synthetic isolated saRNA encapsulated in a liposome, wherein the saRNA up-regulates expression of C/EBPα gene, wherein the saRNA is double-stranded and comprises a sense strand and an antisense strand comprising SEQ ID No. 109 (CEBPA51) or SEQ ID No. 93 (AW51), wherein the liposome comprises 1-palmitoyl-2-oleoyl-sn-glycero-3-phosphocholine (POPC), 1,2-dioleoyl-sn-glycero-3-phosphoethanolamine (DOPE), cholesteryl-hemi succinate (CHEMS), and 4-(2-aminoethyl)-morpholino-cholesterol hemisuccinate (MOCHOL), and wherein the saRNA has a concentration of about 2 mg/mL to about 5 mg/mL.

2. The pharmaceutical composition of claim 1, wherein the molar ratio of POPC:DOPE:CHEMS:MOCHOL is around 6:24:23:47.

3. The pharmaceutical composition of claim 1, wherein the size of the liposome is between about 50 nm to about 150 nm.

4. The pharmaceutical composition of claim 3, wherein the size of the liposome is between 100 nm to about 120 nm.

5. The pharmaceutical composition of claim 1, wherein the antisense strand and/or the sense strand of the saRNA comprises a 3' overhang.

6. The pharmaceutical composition of claim 1, wherein the sense strand of the saRNA comprises at least one chemical modification.

7. The pharmaceutical composition of claim 6, wherein the sense strand of the saRNA comprises at least 2 modifications.

8. The pharmaceutical composition of claim 6, wherein the modification comprises any of 2'-F, 2'-OMe, inverted deoxyribose, or phosphorothioate linkage between nucleotides.

9. The pharmaceutical composition of claim 1, wherein the sense strand of the saRNA comprises SEQ ID No. 110 (CEBPA51) or SEQ ID No. 94 (AW51).

10. The pharmaceutical composition of claim 1, wherein the saRNA has an antisense strand of SEQ ID No. 109 and a sense strand of SEQ ID No. 110.

11. The pharmaceutical composition of claim 1, wherein the saRNA has a concentration of about 2.5 mg/mL.

12. The pharmaceutical composition of claim 1, wherein the pharmaceutical composition has a pH between about 7.2 to about 7.8.

13. The pharmaceutical composition of claim 12, wherein the pharmaceutical composition has a pH of about 7.5.

14. The pharmaceutical composition of claim 1, wherein the pharmaceutical composition has a phosphate buffer.

15. The pharmaceutical composition of claim 14, wherein the phosphate buffer comprises disodium hydrogen phosphate, dihydrate and potassium dihydrogen phosphate.

16. The pharmaceutical composition of claim 1, wherein the pharmaceutical composition comprises a cryoprotectant.

17. The pharmaceutical composition of claim 16, wherein the cryoprotectant is sucrose.

18. The pharmaceutical composition of claim 1, wherein the pharmaceutical composition comprises an ionic strength adjuster.

19. The pharmaceutical composition of claim 18, wherein the ionic strength adjuster is potassium chloride.

20. A method of treating hepatocellular carcinoma (HCC) of a subject comprising administering the pharmaceutical composition in claim 1 to the subject.

21. The method of claim 20, wherein the HCC is advanced HCC.

22. The method of claim 20, wherein the dose of the pharmaceutical composition is between about 20 to about 160 mg/m$^2$.

23. The method of claim 20, wherein the pharmaceutical composition is administered once a week for 3 weeks on Day 1, Day 8 and Day 15 by intravenous infusion.

\* \* \* \* \*

SEQUENCE LISTING

<160> NUMBER OF SEQ ID NOS: 129

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
cggucauugu cacugguca                                                  19

<210> SEQ ID NO 2
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
ugaccaguga caaugaccg                                                  19

<210> SEQ ID NO 3
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
agcugaaagg auucauccu                                                  19

<210> SEQ ID NO 4
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
aggaugaauc cuuccagcu                                                  19

<210> SEQ ID NO 5
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
acauagnccc agugauuaa                                                  19

<210> SEQ ID NO 6
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
uuaaucacug ggacuaugu                                                  19

```
<210> SEQ ID NO 7
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gaauaagacu uuguccaau                                                     19

<210> SEQ ID NO 8
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
auuggacaaa gucuuauuc                                                     19

<210> SEQ ID NO 9
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
gcgcggauuc ucuuucaaa                                                     19

<210> SEQ ID NO 10
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
uuugaaagag aauccgcgc                                                     19

<210> SEQ ID NO 11
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
ccaggaacuc gucguugaa                                                     19

<210> SEQ ID NO 12
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
uucaacgacg aguuccugg                                                     19
```

```
<210> SEQ ID NO 13
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
agaaguuggc cacuuccau                                                   19

<210> SEQ ID NO 14
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
auggagucgg ccgacuucu                                                   19

<210> SEQ ID NO 15
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
aagaggucgg agaggaagu                                                   19

<210> SEQ ID NO 16
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16 aguccuggc cgaccuguu                                                    19

<210> SEQ ID NO 17
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
uuguacucgu cgcugugcu                                                   19

<210> SEQ ID NO 18
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
agaacagcaa cgaguaccg                                                   19
```

```
<210> SEQ ID NO 19
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
uacucgucgc ugugcuugu                                                        19

<210> SEQ ID NO 20
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
acaagaacag caacgagua                                                        19

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 21
agaaguuggc cacuuccaug gggga                                                 25

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 22
tcccccaugg agucggccga cuucuac                                               27

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 23
aagaggucgg agaggaaguc gucgt                                                 25

<210> SEQ ID NO 24
<211> LENGTH: 27
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 24
acgacgaguu ccuggccgac cuguucc                                            27

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 25
uuguacucgu cgcugugcuu gucca                                              25

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 26
tggacaagaa cagcaacgag uaccggg                                            27

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 27
uacucgucgc ugugcuuguc caccg                                              25

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 28
cgguggacaa gaacagcaac gaguacc                                            27
```

```
<210> SEQ ID NO 29
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
cugaguaauc gcuuaaagau u                                              21

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
ucuuuaagcg auuacucagu u                                              21

<210> SEQ ID NO 31
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
gaaacuuuag cgagucagau u                                              21

<210> SEQ ID NO 32
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
ucugacucgc uaaaguuucu u                                              21

<210> SEQ ID NO 33
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
acuacugagu gacaguagau u                                              21

<210> SEQ ID NO 34
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Sense strand starting at position 17 of SEQ ID
      NO: 67

<400> SEQUENCE: 34
gguauacauc cucagagcu                                                 19
```

```
<210> SEQ ID NO 35
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Antisense strand to SEQ ID NO: 34

<400> SEQUENCE: 35
agcucugagg auguauacc                                                19

<210> SEQ ID NO 36
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Sense strand starting at position 46 of SEQ ID
      NO: 67

<400> SEQUENCE: 36
cuagcuuucu ggugugacu                                                19

<210> SEQ ID NO 37
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Antisense strand to SEQ ID NO: 36

<400> SEQUENCE: 37
agucacacca gaaagcuag                                                19

<210> SEQ ID NO 38
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Sense strand starting at position 305 of SEQ ID
      NO: 67

<400> SEQUENCE: 38
cgggcuuguc gggaucuca                                                19

<210> SEQ ID NO 39
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Antisense strand to SEQ ID NO: 37

<400> SEQUENCE: 39
ugagaucccg acaagcccg                                                19
```

```
<210> SEQ ID NO 40
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Sense strand starting at position 457 of SEQ ID
      NO: 67

<400> SEQUENCE: 40
gcauuggagc ggugaguuu                                               19

<210> SEQ ID NO 41
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Antisense strand to SEQ ID NO: 40

<400> SEQUENCE: 41
aaacucaccg cuccaaugc                                               19

<210> SEQ ID NO 42
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Sense strand starting at position 486 of SEQ ID
      NO: 67

<400> SEQUENCE: 42
ggcacaaggu uauccuaaa                                               19

<210> SEQ ID NO 43
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Antisense strand to SEQ ID NO: 42

<400> SEQUENCE: 43
uuuaggauaa ccuugugcc                                               19

<210> SEQ ID NO 44
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Sense strand starting at position 487 of SEQ ID
      NO: 67

<400> SEQUENCE: 44
gcacaagguu auccuaaau                                               19
```

```
<210> SEQ ID NO 45
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Antisense strand to SEQ ID NO: 44

<400> SEQUENCE: 45
auuuaggaua accuugugc                                                    19

<210> SEQ ID NO 46
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Sense strand starting at position 883 of SEQ ID
      NO: 67

<400> SEQUENCE: 46
cggucauugu cacgguca                                                     19

<210> SEQ ID NO 47
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Antisense strand to SEQ ID NO: 46

<400> SEQUENCE: 47
ugaccaguga caaugaccg                                                    19

<210> SEQ ID NO 48
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Sense strand starting at position 1616 of SEQ
      ID NO: 67

<400> SEQUENCE: 48
ccaggaacuc gucguugaa                                                    19

<210> SEQ ID NO 49
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Antisense strand to SEQ ID NO: 48

<400> SEQUENCE: 49
uucaacgacg aguuccugg                                                    19
```

```
<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
cggucauugu cacuggucau u                                              21

<210> SEQ ID NO 51
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
ugaccaguga caaugaccgu u                                              21

<210> SEQ ID NO 52
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2'O-Me modified nucleotide
<220> FEATURE:
<221> NAME/KEY: modified_base
<222> LOCATION: (3)..(3)
<223> OTHER INFORMATION: 2'F modified nucleotide
<220> FEATURE:
<221> NAME/KEY: modified_base
<222> LOCATION: (4)..(4)
<223> OTHER INFORMATION: 2'O-Me modified nucleotide
<220> FEATURE:
<221> NAME/KEY: modified_base
<222> LOCATION: (5)..(5)
<223> OTHER INFORMATION: 2'F modified nucleotide
<220> FEATURE:
<221> NAME/KEY: modified_base
<222> LOCATION: (6)..(6)
<223> OTHER INFORMATION: 2'O-Me modified nucleotide
<220> FEATURE:
<221> NAME/KEY: modified_base
<222> LOCATION: (7)..(7)
<223> OTHER INFORMATION: 2'F modified nucleotide
<220> FEATURE:
<221> NAME/KEY: modified_base
<222> LOCATION: (8)..(8)
<223> OTHER INFORMATION: 2'O-Me modified nucleotide
<220> FEATURE:
<221> NAME/KEY: modified_base
<222> LOCATION: (9)..(9)
<223> OTHER INFORMATION: 2'F modified nucleotide
<220> FEATURE:
<221> NAME/KEY: modified_base
<222> LOCATION: (10)..(10)
<223> OTHER INFORMATION: 2'O-Me modified nucleotide
<220> FEATURE:
<221> NAME/KEY: modified_base
<222> LOCATION: (11)..(11)
<223> OTHER INFORMATION: 2'F modified nucleotide
<220> FEATURE:
<221> NAME/KEY: modified_base
<222> LOCATION: (12)..(12)
<223> OTHER INFORMATION: 2'O-Me modified nucleotide
```

```
<220> FEATURE:
<221> NAME/KEY: modified_base
<222> LOCATION: (13)..(13)
<223> OTHER INFORMATION: 2'F modified nucleotide
<220> FEATURE:
<221> NAME/KEY: modified_base
<222> LOCATION: (14)..(14)
<223> OTHER INFORMATION: 2'O-Me modified nucleotide
<220> FEATURE:
<221> NAME/KEY: modified_base
<222> LOCATION: (15)..(15)
<223> OTHER INFORMATION: 2'F modified nucleotide
<220> FEATURE:
<221> NAME/KEY: modified_base
<222> LOCATION: (16)..(16)
<223> OTHER INFORMATION: 2'O-Me modified nucleotide
<220> FEATURE:
<221> NAME/KEY: modified_base
<222> LOCATION: (17)..(17)
<223> OTHER INFORMATION: 2'F modified nucleotide
<220> FEATURE:
<221> NAME/KEY: modified_base
<222> LOCATION: (18)..(18)
<223> OTHER INFORMATION: 2'O-Me modified nucleotide
<220> FEATURE:
<221> NAME/KEY: modified_base
<222> LOCATION: (19)..(19)
<223> OTHER INFORMATION: 2'F modified nucleotide
<220> FEATURE:
<221> NAME/KEY: modified_base
<222> LOCATION: (20)..(21)
<223> OTHER INFORMATION: 2'O-Me modified nucleotide
<220> FEATURE:
<221> NAME/KEY: misc_feature
<222> LOCATION: (20)..(21)
<223> OTHER INFORMATION: Phosphorothioate linkage

<400> SEQUENCE: 52
cggucauugu cacuggucau u                                              21

<210> SEQ ID NO 53
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2'F modified nucleotide
<220> FEATURE:
<221> NAME/KEY: modified_base
<222> LOCATION: (3)..(3)
<223> OTHER INFORMATION: 2'O-Me modified nucleotide
<220> FEATURE:
<221> NAME/KEY: modified_base
<222> LOCATION: (4)..(4)
<223> OTHER INFORMATION: 2'F modified nucleotide
<220> FEATURE:
<221> NAME/KEY: modified_base
<222> LOCATION: (5)..(5)
<223> OTHER INFORMATION: 2'O-Me modified nucleotide
<220> FEATURE:
<221> NAME/KEY: modified_base
<222> LOCATION: (6)..(6)
<223> OTHER INFORMATION: 2'F modified nucleotide
<220> FEATURE:
<221> NAME/KEY: modified_base
<222> LOCATION: (7)..(7)
<223> OTHER INFORMATION: 2'O-Me modified nucleotide
<220> FEATURE:
<221> NAME/KEY: modified_base
<222> LOCATION: (8)..(8)
<223> OTHER INFORMATION: 2'F modified nucleotide
```

```
<220> FEATURE:
<221> NAME/KEY: modified_base
<222> LOCATION: (9)..(9)
<223> OTHER INFORMATION: 2'O-Me modified nucleotide
<220> FEATURE:
<221> NAME/KEY: modified_base
<222> LOCATION: (10)..(10)
<223> OTHER INFORMATION: 2'F modified nucleotide
<220> FEATURE:
<221> NAME/KEY: modified_base
<222> LOCATION: (11)..(11)
<223> OTHER INFORMATION: 2'O-Me modified nucleotide
<220> FEATURE:
<221> NAME/KEY: modified_base
<222> LOCATION: (12)..(12)
<223> OTHER INFORMATION: 2'F modified nucleotide
<220> FEATURE:
<221> NAME/KEY: modified_base
<222> LOCATION: (13)..(13)
<223> OTHER INFORMATION: 2'O-Me modified nucleotide
<220> FEATURE:
<221> NAME/KEY: modified_base
<222> LOCATION: (14)..(14)
<223> OTHER INFORMATION: 2'F modified nucleotide
<220> FEATURE:
<221> NAME/KEY: modified_base
<222> LOCATION: (15)..(15)
<223> OTHER INFORMATION: 2'O-Me modified nucleotide
<220> FEATURE:
<221> NAME/KEY: modified_base
<222> LOCATION: (16)..(16)
<223> OTHER INFORMATION: 2'F modified nucleotide
<220> FEATURE:
<221> NAME/KEY: modified_base
<222> LOCATION: (17)..(17)
<223> OTHER INFORMATION: 2'O-Me modified nucleotide
<220> FEATURE:
<221> NAME/KEY: modified_base
<222> LOCATION: (18)..(18)
<223> OTHER INFORMATION: 2'F modified nucleotide
<220> FEATURE:
<221> NAME/KEY: modified_base
<222> LOCATION: (19)..(21)
<223> OTHER INFORMATION: 2'O-Me modified nucleotide
<220> FEATURE:
<221> NAME/KEY: misc_feature
<222> LOCATION: (20)..(21)
<223> OTHER INFORMATION: Phosphorothioate linkage

<400> SEQUENCE: 53
ugaccaguga caaugaccgu u                                        21

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(2)
<223> OTHER INFORMATION: 2'O-Me modified nucleotide
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: modified_base
<222> LOCATION: (3)..(3)
<223> OTHER INFORMATION: 2'F modified nucleotide
```

<220> FEATURE:
<221> NAME/KEY: modified_base
<222> LOCATION: (4)..(4)
<223> OTHER INFORMATION: 2'O-Me modified nucleotide
<220> FEATURE:
<221> NAME/KEY: modified_base
<222> LOCATION: (5)..(5)
<223> OTHER INFORMATION: 2'F modified nucleotide
<220> FEATURE:
<221> NAME/KEY: modified_base
<222> LOCATION: (6)..(6)
<223> OTHER INFORMATION: 2'O-Me modified nucleotide
<220> FEATURE:
<221> NAME/KEY: modified_base
<222> LOCATION: (7)..(7)
<223> OTHER INFORMATION: 2'F modified nucleotide
<220> FEATURE:
<221> NAME/KEY: modified_base
<222> LOCATION: (8)..(8)
<223> OTHER INFORMATION: 2'O-Me modified nucleotide
<220> FEATURE:
<221> NAME/KEY: modified_base
<222> LOCATION: (9)..(9)
<223> OTHER INFORMATION: 2'F modified nucleotide
<220> FEATURE:
<221> NAME/KEY: modified_base
<222> LOCATION: (10)..(10)
<223> OTHER INFORMATION: 2'O-Me modified nucleotide
<220> FEATURE:
<221> NAME/KEY: modified_base
<222> LOCATION: (11)..(11)
<223> OTHER INFORMATION: 2'F modified nucleotide
<220> FEATURE:
<221> NAME/KEY: modified_base
<222> LOCATION: (12)..(12)
<223> OTHER INFORMATION: 2'O-Me modified nucleotide
<220> FEATURE:
<221> NAME/KEY: modified_base
<222> LOCATION: (13)..(13)
<223> OTHER INFORMATION: 2'F modified nucleotide
<220> FEATURE:
<221> NAME/KEY: modified_base
<222> LOCATION: (14)..(14)
<223> OTHER INFORMATION: 2'O-Me modified nucleotide
<220> FEATURE:
<221> NAME/KEY: modified_base
<222> LOCATION: (15)..(15)
<223> OTHER INFORMATION: 2'F modified nucleotide
<220> FEATURE:
<221> NAME/KEY: modified_base
<222> LOCATION: (16)..(16)
<223> OTHER INFORMATION: 2'O-Me modified nucleotide
<220> FEATURE:
<221> NAME/KEY: modified_base
<222> LOCATION: (17)..(17)
<223> OTHER INFORMATION: 2'F modified nucleotide
<220> FEATURE:
<221> NAME/KEY: modified_base
<222> LOCATION: (18)..(18)
<223> OTHER INFORMATION: 2'O-Me modified nucleotide
<220> FEATURE:
<221> NAME/KEY: modified_base
<222> LOCATION: (19)..(19)
<223> OTHER INFORMATION: 2'F modified nucleotide
<220> FEATURE:
<221> NAME/KEY: modified_base
<222> LOCATION: (20)..(20)
<223> OTHER INFORMATION: Inverted nucleotide
<220> FEATURE:
<221> NAME/KEY: modified_base
<222> LOCATION: (20)..(20)
<223> OTHER INFORMATION: Deoxy-nucleotide

<400> SEQUENCE: 54
cggucauugu cacuggucat                                         20

```
<210> SEQ ID NO 55
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2'F modified nucleotide
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: modified_base
<222> LOCATION: (3)..(3)
<223> OTHER INFORMATION: 2'O-Me modified nucleotide
<220> FEATURE:
<221> NAME/KEY: modified_base
<222> LOCATION: (4)..(4)
<223> OTHER INFORMATION: 2'F modified nucleotide
<220> FEATURE:
<221> NAME/KEY: modified_base
<222> LOCATION: (5)..(5)
<223> OTHER INFORMATION: 2'O-Me modified nucleotide
<220> FEATURE:
<221> NAME/KEY: modified_base
<222> LOCATION: (6)..(6)
<223> OTHER INFORMATION: 2'F modified nucleotide
<220> FEATURE:
<221> NAME/KEY: modified_base
<222> LOCATION: (7)..(7)
<223> OTHER INFORMATION: 2'O-Me modified nucleotide
<220> FEATURE:
<221> NAME/KEY: modified_base
<222> LOCATION: (8)..(8)
<223> OTHER INFORMATION: 2'F modified nucleotide
<220> FEATURE:
<221> NAME/KEY: modified_base
<222> LOCATION: (9)..(9)
<223> OTHER INFORMATION: 2'O-Me modified nucleotide
<220> FEATURE:
<221> NAME/KEY: modified_base
<222> LOCATION: (10)..(10)
<223> OTHER INFORMATION: 2'F modified nucleotide
<220> FEATURE:
<221> NAME/KEY: modified_base
<222> LOCATION: (11)..(11)
<223> OTHER INFORMATION: 2'O-Me modified nucleotide
<220> FEATURE:
<221> NAME/KEY: modified_base
<222> LOCATION: (12)..(12)
<223> OTHER INFORMATION: 2'F modified nucleotide
<220> FEATURE:
<221> NAME/KEY: modified_base
<222> LOCATION: (13)..(13)
<223> OTHER INFORMATION: 2'O-Me modified nucleotide
<220> FEATURE:
<221> NAME/KEY: modified_base
<222> LOCATION: (14)..(14)
<223> OTHER INFORMATION: 2'F modified nucleotide
<220> FEATURE:
<221> NAME/KEY: modified_base
<222> LOCATION: (15)..(15)
<223> OTHER INFORMATION: 2'O-Me modified nucleotide
<220> FEATURE:
<221> NAME/KEY: modified_base
<222> LOCATION: (16)..(16)
<223> OTHER INFORMATION: 2'F modified nucleotide
<220> FEATURE:
<221> NAME/KEY: modified_base
<222> LOCATION: (17)..(17)
<223> OTHER INFORMATION: 2'O-Me modified nucleotide
<220> FEATURE:
<221> NAME/KEY: modified_base
<222> LOCATION: (18)..(18)
<223> OTHER INFORMATION: 2'F modified nucleotide
```

```
<220> FEATURE:
<221> NAME/KEY: modified_base
<222> LOCATION: (19)..(21)
<223> OTHER INFORMATION: 2'O-Me modified nucleotide
<220> FEATURE:
<221> NAME/KEY: misc_feature
<222> LOCATION: (19)..(21)
<223> OTHER INFORMATION: Phosphorothioate linkage

<400> SEQUENCE: 55
ugaccaguga caaugaccgu u                                              21

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Inverted nucleotide
<220> FEATURE:
<221> NAME/KEY: modified_base
<222> LOCATION: (1)..(1)
<223> OTHER INFORMATION: Deoxy-nucleotide
<220> FEATURE:
<221> NAME/KEY: modified_base
<222> LOCATION: (2)..(3)
<223> OTHER INFORMATION: 2'O-Me modified nucleotide
<220> FEATURE:
<221> NAME/KEY: modified_base
<222> LOCATION: (4)..(4)
<223> OTHER INFORMATION: 2'F modified nucleotide
<220> FEATURE:
<221> NAME/KEY: modified_base
<222> LOCATION: (5)..(5)
<223> OTHER INFORMATION: 2'O-Me modified nucleotide
<220> FEATURE:
<221> NAME/KEY: modified_base
<222> LOCATION: (6)..(6)
<223> OTHER INFORMATION: 2'F modified nucleotide
<220> FEATURE:
<221> NAME/KEY: modified_base
<222> LOCATION: (7)..(7)
<223> OTHER INFORMATION: 2'O-Me modified nucleotide
<220> FEATURE:
<221> NAME/KEY: modified_base
<222> LOCATION: (8)..(8)
<223> OTHER INFORMATION: 2'F modified nucleotide
<220> FEATURE:
<221> NAME/KEY: modified_base
<222> LOCATION: (9)..(9)
<223> OTHER INFORMATION: 2'O-Me modified nucleotide
<220> FEATURE:
<221> NAME/KEY: modified_base
<222> LOCATION: (10)..(10)
<223> OTHER INFORMATION: 2'F modified nucleotide
<220> FEATURE:
<221> NAME/KEY: modified_base
<222> LOCATION: (11)..(11)
<223> OTHER INFORMATION: 2'O-Me modified nucleotide
<220> FEATURE:
<221> NAME/KEY: modified_base
<222> LOCATION: (12)..(12)
<223> OTHER INFORMATION: 2'F modified nucleotide
<220> FEATURE:
<221> NAME/KEY: modified_base
<222> LOCATION: (13)..(13)
<223> OTHER INFORMATION: 2'O-Me modified nucleotide
```

```
<220> FEATURE:
<221> NAME/KEY: modified_base
<222> LOCATION: (14)..(14)
<223> OTHER INFORMATION: 2'F modified nucleotide
<220> FEATURE:
<221> NAME/KEY: modified_base
<222> LOCATION: (15)..(15)
<223> OTHER INFORMATION: 2'O-Me modified nucleotide
<220> FEATURE:
<221> NAME/KEY: modified_base
<222> LOCATION: (16)..(16)
<223> OTHER INFORMATION: 2'F modified nucleotide
<220> FEATURE:
<221> NAME/KEY: modified_base
<222> LOCATION: (17)..(17)
<223> OTHER INFORMATION: 2'O-Me modified nucleotide
<220> FEATURE:
<221> NAME/KEY: modified_base
<222> LOCATION: (18)..(18)
<223> OTHER INFORMATION: 2'F modified nucleotide
<220> FEATURE:
<221> NAME/KEY: modified_base
<222> LOCATION: (19)..(19)
<223> OTHER INFORMATION: 2'O-Me modified nucleotide
<220> FEATURE:
<221> NAME/KEY: modified_base
<222> LOCATION: (20)..(20)
<223> OTHER INFORMATION: 2'F modified nucleotide
<220> FEATURE:
<221> NAME/KEY: modified_base
<222> LOCATION: (21)..(21)
<223> OTHER INFORMATION: Inverted nucleotide
<220> FEATURE:
<221> NAME/KEY: modified_base
<222> LOCATION: (21)..(21)
<223> OTHER INFORMATION: Deoxy-nucleotide

<400> SEQUENCE: 56
tcggucauug ucacugguca t                                            21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Inverted nucleotide
<220> FEATURE:
<221> NAME/KEY: modified_base
<222> LOCATION: (1)..(1)
<223> OTHER INFORMATION: Deoxy-nucleotide
<220> FEATURE:
<221> NAME/KEY: modified_base
<222> LOCATION: (2)..(2)
<223> OTHER INFORMATION: 2'F modified nucleotide
<220> FEATURE:
<221> NAME/KEY: modified_base
<222> LOCATION: (3)..(4)
<223> OTHER INFORMATION: Deoxy-nucleotide
<220> FEATURE:
<221> NAME/KEY: modified_base
<222> LOCATION: (5)..(6)
<223> OTHER INFORMATION: 2'F modified nucleotide
<220> FEATURE:
<221> NAME/KEY: modified_base
<222> LOCATION: (7)..(7)
<223> OTHER INFORMATION: Deoxy-nucleotide
```

```
<220> FEATURE:
<221> NAME/KEY: modified_base
<222> LOCATION: (8)..(9)
<223> OTHER INFORMATION: 2'F modified nucleotide
<220> FEATURE:
<221> NAME/KEY: modified_base
<222> LOCATION: (10)..(10)
<223> OTHER INFORMATION: Deoxy-nucleotide
<220> FEATURE:
<221> NAME/KEY: modified_base
<222> LOCATION: (11)..(12)
<223> OTHER INFORMATION: 2'F modified nucleotide
<220> FEATURE:
<221> NAME/KEY: modified_base
<222> LOCATION: (13)..(13)
<223> OTHER INFORMATION: Deoxy-nucleotide
<220> FEATURE:
<221> NAME/KEY: modified_base
<222> LOCATION: (14)..(15)
<223> OTHER INFORMATION: 2'F modified nucleotide
<220> FEATURE:
<221> NAME/KEY: modified_base
<222> LOCATION: (16)..(17)
<223> OTHER INFORMATION: Deoxy-nucleotide
<220> FEATURE:
<221> NAME/KEY: modified_base
<222> LOCATION: (18)..(19)
<223> OTHER INFORMATION: 2'F modified nucleotide
<220> FEATURE:
<221> NAME/KEY: modified_base
<222> LOCATION: (20)..(21)
<223> OTHER INFORMATION: Deoxy-nucleotide
<220> FEATURE:
<221> NAME/KEY: modified_base
<222> LOCATION: (21)..(21)
<223> OTHER INFORMATION: Inverted nucleotide

<400> SEQUENCE: 57
tcggucauug ucacugguca t                                              21

<210> SEQ ID NO 58
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'F modified nucleotide
<220> FEATURE:
<221> NAME/KEY: modified_base
<222> LOCATION: (2)..(3)
<223> OTHER INFORMATION: 2'O-Me modified nucleotide
<220> FEATURE:
<221> NAME/KEY: modified_base
<222> LOCATION: (4)..(5)
<223> OTHER INFORMATION: 2'F modified nucleotide
<220> FEATURE:
<221> NAME/KEY: modified_base
<222> LOCATION: (6)..(7)
<223> OTHER INFORMATION: 2'O-Me modified nucleotide
<220> FEATURE:
<221> NAME/KEY: modified_base
<222> LOCATION: (8)..(8)
<223> OTHER INFORMATION: 2'F modified nucleotide
<220> FEATURE:
<221> NAME/KEY: modified_base
<222> LOCATION: (9)..(10)
<223> OTHER INFORMATION: 2'O-Me modified nucleotide
<220> FEATURE:
<221> NAME/KEY: modified_base
<222> LOCATION: (11)..(11)
<223> OTHER INFORMATION: 2'F modified nucleotide
```

```
<220> FEATURE:
<221> NAME/KEY: modified_base
<222> LOCATION: (12)..(13)
<223> OTHER INFORMATION: 2'O-Me modified nucleotide
<220> FEATURE:
<221> NAME/KEY: modified_base
<222> LOCATION: (14)..(14)
<223> OTHER INFORMATION: 2'F modified nucleotide
<220> FEATURE:
<221> NAME/KEY: modified_base
<222> LOCATION: (15)..(16)
<223> OTHER INFORMATION: 2'O-Me modified nucleotide
<220> FEATURE:
<221> NAME/KEY: modified_base
<222> LOCATION: (17)..(18)
<223> OTHER INFORMATION: 2'F modified nucleotide
<220> FEATURE:
<221> NAME/KEY: modified_base
<222> LOCATION: (19)..(21)
<223> OTHER INFORMATION: 2'O-Me modified nucleotide
<220> FEATURE:
<221> NAME/KEY: misc_feature
<222> LOCATION: (20)..(21)
<223> OTHER INFORMATION: Phosphorothioate linkage

<400> SEQUENCE: 58
ugaccaguga caaugaccgu u                                              21

<210> SEQ ID NO 59
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2'O-Me modified nucleotide
<220> FEATURE:
<221> NAME/KEY: modified_base
<222> LOCATION: (3)..(3)
<223> OTHER INFORMATION: 2'F modified nucleotide
<220> FEATURE:
<221> NAME/KEY: modified_base
<222> LOCATION: (4)..(4)
<223> OTHER INFORMATION: 2'O-Me modified nucleotide
<220> FEATURE:
<221> NAME/KEY: modified_base
<222> LOCATION: (5)..(5)
<223> OTHER INFORMATION: 2'F modified nucleotide
<220> FEATURE:
<221> NAME/KEY: modified_base
<222> LOCATION: (6)..(6)
<223> OTHER INFORMATION: 2'O-Me modified nucleotide
<220> FEATURE:
<221> NAME/KEY: modified_base
<222> LOCATION: (7)..(7)
<223> OTHER INFORMATION: 2'F modified nucleotide
<220> FEATURE:
<221> NAME/KEY: modified_base
<222> LOCATION: (8)..(8)
<223> OTHER INFORMATION: 2'O-Me modified nucleotide
<220> FEATURE:
<221> NAME/KEY: modified_base
<222> LOCATION: (9)..(9)
<223> OTHER INFORMATION: 2'F modified nucleotide
<220> FEATURE:
<221> NAME/KEY: modified_base
<222> LOCATION: (10)..(10)
<223> OTHER INFORMATION: 2'O-Me modified nucleotide
<220> FEATURE:
<221> NAME/KEY: modified_base
<222> LOCATION: (11)..(11)
<223> OTHER INFORMATION: 2'F modified nucleotide
```

```
<220> FEATURE:
<221> NAME/KEY: modified_base
<222> LOCATION: (12)..(12)
<223> OTHER INFORMATION: 2'O-Me modified nucleotide
<220> FEATURE:
<221> NAME/KEY: modified_base
<222> LOCATION: (13)..(13)
<223> OTHER INFORMATION: 2'F modified nucleotide
<220> FEATURE:
<221> NAME/KEY: modified_base
<222> LOCATION: (14)..(14)
<223> OTHER INFORMATION: 2'O-Me modified nucleotide
<220> FEATURE:
<221> NAME/KEY: modified_base
<222> LOCATION: (15)..(15)
<223> OTHER INFORMATION: 2'F modified nucleotide
<220> FEATURE:
<221> NAME/KEY: modified_base
<222> LOCATION: (16)..(16)
<223> OTHER INFORMATION: 2'O-Me modified nucleotide
<220> FEATURE:
<221> NAME/KEY: modified_base
<222> LOCATION: (17)..(17)
<223> OTHER INFORMATION: 2'F modified nucleotide
<220> FEATURE:
<221> NAME/KEY: modified_base
<222> LOCATION: (18)..(18)
<223> OTHER INFORMATION: 2'O-Me modified nucleotide
<220> FEATURE:
<221> NAME/KEY: modified_base
<222> LOCATION: (19)..(19)
<223> OTHER INFORMATION: 2'F modified nucleotide
<220> FEATURE:
<221> NAME/KEY: modified_base
<222> LOCATION: (20)..(20)
<223> OTHER INFORMATION: 2'O-Me modified nucleotide
<220> FEATURE:
<221> NAME/KEY: modified_base
<222> LOCATION: (21)..(21)
<223> OTHER INFORMATION: 2'F modified nucleotide
<220> FEATURE:
<221> NAME/KEY: modified_base
<222> LOCATION: (22)..(23)
<223> OTHER INFORMATION: 2'O-Me modified nucleotide
<220> FEATURE:
<221> NAME/KEY: misc_feature
<222> LOCATION: (22)..(23)
<223> OTHER INFORMATION: Phosphorothioate linkage

<400> SEQUENCE: 59
gcggucauug ucacuggucu uuu                                               23

<210> SEQ ID NO 60
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2'F modified nucleotide
<220> FEATURE:
<221> NAME/KEY: modified_base
<222> LOCATION: (3)..(3)
<223> OTHER INFORMATION: 2'O-Me modified nucleotide
<220> FEATURE:
<221> NAME/KEY: modified_base
<222> LOCATION: (4)..(4)
<223> OTHER INFORMATION: 2'F modified nucleotide
<220> FEATURE:
<221> NAME/KEY: modified_base
<222> LOCATION: (5)..(5)
<223> OTHER INFORMATION: 2'O-Me modified nucleotide
```

```
<220> FEATURE:
<221> NAME/KEY: modified_base
<222> LOCATION: (6)..(6)
<223> OTHER INFORMATION: 2'F modified nucleotide
<220> FEATURE:
<221> NAME/KEY: modified_base
<222> LOCATION: (7)..(7)
<223> OTHER INFORMATION: 2'O-Me modified nucleotide
<220> FEATURE:
<221> NAME/KEY: modified_base
<222> LOCATION: (8)..(8)
<223> OTHER INFORMATION: 2'F modified nucleotide
<220> FEATURE:
<221> NAME/KEY: modified_base
<222> LOCATION: (9)..(9)
<223> OTHER INFORMATION: 2'O-Me modified nucleotide
<220> FEATURE:
<221> NAME/KEY: modified_base
<222> LOCATION: (10)..(10)
<223> OTHER INFORMATION: 2'F modified nucleotide
<220> FEATURE:
<221> NAME/KEY: modified_base
<222> LOCATION: (11)..(11)
<223> OTHER INFORMATION: 2'O-Me modified nucleotide
<220> FEATURE:
<221> NAME/KEY: modified_base
<222> LOCATION: (12)..(12)
<223> OTHER INFORMATION: 2'F modified nucleotide
<220> FEATURE:
<221> NAME/KEY: modified_base
<222> LOCATION: (13)..(13)
<223> OTHER INFORMATION: 2'O-Me modified nucleotide
<220> FEATURE:
<221> NAME/KEY: modified_base
<222> LOCATION: (14)..(14)
<223> OTHER INFORMATION: 2'F modified nucleotide
<220> FEATURE:
<221> NAME/KEY: modified_base
<222> LOCATION: (15)..(15)
<223> OTHER INFORMATION: 2'O-Me modified nucleotide
<220> FEATURE:
<221> NAME/KEY: modified_base
<222> LOCATION: (16)..(16)
<223> OTHER INFORMATION: 2'F modified nucleotide
<220> FEATURE:
<221> NAME/KEY: modified_base
<222> LOCATION: (17)..(17)
<223> OTHER INFORMATION: 2'O-Me modified nucleotide
<220> FEATURE:
<221> NAME/KEY: modified_base
<222> LOCATION: (18)..(18)
<223> OTHER INFORMATION: 2'F modified nucleotide
<220> FEATURE:
<221> NAME/KEY: modified_base
<222> LOCATION: (19)..(19)
<223> OTHER INFORMATION: 2'O-Me modified nucleotide
<220> FEATURE:
<221> NAME/KEY: modified_base
<222> LOCATION: (20)..(20)
<223> OTHER INFORMATION: 2'F modified nucleotide
<220> FEATURE:
<221> NAME/KEY: modified_base
<222> LOCATION: (21)..(23)
<223> OTHER INFORMATION: 2'O-Me modified nucleotide
<220> FEATURE:
<221> NAME/KEY: misc_feature
<222> LOCATION: (22)..(23)
<223> OTHER INFORMATION: Phosphorothioate linkage

<400> SEQUENCE: 60
aagaccagug acaaugaccg cuu                                              23

<210> SEQ ID NO 61
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(2)
<223> OTHER INFORMATION: 2'O-Me modified nucleotide
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: modified_base
<222> LOCATION: (3)..(3)
<223> OTHER INFORMATION: 2'F modified nucleotide
<220> FEATURE:
<221> NAME/KEY: modified_base
<222> LOCATION: (4)..(4)
<223> OTHER INFORMATION: 2'O-Me modified nucleotide
<220> FEATURE:
<221> NAME/KEY: modified_base
<222> LOCATION: (5)..(5)
<223> OTHER INFORMATION: 2'F modified nucleotide
<220> FEATURE:
<221> NAME/KEY: modified_base
<222> LOCATION: (6)..(6)
<223> OTHER INFORMATION: 2'O-Me modified nucleotide
<220> FEATURE:
<221> NAME/KEY: modified_base
<222> LOCATION: (7)..(7)
<223> OTHER INFORMATION: 2'F modified nucleotide
<220> FEATURE:
<221> NAME/KEY: modified_base
<222> LOCATION: (8)..(8)
<223> OTHER INFORMATION: 2'O-Me modified nucleotide
<220> FEATURE:
<221> NAME/KEY: modified_base
<222> LOCATION: (9)..(9)
<223> OTHER INFORMATION: 2'F modified nucleotide
<220> FEATURE:
<221> NAME/KEY: modified_base
<222> LOCATION: (10)..(10)
<223> OTHER INFORMATION: 2'O-Me modified nucleotide
<220> FEATURE:
<221> NAME/KEY: modified_base
<222> LOCATION: (11)..(11)
<223> OTHER INFORMATION: 2'F modified nucleotide
<220> FEATURE:
<221> NAME/KEY: modified_base
<222> LOCATION: (12)..(12)
<223> OTHER INFORMATION: 2'O-Me modified nucleotide
<220> FEATURE:
<221> NAME/KEY: modified_base
<222> LOCATION: (13)..(13)
<223> OTHER INFORMATION: 2'F modified nucleotide
<220> FEATURE:
<221> NAME/KEY: modified_base
<222> LOCATION: (14)..(14)
<223> OTHER INFORMATION: 2'O-Me modified nucleotide
<220> FEATURE:
<221> NAME/KEY: modified_base
<222> LOCATION: (15)..(15)
<223> OTHER INFORMATION: 2'F modified nucleotide
<220> FEATURE:
<221> NAME/KEY: modified_base
<222> LOCATION: (16)..(16)
<223> OTHER INFORMATION: 2'O-Me modified nucleotide
<220> FEATURE:
<221> NAME/KEY: modified_base
<222> LOCATION: (17)..(17)
<223> OTHER INFORMATION: 2'F modified nucleotide
<220> FEATURE:
<221> NAME/KEY: modified_base
<222> LOCATION: (18)..(18)
<223> OTHER INFORMATION: 2'O-Me modified nucleotide
```

<220> FEATURE:
<221> NAME/KEY: modified_base
<222> LOCATION: (19)..(19)
<223> OTHER INFORMATION: 2'F modified nucleotide
<220> FEATURE:
<221> NAME/KEY: modified_base
<222> LOCATION: (20)..(20)
<223> OTHER INFORMATION: 2'O-Me modified nucleotide
<220> FEATURE:
<221> NAME/KEY: modified_base
<222> LOCATION: (21)..(21)
<223> OTHER INFORMATION: 2'F modified nucleotide
<220> FEATURE:
<221> NAME/KEY: modified_base
<222> LOCATION: (22)..(22)
<223> OTHER INFORMATION: Inverted nucleotide
<220> FEATURE:
<221> NAME/KEY: modified_base
<222> LOCATION: (22)..(22)
<223> OTHER INFORMATION: Deoxy-nucleotide

<400> SEQUENCE: 61
gcggucauug ucacuggucu ut                                              22

<210> SEQ ID NO 62
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2'F modified nucleotide
<220> FEATURE:
<221> NAME/KEY: modified_base
<222> LOCATION: (3)..(3)
<223> OTHER INFORMATION: 2'O-Me modified nucleotide
<220> FEATURE:
<221> NAME/KEY: modified_base
<222> LOCATION: (4)..(4)
<223> OTHER INFORMATION: 2'F modified nucleotide
<220> FEATURE:
<221> NAME/KEY: modified_base
<222> LOCATION: (5)..(5)
<223> OTHER INFORMATION: 2'O-Me modified nucleotide
<220> FEATURE:
<221> NAME/KEY: modified_base
<222> LOCATION: (6)..(6)
<223> OTHER INFORMATION: 2'F modified nucleotide
<220> FEATURE:
<221> NAME/KEY: modified_base
<222> LOCATION: (7)..(7)
<223> OTHER INFORMATION: 2'O-Me modified nucleotide
<220> FEATURE:
<221> NAME/KEY: modified_base
<222> LOCATION: (8)..(8)
<223> OTHER INFORMATION: 2'F modified nucleotide
<220> FEATURE:
<221> NAME/KEY: modified_base
<222> LOCATION: (9)..(9)
<223> OTHER INFORMATION: 2'O-Me modified nucleotide
<220> FEATURE:
<221> NAME/KEY: modified_base
<222> LOCATION: (10)..(10)
<223> OTHER INFORMATION: 2'F modified nucleotide
<220> FEATURE:
<221> NAME/KEY: modified_base
<222> LOCATION: (11)..(11)
<223> OTHER INFORMATION: 2'O-Me modified nucleotide
<220> FEATURE:
<221> NAME/KEY: modified_base
<222> LOCATION: (12)..(12)
<223> OTHER INFORMATION: 2'F modified nucleotide

```
<220> FEATURE:
<221> NAME/KEY: modified_base
<222> LOCATION: (13)..(13)
<223> OTHER INFORMATION: 2'O-Me modified nucleotide
<220> FEATURE:
<221> NAME/KEY: modified_base
<222> LOCATION: (14)..(14)
<223> OTHER INFORMATION: 2'F modified nucleotide
<220> FEATURE:
<221> NAME/KEY: modified_base
<222> LOCATION: (15)..(15)
<223> OTHER INFORMATION: 2'O-Me modified nucleotide
<220> FEATURE:
<221> NAME/KEY: modified_base
<222> LOCATION: (16)..(16)
<223> OTHER INFORMATION: 2'F modified nucleotide
<220> FEATURE:
<221> NAME/KEY: modified_base
<222> LOCATION: (17)..(17)
<223> OTHER INFORMATION: 2'O-Me modified nucleotide
<220> FEATURE:
<221> NAME/KEY: modified_base
<222> LOCATION: (18)..(18)
<223> OTHER INFORMATION: 2'F modified nucleotide
<220> FEATURE:
<221> NAME/KEY: modified_base
<222> LOCATION: (19)..(19)
<223> OTHER INFORMATION: 2'O-Me modified nucleotide
<220> FEATURE:
<221> NAME/KEY: modified_base
<222> LOCATION: (20)..(20)
<223> OTHER INFORMATION: 2'F modified nucleotide
<220> FEATURE:
<221> NAME/KEY: misc_feature
<222> LOCATION: (20)..(21)
<223> OTHER INFORMATION: Phosphorothioate linkage
<220> FEATURE:
<221> NAME/KEY: modified_base
<222> LOCATION: (21)..(23)
<223> OTHER INFORMATION: 2'O-Me modified nucleotide
<220> FEATURE:
<221> NAME/KEY: misc_feature
<222> LOCATION: (22)..(23)
<223> OTHER INFORMATION: Phosphorothioate linkage

<400> SEQUENCE: 62
aagaccagug acaaugaccg cuu                                              23

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Inverted nucleotide
<220> FEATURE:
<221> NAME/KEY: modified_base
<222> LOCATION: (1)..(1)
<223> OTHER INFORMATION: Deoxy-nucleotide
<220> FEATURE:
<221> NAME/KEY: modified_base
<222> LOCATION: (2)..(3)
<223> OTHER INFORMATION: 2'O-Me modified nucleotide
<220> FEATURE:
<221> NAME/KEY: modified_base
<222> LOCATION: (4)..(4)
<223> OTHER INFORMATION: 2'F modified nucleotide
```

```
-continued

<220> FEATURE:
<221> NAME/KEY: modified_base
<222> LOCATION: (5)..(5)
<223> OTHER INFORMATION: 2'O-Me modified nucleotide
<220> FEATURE:
<221> NAME/KEY: modified_base
<222> LOCATION: (6)..(6)
<223> OTHER INFORMATION: 2'F modified nucleotide
<220> FEATURE:
<221> NAME/KEY: modified_base
<222> LOCATION: (7)..(7)
<223> OTHER INFORMATION: 2'O-Me modified nucleotide
<220> FEATURE:
<221> NAME/KEY: modified_base
<222> LOCATION: (8)..(8)
<223> OTHER INFORMATION: 2'F modified nucleotide
<220> FEATURE:
<221> NAME/KEY: modified_base
<222> LOCATION: (9)..(9)
<223> OTHER INFORMATION: 2'O-Me modified nucleotide
<220> FEATURE:
<221> NAME/KEY: modified_base
<222> LOCATION: (10)..(10)
<223> OTHER INFORMATION: 2'F modified nucleotide
<220> FEATURE:
<221> NAME/KEY: modified_base
<222> LOCATION: (11)..(11)
<223> OTHER INFORMATION: 2'O-Me modified nucleotide
<220> FEATURE:
<221> NAME/KEY: modified_base
<222> LOCATION: (12)..(12)
<223> OTHER INFORMATION: 2'F modified nucleotide
<220> FEATURE:
<221> NAME/KEY: modified_base
<222> LOCATION: (13)..(13)
<223> OTHER INFORMATION: 2'O-Me modified nucleotide
<220> FEATURE:
<221> NAME/KEY: modified_base
<222> LOCATION: (14)..(14)
<223> OTHER INFORMATION: 2'F modified nucleotide
<220> FEATURE:
<221> NAME/KEY: modified_base
<222> LOCATION: (15)..(15)
<223> OTHER INFORMATION: 2'O-Me modified nucleotide
<220> FEATURE:
<221> NAME/KEY: modified_base
<222> LOCATION: (16)..(16)
<223> OTHER INFORMATION: 2'F modified nucleotide
<220> FEATURE:
<221> NAME/KEY: modified_base
<222> LOCATION: (17)..(17)
<223> OTHER INFORMATION: 2'O-Me modified nucleotide
<220> FEATURE:
<221> NAME/KEY: modified_base
<222> LOCATION: (18)..(18)
<223> OTHER INFORMATION: 2'F modified nucleotide
<220> FEATURE:
<221> NAME/KEY: modified_base
<222> LOCATION: (19)..(19)
<223> OTHER INFORMATION: 2'O-Me modified nucleotide
<220> FEATURE:
<221> NAME/KEY: modified_base
<222> LOCATION: (20)..(20)
<223> OTHER INFORMATION: 2'F modified nucleotide
<220> FEATURE:
<221> NAME/KEY: modified_base
<222> LOCATION: (21)..(21)
<223> OTHER INFORMATION: 2'O-Me modified nucleotide
<220> FEATURE:
<221> NAME/KEY: modified_base
<222> LOCATION: (22)..(22)
<223> OTHER INFORMATION: 2'F modified nucleotide
<220> FEATURE:
<221> NAME/KEY: modified_base
<222> LOCATION: (23)..(23)
<223> OTHER INFORMATION: Inverted nucleotide
```

```
<220> FEATURE:
<221> NAME/KEY: modified_base
<222> LOCATION: (23)..(23)
<223> OTHER INFORMATION: Deoxy-nucleotide

<400> SEQUENCE: 63
tgcggucauu gucacugguc uut                                               23

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Inverted nucleotide
<220> FEATURE:
<221> NAME/KEY: modified_base
<222> LOCATION: (1)..(2)
<223> OTHER INFORMATION: Deoxy-nucleotide
<220> FEATURE:
<221> NAME/KEY: modified_base
<222> LOCATION: (3)..(3)
<223> OTHER INFORMATION: 2'F modified nucleotide
<220> FEATURE:
<221> NAME/KEY: modified_base
<222> LOCATION: (4)..(5)
<223> OTHER INFORMATION: Deoxy-nucleotide
<220> FEATURE:
<221> NAME/KEY: modified_base
<222> LOCATION: (6)..(7)
<223> OTHER INFORMATION: 2'F modified nucleotide
<220> FEATURE:
<221> NAME/KEY: modified_base
<222> LOCATION: (8)..(8)
<223> OTHER INFORMATION: Deoxy-nucleotide
<220> FEATURE:
<221> NAME/KEY: modified_base
<222> LOCATION: (9)..(10)
<223> OTHER INFORMATION: 2'F modified nucleotide
<220> FEATURE:
<221> NAME/KEY: modified_base
<222> LOCATION: (11)..(11)
<223> OTHER INFORMATION: Deoxy-nucleotide
<220> FEATURE:
<221> NAME/KEY: modified_base
<222> LOCATION: (12)..(13)
<223> OTHER INFORMATION: 2'F modified nucleotide
<220> FEATURE:
<221> NAME/KEY: modified_base
<222> LOCATION: (14)..(14)
<223> OTHER INFORMATION: Deoxy-nucleotide
<220> FEATURE:
<221> NAME/KEY: modified_base
<222> LOCATION: (15)..(16)
<223> OTHER INFORMATION: 2'F modified nucleotide
<220> FEATURE:
<221> NAME/KEY: modified_base
<222> LOCATION: (17)..(18)
<223> OTHER INFORMATION: Deoxy-nucleotide
<220> FEATURE:
<221> NAME/KEY: modified_base
<222> LOCATION: (19)..(22)
<223> OTHER INFORMATION: 2'F modified nucleotide
<220> FEATURE:
<221> NAME/KEY: modified_base
<222> LOCATION: (23)..(23)
<223> OTHER INFORMATION: Inverted nucleotide
```

```
<220> FEATURE:
<221> NAME/KEY: modified_base
<222> LOCATION: (23)..(23)
<223> OTHER INFORMATION: Deoxy-nucleotide

<400> SEQUENCE: 64
tgcggucauu gucacugguc uut                                              23

<210> SEQ ID NO 65
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2'O-Me modified nucleotide
<220> FEATURE:
<221> NAME/KEY: modified_base
<222> LOCATION: (3)..(4)
<223> OTHER INFORMATION: 2'F modified nucleotide
<220> FEATURE:
<221> NAME/KEY: modified_base
<222> LOCATION: (5)..(6)
<223> OTHER INFORMATION: 2'O-Me modified nucleotide
<220> FEATURE:
<221> NAME/KEY: modified_base
<222> LOCATION: (7)..(7)
<223> OTHER INFORMATION: 2'F modified nucleotide
<220> FEATURE:
<221> NAME/KEY: modified_base
<222> LOCATION: (8)..(9)
<223> OTHER INFORMATION: 2'O-Me modified nucleotide
<220> FEATURE:
<221> NAME/KEY: modified_base
<222> LOCATION: (10)..(10)
<223> OTHER INFORMATION: 2'F modified nucleotide
<220> FEATURE:
<221> NAME/KEY: modified_base
<222> LOCATION: (11)..(12)
<223> OTHER INFORMATION: 2'O-Me modified nucleotide
<220> FEATURE:
<221> NAME/KEY: modified_base
<222> LOCATION: (13)..(13)
<223> OTHER INFORMATION: 2'F modified nucleotide
<220> FEATURE:
<221> NAME/KEY: modified_base
<222> LOCATION: (14)..(15)
<223> OTHER INFORMATION: 2'O-Me modified nucleotide
<220> FEATURE:
<221> NAME/KEY: modified_base
<222> LOCATION: (16)..(17)
<223> OTHER INFORMATION: 2'F modified nucleotide
<220> FEATURE:
<221> NAME/KEY: modified_base
<222> LOCATION: (18)..(18)
<223> OTHER INFORMATION: 2'O-Me modified nucleotide
<220> FEATURE:
<221> NAME/KEY: modified_base
<222> LOCATION: (19)..(21)
<223> OTHER INFORMATION: 2'F modified nucleotide
<220> FEATURE:
<221> NAME/KEY: modified_base
<222> LOCATION: (22)..(23)
<223> OTHER INFORMATION: 2'O-Me modified nucleotide
<220> FEATURE:
<221> NAME/KEY: misc_feature
<222> LOCATION: (22)..(23)
<223> OTHER INFORMATION: Phosphorothioate linkage

<400> SEQUENCE: 65
gaccagugac aaugaccgcu uuu                                              23
```

```
<210> SEQ ID NO 66
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2'O-Me modified nucleotide
<220> FEATURE:
<221> NAME/KEY: modified_base
<222> LOCATION: (3)..(3)
<223> OTHER INFORMATION: 2'F modified nucleotide
<220> FEATURE:
<221> NAME/KEY: modified_base
<222> LOCATION: (4)..(4)
<223> OTHER INFORMATION: 2'O-Me modified nucleotide
<220> FEATURE:
<221> NAME/KEY: modified_base
<222> LOCATION: (5)..(5)
<223> OTHER INFORMATION: 2'F modified nucleotide
<220> FEATURE:
<221> NAME/KEY: modified_base
<222> LOCATION: (6)..(6)
<223> OTHER INFORMATION: 2'O-Me modified nucleotide
<220> FEATURE:
<221> NAME/KEY: modified_base
<222> LOCATION: (7)..(7)
<223> OTHER INFORMATION: 2'F modified nucleotide
<220> FEATURE:
<221> NAME/KEY: modified_base
<222> LOCATION: (8)..(8)
<223> OTHER INFORMATION: 2'O-Me modified nucleotide
<220> FEATURE:
<221> NAME/KEY: modified_base
<222> LOCATION: (9)..(9)
<223> OTHER INFORMATION: 2'F modified nucleotide
<220> FEATURE:
<221> NAME/KEY: modified_base
<222> LOCATION: (10)..(10)
<223> OTHER INFORMATION: 2'O-Me modified nucleotide
<220> FEATURE:
<221> NAME/KEY: modified_base
<222> LOCATION: (11)..(11)
<223> OTHER INFORMATION: 2'F modified nucleotide
<220> FEATURE:
<221> NAME/KEY: modified_base
<222> LOCATION: (12)..(12)
<223> OTHER INFORMATION: 2'O-Me modified nucleotide
<220> FEATURE:
<221> NAME/KEY: modified_base
<222> LOCATION: (13)..(13)
<223> OTHER INFORMATION: 2'F modified nucleotide
<220> FEATURE:
<221> NAME/KEY: modified_base
<222> LOCATION: (14)..(14)
<223> OTHER INFORMATION: 2'O-Me modified nucleotide
<220> FEATURE:
<221> NAME/KEY: modified_base
<222> LOCATION: (15)..(15)
<223> OTHER INFORMATION: 2'F modified nucleotide
<220> FEATURE:
<221> NAME/KEY: modified_base
<222> LOCATION: (16)..(16)
<223> OTHER INFORMATION: 2'O-Me modified nucleotide
<220> FEATURE:
<221> NAME/KEY: modified_base
<222> LOCATION: (17)..(17)
<223> OTHER INFORMATION: 2'F modified nucleotide
<220> FEATURE:
<221> NAME/KEY: modified_base
<222> LOCATION: (18)..(18)
<223> OTHER INFORMATION: 2'O-Me modified nucleotide
<220> FEATURE:
<221> NAME/KEY: modified_base
<222> LOCATION: (19)..(19)
<223> OTHER INFORMATION: 2'F modified nucleotide
```

-continued

```
<220> FEATURE:
<221> NAME/KEY: modified_base
<222> LOCATION: (20)..(20)
<223> OTHER INFORMATION: 2'O-Me modified nucleotide
<220> FEATURE:
<221> NAME/KEY: modified_base
<222> LOCATION: (21)..(21)
<223> OTHER INFORMATION: 2'F modified nucleotide
<220> FEATURE:
<221> NAME/KEY: modified_base
<222> LOCATION: (22)..(23)
<223> OTHER INFORMATION: 2'O-Me modified nucleotide
<220> FEATURE:
<221> NAME/KEY: misc_feature
<222> LOCATION: (22)..(23)
<223> OTHER INFORMATION: Phosphorothioate linkage

<400> SEQUENCE: 66
ugaaaggauu cauccuccuu uuu                                            23

<210> SEQ ID NO 67
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2'F modified nucleotide
<220> FEATURE:
<221> NAME/KEY: modified_base
<222> LOCATION: (3)..(3)
<223> OTHER INFORMATION: 2'O-Me modified nucleotide
<220> FEATURE:
<221> NAME/KEY: modified_base
<222> LOCATION: (4)..(4)
<223> OTHER INFORMATION: 2'F modified nucleotide
<220> FEATURE:
<221> NAME/KEY: modified_base
<222> LOCATION: (5)..(5)
<223> OTHER INFORMATION: 2'O-Me modified nucleotide
<220> FEATURE:
<221> NAME/KEY: modified_base
<222> LOCATION: (6)..(6)
<223> OTHER INFORMATION: 2'F modified nucleotide
<220> FEATURE:
<221> NAME/KEY: modified_base
<222> LOCATION: (7)..(7)
<223> OTHER INFORMATION: 2'O-Me modified nucleotide
<220> FEATURE:
<221> NAME/KEY: modified_base
<222> LOCATION: (8)..(8)
<223> OTHER INFORMATION: 2'F modified nucleotide
<220> FEATURE:
<221> NAME/KEY: modified_base
<222> LOCATION: (9)..(9)
<223> OTHER INFORMATION: 2'O-Me modified nucleotide
<220> FEATURE:
<221> NAME/KEY: modified_base
<222> LOCATION: (10)..(10)
<223> OTHER INFORMATION: 2'F modified nucleotide
<220> FEATURE:
<221> NAME/KEY: modified_base
<222> LOCATION: (11)..(11)
<223> OTHER INFORMATION: 2'O-Me modified nucleotide
<220> FEATURE:
<221> NAME/KEY: modified_base
<222> LOCATION: (12)..(12)
<223> OTHER INFORMATION: 2'F modified nucleotide
<220> FEATURE:
<221> NAME/KEY: modified_base
<222> LOCATION: (13)..(13)
<223> OTHER INFORMATION: 2'O-Me modified nucleotide
```

-continued

<220> FEATURE:
<221> NAME/KEY: modified_base
<222> LOCATION: (14)..(14)
<223> OTHER INFORMATION: 2'F modified nucleotide
<220> FEATURE:
<221> NAME/KEY: modified_base
<222> LOCATION: (15)..(15)
<223> OTHER INFORMATION: 2'O-Me modified nucleotide
<220> FEATURE:
<221> NAME/KEY: modified_base
<222> LOCATION: (16)..(16)
<223> OTHER INFORMATION: 2'F modified nucleotide
<220> FEATURE:
<221> NAME/KEY: modified_base
<222> LOCATION: (17)..(17)
<223> OTHER INFORMATION: 2'O-Me modified nucleotide
<220> FEATURE:
<221> NAME/KEY: modified_base
<222> LOCATION: (18)..(18)
<223> OTHER INFORMATION: 2'F modified nucleotide
<220> FEATURE:
<221> NAME/KEY: modified_base
<222> LOCATION: (19)..(19)
<223> OTHER INFORMATION: 2'O-Me modified nucleotide
<220> FEATURE:
<221> NAME/KEY: modified_base
<222> LOCATION: (20)..(20)
<223> OTHER INFORMATION: 2'F modified nucleotide
<220> FEATURE:
<221> NAME/KEY: modified_base
<222> LOCATION: (21)..(23)
<223> OTHER INFORMATION: 2'O-Me modified nucleotide
<220> FEATURE:
<221> NAME/KEY: misc_feature
<222> LOCATION: (22)..(23)
<223> OTHER INFORMATION: Phosphorothioate linkage

<400> SEQUENCE: 67
aaaggaggau gaauccuuuc auu                                        23

<210> SEQ ID NO 68
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(2)
<223> OTHER INFORMATION: 2'O-Me modified nucleotide
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: modified_base
<222> LOCATION: (3)..(3)
<223> OTHER INFORMATION: 2'F modified nucleotide
<220> FEATURE:
<221> NAME/KEY: modified_base
<222> LOCATION: (4)..(4)
<223> OTHER INFORMATION: 2'O-Me modified nucleotide
<220> FEATURE:
<221> NAME/KEY: modified_base
<222> LOCATION: (5)..(5)
<223> OTHER INFORMATION: 2'F modified nucleotide
<220> FEATURE:
<221> NAME/KEY: modified_base
<222> LOCATION: (6)..(6)
<223> OTHER INFORMATION: 2'O-Me modified nucleotide

```
<220> FEATURE:
<221> NAME/KEY: modified_base
<222> LOCATION: (7)..(7)
<223> OTHER INFORMATION: 2'F modified nucleotide
<220> FEATURE:
<221> NAME/KEY: modified_base
<222> LOCATION: (8)..(8)
<223> OTHER INFORMATION: 2'O-Me modified nucleotide
<220> FEATURE:
<221> NAME/KEY: modified_base
<222> LOCATION: (9)..(9)
<223> OTHER INFORMATION: 2'F modified nucleotide
<220> FEATURE:
<221> NAME/KEY: modified_base
<222> LOCATION: (10)..(10)
<223> OTHER INFORMATION: 2'O-Me modified nucleotide
<220> FEATURE:
<221> NAME/KEY: modified_base
<222> LOCATION: (11)..(11)
<223> OTHER INFORMATION: 2'F modified nucleotide
<220> FEATURE:
<221> NAME/KEY: modified_base
<222> LOCATION: (12)..(12)
<223> OTHER INFORMATION: 2'O-Me modified nucleotide
<220> FEATURE:
<221> NAME/KEY: modified_base
<222> LOCATION: (13)..(13)
<223> OTHER INFORMATION: 2'F modified nucleotide
<220> FEATURE:
<221> NAME/KEY: modified_base
<222> LOCATION: (14)..(14)
<223> OTHER INFORMATION: 2'O-Me modified nucleotide
<220> FEATURE:
<221> NAME/KEY: modified_base
<222> LOCATION: (15)..(15)
<223> OTHER INFORMATION: 2'F modified nucleotide
<220> FEATURE:
<221> NAME/KEY: modified_base
<222> LOCATION: (16)..(16)
<223> OTHER INFORMATION: 2'O-Me modified nucleotide
<220> FEATURE:
<221> NAME/KEY: modified_base
<222> LOCATION: (17)..(17)
<223> OTHER INFORMATION: 2'F modified nucleotide
<220> FEATURE:
<221> NAME/KEY: modified_base
<222> LOCATION: (18)..(18)
<223> OTHER INFORMATION: 2'O-Me modified nucleotide
<220> FEATURE:
<221> NAME/KEY: modified_base
<222> LOCATION: (19)..(19)
<223> OTHER INFORMATION: 2'F modified nucleotide
<220> FEATURE:
<221> NAME/KEY: modified_base
<222> LOCATION: (20)..(20)
<223> OTHER INFORMATION: 2'O-Me modified nucleotide
<220> FEATURE:
<221> NAME/KEY: modified_base
<222> LOCATION: (21)..(21)
<223> OTHER INFORMATION: 2'F modified nucleotide
<220> FEATURE:
<221> NAME/KEY: modified_base
<222> LOCATION: (22)..(22)
<223> OTHER INFORMATION: Inverted nucleotide
<220> FEATURE:
<221> NAME/KEY: modified_base
<222> LOCATION: (22)..(22)
<223> OTHER INFORMATION: Deoxy-nucleotide

<400> SEQUENCE: 68
ugaaaggauu cauccuccuu ut                                          22

<210> SEQ ID NO 69
<211> LENGTH: 23
<212> TYPE: RNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2'F modified nucleotide
<220> FEATURE:
<221> NAME/KEY: modified_base
<222> LOCATION: (3)..(3)
<223> OTHER INFORMATION: 2'O-Me modified nucleotide
<220> FEATURE:
<221> NAME/KEY: modified_base
<222> LOCATION: (4)..(4)
<223> OTHER INFORMATION: 2'F modified nucleotide
<220> FEATURE:
<221> NAME/KEY: modified_base
<222> LOCATION: (5)..(5)
<223> OTHER INFORMATION: 2'O-Me modified nucleotide
<220> FEATURE:
<221> NAME/KEY: modified_base
<222> LOCATION: (6)..(6)
<223> OTHER INFORMATION: 2'F modified nucleotide
<220> FEATURE:
<221> NAME/KEY: modified_base
<222> LOCATION: (7)..(7)
<223> OTHER INFORMATION: 2'O-Me modified nucleotide
<220> FEATURE:
<221> NAME/KEY: modified_base
<222> LOCATION: (8)..(8)
<223> OTHER INFORMATION: 2'F modified nucleotide
<220> FEATURE:
<221> NAME/KEY: modified_base
<222> LOCATION: (9)..(9)
<223> OTHER INFORMATION: 2'O-Me modified nucleotide
<220> FEATURE:
<221> NAME/KEY: modified_base
<222> LOCATION: (10)..(10)
<223> OTHER INFORMATION: 2'F modified nucleotide
<220> FEATURE:
<221> NAME/KEY: modified_base
<222> LOCATION: (11)..(11)
<223> OTHER INFORMATION: 2'O-Me modified nucleotide
<220> FEATURE:
<221> NAME/KEY: modified_base
<222> LOCATION: (12)..(12)
<223> OTHER INFORMATION: 2'F modified nucleotide
<220> FEATURE:
<221> NAME/KEY: modified_base
<222> LOCATION: (13)..(13)
<223> OTHER INFORMATION: 2'O-Me modified nucleotide
<220> FEATURE:
<221> NAME/KEY: modified_base
<222> LOCATION: (14)..(14)
<223> OTHER INFORMATION: 2'F modified nucleotide
<220> FEATURE:
<221> NAME/KEY: modified_base
<222> LOCATION: (15)..(15)
<223> OTHER INFORMATION: 2'O-Me modified nucleotide
<220> FEATURE:
<221> NAME/KEY: modified_base
<222> LOCATION: (16)..(16)
<223> OTHER INFORMATION: 2'F modified nucleotide
<220> FEATURE:
<221> NAME/KEY: modified_base
<222> LOCATION: (17)..(17)
<223> OTHER INFORMATION: 2'O-Me modified nucleotide
<220> FEATURE:
<221> NAME/KEY: modified_base
<222> LOCATION: (18)..(18)
<223> OTHER INFORMATION: 2'F modified nucleotide
<220> FEATURE:
<221> NAME/KEY: modified_base
<222> LOCATION: (19)..(19)
<223> OTHER INFORMATION: 2'O-Me modified nucleotide
<220> FEATURE:
<221> NAME/KEY: modified_base
<222> LOCATION: (20)..(20)
<223> OTHER INFORMATION: 2'F modified nucleotide
```

```
<220> FEATURE:
<221> NAME/KEY: modified_base
<222> LOCATION: (21)..(23)
<223> OTHER INFORMATION: 2'O-Me modified nucleotide
<220> FEATURE:
<221> NAME/KEY: misc_feature
<222> LOCATION: (21)..(23)
<223> OTHER INFORMATION: Phosphorothioate linkage

<400> SEQUENCE: 69
aaaggaggau gaauccuuuc auu                                          23

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Inverted nucleotide
<220> FEATURE:
<221> NAME/KEY: modified_base
<222> LOCATION: (1)..(1)
<223> OTHER INFORMATION: Deoxy-nucleotide
<220> FEATURE:
<221> NAME/KEY: modified_base
<222> LOCATION: (2)..(3)
<223> OTHER INFORMATION: 2'O-Me modified nucleotide
<220> FEATURE:
<221> NAME/KEY: modified_base
<222> LOCATION: (4)..(4)
<223> OTHER INFORMATION: 2'F modified nucleotide
<220> FEATURE:
<221> NAME/KEY: modified_base
<222> LOCATION: (5)..(5)
<223> OTHER INFORMATION: 2'O-Me modified nucleotide
<220> FEATURE:
<221> NAME/KEY: modified_base
<222> LOCATION: (6)..(6)
<223> OTHER INFORMATION: 2'F modified nucleotide
<220> FEATURE:
<221> NAME/KEY: modified_base
<222> LOCATION: (7)..(7)
<223> OTHER INFORMATION: 2'O-Me modified nucleotide
<220> FEATURE:
<221> NAME/KEY: modified_base
<222> LOCATION: (8)..(8)
<223> OTHER INFORMATION: 2'F modified nucleotide
<220> FEATURE:
<221> NAME/KEY: modified_base
<222> LOCATION: (9)..(9)
<223> OTHER INFORMATION: 2'O-Me modified nucleotide
<220> FEATURE:
<221> NAME/KEY: modified_base
<222> LOCATION: (10)..(10)
<223> OTHER INFORMATION: 2'F modified nucleotide
<220> FEATURE:
<221> NAME/KEY: modified_base
<222> LOCATION: (11)..(11)
<223> OTHER INFORMATION: 2'O-Me modified nucleotide
<220> FEATURE:
<221> NAME/KEY: modified_base
<222> LOCATION: (12)..(12)
<223> OTHER INFORMATION: 2'F modified nucleotide
<220> FEATURE:
<221> NAME/KEY: modified_base
<222> LOCATION: (13)..(13)
<223> OTHER INFORMATION: 2'O-Me modified nucleotide
```

```
<220> FEATURE:
<221> NAME/KEY: modified_base
<222> LOCATION: (14)..(14)
<223> OTHER INFORMATION: 2'F modified nucleotide
<220> FEATURE:
<221> NAME/KEY: modified_base
<222> LOCATION: (15)..(15)
<223> OTHER INFORMATION: 2'O-Me modified nucleotide
<220> FEATURE:
<221> NAME/KEY: modified_base
<222> LOCATION: (16)..(16)
<223> OTHER INFORMATION: 2'F modified nucleotide
<220> FEATURE:
<221> NAME/KEY: modified_base
<222> LOCATION: (17)..(17)
<223> OTHER INFORMATION: 2'O-Me modified nucleotide
<220> FEATURE:
<221> NAME/KEY: modified_base
<222> LOCATION: (18)..(18)
<223> OTHER INFORMATION: 2'F modified nucleotide
<220> FEATURE:
<221> NAME/KEY: modified_base
<222> LOCATION: (19)..(19)
<223> OTHER INFORMATION: 2'O-Me modified nucleotide
<220> FEATURE:
<221> NAME/KEY: modified_base
<222> LOCATION: (20)..(20)
<223> OTHER INFORMATION: 2'F modified nucleotide
<220> FEATURE:
<221> NAME/KEY: modified_base
<222> LOCATION: (21)..(21)
<223> OTHER INFORMATION: 2'O-Me modified nucleotide
<220> FEATURE:
<221> NAME/KEY: modified_base
<222> LOCATION: (22)..(22)
<223> OTHER INFORMATION: 2'F modified nucleotide
<220> FEATURE:
<221> NAME/KEY: modified_base
<222> LOCATION: (23)..(23)
<223> OTHER INFORMATION: Inverted nucleotide
<220> FEATURE:
<221> NAME/KEY: modified_base
<222> LOCATION: (23)..(23)
<223> OTHER INFORMATION: Deoxy-nucleotide

<400> SEQUENCE: 70
tugaaaggau ucauccuccu uut                                            23

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: Inverted nucleotide
<220> FEATURE:
<221> NAME/KEY: modified_base
<222> LOCATION: (1)..(1)
<223> OTHER INFORMATION: Deoxy-nucleotide
<220> FEATURE:
<221> NAME/KEY: modified_base
<222> LOCATION: (2)..(2)
<223> OTHER INFORMATION: 2'F modified nucleotide
<220> FEATURE:
<221> NAME/KEY: modified_base
<222> LOCATION: (3)..(9)
<223> OTHER INFORMATION: Deoxy-nucleotide
```

```
<220> FEATURE:
<221> NAME/KEY: modified_base
<222> LOCATION: (10)..(12)
<223> OTHER INFORMATION: 2'F modified nucleotide
<220> FEATURE:
<221> NAME/KEY: modified_base
<222> LOCATION: (13)..(13)
<223> OTHER INFORMATION: Deoxy-nucleotide
<220> FEATURE:
<221> NAME/KEY: modified_base
<222> LOCATION: (14)..(22)
<223> OTHER INFORMATION: 2'F modified nucleotide
<220> FEATURE:
<221> NAME/KEY: modified_base
<222> LOCATION: (23)..(23)
<223> OTHER INFORMATION: Inverted nucleotide
<220> FEATURE:
<221> NAME/KEY: modified_base
<222> LOCATION: (23)..(23)
<223> OTHER INFORMATION: Deoxy-nucleotide

<400> SEQUENCE: 71
tugaaaggau ucauccuccu uut                                              23

<210> SEQ ID NO 72
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(7)
<223> OTHER INFORMATION: 2'O-Me modified nucleotide
<220> FEATURE:
<221> NAME/KEY: modified_base
<222> LOCATION: (8)..(8)
<223> OTHER INFORMATION: 2'F modified nucleotide
<220> FEATURE:
<221> NAME/KEY: modified_base
<222> LOCATION: (9)..(11)
<223> OTHER INFORMATION: 2'O-Me modified nucleotide
<220> FEATURE:
<221> NAME/KEY: modified_base
<222> LOCATION: (12)..(18)
<223> OTHER INFORMATION: 2'F modified nucleotide
<220> FEATURE:
<221> NAME/KEY: modified_base
<222> LOCATION: (19)..(19)
<223> OTHER INFORMATION: 2'O-Me modified nucleotide
<220> FEATURE:
<221> NAME/KEY: modified_base
<222> LOCATION: (20)..(21)
<223> OTHER INFORMATION: 2'F modified nucleotide
<220> FEATURE:
<221> NAME/KEY: modified_base
<222> LOCATION: (22)..(23)
<223> OTHER INFORMATION: 2'O-Me modified nucleotide
<220> FEATURE:
<221> NAME/KEY: misc_feature
<222> LOCATION: (22)..(23)
<223> OTHER INFORMATION: Phosphorothioate linkage

<400> SEQUENCE: 72
aggaggauga auccuuucau uuu                                              23

<210> SEQ ID NO 73
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 73
gcggucauug ucacuggucu u                                              21

<210> SEQ ID NO 74
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
ugaaaggauu cauccuccuu u                                              21

<210> SEQ ID NO 75
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
gaccagugac aaugaccgcu u                                              21

<210> SEQ ID NO 76
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
aggaggauga auccuuucau u                                              21

<210> SEQ ID NO 77
<211> LENGTH: 4001
<212> TYPE: DNA
<213> ORGANISM: Homo sapiens

<400> SEQUENCE: 77
tccctctccc accagggta  tacatcctca gagctgaccc acgacctagc tttctggtgt     60
gactcggggt gggggctccc actggtcacc tggtgacccc catcgcagtg agttccgccc    120 caagggaag  cccagcctat agcaggctgg ggtgggtgt  gtgcggaggg aggtgggaga    180
ggcgtggaac tagagaccct ccaccttcat gtagaactag gggaacaacc ttaggttcca    240
agccccaagt ccctatgttt ccaccccttt ctaaggacag gcgtggagga gcggctgggg    300
ctggcgggct tgtcgggatc tcagctccct gagccctcct cctgccacgg gcctgctccc    360
ctccttctct catggggtc  tgctgtagcc tcgggaagga ggcaggaaac ctccaaataa    420
aatgacaagg cacgatttgc tccccctact cagtaggcat tggagcggtg agtttgcatt    480
tccaaggcac aaggttatcc taaatactag agttgccggg ctcccagctc agccccaaga    540
attctcccct cctcgcaggg agaagccacc gcctggcccc ctcatcttag acgcaccaag    600
tccggcgcag aggaagggag gggacacgcg gagcaggcca ggctttcagg aggcaccgga    660
atctcctagt cctggctcgc acggctcggg caagcctcga gatccggcga ccccaaacca    720
ctccctgggt ccccgccgga ggctggccca ggcggtccc  acagccgcgc gcctcacgcg    780
cagttgccca tggccttgac caaggagctc tctggcagct ggcggaagat gccccgcagc    840
```

```
gtgtccagtt cgcggctcag ctgttccacc cgcttgcgca ggcggtcatt gtcactggtc    900
agctccagca ccttctgctg cgtctccacg ttgcgctgct tggccttgtc gcggctcttg    960
cgcaccgcga tgttgttgcg ctcgcgccgc acccggtact cgttgctgtt cttgtccacc   1020
gacttcttgg ccttgcccgc gccgctgccg ccactcgcgc ggaggtcggg gtgcgcggcg   1080
cccagcccct tgagcgcgct gccagggccc ggcaggccgg cggcaccgag cgcgggcgcg   1140
gggtgcgggc tgggcacggg cgtgggcggc ggcgtggggt gaccgggctg caggtgcatg   1200
gtggtctggc cgcagtgcgc gatctggaac tgcaggtgcg gggcggccag gtgcgcgggc   1260
ggcgggtgcg ggtgcgggtg cgagggcggc ggcggcggcg gcggctggta agggaagagg   1320
ccggccagcg ccagctgctt ggcttcatcc tcctcgcggg gctcctgctt gatcaccagc   1380
ggccgcagcg ccggcgcccc gacgcgctcg tacaggggct ccagcctgcc gtccaggtag   1440
ccggcggccg cgcagccgta gccgggcggg ggcccgtgcg ctcccccggg catgacggcg   1500
ccgccgggc ccgcgggcgc gcccgggtag tcaaagtcgc cgccgccgcc gccgcccgtg   1560
gggcccacgg ccgccttggc cttctcctgc tgccggctgt gctggaacag gtcggccagg   1620
aactcgtcgt tgaaggcggc cgggtcgatg taggcgctga tgtcgatgga cgtctcgtgc   1680
tcgcagatgc cgcccagcgg ctccggggcg gcaggtgggg cggaggctg cgcggggccc   1740
gcgccccggg gaaagccgaa ggcggcgctg ctgggcgcgt gcgggggct ctgcaggtgg   1800
ctgctcatcg ggggccgcgg ctccgcctcg tagaagtcgg ccgactccat gggggagtta   1860
gagttctccc ggcatggcga gcctcggcgg cctccagcct gcgcggggcg tcgccgccgc   1920
ccacccggag accctgctcg cccgcgcccg cgcacctccg ggtcgcgaat ggcccggccc   1980
gcgccggccc agcttttata cccggcaggc cgcgtcgccc cctagagtcc gaggcggcct   2040
ctgtccccgg gctgcggcgg cgcggcgcct gctgggtcct agcgcgcggc cggcatgggg   2100
cggcgaacca gcgcggcaca gcgccgcgct ccccaggcag gccgcggcgc aacgcccacc   2160
gcctccagcg cgcccagcag agccgcggcg ctcgctccaa gctccgcccc cggcccggcc   2220
gtcgccccc gcccacgtg gtcggtagcg ggggccccct cctcctgcct gccctaggcg   2280
cccgtatcca gccacggccg ggagcccagg agtatcccga ggctgcacgg ggtaggggtg   2340
gggggcggag ggcgagtctt ggtcttgagc tgctggggcg cggattctct ttcaaagcca   2400
gaaccaggcc tgtcccggac ccgcgtcccg gggaggctgc agcgcagagc agcggggctg   2460
gggccggtgg ggggccgttt gggacgcgcg gagaggtcct gagcgcggtg gctctgcgtc   2520
tcctagctct gatctccagg ctaccccgt gattccgcgc agaggtacct ctcggaggac   2580
gccggggtcc catgggcggc gccgcgcagg gcgctaggac cccgcgggga gcggaggcgg   2640
cctcggcccg ggagcctgga ggacctggcc ggtcgatccg cccgggctgg aaaactttct   2700
ttataattac ttctccaggt cggagcgcgc ggcttgctag gcgcgcgggg ccggcgctgt   2760
taccggcgt ggagtcgccg attttttttc ctgcggacc gcggggcccc ccagactagc   2820
ggagctggac gccggggcga gcacggggag gggcgcaccg agggaggaga caaacttaac   2880
tctggggccg ggattccgag gcggggggccg cagccctcga ggcccgaagc caccgcttcc   2940
tcccccgcct cccattcag gtgggcgcca acgcgggag cgaggtgtc caggccgccg   3000
ggctgccagg tccgagcacg cacagggaga actctgccca gtggttcgcc gggcgctgta   3060
gtccccggga tcctagggac cgaggcggcc aggccctggg gccccttgag tgcggcagct   3120
aatgctctca ccgcggcggg ggaaggagct tgccaccgag accccagcc acgtgcgtcc   3180
ctcgcattct ttaccggggc cggggtggcg gctacggacc gtcagctggg cccagatgga   3240
```

-continued

```
gtcttgggag ccctcaagtg tctcctgtcc ttgcccgcgc cgcccctcgc cactggcgct    3300
gaggcctgac gccgcctgcg tcccggctag aggcgcgctt gcctacaggt gagggaagac    3360 cccttcacc gacagtggcc ttaggcctgg caaggcgcca cgacccgccc aggagccccg    3420
gagggggcac agctaaaaac accgctggag agccccgagc ttccacgacg atcgcagtaa    3480
agaagcagtt tcatctgggc aacgcacact gcgctttaat caagttccta ttcaacatag    3540
tcccagtgat taatagccca actgcttcgt tttcggtcca gagctcataa acaagatatt    3600
tttagcttga cgcttttgga cgggagggag taaaaaccag atacgttaaa taaatatccc    3660
gatgtgagcc ggagagctgc ttgctgagcc aaatgcagga cccattcata tagcattcac    3720
ctgtggaggg agacctggac ggaaatcaaa aagcaccaag agcgatttgc gttttttct    3780 gcggtgctaa aactaatggc ttttcctacc taggaacaaa gaaacgccac tgtacatgca    3840
cggttcccgg cctgtggagt tgtgggagga aggcgatgtc tggcctttt tgcacagctg    3900 ctgttgcctg cccagagatc gggaactctg ccccgtagga ctggaagaaa cctcagtaat    3960
gggaataaga ctttgtccaa taggggggctg atgaatgtgt g                       4001
```

<210> SEQ ID NO 78
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-OMe modified nucleotide
<220> FEATURE:
<221> NAME/KEY: modified_base
<222> LOCATION: (7)..(7)
<223> OTHER INFORMATION: 2'-OMe modified nucleotide
<220> FEATURE:
<221> NAME/KEY: misc_feature
<222> LOCATION: (19)..(21)
<223> OTHER INFORMATION: Phosphorothioate linkages
<220> FEATURE:
<221> NAME/KEY: modified_base
<222> LOCATION: (20)..(21)
<223> OTHER INFORMATION: 2'-OMe modified nucleotide

<400> SEQUENCE: 78
cuuacgcuga guacuucgau u                                              21

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (4)..(4)
<223> OTHER INFORMATION: 2'-OMe modified nucleotide
<220> FEATURE:
<221> NAME/KEY: modified_base
<222> LOCATION: (9)..(9)
<223> OTHER INFORMATION: 2'-OMe modified nucleotide
<220> FEATURE:
<221> NAME/KEY: modified_base
<222> LOCATION: (15)..(16)
<223> OTHER INFORMATION: 2'-OMe modified nucleotide

```
<220> FEATURE:
<221> NAME/KEY: modified_base
<222> LOCATION: (19)..(19)
<223> OTHER INFORMATION: 2'-OMe modified nucleotide
<220> FEATURE:
<221> NAME/KEY: misc_feature
<222> LOCATION: (20)..(21)
<223> OTHER INFORMATION: Phosphorothioate linkages

<400> SEQUENCE: 79
ggaugaagug gagauuagut t                                              21

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: 2'F modified nucleotide
<220> FEATURE:
<221> NAME/KEY: modified_base
<222> LOCATION: (7)..(10)
<223> OTHER INFORMATION: 2'F modified nucleotide
<220> FEATURE:
<221> NAME/KEY: modified_base
<222> LOCATION: (14)..(17)
<223> OTHER INFORMATION: 2'F modified nucleotide
<220> FEATURE:
<221> NAME/KEY: modified_base
<222> LOCATION: (19)..(19)
<223> OTHER INFORMATION: 2'F modified nucleotide
<220> FEATURE:
<221> NAME/KEY: misc_feature
<222> LOCATION: (20)..(21)
<223> OTHER INFORMATION: Phosphorothioate linkage

<400> SEQUENCE: 80
ggaucaucuc aagucuuact t                                              21

<210> SEQ ID NO 81
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
ucuacuguca cucaguaguu u                                              21

<210> SEQ ID NO 82
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-OMe modified nucleotide
<220> FEATURE:
<221> NAME/KEY: modified_base
<222> LOCATION: (7)..(7)
<223> OTHER INFORMATION: 2'-OMe modified nucleotide
<220> FEATURE:
<221> NAME/KEY: modified_base
<222> LOCATION: (9)..(9)
<223> OTHER INFORMATION: 2'-OMe modified nucleotide
```

```
<220> FEATURE:
<221> NAME/KEY: modified_base
<222> LOCATION: (14)..(14)
<223> OTHER INFORMATION: 2'-OMe modified nucleotide
<220> FEATURE:
<221> NAME/KEY: misc_feature
<222> LOCATION: (19)..(21)
<223> OTHER INFORMATION: Phosphorothioate linkages
<220> FEATURE:
<221> NAME/KEY: modified_base
<222> LOCATION: (19)..(21)
<223> OTHER INFORMATION: 2'-OMe modified nucleotide

<400> SEQUENCE: 82
ucgaaguacu cagcguaagu u                                              21

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(3)
<223> OTHER INFORMATION: 2'-OMe modified nucleotide
<220> FEATURE:
<221> NAME/KEY: modified_base
<222> LOCATION: (10)..(10)
<223> OTHER INFORMATION: 2'-OMe modified nucleotide
<220> FEATURE:
<221> NAME/KEY: modified_base
<222> LOCATION: (15)..(15)
<223> OTHER INFORMATION: 2'-OMe modified nucleotide
<220> FEATURE:
<221> NAME/KEY: misc_feature
<222> LOCATION: (20)..(21)
<223> OTHER INFORMATION: Phosphorothioate linkages

<400> SEQUENCE: 83
acuaaucucc acuucaucct t                                              21

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'F modified nucleotide
<220> FEATURE:
<221> NAME/KEY: modified_base
<222> LOCATION: (7)..(9)
<223> OTHER INFORMATION: 2'F modified nucleotide
<220> FEATURE:
<221> NAME/KEY: modified_base
<222> LOCATION: (14)..(14)
<223> OTHER INFORMATION: 2'F modified nucleotide
<220> FEATURE:
<221> NAME/KEY: modified_base
<222> LOCATION: (17)..(19)
<223> OTHER INFORMATION: 2'F modified nucleotide
<220> FEATURE:
<221> NAME/KEY: misc_feature
<222> LOCATION: (20)..(21)
<223> OTHER INFORMATION: Phosphorothioate linkage
```

```
<400> SEQUENCE: 84
guaagacuug agaugaucct t                                               21

<210> SEQ ID NO 85
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
gcggucauug ucacuggucu u                                               21

<210> SEQ ID NO 86
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
gaccagugac aaugaccgcu u                                               21

<210> SEQ ID NO 87
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
ugaaaggauu cauccuccuu u                                               21

<210> SEQ ID NO 88
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
aggaggauga auccuuucau u                                               21

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (20)..(21)
<223> OTHER INFORMATION: Phosphorothioate linkage

<400> SEQUENCE: 89
ggaugaagug gagauuagut t                                               21

<210> SEQ ID NO 90
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 90
acuaaucucc acuucaucct t                                              21

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: modified_base
<222> LOCATION: (5)..(5)
<223> OTHER INFORMATION: 2'-OMe modified nucleotide
<220> FEATURE:
<221> NAME/KEY: modified_base
<222> LOCATION: (7)..(8)
<223> OTHER INFORMATION: 2'-OMe modified nucleotide
<220> FEATURE:
<221> NAME/KEY: modified_base
<222> LOCATION: (12)..(12)
<223> OTHER INFORMATION: 2'-OMe modified nucleotide
<220> FEATURE:
<221> NAME/KEY: modified_base
<222> LOCATION: (14)..(17)
<223> OTHER INFORMATION: 2'-OMe modified nucleotide
<220> FEATURE:
<221> NAME/KEY: misc_feature
<222> LOCATION: (20)..(21)
<223> OTHER INFORMATION: Phosphorothioate linkage

<400> SEQUENCE: 91
cuuacgcuga guacuucgat t                                              21

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 2'-OMe modified nucleotide
<220> FEATURE:
<221> NAME/KEY: modified_base
<222> LOCATION: (11)..(11)
<223> OTHER INFORMATION: 2'-OMe modified nucleotide
<220> FEATURE:
<221> NAME/KEY: modified_base
<222> LOCATION: (16)..(16)
<223> OTHER INFORMATION: 2'-OMe modified nucleotide
<220> FEATURE:
<221> NAME/KEY: misc_feature
<222> LOCATION: (20)..(21)
<223> OTHER INFORMATION: Phosphorothioate linkage

<400> SEQUENCE: 92
ucgaaguacu cagcguaagt t                                              21

<210> SEQ ID NO 93
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 93
gaccagugac aaugaccgcu u                                              21

<210> SEQ ID NO 94
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
gcggucauug ucacuggucu u                                              21

<210> SEQ ID NO 95
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
acuacugagu gacaguagau u                                              21

<210> SEQ ID NO 96
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
ucuacuguca cucaguaguu u                                              21

<210> SEQ ID NO 97
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
gcggucauug ucacuggucu u                                              21

<210> SEQ ID NO 98
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
gaccagugac aaugaccgcu u                                              21

<210> SEQ ID NO 99
<211> LENGTH: 21
<212> TYPE: RNA
<213> ORGANISM: Artificial Sequence
```

-continued

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Inverted abasic modification

<400> SEQUENCE: 99
gcggucauug ucacuggucu u                                                 21

<210> SEQ ID NO 100
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Inverted abasic modification

<400> SEQUENCE: 100
gaccagugac aaugaccgcu u                                                 21

<210> SEQ ID NO 101
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
gcggucauac acacuggucu u                                                 21

<210> SEQ ID NO 102
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
gaccagugug uaugaccgcu u                                                 21

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: modified_base
<222> LOCATION: (5)..(5)
<223> OTHER INFORMATION: 2'-OMe modified nucleotide
<220> FEATURE:
<221> NAME/KEY: modified_base
<222> LOCATION: (7)..(8)
<223> OTHER INFORMATION: 2'-OMe modified nucleotide
```

```
<220> FEATURE:
<221> NAME/KEY: modified_base
<222> LOCATION: (12)..(12)
<223> OTHER INFORMATION: 2'-OMe modified nucleotide
<220> FEATURE:
<221> NAME/KEY: modified_base
<222> LOCATION: (14)..(17)
<223> OTHER INFORMATION: 2'-OMe modified nucleotide
<220> FEATURE:
<221> NAME/KEY: modified_base
<222> LOCATION: (20)..(21)
<223> OTHER INFORMATION: Phosphorothioate linkage

<400> SEQUENCE: 103
cuuacgcuga guacuucgat t                                          21

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(7)
<223> OTHER INFORMATION: 2'-OMe modified nucleotide
<220> FEATURE:
<221> NAME/KEY: modified_base
<222> LOCATION: (11)..(11)
<223> OTHER INFORMATION: 2'-OMe modified nucleotide
<220> FEATURE:
<221> NAME/KEY: modified_base
<222> LOCATION: (16)..(16)
<223> OTHER INFORMATION: 2'-OMe modified nucleotide
<220> FEATURE:
<221> NAME/KEY: modified_base
<222> LOCATION: (20)..(21)
<223> OTHER INFORMATION: Phosphorothioate linkage

<400> SEQUENCE: 104
ucgaaguacu cagcguaagt t                                          21

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (4)..(4)
<223> OTHER INFORMATION: 2'-OMe modified nucleotide
<220> FEATURE:
<221> NAME/KEY: modified_base
<222> LOCATION: (9)..(9)
<223> OTHER INFORMATION: 2'-OMe modified nucleotide
<220> FEATURE:
<221> NAME/KEY: modified_base
<222> LOCATION: (15)..(16)
<223> OTHER INFORMATION: 2'-OMe modified nucleotide
<220> FEATURE:
<221> NAME/KEY: modified_base
<222> LOCATION: (19)..(19)
<223> OTHER INFORMATION: 2'-OMe modified nucleotide
```

```
<220> FEATURE:
<221> NAME/KEY: modified_base
<222> LOCATION: (20)..(21)
<223> OTHER INFORMATION: Phosphorothioate linkage

<400> SEQUENCE: 105
ggaugaagug gagauuagut t                                              21

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(3)
<223> OTHER INFORMATION: 2'-OMe modified nucleotide
<220> FEATURE:
<221> NAME/KEY: modified_base
<222> LOCATION: (10)..(10)
<223> OTHER INFORMATION: 2'-OMe modified nucleotide
<220> FEATURE:
<221> NAME/KEY: modified_base
<222> LOCATION: (15)..(15)
<223> OTHER INFORMATION: 2'-OMe modified nucleotide
<220> FEATURE:
<221> NAME/KEY: modified_base
<222> LOCATION: (20)..(21)
<223> OTHER INFORMATION: Phosphorothioate linkage

<400> SEQUENCE: 106
acuaaucucc acuucaucct t                                              21

<210> SEQ ID NO 107
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Inverted abasic modification
<220> FEATURE:
<221> NAME/KEY: modified_base
<222> LOCATION: (1)..(2)
<223> OTHER INFORMATION: 2'-OMe modified nucleotide
<220> FEATURE:
<221> NAME/KEY: modified_base
<222> LOCATION: (4)..(4)
<223> OTHER INFORMATION: 2'-OMe modified nucleotide
<220> FEATURE:
<221> NAME/KEY: modified_base
<222> LOCATION: (10)..(10)
<223> OTHER INFORMATION: 2'-OMe modified nucleotide
<220> FEATURE:
<221> NAME/KEY: modified_base
<222> LOCATION: (14)..(14)
<223> OTHER INFORMATION: 2'-OMe modified nucleotide
<220> FEATURE:
<221> NAME/KEY: modified_base
<222> LOCATION: (20)..(21)
<223> OTHER INFORMATION: 2'-OMe modified nucleotide

<400> SEQUENCE: 107
gcggucauug ucacuggucu u                                              21
```

```
<210> SEQ ID NO 108
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe modified nucleotide

<400> SEQUENCE: 108
gaccagugac aaugaccgcu u                                              21

<210> SEQ ID NO 109
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe modified nucleotide

<400> SEQUENCE: 109
gaccagugac aaugaccgcu u                                              21

<210> SEQ ID NO 110
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Inverted abasic modification
<220> FEATURE:
<221> NAME/KEY: modified_base
<222> LOCATION: (1)..(2)
<223> OTHER INFORMATION: 2'-OMe modified nucleotide
<220> FEATURE:
<221> NAME/KEY: modified_base
<222> LOCATION: (4)..(4)
<223> OTHER INFORMATION: 2'-OMe modified nucleotide
<220> FEATURE:
<221> NAME/KEY: modified_base
<222> LOCATION: (10)..(10)
<223> OTHER INFORMATION: 2'-OMe modified nucleotide
<220> FEATURE:
<221> NAME/KEY: modified_base
<222> LOCATION: (14)..(14)
<223> OTHER INFORMATION: 2'-OMe modified nucleotide
<220> FEATURE:
<221> NAME/KEY: modified_base
<222> LOCATION: (20)..(21)
<223> OTHER INFORMATION: 2'-OMe modified nucleotide

<400> SEQUENCE: 110
gcggucauug ucacuggucu u                                              21

<210> SEQ ID NO 111
<211> LENGTH: 23
<212> TYPE: RNA
<213> ORGANISM: Artificial Sequence
<220> FEATURE:
<223> OTHER INFORMATION: Synthetic oligonucleotide
```

```
<220> FEATURE:
<221> NAME/KEY: modified_base
<222> LOCATION: (2)..(2)
<223> OTHER INFORMATION: 2'-OMe modified nucleotide
<220> FEATURE:
<221> NAME/KEY: modified_base
<222> LOCATION: (7)..(7)
<223> OTHER INFORMATION: 2'-OMe modified nucleotide
<220> FEATURE:
<221> NAME/KEY: modified_base
<222> LOCATION: (20)..(23)
<223> OTHER INFORMATION: 2'-OMe modified nucleotide

<400> SEQUENCE: 111
cuuacgcuga guacuucgas usu                                                23

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (4)..(4)
<223> OTHER INFORMATION: 2'-OMe modified nucleotide
<220> FEATURE:
<221> NAME/KEY: modified_base
<222> LOCATION: (9)..(9)
<223> OTHER INFORMATION: 2'-OMe modified nucleotide
<220> FEATURE:
<221> NAME/KEY: modified_base
<222> LOCATION: (15)..(16)
<223> OTHER INFORMATION: 2'-OMe modified nucleotide
<220> FEATURE:
<221> NAME/KEY: modified_base
<222> LOCATION: (19)..(19)
<223> OTHER INFORMATION: 2'-OMe modified nucleotide
<220> FEATURE:
<221> NAME/KEY: modified_base
<222> LOCATION: (20)..(21)
<223> OTHER INFORMATION: Phosphorothioate linkage

<400> SEQUENCE: 112
ggaugaagug gagauuagut t                                                  21

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(6)
<223> OTHER INFORMATION: 2'F modified nucleotide
<220> FEATURE:
<221> NAME/KEY: modified_base
<222> LOCATION: (8)..(11)
<223> OTHER INFORMATION: 2'F modified nucleotide
<220> FEATURE:
<221> NAME/KEY: modified_base
<222> LOCATION: (15)..(18)
<223> OTHER INFORMATION: 2'F modified nucleotide
```

```
<220> FEATURE:
<221> NAME/KEY: modified_base
<222> LOCATION: (20)..(21)
<223> OTHER INFORMATION: Phosphorothioate linkage

<400> SEQUENCE: 113
ggaucaucuc aagucuuact t                                              21

<210> SEQ ID NO 114
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 114
ucuacuguca cucaguaguu u                                              21

<210> SEQ ID NO 115
<211> LENGTH: 23
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (2)..(2)
<223> OTHER INFORMATION: 2'-OMe modified nucleotide
<220> FEATURE:
<221> NAME/KEY: modified_base
<222> LOCATION: (7)..(7)
<223> OTHER INFORMATION: 2'-OMe modified nucleotide
<220> FEATURE:
<221> NAME/KEY: modified_base
<222> LOCATION: (9)..(9)
<223> OTHER INFORMATION: 2'-OMe modified nucleotide
<220> FEATURE:
<221> NAME/KEY: modified_base
<222> LOCATION: (14)..(14)
<223> OTHER INFORMATION: 2'-OMe modified nucleotide
<220> FEATURE:
<221> NAME/KEY: modified_base
<222> LOCATION: (19)..(23)
<223> OTHER INFORMATION: 2'-OMe modified nucleotide

<400> SEQUENCE: 115
ucgaaguacu cagcguaags usu                                            23

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(3)
<223> OTHER INFORMATION: 2'-OMe modified nucleotide
<220> FEATURE:
<221> NAME/KEY: modified_base
<222> LOCATION: (10)..(10)
<223> OTHER INFORMATION: 2'-OMe modified nucleotide
<220> FEATURE:
<221> NAME/KEY: modified_base
<222> LOCATION: (15)..(15)
<223> OTHER INFORMATION: 2'-OMe modified nucleotide
```

```
<220> FEATURE:
<221> NAME/KEY: modified_base
<222> LOCATION: (20)..(21)
<223> OTHER INFORMATION: Phosphorothioate linkages

<400> SEQUENCE: 116
acuaaucucc acuucaucct t                                              21

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(3)
<223> OTHER INFORMATION: 2'F modified nucleotide
<220> FEATURE:
<221> NAME/KEY: modified_base
<222> LOCATION: (8)..(10)
<223> OTHER INFORMATION: 2'F modified nucleotide
<220> FEATURE:
<221> NAME/KEY: modified_base
<222> LOCATION: (15)..(15)
<223> OTHER INFORMATION: 2'F modified nucleotide
<220> FEATURE:
<221> NAME/KEY: modified_base
<222> LOCATION: (18)..(19)
<223> OTHER INFORMATION: 2'F modified nucleotide
<220> FEATURE:
<221> NAME/KEY: modified_base
<222> LOCATION: (20)..(21)
<223> OTHER INFORMATION: Phosphorothioate linkages

<400> SEQUENCE: 117
guaagacuug agaugaucct t                                              21

<210> SEQ ID NO 118
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 118
cggucauugu cacggucau u                                               21

<210> SEQ ID NO 119
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 119
ugaccaguga caaugaccgu u                                              21

<210> SEQ ID NO 120
<211> LENGTH: 21
<212> TYPE: RNA
<213> ORGANISM: Artificial Sequence
<220> FEATURE:
<223> OTHER INFORMATION: Synthetic oligonucleotide
```

```
<400> SEQUENCE: 120
gcggucauug ucacuggucu u                                              21

<210> SEQ ID NO 121
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 121
gaccagugac aaugaccgcu u                                              21

<210> SEQ ID NO 122
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 122
ugaaaggauu cauccuccuu u                                              21

<210> SEQ ID NO 123
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 123
aggaggauga auccuuucau u                                              21

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: Phosphorothioate linkages

<400> SEQUENCE: 124
ggaugaagug gagauuagut t                                              21

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 125
acuaaucucc acuucaucct t                                              21
```

```
<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: modified_base
<222> LOCATION: (5)..(5)
<223> OTHER INFORMATION: 2'-OMe modified nucleotide
<220> FEATURE:
<221> NAME/KEY: modified_base
<222> LOCATION: (7)..(8)
<223> OTHER INFORMATION: 2'-OMe modified nucleotide
<220> FEATURE:
<221> NAME/KEY: modified_base
<222> LOCATION: (12)..(12)
<223> OTHER INFORMATION: 2'-OMe modified nucleotide
<220> FEATURE:
<221> NAME/KEY: modified_base
<222> LOCATION: (14)..(17)
<223> OTHER INFORMATION: 2'-OMe modified nucleotide
<220> FEATURE:
<221> NAME/KEY: modified_base
<222> LOCATION: (20)..(21)
<223> OTHER INFORMATION: Phosphorothioate linkages

<400> SEQUENCE: 126
cuuacgcuga guacuucgat t                                           21

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(7)
<223> OTHER INFORMATION: 2'-OMe modified nucleotide
<220> FEATURE:
<221> NAME/KEY: modified_base
<222> LOCATION: (11)..(11)
<223> OTHER INFORMATION: 2'-OMe modified nucleotide
<220> FEATURE:
<221> NAME/KEY: modified_base
<222> LOCATION: (16)..(16)
<223> OTHER INFORMATION: 2'-OMe modified nucleotide
<220> FEATURE:
<221> NAME/KEY: modified_base
<222> LOCATION: (20)..(21)
<223> OTHER INFORMATION: Phosphorothioate linkages

<400> SEQUENCE: 127
ucgaaguacu cagcguaagt t                                           21

<210> SEQ ID NO 128
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (1)..(1)
<223> OTHER INFORMATION: Inverted abasic modification
<220> FEATURE:
<221> NAME/KEY: modified_base
<222> LOCATION: (1)..(2)
<223> OTHER INFORMATION: 2'-OMe modified nucleotide
<220> FEATURE:
<221> NAME/KEY: modified_base
<222> LOCATION: (4)..(4)
<223> OTHER INFORMATION: 2'-OMe modified nucleotide
<220> FEATURE:
<221> NAME/KEY: modified_base
<222> LOCATION: (10)..(10)
<223> OTHER INFORMATION: 2'-OMe modified nucleotide
<220> FEATURE:
<221> NAME/KEY: modified_base
<222> LOCATION: (14)..(14)
<223> OTHER INFORMATION: 2'-OMe modified nucleotide
<220> FEATURE:
<221> NAME/KEY: modified_base
<222> LOCATION: (20)..(21)
<223> OTHER INFORMATION: 2'-OMe modified nucleotide

<400> SEQUENCE: 128
gcggucauug ucacuggucu u                                              21

<210> SEQ ID NO 129
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe modified nucleotide

<400> SEQUENCE: 129
gaccagugac aaugaccgcu u                                              21
```